US009993544B2

(12) United States Patent
Meyers et al.

(10) Patent No.: US 9,993,544 B2
(45) Date of Patent: Jun. 12, 2018

(54) RECOMBINANT CLASSICAL SWINE FEVER VIRUS (CSFV) COMPRISING SUBSTITUTION IN THE TAV EPITOPE OF THE E2 PROTEIN

(71) Applicant: Boehringer Ingelheim Vetmedica GmbH, Ingelheim am Rhein (DE)

(72) Inventors: Gregor Meyers, Neuenkirchen-Wampen (DE); Sabine Wirtz, Aachen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days. days.

(21) Appl. No.: 15/312,249

(22) PCT Filed: May 22, 2015

(86) PCT No.: PCT/EP2015/061473
§ 371 (c)(1),
(2) Date: Nov. 18, 2016

(87) PCT Pub. No.: WO2015/177369
PCT Pub. Date: Nov. 26, 2015

(65) Prior Publication Data
US 2017/0119870 A1    May 4, 2017

(30) Foreign Application Priority Data
May 23, 2014    (EP) ..................................... 14169703

(51) Int. Cl.
*A61K 39/12* (2006.01)
*G01N 33/569* (2006.01)
*C12N 7/00* (2006.01)
*A61K 39/00* (2006.01)

(52) U.S. Cl.
CPC .............. *A61K 39/12* (2013.01); *C12N 7/00* (2013.01); *G01N 33/56983* (2013.01); *A61K 2039/5254* (2013.01); *A61K 2039/552* (2013.01); *C12N 2770/24321* (2013.01); *C12N 2770/24322* (2013.01); *C12N 2770/24334* (2013.01); *C12N 2770/24362* (2013.01); *G01N 2333/185* (2013.01)

(58) Field of Classification Search
None
See application file for complete search history.

(56) References Cited

U.S. PATENT DOCUMENTS

| | | | | |
|---|---|---|---|---|
| 9,636,389 | B2 * | 5/2017 | Fachinger | A61K 39/105 |
| 2009/0232846 | A1 * | 9/2009 | Beer | C12N 7/00 |
| | | | | 424/218.1 |
| 2011/0150770 | A1 * | 6/2011 | Bautista | A61K 39/125 |
| | | | | 424/9.2 |
| 2017/0119870 | A1 * | 5/2017 | Meyers | A61K 39/12 |

FOREIGN PATENT DOCUMENTS

| | | | |
|---|---|---|---|
| SK | 000287626 | * | 4/2011 |
| WO | WO 2005/111201 | * | 11/2005 |
| WO | 2007143442 A2 | | 12/2007 |
| WO | 2010074575 A2 | | 7/2010 |
| WO | 2011144360 A1 | | 11/2011 |
| WO | 2015177369 A1 | | 11/2015 |

OTHER PUBLICATIONS

Becher et al. (Virology. 2003; 31: 96-104).*
International Search Report and Written Opinion for PCT/EP2015/061472 dated Sep. 21, 2015.
Rasmussen et al., "Efficient generation of recombinant RNA viruses using targeted recombination-mediated mutagenesis of bacterial artificial chromosomes containing full-length cDNA." BMC Genomics, vol. 14:819, 2013, pp. 1-10.
Reimann et al., "Characterization of a new chimeric marker vaccine candidate with a mutated antigenic E2-epitope." Veterinary Microbiology, vol. 142, 2010, pp. 45-50.

* cited by examiner

*Primary Examiner* — Shanon A. Foley
(74) *Attorney, Agent, or Firm* — Judy Jarecki-Black

(57) ABSTRACT

The present invention relates i.a. to a CSFV (classical swine fever virus) comprising a substitution of proline to lysine at amino acid position 44 of the E2 protein and a substitution of threonine to aspartic acid at amino acid position 45 of the E2 protein. Further, the present invention provides an immunogenic composition comprising the CSFV of the present invention and the use of the immunogenic composition for reducing the incidence of or severity in an animal of one or more clinical signs associated with CSF. Moreover, the present invention provides a method of differentiating animals infected with CSFV from animals vaccinated with the immunogenic composition of the present invention.

15 Claims, No Drawings

RECOMBINANT CLASSICAL SWINE FEVER VIRUS (CSFV) COMPRISING SUBSTITUTION IN THE TAV EPITOPE OF THE E2 PROTEIN

SEQUENCE LISTING

This application contains a sequence listing in accordance with 37 C.F.R. 1.821-1.825. The sequence listing accompanying this application is hereby incorporated by reference in its entirety.

BACKGROUND

Classical swine fever virus (CSFV), formerly named hog cholera virus, is responsible for classical swine fever (CSF) or hog cholera (HC) (Moennig and Plagemann, 1992. Adv. Virus Res. 41: 53-91; Thiel et al., 1996. eds. Fields, B. N., Knipe, D. M., & Howley, P. M. (Lippincott-Raven, Philadelphia), pp. 1059-1073). Classical swine fever is caused by a small enveloped RNA-Pestvirus within the family Flaviviridae. The natural hosts of the swinel fever virus are solely domesticated and wild swine species.

Pestiviruses are causative agents of economically important diseases of animals in many countries worldwide. Presently known virus isolates have been grouped into four different species: Bovine viral diarrhea virus (BVDV) type 1 (BVDV-1) and type 2 (BVDV-2), CSFV and Border disease virus (BDV) which together form one genus within the family Flaviviridae.

Pestiviruses are small enveloped viruses with a single stranded RNA genome of positive polarity lacking both 5' cap and 3' poly(A) sequences. The viral genome codes for a polyprotein of about 4000 amino acids giving rise to final cleavage products by co- and posttranslational processing involving cellular and viral proteases. The viral proteins are arranged in the polyprotein in the order NH2-Npro-C-Erns-E1-E2-p7-NS2-NS3-NS4A-NS4B-NS5A-NS5B—COOH (Lindenbach and Rice, 2001. eds. Knipe, D. M., & Howley, P. M. (Lippincott-Raven, Philadelphia), pp. 991-1042). Protein C (=core- or capsidprotein) and the glycoproteins Erns, E1 and E2 represent structural components of the pestivirus virion as demonstrated for CSFV (Thiel et al., 1991. J. Virol. 65: 4705-4712). This also holds true for BVDV. E2 and to a lesser extent Erns were found to be targets for antibody neutralization (Donis et al., 1988. J. Gen. Virol. 69: 77-86; Paton et al., 1992. Virology 190: 763-772; van Rijn et al., 1993 J. Gen. Virol. 74: 2053-2060; Weiland et al., 1990. J. Virology 64:3563-3569; Weiland et al., 1992. J. Virology 66:3677-3682). Erns lacks a typical membrane anchor and is secreted in considerable amounts from the infected cells (Fetzer et al., 2005. J. Virol. 79, 11901-11913; Tews and Meyers 2007. J. Biol. Chem. 282, 32730-32741; Rümenapf et al., 1993. J. Virol. 67, 3288-3295; Magkouras et al., 2008. J. Gen. Virol. 89, 2501-2506); this protein has been reported to exhibit RNase activity (Hulst et al., 1994. Virology 200: 558-565; Schneider et al., 1993. Science 261: 1169-1171; Windisch et al., 1996. J. Virol. 70: 352-358). The function of this enzymatic activity for the viral life cycle is presently unknown. The enzymatic activity depends on the presence of two stretches of amino acids conserved between the pestivirus Erns and different known RNases of plant and fungal origin. Both of these conserved sequences contain a histidine residue (Schneider et al., 1993. Science 261: 1169-1171). Inactivation of the RNase activity residing within the Erns results in an attenuated apathogenic pestivirus which is capable to be used as a modified live vaccine (WO 99/64604).

Vaccines comprising attenuated or killed viruses or viral proteins expressed in heterologous expression systems have been generated for CSFV and BVDV and are presently used. The international patent application WO2005/111201 A1 provides a new generation of a modified live pestivirus vaccine, which comprises a multiple modified pestivirus, having at least one mutation in the coding sequence for glycoprotein Erns and at least another mutation in the coding sequence for Npro, wherein said mutation in the coding sequence for glycoprotein Erns leads to inactivation of RNase activity residing in Erns and/or said mutation in the coding sequence for Npro leads to inactivation of said Npro. In addition, vaccines based on the Chinese viral strain "C" or a derivative thereof has been described (so-called "C-strain vaccines"). It has been shown that four days after application of the vaccine, a complete protection of the animals against virulent CSFV challenge infection can be demonstrated. Further, seven days after vaccination, a complete protection is provided from vertical transmission of challenge virus in carrier animals (de Smit et al., 2001. Vaccine 19: 1467-1476).

However, attempts have been made within the European Union to eradicate CSF through rigorous measures without prophylactic vaccination, which has been forbidden since 1990. Vaccination does represent a legally approved option only as an emergency vaccination in cases when swine fever appears (Art. 19 of the Counsel Directive 2001/89/EC).

Therefore, there is a significant demand for a highly efficient vaccine which allows differentiation between vaccinated and infected animals. Furthermore the vaccine shall exhibit all the advantages of traditional modified live vaccines.

Markers for discrimination between vaccinated and infected animals already have been described. Inter alia the TAV epitope having the amino acids TAVSPTTLR (SEQ ID NO:1) from amino acid position 829 to 837 of the polyprotein (containing Npro-C-Erns-E1-E2-p7-N52-N53-NS4A-NS4B-NS5A-NS5B) and the positions 40 to 48 of the E2 protein, respectively, has been mutated.

WO 2010/074575 A2 for example disclose mutations in the TAV epitope of the E2 protein. The substitution of the proline to asparagine (or two asparagines) has been described as well as mutants having a further asparagine substitution. However, WO 2010/074575 A2 rather concentrates on deletion mutants. Only deletion mutants have been tested in animal experiments.

WO 2011/144360 A1 for example disclose escape variants having an amino acid substitution at amino acid position 830 (alanine to valine), at amino acid position 833 (proline to serine) and at amino acid position 839 (glutamic acid to glycine).

Further, in WO 2007/143442 A2 the CSFV E2 has been mutated to the homologous amino acid sequence of BVDV strain NADL E2 for identifying live attenuated CSFV vaccines.

However, the stability of different substitutions within the TAV epitope in cell culture and after re-isolation of vaccinated animals, so far have not been studied.

In light of this, the problem of the present invention is to provide a stable mutated TAV epitope for generating modified live vaccines which enables discrimination between vaccinated and infected animals.

DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "a or an epitope" includes a plurality of epitopes, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the virus strains, the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art.

Generally, the present invention provides a CSFV (classical swine fever virus) comprising a substitution of proline to lysine at amino acid position 44 of the E2 protein and a substitution of threonine to aspartic acid at amino acid position 45 of the E2 protein.

The term "CSFV" as used herein refers to all viruses belonging to species of classical swine fever virus (CSFV) in the genus Pestivirus within the family Flaviviridae.

The term "substitution" means that an amino acid is replaced by another amino acid at the same position. Thus, the term substitution covers the removal/deletion of an amino acid, followed by insertion of another amino acid at the same position.

The term "E2 protein" refers to the processed E2 protein which results as final cleavage product from the polyprotein (Npro-C-Erns-E1-E2-p7-NS2-NS3-NS4A-NS4B-NS5A-NS5B) of the CSFV.

The term "amino acid position" refers to the amino acid position in the processed E2 protein from the N-terminal. The TAV epitope having the amino acids TAVSPTTLR (SEQ ID NO: 1) is located within positions 40 to 48 of the processed E2 protein. However, the localization of the TAV epitope can further be defined in relation to the polyprotein (containing Npro-C-Erns-E1-E2-p7-N52-N53-NS4A-NS4B-NS5A-NS5B). The TAV epitope having the amino acids TAVSPTTLR (SEQ ID NO: 1) is located within positions 829 to 837 of the E2 polyprotein. With polyprotein is meant the about 4000 amino acid hypothetical polyprotein that is formed upon translation of the viral RNA. Said polyprotein is processed to form the final cleavage products Npro-C-Erns-E1-E2-p7-NS2-NS3-NS4A-NS4B-NS5A-NS5B.

In one aspect of the present invention said amino acid substitution is within the TAV epitope of the E2 protein having the amino acid sequence TAVSPTTLR (SEQ ID NO:1).

In one aspect of the present invention said amino acid substitution is within the TAV epitope of the E2 protein having the amino acid sequence TAVSPTTLRT (SEQ ID NO:17).

In one aspect of the present invention the amino acid substitution within the TAV epitope of the E2 protein results in the TAV epitope sequence TAVSKDTLRT (SEQ ID NO:22).

In one aspect of the present invention the amino acid substitution within the TAV epitope of the E2 protein is a stable amino acid substitution.

The term "TAV epitope" refers to an epitope within the E2 protein. The CSFV E2 protein contains a recently identified epitope that comprises the amino acid sequence TAVSPTTLR (SEQ ID NO:1) (residues 40 to 48 of the E2 protein or residues 829-837 of the CSFV polyprotein; using single letter code for amino acids). This epitope is evolutionarily conserved and specific for CSFV and a target for neutralizing antibodies (Lin et al., 2000. J Virol 74: 11619-25).

The term "stable amino acid substitution" refers to an amino acid substitution which is still present after several passages of the CSFV virus in cell culture. Preferably, the amino acid substitution within the TAV epitope of the E2 protein is still present after at least 3 passages, more preferably after at least 6 passages, even more preferably after at least 9 passages, even more preferably after at least 12 passages, even more preferably after at least 15 passages, even more preferably after at least 20 passages, even more preferably after at least 30 passages, even more preferably after at least 50 passages, even more preferably after 100 passages, most preferred after 250 passages of the CSFV in cell culture. The term "cell culture" or "passages in cell culture" is known by the person skilled in the art. The term relates to the propagation of the virus in cells cultured outside the organism. Said term also refers to the propagation of cells outside the organism in a cell system. Such cell system comprises host cells (such as SK-6 cells or PK-15 cells and the alike) and cell culture medium suitable for the propagation of such cells outside of the organism. Suitable cell culture media are known to a person skilled in the art and are commercially available. They may comprise nutrients, salts, growth factors, antibiotics, serum (e.g. fetal calf serum) and pH-indicators (e.g. phenol red). Whether an amino acid is still present within the TAV epitope of the E2 protein can be determined by the person skilled in the art without further ado. Further, the term "stable amino acid substitution" also refers to an amino acid substitution which is still present after re-isolation of the CSFV from vaccinated animals which prior have been vaccinated with the CSFV of the present invention. Preferably, the amino acid substitution within the TAV epitope of the E2 protein is still present at least 3 days, more preferably at least 4 days, even more preferably at least 5 days, even more preferably at least 6 days, even more preferably at least 7 days, even more preferably at least 8 days, even more preferably at least 9 days, even more preferably at least 10 days, even more preferably at least 12 days, even more preferably at least 15 days, even more preferably at least 20 days, even more preferably at least 25 days, even more preferably at least 35 days, even more preferably at least 50 days, most preferred at least 100 days after the vaccination in the re-isolated CSFV from vaccinated animals which prior have been vaccinated with the CSFV of the present invention. The vaccination, re-isolation of the CSFV and the determination whether an amino acid is still present within the TAV epitope of the E2 protein can be done by the person skilled in the art without further ado.

It has been found that not all substitutions within the TAV epitope at positions 44, 45 and 46 of the E2 protein have the same stability. In contrast, it has been found that most substitutions tested are not suitable for generating marker or DIVA vaccines due to exemplary reversions in the sequence at said positions within the TAV epitope. However, surprisingly, it has been found that a substitution of proline to lysine at amino acid position 44 of the E2 protein and a substitution of threonine to aspartic acid at amino acid position 45 within the TAV epitope of the E2 protein is highly suitable for generating marker or DIVA vaccines due to the stability of said substitutions. Said substitution within the TAV epitope according to the present invention is stable after several passages of the CSFV virus according to the invention in cell culture. Further, the substitution within the TAV epitope according to the present invention is still present after re-isolation of the CSFV from vaccinated animals which prior have been vaccinated with the CSFV of the present invention. Thus, stability of the substitution in the TAV epitope according to the present invention has been shown. Moreover, it has been shown that the substitution within the TAV epitope according to the present invention cannot be recognized by antibodies specific for the intact (wildtype) TAV epitope of the E2 protein. Thus, the substitution within the TAV epitope according to the present invention can be used as a negative marker for generating marker or DIVA vaccines.

In one aspect of the present invention the amino acid substitution within the TAV epitope of the E2 protein results in a TAV epitope sequence as shown in SEQ ID NO: 22.

Preferably, the CSFV is the Alfort Tübingen strain. The Alfort Tübingen strain has been described in the prior art and its genome sequence is available (Meyers et al., 1989. Virology 171: 555-567; WO2009156448 A1).

The amino acid sequence as shown in SEQ ID NO: 2 refers to the sequence of the Alfort Tübingen wildtype strain.

In another aspect of the present invention the CSFV has an amino acid as shown in SEQ ID NO: 3.

The amino acid sequence as shown in SEQ ID NO: 3 refers to the sequence of the Alfort Tübingen strain having the substitution of proline to lysine at amino acid position 44 of the E2 protein and a substitution of threonine to aspartic acid at amino acid position 45 of the E2 protein.

Further, the amino acid sequence as shown in SEQ ID NO: 4 refers to the sequence of the Alfort Tübingen strain having the substitution within the TAV epitope according to the present invention and, further, having a deletion at amino acid position 346 of Erns Protein.

Further, the amino acid sequence as shown in SEQ ID NO: 5 refers to the sequence of the Alfort Tübingen strain having the substitution within the TAV epitope according to the present invention and, further, having a deletion of the Npro coding sequence except for the first two amino terminal amino acids.

Moreover, the amino acid sequence as shown in SEQ ID NO: 6 refers to the sequence of the Alfort Tübingen strain having the substitution within the TAV epitope according to the present invention and, further, having a deletion at amino acid position 346 of Erns Protein and a deletion of the Npro coding sequence except for the last two amino terminal amino acids.

In another aspect of the present invention the CSFV is a recombinant CSFV.

The term "recombinant" refers to a CSFV that has been altered, rearranged, or modified by genetic engineering. However, the term does not refer to alterations in polynucleotide or amino acid sequence that result from naturally occurring events, such as spontaneous mutations.

In another aspect of the present invention the CSFV is attenuated.

The term "attenuated" means that the virulence of the CSFV has been reduced. In the present invention "attenuation" is synonymous with "avirulent". In the present invention, an attenuated CSFV is one in which the virulence has been reduced so that it does not cause clinical signs of a CSFV infection but is capable of inducing an immune response in the target animal, but may also mean that the clinical signs are reduced in incidence or severity in animals infected with the attenuated CSFV in comparison with a "control group" of animals infected with non-attenuated CSFV and not receiving the attenuated virus. In this context, the term "reduce/reduced" means a reduction of at least 10%, preferably 25%, even more preferably 50%, most preferably of more than 100% as compared to the control group as defined above. Thus, an attenuated CSFV strain is one that suitable for incorporation into an immunogenic composition.

The attenuation of the CSFV can be done by serial passaging. The attenuation by serial passaging of the CSFV in cell culture is well known by the person skilled in the art and can be done by the person skilled in the art without further ado. Further, attenuation can be achieved by mutating the CSFV. Attenuated CSFV strains can be generated by mutation of the Erns gene (WO 99/64604, WO2005/111201, WO 2009/156448 A1, Mayer et a I., 2003. Virus Res. 98: 105-16, Meyers et al., 1999. J. Virol. 73: 10224-10235, Widjojoatmodjo et al., 2000. J. Virol. 74: 2973-80); by deletion of Npro from CSFV virulent strains (Tratschin, J., et al., 1998. J. Virol. 72: 7681-7684), by combining mutations in Erns and deletion of Npro (WO2005/111201, WO 2009/156448 A1), by combining mutations in Erns and E2 (van Gen nip et al. 2004. J. Virol, 78: 3812-3823), by mutation of the E1 gene (Risatti et al., 2005. Virology 343: 116-127): and by mutation of the E2 gene (Risatti et al., 2007. Virology 364: 371-82). A preferred attenuated CSFV strain comprises an insertion in the 3'-terminal non-coding region. For example, an insertion of 12 nucleotides in the 3' untranslated region leads to attenuation of CSFV (Wang et al., 2008. Virology 374: 390-8). Said insertion preferably comprises a sequence of 12 nucleotides consisting of 5'-CUUUUUUCUUUU (SEQ ID NO: 38).

In another aspect of the present invention the CSFV has a mutation in the coding sequence for glycoprotein Erns and/or a mutation in the coding sequence for Npro.

The term "mutation" refers to modifications in the nucleic acid molecules either in the non-coding or coding part. The term mutation comprises modifications in the nucleic acid molecules encoding the proteins/amino acids according to the invention leading to an alteration of the encoded amino acid. However, the term mutation does also comprise silent mutations. A silent mutation only changes the genome of the virus but does not result in an alteration of the amino acid. Said mutations relate to, but are not limited to, substitutions (replacement of one or several nucleotides/base pairs), deletions (removal of one or several nucleotides/base pairs), and/or insertions (addition of one or several nucleotides/base pairs). As used herein, mutation may be a single mutation or several mutations, therefore, often the term "mutation (s)" used and relates to both a single mutation and several mutations. Said mutations include, but are not limited to point mutations (single nucleotide mutations) or larger mutations wherein e.g. parts of the encoding nucleic acid molecules are deleted, substituted and/or additional coding nucleic acid is inserted. Said mutations may result in a modified expressed polypeptide due to the change in the coding sequence. However, the term mutation is well known to the person skilled in the art and the person skilled in the art can generate mutations without further ado. Mutations within the coding sequence for Npro and Erns already have been described in the prior art as set forth above (see exemplary WO 99/64604, WO2005/111201 A, WO2009/156448 A1).

The term "N pro" as understood herein relates to the first protein encoded by the viral open reading frame and cleaves itself from the rest of the synthesized polyprotein (Stark, et al., J. Virol. 67:7088-7093 (1993); Wiskerchen, et al., Virol. 65:4508-4514 (1991)). Said term, depending on the context, may also relate to the remaining "Npro" amino acids after mutation of the encoding nucleotide sequence or to the coding nucleotide sequence for said protein itself. "Protease activity residing in Npro" relates to the polypeptide cleavage activity of said "Npro".

"Erns" as used herein relates to the glycoprotein Erns which represents a structural component of the pestivirus virion (Thiel et al., 1991. J. Virol. 65: 4705-4712). Erns lacks a typical membrane anchor and is secreted in considerable amounts from the infected cells; this protein has been reported to exhibit RNase activity (Hulst et al., 1994. Virology 200: 558-565; Schneider et al., 1993. Science 261: 1169-1171; Windisch et al., 1996. J. Virol. 70: 352-358). It should be noted that the term glycoprotein E0 is often used synonymously to glycoprotein Erns in publications. Said term, depending on the context, may also relate to the mutated "Erns" protein after mutation of the encoding nucleotide sequence or to the coding nucleotide sequence for said protein itself. "RNase activity residing in glycoprotein Erns" relates to the RNA cleavage activity of said glycoprotein, i.e. the ability of the glycoprotein Erns to hydrolyze RNA. The term "inactivation of the RNase activity residing in said glycoprotein" refers to the inability or reduced capability of a modified glycoprotein Erns to hydrolyze RNA as compared to the unmodified wild type of said glycoprotein Erns.

In another aspect of the present invention the mutation in the coding sequence for glycoprotein Erns leads to inactivation of RNase activity residing in Erns.

The term "inactivation of RNase" means RNase activity not significantly above the level measured for noninfected control cells in an RNase assay as described in Meyers et al., 1999 (J Virol 73: 10224-10235). "Not significantly above the level measured for noninfected control cells in an RNase assay as described in Meyers et al., 1999 (J Virol 73: 10224-10235), means for example, that the RNase activity is less than 150% compared to the noninfected control cells. The putative active site of the RNase is represented by the conserved Erns sequences SLHGIWPEKICKG (SEQ ID NO: 32) and/or LQRHEWNKHGWCNWYNIDPW (SEQ ID NO: 33) as exemplarily shown for the Alfort/Tübingen CSFV strain. Thus, preferably, the invention further relates to a CSFV having the mutation ins the TAV epitope as described herein, wherein said RNase negative mutation(s) in the coding sequence for glycoprotein Erns are located in the nucleotide sequence coding for the conserved Erns sequence SLHGIWPEKICTG (SEQ ID NO: 34) and/or LQRHEWNKHGWCNWFHIEPW (SEQ ID NO: 35). These sequences are representing the putative active site of the RNase. The sequences SLHGIWPEKIC (SEQ ID NO: 36) and RHEWNKHGWCNW (SEQ ID NO: 37) of the putative Erns active site are even more conserved across pestiviruses. Suitable modifications of the glycoprotein Erns which result in RNase negative Erns glycoproteins are for example, the single substitutions/deletions: S295G, H297K, H297L, H297R, H297del, W300G, P301del, E302A, C305G, R340G, E342del, W343G, K345A, H346K, H346L, H346del, H346Q, H346SV, K345R, W348P, W348G, W348L, W348K, W348H; the double substitutions/deletions: H297L/H346L, K345del/H346del, H346del/G347del, E342del/H346del, W300G/E302A, H297K/H346K, H297K/H346L and the triple deletions: L296del/H297del/G297del, K345del/H346del/G347del.

In another aspect of the present invention the mutation in the coding sequence for glycoprotein Erns is a deletion at amino acid position 346 of glycoprotein Erns.

The amino acid position refers to the position in the polyprotein as defined above.

In another aspect of the present invention the glycoprotein Erns has lost its ability to build dimers. Such loss of dimerization results also in attenuation. Examples of such dimerization deficient CSFV mutants, which can be used together with the modified TAV as described herein, are disclosed in an exemplarily manner in the international patent application WO2009/156448. For example the deletion of the last cysteine residue of the Erns glycoprotein, in particular of cysteine residue at amino acid position 438 of Erns protein, may result in the loss of dimerization and in attenuation, provided that such modification is not substituted by any other modification. The amino acid position refers to the position in the polyprotein as defined above.

In another aspect of the present invention the mutation in the coding sequence for Npro leads to inactivation of said N pro.

The term "inactivation of Npro" as used herein means the prevention or considerable reduction of the probable immunemodulating activity of Npro by mutation. In a preferred embodiment this mutation prevents or considerably reduces the interference of Npro with the induction of an interferon response by the infected cells as described by Ruggli et al., 2003 (J. Virol. 77:7645-7654). In this case, the inactivation of Npro would allow the cell to mount a normal interferon response.

In another aspect of the present invention the mutation in the coding sequence for Npro is a deletion of the Npro coding sequence except for the first two amino terminal amino acids. The international patent application WO2005/111201 provides various modifications within the Npro coding sequence, which mutations are incorporated herein by reference. Inactivation of the Npro is achieved in CSFV of the specified formula described more in detail below, wherein between 0 and all amino acids of Npro coding sequence are present; ubiquitin or LC3 or another sequence serving as processing signal (e.g. SUMO-1, NEDD8, GATE-16, GABA(A)RAP, or proteases like e.g. Intein, picornavirus 3C, caridovirus 2A, or p15 of rabbit hemorrhagic disease virus, or sequences like aphtovirus 2A that lead to discontinuous translation) is present or absent. In case a processing signal is present, the coding sequence of the processing signal is inserted at or close to the C-terminal end of the (remaining part of the) Npro coding sequence. Only in the case that a processing signal is present, any number of amino acids coding for Npro (=Npro amino acids) may be present. In case no processing signal sequence is inserted, a maximum of about 12 amino acids, preferably amino-terminal amino acids, of Npro coding sequence may be present, the remaining amino acids have to be deleted. Thus, the invention relates to a CSFV having the mutation within the TAV coding sequence as described herein and a mutation within the Npro coding region, wherein said mutation(s) in the coding sequence for Npro lead to an encoded polyprotein as characterized by the following formula:

$$[N^{pro}]_x\text{-}[PS]_y\text{-}[C\text{-term}]$$

and wherein:

$[N^{pro}]$ relates to the $N^{pro}$ portion of said polyprotein, wherein "x" represents the number of amino acids of the $N^{pro}$ present in the polyprotein;

[PS] relates to a processing signal selected from: ubiquitin, LC3, SUMO-1, NEDD8, GATE-16 or GABA(A)RAP or proteases like e.g. Intein, picornavirus 3C, caridovirus 2A, or p15 of rabbit hemorrhagic disease virus or any processing signal known to the skilled person that ensures the generation of a functional N-terminal of the C-protein. "Y" may be=0, which means that no processing signal is present (=PS is absent), or "Y" may be=1, which means that a processing signal is present (=PS present).

[C-term] relates to the complete pestivirus polyproteine, in particular the complete CSFV polyprotein except for $N^{pro}$, but including the capsid (C)-protein and any other protein present in the pestivirus polyprotein, in particular in the CSFV polyprotein including the carboxy-terminal NS5B. Preferably, the glycoprotein Erns in said [C-term] is mutated, in such that the RNase activity residing in the glycoprotein Erns is inactivated. The term "any other protein present in the pestivirus polyprotein/CSFV polyprotein" relates to $E^{rns}$, E1, E2, p7, NS2, NS3, NS4A, NS4B and NS5A, wherein glycoprotein Erns is mutated, preferably as disclosed herein (see above), in such that the RNase activity residing in the glycoprotein $E^{rns}$ is inactivated. Preferably, the pestivirus, in particular the CSFV according to the invention has a C-protein which is not mutated except for the amino acid at position 2 which is changed from D to N. Therefore, [C-term*] is the same as [C-term] but with a mutation at position 2 of the C-protein (N instead of D); if "y" is =0 (means no [PS] present) then"x" is 0 to 12, (means no $N^{pro}$ specific amino acid or 1 to 12 amino acids of $N^{pro}$, preferably of the N-terminus of $N^{pro}$, are present); if "y" is =1 (means [PS] is present) then "x" is 0 to 168; (means no $N^{pro}$ specific amino acid or 1 to all 168 amino acids of $N^{pro}$, preferably of the N-terminus of $N^{pro}$, are present).

The term "deletion of Npro coding sequence except for the last two amino terminal amino acids" as used herein refers to the deletion of almost the complete Npro coding region. However, two aminoterminal amino acids remain. The complete Npro coding region is deleted, except for codons 1 to 2, thus amino acids M and G of Npro remain.

In another aspect of the present invention the CSFV is a C (Chinese)-strain.

The term "C-(Chinese) strain" is well known to the person skilled in the art. The so-called "Chinese" or "C"-strains are available in its pathogenic form or has been attenuated by repeated passage in rabbits and cell culture. Preferably, the CSFV strain is the Cedipest C-strain, which is a C-strain virus that was adapted to suspension cultures of the swine kidney cell line SK6 (Terpstra et al., 1990. Dtsch Tierarztl Wochenschr. 97:77-9). Pigs inoculated with 400-600 TCID50 of the Cedipest strain are fully protected against challenge with greater than 100 pig LD50 of a virulent strain of CSFV at 7 days and at 6 month post vaccination. More preferably, the CSFV strain is a C-(Chinese) strain Riems (SEQ ID NO: 7) or a C-(Chinese) strain as described in Moormann et al., 1996 (J Virol. 70(2):763-70).

The amino acid sequence as shown in SEQ ID NO: 7 refers to the sequence of the wildtype C-(Chinese) strain Riems.

The amino acid sequence as shown in SEQ ID NO: 8 refers to the sequence of the C-(Chinese) strain Riems having the substitution of proline to lysine at amino acid position 44 of the E2 protein and a substitution of threonine to aspartic acid at amino acid position 45 of the E2 protein.

Further, the amino acid sequence as shown in SEQ ID NO: 9 refers to the sequence of the C-(Chinese) strain Riems having the substitution within the TAV epitope according to the present invention and, further, having a deletion at amino acid position 346 of Erns Protein.

Further, the amino acid sequence as shown in SEQ ID NO: 10 refers to the sequence of the C-(Chinese) strain Riems having the substitution within the TAV epitope according to the present invention and, further, having a deletion of the Npro coding sequence except for the last two amino terminal amino acids.

Moreover, the amino acid sequence as shown in SEQ ID NO: 11 refers to the sequence of the C-(Chinese) strain Riems having the substitution within the TAV epitope according to the present invention and, further, having a deletion at amino acid position 346 of Erns glycoprotein and a deletion of the Npro coding sequence except for the last two amino terminal amino acids.

The amino acid sequence as shown in SEQ ID NO: 12 refers to the sequence of the wildtype C-(Chinese) strain as described in Moormann et al., 1996 (J Virol. 70(2):763-70).

The amino acid sequence as shown in SEQ ID NO: 13 refers to the sequence of the C-(Chinese) strain as described in Moormann et al., 1996 (J Virol. 70(2):763-70) having the substitution of proline to lysine at amino acid position 44 of the E2 protein and a substitution of threonine to aspartic acid at amino acid position 45 of the E2 protein.

Further, the amino acid sequence as shown in SEQ ID NO: 14 refers to the sequence of the C-(Chinese) strain as described in Moormann et al., 1996 (J Virol. 70(2):763-70) having the substitution within the TAV epitope according to the present invention and, further, having a deletion at amino acid position 346 of Erns Protein.

Further, the amino acid sequence as shown in SEQ ID NO: 15 refers to the sequence of the C-(Chinese) strain as described in Moormann et al., 1996 (J Virol. 70(2):763-70) having the substitution within the TAV epitope according to the present invention and, further, having a deletion of the Npro coding sequence except for the last two amino terminal amino acids.

Moreover, the amino acid sequence as shown in SEQ ID NO: 16 refers to the sequence of the C-(Chinese) strain as described in Moormann et al., 1996 (J Virol. 70(2):763-70) having the substitution within the TAV epitope according to the present invention and, further, having a deletion at amino acid position 346 of Erns Protein and a deletion of the Npro coding sequence except for the last two amino terminal amino acids.

The present invention also provides a nucleic acid coding for a CSFV according to the present invention.

The term "nucleic acid" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificial modified one such as biotinylated polynucleotides. Further, it is to be understood that the CSFV of the present invention may be encoded by a large number of polynucleotides due to the degenerated genetic code.

The present invention also provides a vector comprising the nucleic acid coding for a CSFV according to the present invention.

The term "vector" encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the nucleic acid of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. More preferably, the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. For example, the techniques are described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

The present invention also provides an immunogenic composition comprising the CSFV according to the present invention.

The term "immunogenic composition" as used herein refers to a composition that comprises at least one antigen, which elicits an immunological response in the host to which the immunogenic composition is administered. Such immunological response may be a cellular and/or antibody-mediated immune response to the immunogenic composition of the invention. The host is also described as "subject". Preferably, any of the hosts or subjects described or mentioned herein is an animal.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutical response.

A "protective immunological response" will be demonstrated by either a reduction or lack of clinical signs normally displayed by an infected host, a quicker recovery time and/or a lowered duration of infectivity or lowered pathogen titer in the tissues or body fluids or excretions of the infected host.

An "antigen" as used herein refers to, but is not limited to, components which elicit an immunological response in a host to an immunogenic composition or vaccine of interest comprising such antigen or an immunologically active component thereof. The antigen or immunologically active component may be a microorganism that is whole (in inactivated or modified live form), or any fragment or fraction thereof, which, if administered to a host, can elicit an immunological response in the host. The antigen may be or may comprise complete live organisms in either its original form or as attenuated organisms in a so called modified live vaccine (MLV). The antigen may further comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species, and optionally by subsequent isolation and purification procedures, or by induction of said synthetic processes in the animal needing a vaccine by direct incorporation of genetic material using suitable pharmaceutical compositions (polynucleotide vaccination). The antigen may comprise whole organisms inactivated by appropriate methods in a so called killed vaccine (KV). If the organism is a bacterium, the killed vaccine is called a bacterin.

In case where the host displays a protective immunological response such that resistance to new infection will be enhanced and/or the clinical severity of the disease reduced, the immunogenic composition is described as a "vaccine".

In another aspect of the present invention the immunogenic composition of the present invention is a vaccine.

The term "vaccine" as understood herein is a vaccine for veterinary use comprising antigenic substances and is administered for the purpose of inducing a specific and active immunity against a disease provoked by a CSFV infection.

Preferably, the vaccine according to the invention is an attenuated live vaccine, comprising a live attenuated virus eliciting a protective immune response in the host animal, but does not invoke the viral disease due to a mutation in its genome. Live attenuated vaccines have the advantage over inactivated vaccines that they mimic the natural infection more closely. As a consequence they provide in general a higher level of protection than their inactivated counterparts. The attenuated CSFV as described herein, confer active immunity that may be transferred passively via maternal antibodies against the immunogens it contains and sometimes also against antigenically related organisms. A vaccine of the invention refers to a vaccine as defined above, wherein one immunologically active component is a CSFV or of pestiviral origin or derived from a nucleotide sequence that is more than 70% homologous to any known pestivirus sequence (sense or antisense). However, the present invention also relates to vaccines comprising inactivated CSFV according to the present invention.

A vaccine may additionally comprise further components typical to pharmaceutical compositions.

Additional components to enhance the immune response are constituents commonly referred to as "adjuvants", like e.g. aluminiumhydroxide, mineral or other oils or ancillary molecules added to the vaccine or generated by the body after the respective induction by such additional components, like but not restricted to interferons, interleukins or growth factors A "pharmaceutical composition" essentially consists of one or more ingredients capable of modifying physiological e.g. immunological functions of the organism it is administered to, or of organisms living in or on the organism. The term includes, but is not restricted to, antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties. One non-limiting example of such a pharmaceutical composition, solely given for demonstration purposes, could be prepared as follows: Cell culture supernatant of an infected cell culture is mixed with a stabilizer (e.g. spermidine and/or BSA (bovine serum albumin)) and the mixture is subsequently lyophilized or dehydrated by other methods. Prior to vaccination, said mixture is then rehydrated in aqueous (e.g. saline, PBS (phosphate buffered saline)) or non-aqueous solutions (e.g. oil emulsion, aluminum-based adjuvant).

In another aspect of the present invention the substitution of proline to lysine at amino acid position 44 of the E2 protein and a substitution of threonine to aspartic acid at amino acid position 45 within the TAV epitope of the E2 protein is used as a marker.

The term "marker" as used herein refers to the substituted TAV epitope according to the present invention. The substituted TAV epitope according to the present invention is different from the TAV sequence of a wildtype CSFV (TAV epitope that has not been genetically modified). Thus, the substituted TAV epitope according to the present invention allows the differentiation of naturally infected animals having a non-mutated TAV epitope from vaccinated animals having a substituted TAV epitope according to the present invention by exemplary immuno tests and/or genomic analytical tests.

In another aspect of the present invention the immunogenic composition of the present invention is a marker vaccine or a DIVA (differentiation between infected and vaccinated animals) vaccine.

The term "marker vaccine" or "DIVA (differentiation between infected and vaccinated animals)" refers to a vaccine having a marker as set forth above. Thus, a marker vaccine can be used for differentiating a vaccinated animal from a naturally infected animal. The immunogenic composition of the present invention acts as a marker vaccine because, in contrast to infection with wild-type CSFV, in animals vaccinated with the CSFV of the present invention the substituted TAV epitope according to the present invention can be detected. By exemplary immuno tests and/or genomic analytical tests the substituted TAV epitope according to the present invention can be differentiated from the TAV sequence of a wildtype CSFV (a TAV epitope that has not been genetically modified). Finally, the marker epitope should be specific for the pathogen in order to avoid false-positive serological results which are induced by other organisms that may appear in livestock. However, as set forth above, the TAV epitope is evolutionarily conserved and specific for CSFV (Lin et al., 2000. J Virol 74: 11619-25). Thus, the substituted TAV epitope according to the present invention is highly suitable to be used as a marker vaccine.

Preferably, the marker vaccine according to the invention is an attenuated live vaccine, comprising a live attenuated virus eliciting a protective immune response in the host animal, but does not invoke the viral disease due to a mutation in its genome. Live attenuated vaccines have the advantage over inactivated vaccines that they mimic the natural infection more closely. As a consequence they provide in general a higher level of protection than their inactivated counterparts.

However this does not necessarily mean that the vaccine must replicate in the target animal in order to act as a vaccine. A virus according to the present invention inherently carries its marker-characteristics (e.g. the substituted TAV epitope according to the present invention). Therefore, the virus functions as a marker vaccine in the target animal regardless if it replicates in the target animal or not. Thus, the present invention also relates to marker vaccines comprising inactivated CSFV according to the present invention.

As set forth above, (non-marker-) live attenuated viruses of CSFV have been described in the art and are even commercially available. And thus, as mentioned above, such viruses constitute a very suitable starting material for the construction of viruses according to the invention, i.e. replication-competent CSFV having the substitution in the TAV epitope according to the present invention. Such viruses do inherently behave attenuated compared to their wild-type counterparts, and they can thus be used as a basis for marker viruses in a marker vaccine.

A major advantage of an efficacious marker vaccine is that it allows the detection of pigs acutely infected or infected some time (at least ca. 3 weeks) before taking samples in a vaccinated pig population, and thus offers the possibility to monitor the spread or re-introduction of CSFV in a pig population. Thus, it makes it possible to declare, with a certain level of confidence, that a vaccinated pig population is free of CSFV on the basis of laboratory test results.

The marker vaccine of the present invention is ideally suited for an emergency vaccination in the case of swine fever detection or outbreak. The marker vaccine facilitates fast and effective administration and allows discrimination between animals infected with the field virus (disease-associated) and vaccinated animals.

In another aspect of the present invention the animals treated with the immunogenic composition of the present invention can be differentiated from animals infected with naturally occurring swine fever virus via analysis of samples obtained from said animals using immuno tests and/or genomic analytical tests.

The term "sample" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting.

The term "obtained" may comprise an isolation and/or purification step known to the person skilled in the art, preferably using precipitation, columns ect.

The term "immuno tests" and "genomic analytical tests" are specified below. However, the analysis of said "immuno tests" and "genomic analytical tests", respectively, is the basis for differentiating animals vaccinated with the immunogenic composition according to the present invention and animals infected with the naturally occurring (disease-associated) swine fever virus.

In another aspect of the present invention said immunogenic composition is formulated for a single-dose administration.

Advantageously, the experimental data provided by the present invention disclose that a single dose administration of the immunogenic composition of the present invention reliably and effectively stimulated a protective immune response.

Also, the invention provides the use of the immunogenic composition of the present invention for use as a medicament.

The present invention also relates to a method for immunizing an animal comprising administering to such animal any of the immunogenic compositions according to the present invention.

The term "immunizing" relates to an active immunization by the administration of an immunogenic composition to an animal to be immunized, thereby causing an immunological response against the antigen included in such immunogenic composition.

Preferably, immunization results in lessening of the incidence of the particular CSFV infection in a herd or in the reduction in the severity of clinical signs caused by or associated with the particular CSFV infection.

According to a further aspect, the immunization of an animal in need with the immunogenic compositions as provided herewith, results in preventing infection of a subject by CSFV infection. Even more preferably, immunization results in an effective, long-lasting, immunological-response against CSFV infection. It will be understood that the said period of time will last more than 2 months, preferably more than 3 months, more preferably more than 4 months, more preferably more than 5 months, more preferably more than 6 months. It is to be understood that immunization may not be effective in all animals immunized. However, the term requires that a significant portion of animals of a herd are effectively immunized.

Preferably, a herd of animals is envisaged in this context which normally, i.e. without immunization, would develop clinical signs normally caused by or associated with a CSFV infection. Whether the animals of a herd are effectively immunized can be determined without further ado by the person skilled in the art. Preferably, the immunization shall be effective if clinical signs in at least 33%, at least 50%, at least 60%, at least 70%, at least 80%, or at least 90% of the animals of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to animals that are either not immunized or immunized with an immunogenic composition that was available prior to the present invention but subsequently infected by CSFV.

In one aspect of the present invention the animal is swine.

In one aspect of the present invention the immunogenic composition is administered once. As shown in the Examples the immunogenic composition as provided herein has been proven to be efficacious after the administration of a single dose to an animal of need.

Preferably, the single-dose has a total volume between about 0.5 ml and 2.5 ml, more preferably between about 0.6 ml and 2.0 ml, even more preferably between about 0.7 ml and 1.75 ml, still more preferably between about 0.8 ml and 1.5 ml, even more preferably between about 0.9 ml and 1.25 ml, with a single 1.0 ml dose being the most preferred.

However, the immunogenic composition can be administered twice or several times, with a first dose being administered prior to the administration of a second (booster) dose. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

The amount of the CSFV to be administered may be an amount of the virus that elicits or is able to elicit an immune response in an animal, to which the dose of the virus is administered. The amount that is effective may depend on the ingredients of the vaccine and the schedule of administration. If an inactivated virus or a modified live virus preparation is used, an amount of the vaccine containing about $10^2$ to about $10^9$ $TCID_{50}$ (tissue culture infective dose 50% end point), more preferably $10^4$ to about $10^8$ $TCID_{50}$, and still more preferably from about $10^5$ to about $10^6$ $TCID_{50}$ per dose may be recommended.

In one aspect of the present invention the immunogenic composition is administered intradermal, intratracheal, intravaginal, intramuscular, intranasal, intravenous, intraarterial, intraperitoneal, oral, intrathecal, subcutaneous, intracutaneous, intracardial, intralobal, intramedullar, intrapulmonary, and combinations thereof. However, depending on the nature and mode of action of a compound, the immunogenic composition may be administered by other routes as well.

The present invention also provides a method of reducing the incidence of or severity in an animal of one or more clinical signs associated with CSF, the method comprising the step of administering the immunogenic composition according to the present invention to an animal in need thereof, wherein the reduction of the incidence of or the severity of the one or more clinical signs is relative to an animal not receiving the immunogenic composition.

The term "clinical signs" as used herein refers to signs of infection of an animal from CSFV. The clinical signs are defined further below. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight gain or loss, dehydration, diarrhea, joint swelling, lameness, wasting, paleness of the skin, unthriftiness, and the like. Mittelholzer et al. (Vet. Microbiol., 2000. 74(4): p. 293-308) developed a checklist for the determination of the clinical scores in CSF animal experiments. This checklist contains the parameters liveliness, body tension, body shape, breathing, walking, skin, eyes/conjunctiva, appetite, defecation and leftovers in feeding through.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to subjects that are either not treated or treated with an immunogenic composition that was available prior to the present invention but subsequently infected by CSFV.

In one aspect of the present invention the immunogenic composition is administered once.

As shown in the Examples the immunogenic composition as provided herein has been proven to be efficacious after the administration of a single dose to an animal of need.

However, the immunogenic composition can be administered twice or several times, with a first dose being administered prior to the administration of a second (booster) dose. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

The amount of the CSFV to be administered may be an amount of the virus that elicits or is able to elicit an immune response in an animal, to which the dose of the virus is administered. The amount that is effective may depend on the ingredients of the vaccine and the schedule of administration. If an inactivated virus or a modified live virus preparation is used, an amount of the vaccine containing about $10^2$ to about $10^9$ $TCID_{50}$ (tissue culture infective dose 50% end point), more preferably $10^4$ to about $10^8$ $TCID_{50}$, and still more preferably from about $10^4$ to about $10^6$ $TCID_{50}$ per dose may be recommended.

Preferably, the single-dose has a total volume between about 0.5 ml and 2.5 ml, more preferably between about 0.6 ml and 2.0 ml, even more preferably between about 0.7 ml and 1.75 ml, still more preferably between about 0.8 ml and 1.5 ml, even more preferably between about 0.9 ml and 1.25 ml, with a single 1.0 ml dose being the most preferred.

In another aspect of the present invention the one or more clinical signs are selected from the group consisting of: respiratory distress, labored breathing, coughing, sneezing, rhinitis, tachypnea, dyspnea, pneumonia, red/blue discoloration of the ears and vulva, jaundice, lymphocytic infiltrates, lymphadenopathy, hepatitis, nephritis, anorexia, fever, lethargy, agalatia, diarrhea, nasal extrudate, conjunctivitis, progressive weight loss, reduced weight gain, paleness of the skin, gastric ulcers, macroscopic and microscopic lesions on organs and tissues, lymphoid lesions, mortality, virus induced abortion, stillbirth, malformation of piglets, mummification and combinations thereof.

In another aspect of the present invention the immunogenic composition is administered using a method selected from the group consisting of intradermal, intratracheal, intravaginal, intramuscular, intranasal, intravenous, intraarterial, intraperitoneal, oral, intrathecal, subcutaneous, intracutaneous, intracardial, intralobal, intramedullar, intrapulmonary, and combinations thereof.

In another aspect of the present invention the animal is swine.

The present invention also provides a method of marking a CSFV vaccine comprising introducing a substitution of proline to lysine at amino acid position 44 of the E2 protein and a substitution of threonine to aspartic acid at amino acid position 45 of the E2 protein into a CSFV vaccine.

The term "marking" as used herein refers to the introduction of a "marker" as defined further above into a CSFV or CSFV vaccine. Thus, it has to be understood that the method of the present invention also refers to the marking of a CSFV and is not restricted to a method of making a CSFV vaccine.

Thus, a "marker vaccine" or a "DIVA" as defined further above may be produced by marking a CSFV vaccine according to the method of the present invention.

In another aspect of the present invention said amino acid substitution is within the TAV epitope of the E2 protein having the amino acid sequence TAVSPTTLR (SEQ ID NO: 1).

In one aspect of the present invention said amino acid substitution is within the TAV epitope of the E2 protein having the amino acid sequence TAVSPTTLRT (SEQ ID NO:17).

In another aspect of the present invention the amino acid substitution within the TAV epitope of the E2 protein results in the TAV epitope sequence TAVSKDTLRT (SEQ ID NO:22).

In another aspect of the present invention the CSFV vaccine is an attenuated vaccine.

Attenuated CSFV vaccines already have been defined further above. Further, it has to be understood that the method according to the present invention is not restricted to the production of attenuated CSFV vaccines. In contrast, as set forth above, a virus functions as a marker vaccine in the target animal regardless if it replicates in the target animal or not. Thus, the present invention also relates to marker vaccines comprising inactivated CSFV according to the present invention.

In another aspect of the present invention the CSFV is a C (Chinese)-strain.

However, the term "C (Chinese)-strain" already has been defined further above.

The present invention also provides a method of differentiating animals infected with CSFV from animals vaccinated with the immunogenic composition according to the present invention, comprising: obtaining a sample from an animal, and analyzing said sample in a immuno test and/or genomic analytical test.

The terms "sample" and "obtaining" already have been defined further above.

The term "immuno test" refers to a test comprising an antibody specific for the TAV epitope of the E2 gene of the CSFV. The antibody may be specific for the substituted TAV epitope according to the present invention or for the TAV epitope of a wildtype CSFV (TAV epitope that has not been genetically modified). However, the term "immune test" does also refer to a test comprising substituted TAV epitope peptides according to the present invention or for TAV epitope peptides of a wildtype CSFV (TAV epitope that has not been genetically modified). Examples of immuno tests include any enzyme-immunological or immunochemical detection method such as ELISA (enzyme linked immunosorbent assay), EIA (enzyme immunoassay), RIA (radioimmunoassay), sandwich enzyme immune tests, fluorescent antibody test (FAT) electrochemiluminescence sandwich immunoassays (ECLIA), dissociation-enhanced lanthanide fluoro immuno assay (DELFIA) or solid phase immune tests, immunofluorescent test (IFT), immunohistological staining, Western blot analysis or any other suitable method available to technicians skilled in the art. Depending upon the assay used, the antigens or the antibodies can be labeled by an enzyme, a fluorophore or a radioisotope. See, e.g., Coligan et al. Current Protocols in Immunology, John Wiley & Sons Inc., New York, N.Y. (1994); and Frye et al., Oncogen 4: 1153-1157, 1987.

Preferably, an antibody specific for the TAV epitope of a wildtype CSFV is used to detect CSFV antigen in serum cells (such as leucocytes) or cryostat sections of isolated organs (such as tonsils, spleen, kidney, lymph nodes, distal portions of the ileum) from a pig that is suspected to be infected with CSFV or that is vaccinated with a vaccine according to the invention. In such a case, only the sample of the infected pig will show positive results by said TAV epitope specific antibody. In contrast, the sample of a pig vaccinated with the vaccine of the present invention will show no results by said TAV epitope specific antibody due to the substitution within the TAV epitope according to the present invention. In an alternative test, CSFV is isolated from, for example, organs (such as the tonsils of an animal) or serum cells (such as leukoyctes) infected, suspected to be infected with field CSFV or vaccinated animals and incubated with a suitable cell line (such as SK-6 cells or PK-15 cells) for infection of the cells with the virus. The replicated virus is subsequently detected in the cells using TAV epitope specific antibodies that differentiate between the field (wildtype, disease associated) virus and the recombinant virus according to the invention. Further, peptides could be used to block unspecific cross-reactivity. Moreover, antibodies specific for other epitopes of the wildtype CSFV could be used as a positive control.

More preferably, an ELISA is used, wherein the antibody specific for the TAV epitope of a wildtype CSFV (TAV epitope that has not been genetically modified) is cross-linked to micro-well assay plates for differentiating between infected pigs from pigs vaccinated with the vaccine according to the present invention. Said cross-linking preferably is performed through an anchor protein such as, for example, poly-L-lysine. ELISAs employing such cross-linking are in general more sensitive when compared to ELISAs employing a passively coated technique. The wildtype (disease associated) virus binds to the antibody specific for the TAV epitope of a wildtype CSFV (TAV epitope that has not been genetically modified). The detection of the binding of the wildtype CSFV virus to the antibody specific for the TAV epitope of a wildtype CSFV can be performed by a further antibody specific for CSFV. In such a case, only the sample of the infected pig will show positive results by the TAV epitope specific antibody. In contrast, the CSFV virus of a pig vaccinated with the vaccine according to the present invention will express only the substituted TAV epitope, and, thus, will not bind to the antibody specific for the TAV epitope of a wildtype CSFV (TAV epitope that has not been genetically modified) that has been cross-linked to the micro-well assay plates. Further, peptides could be used to block unspecific cross-reactivity. Moreover, antibodies specific for other epitopes of the wildtype CSFV could be used as a positive control.

Alternatively, the micro-well assay plates may be cross-linked with an antibody specific for CSFV other than the antibody specific for the TAV epitope of a wildtype CSFV (TAV epitope that has not been genetically modified). The wildtype (disease associated) virus binds to the cross linked antibody. The detection of the binding of the wildtype CSFV virus to the cross linked antibody can be performed by the antibody specific for the TAV epitope of a wildtype CSFV (TAV epitope that has not been genetically modified).

As already set forth above the TAV epitope is evolutionarily conserved and specific for CSFV and a target for neutralizing antibodies (Lin et al., 2000. J Virol 74: 11619-25).

Therefore, more preferably, an ELISA is used for detecting in the sample antibodies that are directed against the substituted TAV epitope according to the present invention or the TAV epitope of a wildtype CSFV (TAV epitope that has not been genetically modified). Such a test comprises substituted TAV epitope peptides according to the present invention or for the TAV epitope peptides of a wildtype CSFV (TAV epitope that has not been genetically modified).

Such a test could e.g. comprise wells with a substituted TAV epitope according to the present invention or the TAV epitope of a wildtype CSFV (TAV epitope that has not been genetically modified) cross-linked to micro-well assay plates. Said cross-linking preferably is performed through an anchor protein such as, for example, poly-L-lysine. Expression systems for obtaining a substituted or wildtype TAV epitope are well known to the person skilled in the art. Alternatively, said TAV epitopes could be chemically synthesized. It has to be understood that although the substituted or wildtype TAV epitope as such can be used in a test according to the invention, it can be convenient to use a protein comprising the complete E2 protein or a fragment of the E2 protein comprising the said TAV epitope, instead of the relatively short epitope as such. Especially when the epitope is for example used for the coating of a well in a standard ELISA test, it may be more efficient to use a larger protein comprising the epitope, for the coating step.

Animals vaccinated with the vaccine according to the present invention have not raised antibodies against the wild-type TAV epitope. However, such animals have raised antibodies against the substituted TAV epitope according to the present invention. As a consequence, no antibodies bind to a well coated with the wildtype TAV epitope. In contrast, if a well has been coated with the substituted TAV epitope according to the present invention antibodies bind to said substituted TAV epitope.

Animals infected with the wild-type virus will however have raised antibodies against the wild-type epitope. However, such animals have not raised antibodies against the substituted TAV epitope according to the present invention. As a consequence, no antibodies bind to a well coated with the substituted TAV epitope according to the present invention. In contrast, if a well has been coated with the wildtype TAV epitope antibodies bind to the wildtype TAV epitope.

The binding of the antibodies to the substituted TAV epitope according to the present invention or the TAV epitope of a wildtype CSFV (TAV epitope that has not been genetically modified) can be done by methods well known to the person skilled in the art.

Preferably, the ELISA is a sandwich type ELISA.

More preferably, the ELISA is a competitive ELISA.

However, the different ELISA techniques are well known to the person skilled in the art. ELISA's have been described exemplary by Wensvoort G. et al., 1988 (Vet. Microbiol. 17(2): 129-140), by Robiolo B. et al., 2010 (J. Virol. Methods. 166(1-2): 21-27) and by Colijn, E. O. et al., 1997 (Vet. Microbiology 59: 15-25).

The term "genomic analytical test" refers to a genomic analytical method based upon the polymerase chain reaction (PCR), reverse transcription polymerase chain reaction (RT-PCR), real-time PCR (r-PCR) or real time reverse transcription PCR (rRT-PCR), Templex-PCR, nucleic-acid sequence based amplification (NASBA), and isothermal amplification methods using polymerases and specific oligonucleotides as primers. The aforementioned amplification methods are well known in the art.

Preferably, the test for differentiating an animal that is infected with field CSFV or vaccinated with a recombinant virus of the invention is provided by RNA isolation of the CSFV and reverse transcriptase followed by amplification of the cDNA. The cDNA is then sequenced for detecting whether the TAV epitope is intact and refers to a wildtype CSF. In such a case the pig is infected with the wildtype CSF. However, if the sequence of the TAV epitope is substituted according to the present invention the animal has been vaccinated with the vaccine of the present invention.

Further, when using any real time based technique primers and/or probes may be used recognizing either the modified (substituted according to the present invention) and/or disease-associated (wildtype) viral nucleotide sequence of the TAV epitope. However, such methods are well known in the art.

In another aspect of the present invention the immunological test comprises testing whether antibodies specifically recognizing the intact TAV epitope (TAVSPTTLR (SEQ ID NO:1)) of the CSFV E2 protein are binding to the CSFV E2 protein in the sample.

In another aspect of the present invention the immunological test is an EIA (enzyme immunoassay) or ELISA (enzyme linked immunosorbent assay).

In another aspect of the present invention the ELISA is an indirect ELISA, Sandwich ELISA, a competitive ELISA or blocking ELISA.

In another aspect of the present invention the genomic analytical test is a PCR (polymerase chain reaction), RT-PCR (reverse transcriptase polymerase chain reaction) or real time PCR (polymerase chain reaction).

In another aspect of the present invention the sample is a serum sample.

In another aspect of the present invention the animal is swine.

EXAMPLES

The following examples are only intended to illustrate the present invention. They shall not limit the scope of the claims in any way.

1 Preparation of Basic TAV Epitope Mutants

1.1 Marker Concept

The approach chosen in this work for a DIVA-suitable marker concept was the TAV epitope on the CSFV E2 protein. This linear epitope is located on positions 140-148 of the E2 protein, has the amino acid sequence TAVSPT-TLRT (SEQ ID NO: 17) and is recognized by the monoclonal antibody (A18). The TAV epitope is specific for CSFV, has a degree of evolutional conservation of almost 100% and is a target for neutralizing antibodies (Lin, M., et al., J. Virol., 2000. 74(24): p. 11619-11625). The aim of the experiments was to modify the amino acid sequence of the epitope such that it is no longer recognized by the monoclonal antibody A18 so as to be able to be used as a negative marker in a vaccine yet to be developed. Such a vaccine would, as a consequence, have to be accompanied by a corresponding serological assay system in which the sera of vaccinated animals would give a negative signal, while the sera of field-virus-infected animals would give a positive signal.

1.2 Preparation of the Marker

The marker was prepared using a Quik Change®-PCR. The following plasmids were generated: pSW14 (TAVNKDTLR (SEQ ID NO: 18)), pSW15 (TAVNQDTLR (SEQ ID NO: 19)), pSW16 (TAVSAATVR (SEQ ID NO: 20)) and pSW17 (TAVSASSVR (SEQ ID NO: 21)).

1.3 Preparation of the Basic TAV Epitope Mutants

The generated clones pSW14-17 were linearized with a restriction enzyme and thereafter transcribed in vitro. The integrity of the RNAs thus obtained was first checked by formaldehyde agarose gel electrophoresis. Thereafter, they were used for the electroporation of SK-6 cells. This was followed by two different antibody stainings for indirect immunofluorescence experiments. Firstly, the cells were stained with the monoclonal antibody 24/16 (detects $E^{rns}$) and secondly with the monoclonal antibody A18. In the 24/16 staining, all the mutants gave a positive signal. This demonstrated that replicating viruses were present. In the A18 staining, all the mutants gave a negative signal. This demonstrated that the intended marker concept has worked.

1.4 Testing the Marker Concept

The infected cells were freeze-thawed and used for infecting fresh SK-6 cells. The viruses thus obtained were then passaged three times so as to be able to verify the stability of the introduced mutations. The passages 3 and 6 of the basic TAV epitope mutants were used for extracting viral RNA, and the RNAs obtained were employed in RT-PCRs. The RT-PCRs' products were then analyzed by sequencing. It emerged that, in the third passage, one of the amino acid substitutions which had been introduced had reverted in each of the four viral mutants. In pSW14 and pSW15, the asparagine codon introduced had been replaced by another serine codon, and in pSW16 and pSW17, the valine codon which had been inserted had been replaced by another leucine codon (Table 2).

TABLE 2

Sequencing results of the basic TAV epitope mutants after passage 3 on SK-6.
In pSW14 and pSW15, the asparagine codons have reverted to serine codons.
In pSW16 and pSW17, the valine codons have reverted to leucine codons.

| | viral mutants | | | |
|---|---|---|---|---|
| Plasmid | pSW14 | pSW15 | pSW16 | pSW17 |
| Original plasmid | TAVNKDTLRT (SEQ ID NO: 28) | TAVNQDTLRT (SEQ ID NO: 29) | TAVSAATVRT (SEQ ID NO: 30) | TAVSASSVRT (SEQ ID NO: 31) |
| Passages 3 and 6 on SK-6 | TAVSKDTLRT (SEQ ID NO: 22) | TAVSQDTLRT (SEQ ID NO: 23) | TAVSAATLRT (SEQ ID NO: 24) | TAVSASSLRT (SEQ ID NO: 25) |

TABLE 1

The amino acid substitutions in the TAV epitope. The substitutions are shown in bold.

| Plasmid name | Inserted amino acid substitutions in the TAV epitope TAVSPTTLRT (SEQ ID NO: 17) |
|---|---|
| pSW14 | TAVNKDTLR (SEQ ID NO: 18) |
| pSW15 | TAVNQDTLR (SEQ ID NO: 19) |
| pSW16 | TAVSAATVR (SEQ ID NO: 20) |
| pSW17 | TAVSASSVR (SEQ ID NO: 21) |

Amino acid substitutions are shown in bold.

Thereafter, the basic TAV epitope mutants were passaged three more times on SK-6 cells. Passage 6 was then used to obtain more RNA, which was employed in RT-PCRs, and the PCR products were subsequently sequenced. The sequencing results were identical to those of the third passage.

Since no novel modifications of the amino acid sequence had occurred, it was considered to be likely that the reversions of the third passage would also remain stable in further passages.

1.5 Indirect Immunofluorescence

The basic TAV epitope mutants (passage 6) were employed in an indirect immunofluorescence assay so as to verify the functionality of the marker concept. Various antibody stainings were assayed as internal positive controls: 24/16 (detects $E^{rns}$), code 4 (detects NS3) and f48 (detects E2). All four mutants gave a positive signal in these stainings. This demonstrates that a replicable CSF virus was present in the cells. All four mutants gave the desired negative signal in the A18 staining (specifically recognizes the TAV epitope). The conclusion of this result is that the reversions detected in the sequencing have no effect on the functionality of the inserted TAV epitope markers, and the latter remain intact.

1.6 Growth Characteristics of the Basic TAV Epitope Mutants

The 6$^{th}$ passages of the basic TAV epitope mutants were titrated, and growth curves were then constructed to compare the growth kinetics of the mutants with a CSFV Alfort/Tübingen wild-type virus. The growth behaviour of all mutants was comparable to that of the wild type (data not shown).

2 TAV Epitope DIVA Vaccine Candidates

So far, it was demonstrated that the negative markers introduced into the TAV epitope remain functional in preventing the mAb A18 from binding, despite the partial reversions which were observed, and that they remain stable over six passages of the viruses on SK-6 cells. Since, however, the basic TAV epitope mutants corresponded to a CSFV Alfort/Tübingen wild-type virus except for the introduced markers, it was expected that their pathogenicity in the natural host would likewise be comparable to that of the wild-type virus. The purpose of the next step, therefore, was to combine the TAV epitope markers with mutations which result in the development of an attenuated viral phenotype.

2.1 Preparation of the Viral Mutants from cDNA Constructs (Approach 1)

In a first approach, it was attempted to generate a set of three viral mutants, all of which contained the TAV epitope markers analogous to pSW17 (TAVASSLRT) (SEQ ID NO: 26). Additionally, in the first mutant, N$^{pro}$ was deleted, in the second one, it was exclusively the Erns RNase activity that was eliminated, and the third mutant contained the dual deletion (Δ N$^{pro}$/RNase−). The Npro deletion mutant contains two remaining codons (M, G), and the intrinsic Erns RNase activity was eliminated by deleting codon 346 Erns (Schürmann, E.-M., *Viren der Bovinen Virusdiarrhoe und der Klassischen Schweinepest—Einfluss von Mutationen auf Persistenzentwicklung, Virulenz und Induktion einer Interferonantwort*, in Fachbereich Veterinärmedizin 2010, Justus-Liebig-Universität: Giessen). The resulting overall clones pSW67 (dual deletion/TAVASSVRT (SEQ ID NO: 27)), pSW68 (RNase−/TAVASSVRT (SEQ ID NO:27)), and pSW69 (Δ N$^{pro}$/TAVASSVRT (SEQ ID NO:27)), were then tested by sequencing. It emerged that all three contained the desired mutations.

The full length clones were linearized with a restriction enzyme and then transcribed in vitro. The RNA thus obtained was first studied by denaturing agarose gel electrophoresis and then employed for the electroporation of SK-6 cells.

The RNAs of plasmids pSW67 (dual deletion/TAVASSVRT (SEQ ID NO: 27)), pSW 69 (Npro Δ/TAVASSVRT (SEQ ID NO:27)) and of a CSFV Alfort/Tübingen wild type were electroporated in a first approach. This was followed by indirect immunofluorescence experiments with two different antibodies. Cells were stained firstly with the monoclonal antibody 24/16 (detects Erns) and secondly with the monoclonal antibody A18. Although a negative signal was obtained for all batches in the first 24/16 staining experiment, the cells were nevertheless freeze-thawed and used for the infection of fresh SK-6 cells. The first passage of virus EP#69/2 then gave the desired positive signal in the 24/16 staining and the expected negative signal in the A18 staining. This virus was therefore passaged on. The results of the first immunofluorescence were reproduced in the fifth passage. The first passage of virus EP#67/2 gave a positive result in the 24/16 staining, but the A18 staining was also positive (Table 3).

TABLE 3

Results of the indirect immunofluorescence of EP#67/2 and EP#69/2 (cloning 1). (+ = positive; − = negative; / = not present). Virus EP#69/2 showed the negative TAV epitope marker consistently over 5 passages. The control staining with mAb 24/16 (detects Erns) was positive, while the A18 staining (detects TAV epitope) was negative. Virus EP#67/2, in contrast, gave a positive signal in both stainings from passage 2 onwards.

| | Virus | | | | | | | | | | | |
|---|---|---|---|---|---|---|---|---|---|---|---|---|
| | EP#67/2 | | | | EP#69/2 | | | | WT | | | mock |
| | Mutations | | | | | | | | | | | |
| | N$^{pro}$ Δ/RNAse−/ TAVASSLRT (SEQ ID NO: 26) | | | | N$^{pro}$ Δ/ TAVASSLRT (SEQ ID NO: 26) | | | | TAVSPTTLRT (SEQ ID NO: 17) | | | |
| Passage | 0 | 1 | 2 | 5 | 0 | 1 | 2 | 5 | 0 | 1 | 2 | 5 | / |
| 24/16 | − | + | + | / | − | + | + | + | − | + | + | + | − |
| A18 | − | + | + | / | − | − | − | − | − | + | + | + | − |

In a further batch, the electroporation of pSW67 was repeated together with the electroporation of two different clones of plasmid pSW68. The first passages of EP#68/MP1 and EP#68/MP15 were positive in the 24/16 staining; the A18 staining, however, gave a dubious result in as far as some foci of positive cells were detected. The first passage of EP67/3 was positive in both stainings.

Thereafter, RNA was extracted from cells which had been infected with the fifth passage of EP#69/2, the first passage of EP#68/MP1 or EP#68/MP15 or the second passage of EP#67/MP2. The RNA obtained was employed in RT-PCR experiments, and the PCR products were then studied by sequencing. The results demonstrated that the TAV epitope sequence of all three viruses matched the sequence of the basic TAV epitope mutant pSW17 after passaging (table). Again, the valine codon which had been inserted by mutation had been replaced by a leucine codon.

These results show that the TAV epitope marker analogous to pSW17 (TAVASSLRT (SEQ ID NO: 26)) is not suitable for preparing a DIVA vaccine because the antibody reactions were not unambiguous. It is possible that the antibody is still capable of interacting with the TAV epitope, despite the substitution.

2.2 Preparation of the Viral Mutants from cDNA Constructs (Approach 2)

Two sets of mutants were generated in this second approach. The first set consisted of three mutants, all of which included the TAV epitope markers analogous to pSW16 (TAVSAATVRT (SEQ ID NO:30)). In the first mutant of this set, the N$^{pro}$ coding region was deleted (Npro deletion mutant contains two remaining codons (M, G)), in the second one the RNase activity of the Erns protein was eliminated by deleting codon 346, and in the third mutant these two attenuating mutations were combined as a dual deletion. The second set contained three mutants, all of which included the TAV epitope markers analogous to pSW14 (TAVNKDTLRT (SEQ ID NO:28)). The attenuating mutations were introduced corresponding to those of the first set (approach 1). This resulted in plasmids pSW70 (RNase−/ ΔN$^{pro}$/TAVSAATVRT (SEQ ID NO:30)), pSW71 (RNase−/ TAVSAATVRT (SEQ ID NO:30)), pSW72 (ΔN$^{pro}$/TAV-SAATVRT (SEQ ID NO:30)), pSW73 (RNase−/ΔN$^{pro}$/ TAVNKDTLRT (SEQ ID NO:28)), pSW74 (RNase−/ TAVNKDTLRT (SEQ ID NO:28)) and pSW75 (ΔN$^{pro}$/ TAVNKDTLRT (SEQ ID NO:28)). The existence of the introduced mutations was detected by sequencing.

The full length clone plasmids were linearized using a restriction enzyme, transcribed in vitro, and cells were subsequently electroporated with the resulting RNA. The viruses thus obtained were passaged a total of 5 times on SK-6 cells, and each passage was studied by indirect immunofluorescence. In this approach too, two parallel stainings with 24/16 and A18 were carried out. The controls used were in each case a non-infected cell control and a positive control which had been infected with a CSFV Alfort/Tübingen wild-type virus. Viruses EP#70/1 (TAVSAATVRT (SEQ ID NO:30)/ΔN$^{pro}$/RNase−) and EP#71/1 (TAVSAATVRT (SEQ ID NO:30)/RNase−) unexpectedly gave a positive signal in the A18 staining (Table 4) in several passages and were therefore not used any further.

The remaining mutants EP#72/1(TAVSAATVRT (SEQ ID NO:30)/ΔN$^{pro}$), EP#73/1 (TAVNKDTLRT (SEQ ID NO:28), ΔN$^{pro}$, RNase−), EP#74/1 (TAVNKDTLRT (SEQ ID NO:28), RNase−) and EP#75/1 (TAVNKDTLRT (SEQ ID NO:28), ΔN$^{pro}$) showed the desired result consistently in all passages: 24/16 staining positive, A18 staining negative (Table 5).

RNA was extracted from SK-6 cells which had been infected in each case with the third and fifth virus passages and employed in RT-PCRs. The PCR products were studied by sequencing. It emerged that the viruses EP#70/1 and EP#71/1 had lost their TAV epitope markers and had reverted to the wild-type sequence (Table 4). While the TAV epitope markers analogous to pSW14 and pSW16 were still present in the remaining viruses, even those viruses contained the partial reversions already observed in the basic TAV epitope mutants (Table 5). Since, however, these partial reversions appear not to adversely affect the functionality of the TAV epitope markers, two viruses from this set (EP#74/1 and EP#75/1) were selected for use in an animal experiment.

Table 4:

TABLE 4

TAV epitope combination mutants EP#70/1, EP#71/1 and EP#72/1. (+ = positive, − = negative, (+) = weak positive signal). Viruses EP#70/1 and EP#71/1 no longer showed the desired TAV epitope marker from passage 2 and 3, respectively, on SK-6 cells. From this point in time, both viruses gave a positive signal with both antibodies in an indirect immunofluorescence staining. Sequencing revealed that these viruses had reverted to the wild-type sequence in the TAV epitope region. Virus EP#72/2 in contrast, consistently showed the desired TAV marker over five passages: A18 negative, 24/16 positive. Sequencing revealed the TAV epitope marker TAVSAATLRT (SEQ ID NO: 24) and the Npro deletion for this virus.

| | Virus | | | | | | | | | | | | | | | | | | |
|---|---|---|---|---|---|---|---|---|---|---|---|---|---|---|---|---|---|---|---|
| | EP#70/1 | | | | | | EP#71/1 | | | | | | EP#72/1 | | | | | | mock |
| | Mutations | | | | | | | | | | | | | | | | | | |
| | TAVSPTTLRT (SEQ ID NO: 17)/ΔNpro/RNase− | | | | | | TAVSPTTLRT (SEQ ID NO: 17)/RNase− | | | | | | TAVSAATLRT (SEQ ID NO: 24)/ΔN$^{pro}$ | | | | | | / |
| Passage | 0 | 1 | 2 | 3 | 4 | 5 | 0 | 1 | 2 | 3 | 4 | 5 | 0 | 1 | 2 | 3 | 4 | 5 | / |
| 24/16 | + | + | + | + | + | + | + | + | + | + | + | + | + | + | + | + | + | + | − |
| A18 | − | − | − | (+) | + | + | − | − | (+) | − | − | − | − | − | − | − | − | − | − |

Table 5:

TABLE 5

TAV epitope combination mutants EP#173/1, EP#74/1 and EP#75/1 (+ = positive, − = negative). Viruses EP#73/1, EP#74/1 and EP#75/1 were consistently negative in an indirect immunofluorescence staining with A18 and consistently positive in the control staining with 24/16 over five passages. Sequencing detected the existence of all introduced mutations (TAV epitope marker and attenuating mutations).

| | Virus | | | | | | | | | | | | | | | | | | | | | | | |
|---|---|---|---|---|---|---|---|---|---|---|---|---|---|---|---|---|---|---|---|---|---|---|---|---|
| | EP#73/1 | | | | | | EP74/1 | | | | | | EP#75/1 | | | | | | WT | | | | | |
| | Mutations | | | | | | | | | | | | | | | | | | | | | | | |
| | TAVSKDTLRT (SEQ ID, NO: 22), ΔN$^{pro}$/RNAse− | | | | | | TAVSKDTLRT (SEQ ID NO: 22)/RNAse− | | | | | | TAVSKDTLRT (SEQ ID NO: 22), ΔN$^{pro}$ | | | | | | TAVSPTTLRT (SEQ ID NO: 17) | | | | | |
| Passage | 0 | 1 | 2 | 3 | 4 | 5 | 0 | 1 | 2 | 3 | 4 | 5 | 0 | 1 | 2 | 3 | 4 | 5 | 0 | 1 | 2 | 3 | 4 | 5 |
| 24/16 | + | + | + | + | + | + | + | + | + | + | + | + | + | + | + | + | + | + | + | + | + | + | + | + |
| A18 | − | − | − | − | − | − | − | − | − | − | − | − | − | − | − | − | − | − | + | + | + | + | + | + |

These results demonstrate that, due to reversion, the TAV epitope marker analogous to pSW16 (TAVSAATLRT (SEQ ID NO:24)) is not suitable for the preparation of a DIVA vaccine.

However, the results demonstrate that, due to its stability, the TAV epitope marker analogous to pSW14 (TAVSKDTLRT (SEQ ID NO:22)) is suitable for the preparation of a DIVA vaccine.

3. Animal Experiment Studies with CSFV DIVA Vaccine Mutants

The aim of the animal experiment was to test two different DIVA vaccine candidates which included the same TAV epitope marker (TAVSKDTLRT (SEQ ID NO:22), analogous to pSW14) in combination with different attenuating mutations (EP#73/2: dual deletion mutant=combination of Npro deletion and elimination of the Erns RNase activity by deleting the codon 346 Erns/EP#74/1: exclusively deletion of codon 346 Erns). It was the intention to study in this experiment whether these two candidates are capable of providing durable protection against challenge with the highly pathogenic CSFV strain "Eystrup". Another aim was the analysis of the viruses' efficiency in respect of the induction of CSFV-specific neutralizing antibodies and the stability of the introduced mutations in the animal passage.

3.1 Characterization of the Viruses Employed

The CSFV mutant EP#73/2 combines two attenuating mutations—the deletion of the genomic region which codes for the Npro NS protein, and the deletion of histidine 346 Erns, which results in the elimination of the Erns RNase activity—with the TAV epitope marker TAVSKDTLRT (SEQ ID NO:22). The CSFV mutant EP#74/1 only contains one attenuating mutation—the deletion of codon 346 Erns, which results in the elimination of the RNase—and the TAV epitope marker TAVSKDTLRT (SEQ ID NO:22). "Eystrup" is a highly pathogenic CSFV field strain.

3.2 Verification of the Marker Concept by Means of Indirect Immunofluorescence

The TAV epitope marker used in mutants EP#73/2 and EP#74/1 acts as a negative marker in respect of the DIVA criterion: the mAb A18, which is directed specifically against the TAV epitope, is no longer capable of recognizing the modified epitopes in the two viruses. Therefore, SK-6 cells which have been infected with EP#73/2 (passage 6) or with EP#74/1 (passage 6), gave a negative signal in the indirect immunofluorescence assay with A18, while the wild-type virus gave a positive signal. By way of internal positive control, SK-6 cells were likewise infected with the same viruses and then stained with the monoclonal antibody f48, which likewise detects the E2 protein. As expected, all viruses were positive in this staining.

3.3 Growth Characteristics

The growth behaviour of the two TAV epitope combination mutants (EP#73/2/EP#74/1) was compared with that of an Alfort/Tübingen CSF wild-type virus. It emerged that the growth characteristics of the RNase-negative mutant with TAV epitope marker EP#74/1 was very similar to that of the wild-type virus. In contrast, the dual deletion mutant with TAV epitope marker EP#73/2 was markedly inferior, and the mutant showed a growth reduction of 1-2 Log levels over the wild-type virus (data not shown). This was not surprising as a similarly inferior growth had already been described in the literature for mutants.

3.4 Experimental Animals

Fifteen days before the intended vaccination, twelve piglets (bodyweight approx. 20 kg) were penned in the experimental unit of the Friedrich-Loeffler Institute on the island of Riems so as to allow for a suitable acclimatization period. The animals were divided into three groups of four animals each. The piglets were vaccinated either intramuscularly with DMEM ("mock" control group: four animals in pen 140/1), with virus EP#73/2 (four animals in pen 141/1) or with virus EP#74/1 (four animals in pen 141/6) (2.2.3.1.). Twenty-four days after the vaccination, all animals were challenged with the highly pathogenic CSFV strain "Eystrup", likewise intramuscularly.

3.5 Schedule

The animals were observed daily from day −7 dpv (days post vaccination) up to and including day 48 dpv, the body temperature was taken, and the clinical symptoms were documented by means of a point scale. Heparin blood samples (for the leukocyte count and for obtaining leukocyte concentrate) and native blood samples (for obtaining serum) were taken on the stated days.

3.6 Infection and Titration of the Viruses for Vaccination and Challenge

The CSFV DIVA vaccine candidates (pen 141/1: EP#73/2/pen 141/6: EP74/1) and DMEM as the "mock" control (pen 140/1) were applied intramuscularly to the animals on day 0 dpv. Each animal received a dose of $10^{5.8}$ KID$_{50}$/ml in a total volume of 3.6 ml of DMEM, distributed into two aliquots of in each case 1.8 ml, which were injected individually into the right and the left *musculus brachiocephalicus*. Twenty-four days after the vaccination, each animal received a dose of $10^{6.5}$ KID$_{50}$/ml of the CSFV strain "Eystrup" in a total volume of 1 ml of DMEM as one injection into the *musculus brachiocephalicus*, which constituted the challenge. To control the virus titre, samples were retained for backtitration and then titrated. The amount of virus which, according to these titrations, had actually been administered to the animals differed only very slightly from the previously calculated vaccination doses (Table 6).

Table 6:

TABLE 6

Backtitration results. The titres determined in the backtitrations differ only slightly from the expected titres. No dilution was prepared for virus EP#73/2, but the original virus was applied undiluted instead.

| | Pen 141/1 EP#73/2 (dual mutant; TAVSKDTLRT (SEQ ID NO: 22)) Titre | | Pen 141/6 EP#74/1 (RNAse−; TAVSKDTLRT (SEQ ID NO: 22)) Titre | | All groups Challenge "Eystrup" Titre | |
|---|---|---|---|---|---|---|
| | Backtitration (KID$_{50}$/ml) | Expected (KID$_{50}$/ml) | Backtitration (KID$_{50}$/ml) | Expected (KID$_{50}$/ml) | Backtitration (KID$_{50}$/ml) | Expected (KID$_{50}$/ml) |
| Original virus (immediately after −70° C.) | $10^{5.94}$ | $10^{5.25}$ | $10^{6.86}$ | $10^{6.25}$ | $10^{6.94}$ | $10^{7.5}$ |

TABLE 6-continued

Backtitration results. The titres determined in the backtitrations differ only slightly from the expected titres. No dilution was prepared for virus EP#73/2, but the original virus was applied undiluted instead.

| | Pen 141/1 EP#73/2 (dual mutant; TAVSKDTLRT (SEQ ID NO: 22)) Titre | | Pen 141/6 EP#74/1 (RNAse−; TAVSKDTLRT (SEQ ID NO: 22)) Titre | | All groups Challenge "Eystrup" Titre | |
|---|---|---|---|---|---|---|
| | Backtitration ($KID_{50}$/ml) | Expected ($KID_{50}$/ml) | Backtitration ($KID_{50}$/ml) | Expected ($KID_{50}$/ml) | Backtitration ($KID_{50}$/ml) | Expected ($KID_{50}$/ml) |
| Dilution applied (applied i.n. + i.m.) | n.b. | n.b. | $10^{5.63}$ | $10^{5.24}$ | $10^{5.75}$ | $10^{6.5}$ |
| Dilution (transport into the pen "on ice", afterwards −70° C.) | $10^{5.75}$ | $10^{5.25}$ | $10^{5.63}$ | $10^{5.24}$ | $10^{5.82}$ | $10^{6.5}$ |

3.7 Clinical Score

Clinical scores were allocated to show the clinical course of a CSFV infection by way of comparison between several animals or groups of animals. This was done using a scheme designed by Mittelholzer et al. (Vet. Microbiol., 2000. 74(4): p. 293-308), which was modified in respect of the defecation.

The clinical score was determined daily between day −7 dpv and day 48 dpv. All animals in groups 141/1 (EP#73/2: dual mutant with TAV epitope marker) and 141/6 (EP#74/1: RNase-negative mutant with TAV epitope marker) showed no signs at all of clinical disease after the vaccination. As expected, the animals in the "mock" control group (140/1) likewise remained clinically normal during this phase of the experiment. Following challenge with "Eystrup" 24 days dpv, all animals in the test groups (141/1 and 141/6) remained clinically healthy and showed no signs at all of suffering from classical swine fever. In contrast, the animals in the "mock" control group were so ill four days after the challenge that they had to be killed for legal reasons (protection of animals).

3.8 Body Temperature

The animals' body temperature was taken daily from day −7 dpv up to day 48 dpv. In the "mock" control group, all animals were febrile after challenge with "Eystrup". Five days after the challenge (i.e. on day 29 dpv), all animals of this group were killed for legal reasons (protection of animals). No animal in groups 141/1 (EP#73/2) and 141/6 (EP#74/1) showed a significant increase in body temperature, either after the vaccination or after the challenge. In group 141/1, the body temperature of the animals remained below 40° C. during the entire experiment. The body temperatures of the animals in group 141/6 varied to a higher degree, and one animal showed a maximum temperature of 40.8° C. at one time of measurement.

3.9 Leukocyte Count

The animals' total leukocyte counts were determined. All the animals in the test groups (pens 141/1 and 141/6) showed a marked drop in the leukocyte numbers three to seven days after the vaccination. However, a drop in leukocyte counts (albeit less pronounced) was also observed in the "mock" control group after the vaccination. Another remarkable fact was that all animals had slightly increased leukocyte counts before the beginning of the experiment (on day −4 dpv) (animal 82/1 in pen 140/1 showed the most significant increase with approx. 35 000 leukocytes/μl blood), which, over the course of the animal experiment, shifted towards the physiological range. Four days after the challenge with "Eystrup", a rapid drop in total leukocyte counts was observed in all animals of the non-vaccinated control group (drop of approx. 8000 leukocytes/μl blood within seven days). All animals of this group had to be destroyed on day 5 after the challenge (day 29 dpv) for legal reasons (protection of animals). The leukocyte counts of the animals in the test groups (pens 141/1 and 141/6) remained in the physiological range from after the challenge up to the end of the animal experiment.

3.10 Serological Examination (SNT)

Serum neutralization tests were carried out for examining serum samples which had been obtained one day before the vaccination (−1 dpv), on the day of the challenge (24 dpv) and on the day of euthanasia (49 dpv). The animals in the "mock" control group (pen 140/1) had to be killed before the intended end of the animal experiment, so that, in these animals, the serum samples were already obtained on day 26 dpv. At no point in time were CSFV-specific neutralizing antibodies detectable in the sera of the "mock" control group's animals. All animals which lived to the intended end of the animal experiment developed significant titres of CSFV-specific neutralizing antibodies. While these antibodies were already detectable on the day of the challenge in the sera of the animals in the test groups (141/1 and 141/6), they markedly increased again up to the day of euthanasia (49 dpv). Three independent serum neutralization tests were carried out. Animals which revealed neutralizing antibodies did so in all three tests.

3.11 Analysis of the Viruses Reisolated from the Leukocyte Concentrate

Viruses were isolated by cocultivation of SK6 cells with leukocyte concentrate. The experiment was evaluated by indirect immunofluorescence staining with the mAb 24/16. It emerged that viraemia was detected only in the four animals of the group in pen 141/6 (EP#74/1) on one day. The samples which tested positive were studied by sequencing and indirect immunofluorescence.

3.11.1 Sequencing—Result

The RNA obtained from the viruses grown in cell culture was employed in RT-PCRs. The subsequent sequencing of the RT-PCR products revealed that all the viruses which had been reisolated from the animals still contained the introduced mutations.

| Primer/Virus | | EP#74/1 | | |
|---|---|---|---|---|
| Animal number | 93/9 | 94/10 | 99/11 | 100/12 |
| SW86 | | TAVSKDTLRT (SEQ ID NO: 22) | | |
| olXhoI | | $N^{pro}+$ | | |
| SW88r | | H 346 $E^{rns}$deleted | | |

3.11.2 Indirect Immunofluorescence—Result

Leukocyte concentrate from the animals of pen 141/6 (EP#74/1) of day 7 dpv was used for this purpose. SK-6 cells were infected with these samples and with the leukocyte concentrate from an animal of the wild-type group by way of positive control. After three days, the infected cells and a non-infected "mock" cell control were stained both by the mAb A18, which specifically detects the TAV epitope, and by the mAb f48 (recognizes a different epitope in the E2 protein) as the internal positive control. It emerged that the viruses which had been reisolated from the EP#74/1-vaccinated animals still contained the TAV epitope marker even after animal passage. The cells which were infected with the leukocyte concentrate of these animals were negative in the A18 staining. In contrast, the cells which had been infected with the leukocyte concentrate of the animal from the wild-type group gave a positive signal in the A18 staining.

The control staining with f48 was positive for all samples. This demonstrates that replicable CSF virus was present in all tested samples.

3.12 Summary of the Animal Experiment

All animals which had been vaccinated with one of the two vaccine candidates (EP#73/2 or EP#74/1) were protected against challenge with "Eystrup" since they showed no signs of clinical disease, no increased body temperature and no pathological changes in leukocyte counts after challenge.

It was possible to reisolate virus from the animals' leukocyte concentrate and to study it by sequencing and with the aid of indirect immunofluorescence. Sequencing revealed that the inserted TAV epitope marker (TAVSKDTLRT) (SEQ ID NO:22) was still present in the leukocyte concentrate of all animals of group 141/6 on day 7.

Furthermore, indirect immunofluorescence showed that the negative TAV epitope marker concept was still functional in the viruses which had been reisolated on day 7 dpv from the leukocyte concentrate of the animals of group 141/6.

In summary, the results of this experiment allow the conclusion that the TAV epitope marker (TAVSKDTLRT) (SEQ ID NO: 22) is suitable for preparing a DIVA vaccine.

The invention claimed is:

1. A CSFV (classical swine fever virus) comprising a substitution mutation in the E2 protein comprising substitution of proline to lysine at amino acid position 44 of the E2 protein and a substitution of threonine to aspartic acid at amino acid position 45 of the E2 protein, wherein the amino acid substitution within the TAV epitope of the E2 protein results in the TAV epitope sequence TAVSKDTLRT (SEQ ID NO:22) or, wherein the CSFV has the amino acid sequence SEQ ID NO: 3.

2. The CSFV according to claim 1, wherein said amino acid substitution is within the wild-type TAV epitope of the E2 protein having the amino acid sequence TAVSPTTLR.

3. The CSFV according to claim 1, wherein said amino acid substitution within the TAV epitope of the E2 protein is a stable amino acid substitution.

4. The CSFV according to claim 1, wherein the CSFV is attenuated.

5. The CSFV according to claim 1, wherein the CSFV has a mutation in the coding sequence for glycoprotein Erns and/or a mutation in the coding sequence for Npro, wherein the mutation in the coding sequence for glycoprotein Erns results in an inactivated RNase activity and wherein the mutation in the Npro coding sequence results in an non-functional Npro protein.

6. The CSFV according to claim 1, wherein the CSFV is a C (Chinese)-strain.

7. A nucleic acid coding for a CSFV according claim 1, or, a vector comprising said nucleic acid.

8. An immunogenic composition comprising the CSFV according claim 1, wherein the CSFV is attenuated.

9. The immunogenic composition according to claim 8, wherein said immunogenic composition is a marker vaccine or a DIVA (differentiation between infected and vaccinated animals) vaccine.

10. A method of marking a CSFV vaccine comprising introducing a substitution mutation in the E2 protein comprising substitution proline to lysine at amino acid position 44 of the E2 protein and a substitution of threonine to aspartic acid at amino acid position 45 of the E2 protein into a CSFV vaccine, wherein the amino acid substitution within the TAV epitope of the E2 protein results in the TAV epitope sequence TAVSKDTLRT (SEQ ID NO:22) or, wherein the CSFV has an amino acid as shown in SEQ ID NO: 3.

11. The method according to claim 10, wherein said amino acid substitution is within the TAV epitope of the E2 protein having the amino acid sequence TAVSPTTLR or, wherein the amino acid substitution within the TAV epitope of the E2 protein results in the TAV epitope sequence TAVSKDTLRT (SEQ ID NO:22).

12. The method according to claim 10, wherein the CSFV vaccine is an attenuated vaccine, and/or, wherein the CSFV is a C (Chinese)-strain.

13. A method of differentiating an animal naturally infected with CSFV from an animal vaccinated with an immunogenic composition comprising the mutated CSFV TAV epitope TAVSKDTLRT (SEQ ID. NO:22), comprising
   a. obtaining a biological sample from an animal,
   b. contacting said biological sample with at least one probe capable of detecting the presence of either a peptide comprising the mutated TAV epitope sequence TAVSKDTLRT (SEQ ID. NO:22) or a peptide comprising the wild-type TAV epitope sequence TAVSPTTLR (SEQ ID NO:1) of the CSFV E2 protein; and c. detecting the presence of the probe-binding to either the peptide comprising the mutated TAV epitope (SEQ ID NO:22) or the peptide comprising the wild-type TAV epitope sequence (SEQ ID NO:1) in the biological sample, of step (b);

wherein the presence of probe-bound-peptide comprising mutated TAV epitope (SEQ ID NO:22) complexes or probe-bound-peptide comprising wild type TAV epitope (SEQ ID NO:1) complexes differentiate the animal naturally infected with CSFV having the non-mutated TAV epitope (SEQ ID NO:1) from the animal vaccinated with the immunogenic composition comprising the mutated CSFV TAV epitope (SEQ ID NO:22).

14. The method according to claim 13, wherein the immuno test is an EIA (enzyme immunoassay) or ELISA (enzyme linked immunosorbent assay).

15. The CSFV according to claim 5, wherein the CSFV mutation in the glycoprotein Erns is a deletion of amino acid at amino acid position 346 of glycoprotein Erns and the mutation in the coding sequence for Npro is a deletion of the Npro coding sequence except for the last two amino terminal amino acids.

* * * * *

SEQUENCE LISTING

```
<160> NUMBER OF SEQ ID NOS: 38

<210> SEQ ID NO 1
<211> LENGTH: 9
<212> TYPE: PRT
<213> ORGANISM: CSFV

<400> SEQUENCE: 1

Thr Ala Val Ser Pro Thr Thr Leu Arg
1               5

<210> SEQ ID NO 2
<211> LENGTH: 3898
<212> TYPE: PRT
<213> ORGANISM: CSFV

<400> SEQUENCE: 2

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140
```

```
Lys Arg Gly Thr Pro Arg Thr Leu Lys Trp Ile Arg Asn Phe Thr Asn
145                 150                 155                 160

Cys Pro Leu Trp Val Thr Ser Cys Ser Asp Asp Gly Ala Ser Gly Ser
            165                 170                 175

Lys Asp Lys Lys Pro Asp Arg Met Asn Lys Gly Lys Leu Lys Ile Ala
        180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Gly Lys Val
210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
            245                 250                 255

Ile Thr Ile Leu Leu Tyr Gln Pro Val Ala Ala Glu Asn Ile Thr Gln
            260                 265                 270

Trp Asn Leu Ser Asp Asn Gly Thr Asn Gly Ile Gln Arg Ala Met Tyr
        275                 280                 285

Leu Arg Gly Val Asn Arg Ser Leu His Gly Ile Trp Pro Glu Lys Ile
290                 295                 300

Cys Lys Gly Val Pro Thr His Leu Ala Thr Asp Thr Glu Leu Lys Glu
305                 310                 315                 320

Ile Arg Gly Met Met Asp Ala Ser Glu Arg Thr Asn Tyr Thr Cys Cys
                325                 330                 335

Arg Leu Gln Arg His Glu Trp Asn Lys His Gly Trp Cys Asn Trp Tyr
            340                 345                 350

Asn Ile Asp Pro Trp Ile Gln Leu Met Asn Arg Thr Gln Thr Asn Leu
        355                 360                 365

Thr Glu Gly Pro Pro Asp Lys Glu Cys Ala Val Thr Cys Arg Tyr Asp
        370                 375                 380

Lys Asn Thr Asp Val Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
            420                 425                 430

Tyr Gly Asp His Glu Cys Gly Ser Leu Leu Gln Asp Thr Ala Leu Tyr
        435                 440                 445

Leu Leu Asp Gly Met Thr Asn Thr Ile Glu Asn Ala Arg Gln Gly Ala
450                 455                 460

Ala Arg Val Thr Ser Trp Leu Gly Arg Gln Leu Ser Thr Ala Gly Lys
465                 470                 475                 480

Lys Leu Glu Arg Arg Ser Lys Thr Trp Phe Gly Ala Tyr Ala Leu Ser
            485                 490                 495

Pro Tyr Cys Asn Val Thr Arg Lys Ile Gly Tyr Ile Trp Tyr Thr Asn
        500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
        530                 535                 540

Gly Gly His Leu Ser Glu Phe Leu Leu Leu Ser Leu Val Ile Leu Ser
545                 550                 555                 560

Asp Phe Ala Pro Glu Thr Ala Ser Thr Leu Tyr Leu Ile Leu His Tyr
```

```
            565                 570                 575
Ala Ile Pro Gln Ser His Glu Pro Glu Gly Cys Asp Thr Asn Gln
            580                 585                 590

Leu Asn Leu Thr Val Lys Leu Arg Thr Glu Asp Val Val Pro Ser Ser
            595                 600                 605

Val Trp Asn Ile Gly Lys Tyr Val Cys Val Arg Pro Asp Trp Trp Pro
    610                 615                 620

Tyr Glu Thr Lys Val Ala Leu Leu Phe Glu Glu Ala Gly Gln Val Ile
625                 630                 635                 640

Lys Leu Val Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
            660                 665                 670

Gln Val Val Gln Gly Ile Ile Trp Leu Leu Leu Val Thr Gly Ala Gln
            675                 680                 685

Gly Arg Leu Ala Cys Lys Glu Asp Tyr Arg Tyr Ala Ile Ser Ser Thr
    690                 695                 700

Asn Glu Ile Gly Leu Leu Gly Ala Glu Gly Leu Thr Thr Thr Trp Lys
705                 710                 715                 720

Glu Tyr Ser His Gly Leu Gln Leu Asp Asp Gly Thr Val Lys Ala Val
                725                 730                 735

Cys Thr Ala Gly Ser Phe Lys Val Thr Ala Leu Asn Val Val Ser Arg
            740                 745                 750

Arg Tyr Leu Ala Ser Leu His Lys Arg Ala Leu Pro Thr Ser Val Thr
    755                 760                 765

Phe Glu Leu Leu Phe Asp Gly Thr Asn Pro Ala Ile Glu Glu Met Asp
770                 775                 780

Asp Asp Phe Gly Phe Gly Leu Cys Pro Phe Asp Thr Ser Pro Val Ile
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Val Glu Cys Thr Ala Val Ser
            820                 825                 830

Pro Thr Thr Leu Arg Thr Glu Val Val Lys Thr Phe Arg Arg Asp Lys
            835                 840                 845

Pro Phe Pro His Arg Val Asp Cys Val Thr Thr Ile Val Glu Lys Glu
    850                 855                 860

Asp Leu Phe His Cys Lys Leu Gly Gly Asn Trp Thr Cys Val Lys Gly
865                 870                 875                 880

Asp Pro Val Thr Tyr Lys Gly Gly Gln Val Lys Gln Cys Arg Trp Cys
                885                 890                 895

Gly Phe Glu Phe Lys Glu Pro Tyr Gly Leu Pro His Tyr Pro Ile Gly
            900                 905                 910

Lys Cys Ile Leu Thr Asn Glu Thr Gly Tyr Arg Val Val Asp Ser Thr
            915                 920                 925

Asp Cys Asn Arg Asp Gly Val Val Ile Ser Thr Glu Gly Glu His Glu
    930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Glu Gly
                965                 970                 975

Pro Val Arg Lys Thr Ser Cys Thr Phe Asn Tyr Thr Lys Thr Leu Arg
            980                 985                 990
```

```
Asn Lys Tyr Tyr Glu Pro Arg Asp Ser Tyr Phe Gln Gln Tyr Met Leu
        995                 1000                1005

Lys Gly Glu Tyr Gln Tyr Trp Phe Asn Leu Asp Val Thr Asp His
   1010                1015                1020

His Thr Asp Tyr Phe Ala Glu Phe Val Val Leu Val Val Val Ala
   1025                1030                1035

Leu Leu Gly Gly Arg Tyr Val Leu Trp Leu Ile Val Thr Tyr Ile
   1040                1045                1050

Ile Leu Thr Glu Gln Leu Ala Ala Gly Leu Gln Leu Gly Gln Gly
   1055                1060                1065

Glu Val Val Leu Ile Gly Asn Leu Ile Thr His Thr Asp Asn Glu
   1070                1075                1080

Val Val Val Tyr Phe Leu Leu Leu Tyr Leu Val Ile Arg Asp Glu
   1085                1090                1095

Pro Ile Lys Lys Trp Ile Leu Leu Leu Phe His Ala Met Thr Asn
   1100                1105                1110

Asn Pro Val Lys Thr Ile Thr Val Ala Leu Leu Met Ile Ser Gly
   1115                1120                1125

Val Ala Lys Gly Gly Lys Ile Asp Gly Gly Trp Gln Arg Gln Pro
   1130                1135                1140

Val Thr Ser Phe Asp Ile Gln Leu Ala Leu Ala Val Val Val Val
   1145                1150                1155

Val Val Met Leu Leu Ala Lys Arg Asp Pro Thr Thr Phe Pro Leu
   1160                1165                1170

Val Ile Thr Val Ala Thr Leu Arg Thr Ala Lys Ile Thr Asn Gly
   1175                1180                1185

Phe Ser Thr Asp Leu Val Ile Ala Thr Val Ser Ala Ala Leu Leu
   1190                1195                1200

Thr Trp Thr Tyr Ile Ser Asp Tyr Tyr Lys Tyr Lys Thr Trp Leu
   1205                1210                1215

Gln Tyr Leu Val Ser Thr Val Thr Gly Ile Phe Leu Ile Arg Val
   1220                1225                1230

Leu Lys Gly Ile Gly Glu Leu Asp Leu His Ala Pro Thr Leu Pro
   1235                1240                1245

Ser His Arg Pro Leu Phe Tyr Ile Leu Val Tyr Leu Ile Ser Thr
   1250                1255                1260

Ala Val Val Thr Arg Trp Asn Leu Asp Val Ala Gly Leu Leu Leu
   1265                1270                1275

Gln Cys Val Pro Thr Leu Leu Met Val Phe Thr Met Trp Ala Asp
   1280                1285                1290

Ile Leu Thr Leu Ile Leu Ile Leu Pro Thr Tyr Glu Leu Thr Lys
   1295                1300                1305

Leu Tyr Tyr Leu Lys Glu Val Lys Ile Gly Ala Glu Arg Gly Trp
   1310                1315                1320

Leu Trp Lys Thr Asn Tyr Lys Arg Val Asn Asp Ile Tyr Glu Val
   1325                1330                1335

Asp Gln Thr Ser Glu Gly Val Tyr Leu Phe Pro Ser Lys Gln Arg
   1340                1345                1350

Thr Ser Ala Ile Thr Ser Thr Met Leu Pro Leu Ile Lys Ala Ile
   1355                1360                1365

Leu Ile Ser Cys Ile Ser Asn Lys Trp Gln Leu Ile Tyr Leu Leu
   1370                1375                1380
```

-continued

Tyr Leu Ile Phe Glu Val Ser Tyr Tyr Leu His Lys Lys Val Ile
    1385            1390            1395

Asp Glu Ile Ala Gly Gly Thr Asn Phe Val Ser Arg Leu Val Ala
    1400            1405            1410

Ala Leu Ile Glu Val Asn Trp Ala Phe Asp Asn Glu Glu Val Lys
    1415            1420            1425

Gly Leu Lys Lys Phe Phe Leu Leu Ser Ser Arg Val Lys Glu Leu
    1430            1435            1440

Ile Ile Lys His Lys Val Arg Asn Glu Val Val Val Arg Trp Phe
    1445            1450            1455

Gly Asp Glu Glu Ile Tyr Gly Met Pro Lys Leu Ile Gly Leu Val
    1460            1465            1470

Lys Ala Ala Thr Leu Ser Arg Asn Lys His Cys Met Leu Cys Thr
    1475            1480            1485

Val Cys Glu Asp Arg Asp Trp Arg Gly Glu Thr Cys Pro Lys Cys
    1490            1495            1500

Gly Arg Phe Gly Pro Pro Val Val Cys Gly Met Thr Leu Ala Asp
    1505            1510            1515

Phe Glu Glu Lys His Tyr Lys Arg Ile Phe Ile Arg Glu Asp Gln
    1520            1525            1530

Ser Gly Gly Pro Leu Arg Glu Glu His Ala Gly Tyr Leu Gln Tyr
    1535            1540            1545

Lys Ala Arg Gly Gln Leu Phe Leu Arg Asn Leu Pro Val Leu Ala
    1550            1555            1560

Thr Lys Val Lys Met Leu Leu Val Gly Asn Leu Gly Thr Glu Ile
    1565            1570            1575

Gly Asp Leu Glu His Leu Gly Trp Val Leu Arg Gly Pro Ala Val
    1580            1585            1590

Cys Lys Lys Val Thr Glu His Glu Arg Cys Thr Thr Ser Ile Met
    1595            1600            1605

Asp Lys Leu Thr Ala Phe Phe Gly Val Met Pro Arg Gly Thr Thr
    1610            1615            1620

Pro Arg Ala Pro Val Arg Phe Pro Thr Ser Leu Leu Lys Ile Arg
    1625            1630            1635

Arg Gly Leu Glu Thr Gly Trp Ala Tyr Thr His Gln Gly Gly Ile
    1640            1645            1650

Ser Ser Val Asp His Val Thr Cys Gly Lys Asp Leu Leu Val Cys
    1655            1660            1665

Asp Thr Met Gly Arg Thr Arg Val Val Cys Gln Ser Asn Asn Lys
    1670            1675            1680

Met Thr Asp Glu Ser Glu Tyr Gly Val Lys Thr Asp Ser Gly Cys
    1685            1690            1695

Pro Glu Gly Ala Arg Cys Tyr Val Phe Asn Pro Glu Ala Val Asn
    1700            1705            1710

Ile Ser Gly Thr Lys Gly Ala Met Val His Leu Gln Lys Thr Gly
    1715            1720            1725

Gly Glu Phe Thr Cys Val Thr Ala Ser Gly Thr Pro Ala Phe Phe
    1730            1735            1740

Asp Leu Lys Asn Leu Lys Gly Trp Ser Gly Leu Pro Ile Phe Glu
    1745            1750            1755

Ala Ser Ser Gly Arg Val Val Gly Arg Val Lys Val Gly Lys Asn
    1760            1765            1770

Glu Asp Ser Lys Pro Thr Lys Leu Met Ser Gly Ile Gln Thr Val

-continued

```
            1775                1780                1785
Ser Lys Ser Ala Thr Asp Leu Thr Glu Met Val Lys Lys Ile Thr
    1790                1795                1800
Thr Met Asn Arg Gly Glu Phe Arg Gln Ile Thr Leu Ala Thr Gly
    1805                1810                1815
Ala Gly Lys Thr Thr Glu Leu Pro Arg Ser Val Ile Glu Glu Ile
    1820                1825                1830
Gly Arg His Lys Arg Val Leu Val Leu Ile Pro Leu Arg Ala Ala
    1835                1840                1845
Ala Glu Ser Val Tyr Gln Tyr Met Arg Gln Lys His Pro Ser Ile
    1850                1855                1860
Ala Phe Asn Leu Arg Ile Gly Glu Met Lys Glu Gly Asp Met Ala
    1865                1870                1875
Thr Gly Ile Thr Tyr Ala Ser Tyr Gly Tyr Phe Cys Gln Met Ser
    1880                1885                1890
Gln Pro Lys Leu Arg Ala Ala Met Val Glu Tyr Ser Phe Ile Phe
    1895                1900                1905
Leu Asp Glu Tyr His Cys Ala Thr Pro Glu Gln Leu Ala Ile Met
    1910                1915                1920
Gly Lys Ile His Arg Phe Ser Glu Asn Leu Arg Val Val Ala Met
    1925                1930                1935
Thr Ala Thr Pro Ala Gly Thr Val Thr Thr Thr Gly Gln Lys His
    1940                1945                1950
Pro Ile Glu Glu Phe Ile Ala Pro Glu Val Met Lys Gly Glu Asp
    1955                1960                1965
Leu Gly Ser Glu Tyr Leu Asp Ile Ala Gly Leu Lys Ile Pro Val
    1970                1975                1980
Glu Glu Met Lys Asn Asn Met Leu Val Phe Val Pro Thr Arg Asn
    1985                1990                1995
Met Ala Val Glu Ala Ala Lys Lys Leu Lys Ala Lys Gly Tyr Asn
    2000                2005                2010
Ser Gly Tyr Tyr Tyr Ser Gly Glu Asp Pro Ser Asn Leu Arg Val
    2015                2020                2025
Val Thr Ser Gln Ser Pro Tyr Val Val Val Ala Thr Asn Ala Ile
    2030                2035                2040
Glu Ser Gly Val Thr Leu Pro Asp Leu Asp Val Val Val Asp Thr
    2045                2050                2055
Gly Leu Lys Cys Glu Lys Arg Ile Arg Leu Ser Pro Lys Met Pro
    2060                2065                2070
Phe Ile Val Thr Gly Leu Lys Arg Met Ala Val Thr Ile Gly Glu
    2075                2080                2085
Gln Ala Gln Arg Arg Gly Arg Val Gly Arg Val Lys Pro Gly Arg
    2090                2095                2100
Tyr Tyr Arg Ser Gln Glu Thr Pro Val Gly Ser Lys Asp Tyr His
    2105                2110                2115
Tyr Asp Leu Leu Gln Ala Gln Arg Tyr Gly Ile Glu Asp Gly Ile
    2120                2125                2130
Asn Ile Thr Lys Ser Phe Arg Glu Met Asn Tyr Asp Trp Ser Leu
    2135                2140                2145
Tyr Glu Glu Asp Ser Leu Met Ile Thr Gln Leu Glu Ile Leu Asn
    2150                2155                2160
Asn Leu Leu Ile Ser Glu Glu Leu Pro Met Ala Val Lys Asn Ile
    2165                2170                2175
```

```
Met Ala Arg Thr Asp His Pro Glu Pro Ile Gln Leu Ala Tyr Asn
    2180            2185                2190
Ser Tyr Glu Thr Gln Val Pro Val Leu Phe Pro Lys Ile Arg Asn
    2195            2200                2205
Gly Glu Val Thr Asp Thr Tyr Asp Asn Tyr Thr Phe Leu Asn Ala
    2210            2215                2220
Arg Lys Leu Gly Asp Asp Val Pro Pro Tyr Val Tyr Ala Thr Glu
    2225            2230                2235
Asp Glu Asp Leu Ala Val Glu Leu Leu Gly Leu Asp Trp Pro Asp
    2240            2245                2250
Pro Gly Asn Gln Gly Thr Val Glu Ala Gly Arg Ala Leu Lys Gln
    2255            2260                2265
Val Val Gly Leu Ser Thr Ala Glu Asn Ala Leu Leu Val Ala Leu
    2270            2275                2280
Phe Gly Tyr Val Gly Tyr Gln Ala Leu Ser Lys Arg His Ile Pro
    2285            2290                2295
Val Val Thr Asp Ile Tyr Ser Val Glu Asp His Arg Leu Glu Asp
    2300            2305                2310
Thr Thr His Leu Gln Tyr Ala Pro Asn Ala Ile Lys Thr Glu Gly
    2315            2320                2325
Lys Glu Thr Glu Leu Lys Glu Leu Ala Gln Gly Asp Val Gln Arg
    2330            2335                2340
Cys Val Glu Ala Val Thr Asn Tyr Ala Arg Glu Gly Ile Gln Phe
    2345            2350                2355
Met Lys Ser Gln Ala Leu Lys Val Arg Glu Thr Pro Thr Tyr Lys
    2360            2365                2370
Glu Thr Met Asn Thr Val Ala Asp Tyr Val Lys Lys Phe Ile Glu
    2375            2380                2385
Ala Leu Thr Asp Ser Lys Glu Asp Ile Ile Lys Tyr Gly Leu Trp
    2390            2395                2400
Gly Ala His Thr Ala Leu Tyr Lys Ser Ile Gly Ala Arg Leu Gly
    2405            2410                2415
His Glu Thr Ala Phe Ala Thr Leu Val Val Lys Trp Leu Ala Phe
    2420            2425                2430
Gly Gly Glu Ser Ile Ser Asp His Ile Lys Gln Ala Ala Thr Asp
    2435            2440                2445
Leu Val Val Tyr Tyr Ile Ile Asn Arg Pro Gln Phe Pro Gly Asp
    2450            2455                2460
Thr Glu Thr Gln Gln Glu Gly Arg Lys Phe Val Ala Ser Leu Leu
    2465            2470                2475
Val Ser Ala Leu Ala Thr Tyr Thr Tyr Lys Ser Trp Asn Tyr Asn
    2480            2485                2490
Asn Leu Ser Lys Ile Val Glu Pro Ala Leu Ala Thr Leu Pro Tyr
    2495            2500                2505
Ala Ala Lys Ala Leu Lys Leu Phe Ala Pro Thr Arg Leu Glu Ser
    2510            2515                2520
Val Val Ile Leu Ser Thr Ala Ile Tyr Lys Thr Tyr Leu Ser Ile
    2525            2530                2535
Arg Arg Gly Lys Ser Asp Gly Leu Leu Gly Thr Gly Val Ser Ala
    2540            2545                2550
Ala Met Glu Ile Met Ser Gln Asn Pro Val Ser Val Gly Ile Ala
    2555            2560                2565
```

Val Met Leu Gly Val Gly Ala Val Ala His Asn Ala Ile Glu
2570                2575            2580

Ala Ser Glu Gln Lys Arg Thr Leu Leu Met Lys Val Phe Val Lys
2585                2590            2595

Asn Phe Leu Asp Gln Ala Ala Thr Asp Glu Leu Val Lys Glu Ser
2600                2605            2610

Pro Glu Lys Ile Ile Met Ala Leu Phe Glu Ala Val Gln Thr Val
2615                2620            2625

Gly Asn Pro Leu Arg Leu Val Tyr His Leu Tyr Gly Val Phe Tyr
2630                2635            2640

Lys Gly Trp Glu Ala Lys Glu Leu Ala Gln Arg Thr Ala Gly Arg
2645                2650            2655

Asn Leu Phe Thr Leu Ile Met Phe Glu Ala Val Glu Leu Leu Gly
2660                2665            2670

Val Asp Ser Glu Gly Lys Ile Arg Gln Leu Ser Ser Asn Tyr Ile
2675                2680            2685

Leu Glu Leu Leu Tyr Lys Phe Arg Asp Asn Ile Lys Ser Ser Val
2690                2695            2700

Arg Glu Ile Ala Ile Ser Trp Ala Pro Ala Pro Phe Ser Cys Asp
2705                2710            2715

Trp Thr Pro Thr Asp Asp Arg Ile Gly Leu Pro His Asp Asn Tyr
2720                2725            2730

Leu Arg Val Glu Thr Lys Cys Pro Cys Gly Tyr Arg Met Lys Ala
2735                2740            2745

Val Lys Asn Cys Ala Gly Glu Leu Arg Leu Leu Glu Glu Gly Gly
2750                2755            2760

Ser Phe Leu Cys Arg Asn Lys Phe Gly Arg Gly Ser Gln Asn Tyr
2765                2770            2775

Arg Val Thr Lys Tyr Tyr Asp Asp Asn Leu Ser Glu Ile Lys Pro
2780                2785            2790

Val Ile Arg Met Glu Gly His Val Glu Leu Tyr Tyr Lys Gly Ala
2795                2800            2805

Thr Ile Lys Leu Asp Phe Asn Asn Ser Lys Thr Val Leu Ala Thr
2810                2815            2820

Asp Lys Trp Glu Val Asp His Ser Thr Leu Val Arg Ala Leu Lys
2825                2830            2835

Arg Tyr Thr Gly Ala Gly Tyr Arg Gly Ala Tyr Leu Gly Glu Lys
2840                2845            2850

Pro Asn His Lys His Leu Ile Gln Arg Asp Cys Ala Thr Leu Thr
2855                2860            2865

Lys Asp Lys Val Cys Phe Ile Lys Met Lys Arg Gly Cys Ala Phe
2870                2875            2880

Thr Tyr Asp Leu Ser Leu His Asn Leu Thr Arg Leu Ile Glu Leu
2885                2890            2895

Val His Lys Asn Asn Leu Glu Asp Arg Glu Ile Pro Ala Val Thr
2900                2905            2910

Val Thr Thr Trp Leu Ala Tyr Thr Phe Val Asn Glu Asp Ile Gly
2915                2920            2925

Thr Ile Lys Pro Thr Phe Gly Glu Lys Val Thr Pro Glu Lys Gln
2930                2935            2940

Glu Glu Val Val Leu Gln Pro Ala Val Val Val Asp Thr Thr Asp
2945                2950            2955

Val Ala Val Thr Val Val Gly Glu Thr Ser Thr Met Thr Thr Gly

-continued

```
                     2960                2965                2970
Glu Thr Pro Thr Thr Phe Thr Ser Leu Gly Ser Asp Ser Lys Val
                     2975                2980                2985
Arg Gln Val Leu Lys Leu Gly Val Asp Asp Gly Gln Tyr Pro Gly
                     2990                2995                3000
Pro Asn Gln Gln Arg Ala Ser Leu Leu Glu Ala Ile Gln Gly Val
                     3005                3010                3015
Asp Glu Arg Pro Ser Val Leu Ile Leu Gly Ser Asp Lys Ala Thr
                     3020                3025                3030
Ser Asn Arg Val Lys Thr Ala Lys Asn Val Lys Ile Tyr Arg Ser
                     3035                3040                3045
Arg Asp Pro Leu Glu Leu Arg Glu Met Met Lys Arg Gly Lys Ile
                     3050                3055                3060
Leu Val Val Ala Leu Ser Arg Val Asp Thr Ala Leu Leu Lys Phe
                     3065                3070                3075
Val Asp Tyr Lys Gly Thr Phe Leu Thr Arg Glu Thr Leu Glu Ala
                     3080                3085                3090
Leu Ser Leu Gly Lys Pro Lys Lys Arg Asp Ile Thr Lys Ala Glu
                     3095                3100                3105
Ala Gln Trp Leu Leu Arg Leu Glu Asp Gln Ile Glu Glu Leu Pro
                     3110                3115                3120
Asp Trp Phe Ala Ala Lys Glu Pro Ile Phe Leu Glu Ala Asn Ile
                     3125                3130                3135
Lys Arg Asp Lys Tyr His Leu Val Gly Asp Ile Ala Thr Ile Lys
                     3140                3145                3150
Glu Lys Ala Lys Gln Leu Gly Ala Thr Asp Ser Thr Lys Ile Ser
                     3155                3160                3165
Lys Glu Val Gly Ala Lys Val Tyr Ser Met Lys Leu Ser Asn Trp
                     3170                3175                3180
Val Ile Gln Glu Glu Asn Lys Gln Gly Ser Leu Ala Pro Leu Phe
                     3185                3190                3195
Glu Glu Leu Leu Gln Gln Cys Pro Pro Gly Gly Gln Asn Lys Thr
                     3200                3205                3210
Thr His Met Val Ser Ala Tyr Gln Leu Ala Gln Gly Asn Trp Val
                     3215                3220                3225
Pro Val Ser Cys His Val Phe Met Gly Thr Ile Pro Ala Arg Arg
                     3230                3235                3240
Thr Lys Thr His Pro Tyr Glu Ala Tyr Val Lys Leu Arg Glu Leu
                     3245                3250                3255
Val Asp Glu His Lys Met Lys Ala Leu Cys Gly Gly Ser Gly Leu
                     3260                3265                3270
Ser Lys His Asn Glu Trp Val Ile Gly Lys Val Lys Tyr Gln Gly
                     3275                3280                3285
Asn Leu Arg Thr Lys His Met Leu Asn Pro Gly Lys Val Ala Glu
                     3290                3295                3300
Gln Leu His Arg Glu Gly Tyr Arg His Asn Val Tyr Asn Lys Thr
                     3305                3310                3315
Ile Gly Ser Val Met Thr Ala Thr Gly Ile Arg Leu Glu Lys Leu
                     3320                3325                3330
Pro Val Val Arg Ala Gln Thr Asp Thr Thr Asn Phe His Gln Ala
                     3335                3340                3345
Ile Arg Asp Lys Ile Asp Lys Glu Glu Asn Leu Gln Thr Pro Gly
                     3350                3355                3360
```

```
Leu His Lys Lys Leu Met Glu Val Phe Asn Ala Leu Lys Arg Pro
3365                3370                3375

Glu Leu Glu Ala Ser Tyr Asp Ala Val Asp Trp Glu Glu Leu Glu
3380                3385                3390

Arg Gly Ile Asn Arg Lys Gly Ala Ala Gly Phe Phe Glu Arg Lys
3395                3400                3405

Asn Ile Gly Glu Val Leu Asp Ser Glu Lys Asn Lys Val Glu Glu
3410                3415                3420

Val Ile Asp Ser Leu Lys Lys Gly Arg Asn Ile Arg Tyr Tyr Glu
3425                3430                3435

Thr Ala Ile Pro Lys Asn Glu Lys Arg Asp Val Asn Asp Asp Trp
3440                3445                3450

Thr Ala Gly Asp Phe Val Asp Glu Lys Lys Pro Arg Val Ile Gln
3455                3460                3465

Tyr Pro Glu Ala Lys Thr Arg Leu Ala Ile Thr Lys Val Met Tyr
3470                3475                3480

Lys Trp Val Lys Gln Lys Pro Val Val Ile Pro Gly Tyr Glu Gly
3485                3490                3495

Lys Thr Pro Leu Phe Gln Ile Phe Asp Lys Val Lys Lys Glu Trp
3500                3505                3510

Asp Gln Phe Gln Asn Pro Val Ala Val Ser Phe Asp Thr Lys Ala
3515                3520                3525

Trp Asp Thr Gln Val Thr Thr Arg Asp Leu Glu Leu Ile Arg Asp
3530                3535                3540

Ile Gln Lys Phe Tyr Phe Lys Lys Lys Trp His Lys Phe Ile Asp
3545                3550                3555

Thr Leu Thr Lys His Met Ser Glu Val Pro Val Ile Ser Ala Asp
3560                3565                3570

Gly Glu Val Tyr Ile Arg Lys Gly Gln Arg Gly Ser Gly Gln Pro
3575                3580                3585

Asp Thr Ser Ala Gly Asn Ser Met Leu Asn Val Leu Thr Met Val
3590                3595                3600

Tyr Ala Phe Cys Glu Ala Thr Gly Val Pro Tyr Lys Ser Phe Asp
3605                3610                3615

Arg Val Ala Lys Ile His Val Cys Gly Asp Asp Gly Phe Leu Ile
3620                3625                3630

Thr Glu Arg Ala Leu Gly Glu Lys Phe Ala Ser Lys Gly Val Gln
3635                3640                3645

Ile Leu Tyr Glu Ala Gly Lys Pro Gln Lys Ile Thr Glu Gly Asp
3650                3655                3660

Lys Met Lys Val Ala Tyr Gln Phe Asp Asp Ile Glu Phe Cys Ser
3665                3670                3675

His Thr Pro Val Gln Val Arg Trp Ser Asp Asn Thr Ser Ser Tyr
3680                3685                3690

Met Pro Gly Arg Asn Thr Thr Thr Ile Leu Ala Lys Met Ala Thr
3695                3700                3705

Arg Leu Asp Ser Ser Gly Glu Arg Gly Thr Ile Ala Tyr Glu Lys
3710                3715                3720

Ala Val Ala Phe Ser Phe Leu Leu Met Tyr Ser Trp Asn Pro Leu
3725                3730                3735

Ile Arg Arg Ile Cys Leu Leu Val Leu Ser Thr Glu Leu Gln Val
3740                3745                3750
```

```
Arg Pro Gly Lys Ser Thr Thr Tyr Tyr Tyr Glu Gly Asp Pro Ile
    3755                3760                3765

Ser Ala Tyr Lys Glu Val Ile Gly His Asn Leu Phe Asp Leu Lys
    3770                3775                3780

Arg Thr Ser Phe Glu Lys Leu Ala Lys Leu Asn Leu Ser Met Ser
    3785                3790                3795

Thr Leu Gly Val Trp Thr Arg His Thr Ser Lys Arg Leu Leu Gln
    3800                3805                3810

Asp Cys Val Asn Val Gly Thr Lys Glu Gly Asn Trp Leu Val Asn
    3815                3820                3825

Ala Asp Arg Leu Val Ser Ser Lys Thr Gly Asn Arg Tyr Ile Pro
    3830                3835                3840

Gly Glu Gly His Thr Leu Gln Gly Lys His Tyr Glu Glu Leu Ile
    3845                3850                3855

Leu Ala Arg Lys Pro Ile Gly Asn Phe Glu Gly Thr Asp Arg Tyr
    3860                3865                3870

Asn Leu Gly Pro Ile Val Asn Val Val Leu Arg Arg Leu Lys Ile
    3875                3880                3885

Met Met Met Ala Leu Ile Gly Arg Gly Val
    3890                3895

<210> SEQ ID NO 3
<211> LENGTH: 3898
<212> TYPE: PRT
<213> ORGANISM: CSFV

<400> SEQUENCE: 3

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
                20                  25                  30

Phe Gly Asn Pro Ser Glu Val His Pro Gln Ser Thr Leu Lys Leu Pro
            35                  40                  45

His Asp Arg Gly Arg Gly Asp Ile Arg Thr Thr Leu Arg Asp Leu Pro
        50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys Ser Asp Asp Gly Ala Ser Gly Ser
                165                 170                 175

Lys Asp Lys Lys Pro Asp Arg Met Asn Lys Gly Lys Leu Lys Ile Ala
            180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Lys Gly Lys Val
    210                 215                 220
```

```
Lys Gly Lys Asn Thr Gln Asp Gly Leu Tyr His Asn Lys Asn Lys Pro
225                 230                 235                 240

Pro Glu Ser Arg Lys Leu Glu Lys Ala Leu Leu Ala Trp Ala Val
            245                 250                 255

Ile Thr Ile Leu Leu Tyr Gln Pro Val Ala Ala Glu Asn Ile Thr Gln
                260                 265                 270

Trp Asn Leu Ser Asp Asn Gly Thr Asn Gly Ile Gln Arg Ala Met Tyr
        275                 280                 285

Leu Arg Gly Val Asn Arg Ser Leu His Gly Ile Trp Pro Glu Lys Ile
    290                 295                 300

Cys Lys Gly Val Pro Thr His Leu Ala Thr Asp Thr Glu Leu Lys Glu
305                 310                 315                 320

Ile Arg Gly Met Met Asp Ala Ser Glu Arg Thr Asn Tyr Thr Cys Cys
                325                 330                 335

Arg Leu Gln Arg His Glu Trp Asn Lys His Gly Trp Cys Asn Trp Tyr
                340                 345                 350

Asn Ile Asp Pro Trp Ile Gln Leu Met Asn Arg Thr Gln Thr Asn Leu
                355                 360                 365

Thr Glu Gly Pro Pro Asp Lys Glu Cys Ala Val Thr Cys Arg Tyr Asp
370                 375                 380

Lys Asn Thr Asp Val Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Gly Asp Ile Leu
                420                 425                 430

Tyr Gly Asp His Glu Cys Gly Ser Leu Leu Gln Asp Thr Ala Leu Tyr
            435                 440                 445

Leu Leu Asp Gly Met Thr Asn Thr Ile Glu Asn Ala Arg Gln Gly Ala
    450                 455                 460

Ala Arg Val Thr Ser Trp Leu Gly Arg Gln Leu Ser Thr Ala Gly Lys
465                 470                 475                 480

Lys Leu Glu Arg Arg Ser Lys Thr Trp Phe Gly Ala Tyr Ala Leu Ser
                485                 490                 495

Pro Tyr Cys Asn Val Thr Arg Lys Ile Gly Tyr Ile Trp Tyr Thr Asn
            500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
    530                 535                 540

Gly Gly His Leu Ser Glu Phe Leu Leu Leu Ser Leu Val Ile Leu Ser
545                 550                 555                 560

Asp Phe Ala Pro Glu Thr Ala Ser Thr Leu Tyr Leu Ile Leu His Tyr
                565                 570                 575

Ala Ile Pro Gln Ser His Glu Glu Pro Gly Cys Asp Thr Asn Gln
                580                 585                 590

Leu Asn Leu Thr Val Lys Leu Arg Thr Glu Asp Val Val Pro Ser Ser
                595                 600                 605

Val Trp Asn Ile Gly Lys Tyr Val Cys Val Arg Pro Asp Trp Trp Pro
            610                 615                 620

Tyr Glu Thr Lys Val Ala Leu Leu Phe Glu Glu Ala Gly Gln Val Ile
625                 630                 635                 640
```

```
Lys Leu Val Leu Arg Ala Leu Arg Asp Leu Thr Arg Val Trp Asn Ser
            645                 650                 655

Ala Ser Thr Thr Ala Phe Leu Ile Cys Leu Ile Lys Val Leu Arg Gly
            660                 665                 670

Gln Val Val Gln Gly Ile Ile Trp Leu Leu Leu Val Thr Gly Ala Gln
            675                 680                 685

Gly Arg Leu Ala Cys Lys Glu Asp Tyr Arg Tyr Ala Ile Ser Ser Thr
            690                 695                 700

Asn Glu Ile Gly Leu Leu Gly Ala Glu Gly Leu Thr Thr Thr Trp Lys
705                 710                 715                 720

Glu Tyr Ser His Gly Leu Gln Leu Asp Asp Gly Thr Val Lys Ala Val
            725                 730                 735

Cys Thr Ala Gly Ser Phe Lys Val Thr Ala Leu Asn Val Val Ser Arg
            740                 745                 750

Arg Tyr Leu Ala Ser Leu His Lys Arg Ala Leu Pro Thr Ser Val Thr
            755                 760                 765

Phe Glu Leu Leu Phe Asp Gly Thr Asn Pro Ala Ile Glu Glu Met Asp
            770                 775                 780

Asp Asp Phe Gly Phe Gly Leu Cys Pro Phe Asp Thr Ser Pro Val Ile
785                 790                 795                 800

Lys Gly Lys Tyr Asn Thr Thr Leu Leu Asn Gly Ser Ala Phe Tyr Leu
            805                 810                 815

Val Cys Pro Ile Gly Trp Thr Gly Val Val Glu Cys Thr Ala Val Ser
            820                 825                 830

Lys Asp Thr Leu Arg Thr Glu Val Val Lys Thr Phe Arg Arg Asp Lys
            835                 840                 845

Pro Phe Pro His Arg Val Asp Cys Val Thr Thr Ile Val Glu Lys Glu
            850                 855                 860

Asp Leu Phe His Cys Lys Leu Gly Gly Asn Trp Thr Cys Val Lys Gly
865                 870                 875                 880

Asp Pro Val Thr Tyr Lys Gly Gly Gln Val Lys Gln Cys Arg Trp Cys
            885                 890                 895

Gly Phe Glu Phe Lys Glu Pro Tyr Gly Leu Pro His Tyr Pro Ile Gly
            900                 905                 910

Lys Cys Ile Leu Thr Asn Glu Thr Gly Tyr Arg Val Val Asp Ser Thr
            915                 920                 925

Asp Cys Asn Arg Asp Gly Val Val Ile Ser Thr Glu Gly Glu His Glu
            930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Glu Gly
            965                 970                 975

Pro Val Arg Lys Thr Ser Cys Thr Phe Asn Tyr Thr Lys Thr Leu Arg
            980                 985                 990

Asn Lys Tyr Tyr Glu Pro Arg Asp Ser Tyr Phe Gln Gln Tyr Met Leu
            995                 1000                1005

Lys Gly Glu Tyr Gln Tyr Trp Phe Asn Leu Asp Val Thr Asp His
            1010                1015                1020

His Thr Asp Tyr Phe Ala Glu Phe Val Val Leu Val Val Val Ala
            1025                1030                1035

Leu Leu Gly Gly Arg Tyr Val Leu Trp Leu Ile Val Thr Tyr Ile
            1040                1045                1050

Ile Leu Thr Glu Gln Leu Ala Ala Gly Leu Gln Leu Gly Gln Gly
```

```
            1055                1060                1065
Glu Val Val Leu Ile Gly Asn Leu Ile Thr His Thr Asp Asn Glu
            1070                1075                1080
Val Val Val Tyr Phe Leu Leu Leu Tyr Leu Val Ile Arg Asp Glu
            1085                1090                1095
Pro Ile Lys Lys Trp Ile Leu Leu Leu Phe His Ala Met Thr Asn
            1100                1105                1110
Asn Pro Val Lys Thr Ile Thr Val Ala Leu Leu Met Ile Ser Gly
            1115                1120                1125
Val Ala Lys Gly Gly Lys Ile Asp Gly Gly Trp Gln Arg Gln Pro
            1130                1135                1140
Val Thr Ser Phe Asp Ile Gln Leu Ala Leu Ala Val Val Val Val
            1145                1150                1155
Val Val Met Leu Leu Ala Lys Arg Asp Pro Thr Thr Phe Pro Leu
            1160                1165                1170
Val Ile Thr Val Ala Thr Leu Arg Thr Ala Lys Ile Thr Asn Gly
            1175                1180                1185
Phe Ser Thr Asp Leu Val Ile Ala Thr Val Ser Ala Ala Leu Leu
            1190                1195                1200
Thr Trp Thr Tyr Ile Ser Asp Tyr Tyr Lys Tyr Lys Thr Trp Leu
            1205                1210                1215
Gln Tyr Leu Val Ser Thr Val Thr Gly Ile Phe Leu Ile Arg Val
            1220                1225                1230
Leu Lys Gly Ile Gly Glu Leu Asp Leu His Ala Pro Thr Leu Pro
            1235                1240                1245
Ser His Arg Pro Leu Phe Tyr Ile Leu Val Tyr Leu Ile Ser Thr
            1250                1255                1260
Ala Val Val Thr Arg Trp Asn Leu Asp Val Ala Gly Leu Leu Leu
            1265                1270                1275
Gln Cys Val Pro Thr Leu Leu Met Val Phe Thr Met Trp Ala Asp
            1280                1285                1290
Ile Leu Thr Leu Ile Leu Ile Leu Pro Thr Tyr Glu Leu Thr Lys
            1295                1300                1305
Leu Tyr Tyr Leu Lys Glu Val Lys Ile Gly Ala Glu Arg Gly Trp
            1310                1315                1320
Leu Trp Lys Thr Asn Tyr Lys Arg Val Asn Asp Ile Tyr Glu Val
            1325                1330                1335
Asp Gln Thr Ser Glu Gly Val Tyr Leu Phe Pro Ser Lys Gln Arg
            1340                1345                1350
Thr Ser Ala Ile Thr Ser Thr Met Leu Pro Leu Ile Lys Ala Ile
            1355                1360                1365
Leu Ile Ser Cys Ile Ser Asn Lys Trp Gln Leu Ile Tyr Leu Leu
            1370                1375                1380
Tyr Leu Ile Phe Glu Val Ser Tyr Tyr Leu His Lys Lys Val Ile
            1385                1390                1395
Asp Glu Ile Ala Gly Gly Thr Asn Phe Val Ser Arg Leu Val Ala
            1400                1405                1410
Ala Leu Ile Glu Val Asn Trp Ala Phe Asp Asn Glu Glu Val Lys
            1415                1420                1425
Gly Leu Lys Lys Phe Phe Leu Leu Ser Ser Arg Val Lys Glu Leu
            1430                1435                1440
Ile Ile Lys His Lys Val Arg Asn Glu Val Val Val Arg Trp Phe
            1445                1450                1455
```

-continued

```
Gly Asp Glu Glu Ile Tyr Gly Met Pro Lys Leu Ile Gly Leu Val
    1460            1465               1470

Lys Ala Ala Thr Leu Ser Arg Asn Lys His Cys Met Leu Cys Thr
    1475            1480               1485

Val Cys Glu Asp Arg Asp Trp Arg Gly Glu Thr Cys Pro Lys Cys
    1490            1495               1500

Gly Arg Phe Gly Pro Pro Val Val Cys Gly Met Thr Leu Ala Asp
    1505            1510               1515

Phe Glu Glu Lys His Tyr Lys Arg Ile Phe Ile Arg Glu Asp Gln
    1520            1525               1530

Ser Gly Gly Pro Leu Arg Glu His Ala Gly Tyr Leu Gln Tyr
    1535            1540               1545

Lys Ala Arg Gly Gln Leu Phe Leu Arg Asn Leu Pro Val Leu Ala
    1550            1555               1560

Thr Lys Val Lys Met Leu Leu Val Gly Asn Leu Gly Thr Glu Ile
    1565            1570               1575

Gly Asp Leu Glu His Leu Gly Trp Val Leu Arg Gly Pro Ala Val
    1580            1585               1590

Cys Lys Lys Val Thr Glu His Glu Arg Cys Thr Thr Ser Ile Met
    1595            1600               1605

Asp Lys Leu Thr Ala Phe Phe Gly Val Met Pro Arg Gly Thr Thr
    1610            1615               1620

Pro Arg Ala Pro Val Arg Phe Pro Thr Ser Leu Leu Lys Ile Arg
    1625            1630               1635

Arg Gly Leu Glu Thr Gly Trp Ala Tyr Thr His Gln Gly Gly Ile
    1640            1645               1650

Ser Ser Val Asp His Val Thr Cys Gly Lys Asp Leu Leu Val Cys
    1655            1660               1665

Asp Thr Met Gly Arg Thr Arg Val Val Cys Gln Ser Asn Asn Lys
    1670            1675               1680

Met Thr Asp Glu Ser Glu Tyr Gly Val Lys Thr Asp Ser Gly Cys
    1685            1690               1695

Pro Glu Gly Ala Arg Cys Tyr Val Phe Asn Pro Glu Ala Val Asn
    1700            1705               1710

Ile Ser Gly Thr Lys Gly Ala Met Val His Leu Gln Lys Thr Gly
    1715            1720               1725

Gly Glu Phe Thr Cys Val Thr Ala Ser Gly Thr Pro Ala Phe Phe
    1730            1735               1740

Asp Leu Lys Asn Leu Lys Gly Trp Ser Gly Leu Pro Ile Phe Glu
    1745            1750               1755

Ala Ser Ser Gly Arg Val Val Gly Arg Val Lys Val Gly Lys Asn
    1760            1765               1770

Glu Asp Ser Lys Pro Thr Lys Leu Met Ser Gly Ile Gln Thr Val
    1775            1780               1785

Ser Lys Ser Ala Thr Asp Leu Thr Glu Met Val Lys Lys Ile Thr
    1790            1795               1800

Thr Met Asn Arg Gly Glu Phe Arg Gln Ile Thr Leu Ala Thr Gly
    1805            1810               1815

Ala Gly Lys Thr Thr Glu Leu Pro Arg Ser Val Ile Glu Glu Ile
    1820            1825               1830

Gly Arg His Lys Arg Val Leu Val Leu Ile Pro Leu Arg Ala Ala
    1835            1840               1845
```

```
Ala Glu Ser Val Tyr Gln Tyr Met Arg Gln Lys His Pro Ser Ile
1850            1855                1860

Ala Phe Asn Leu Arg Ile Gly Glu Met Lys Glu Gly Asp Met Ala
1865            1870                1875

Thr Gly Ile Thr Tyr Ala Ser Tyr Gly Tyr Phe Cys Gln Met Ser
1880            1885                1890

Gln Pro Lys Leu Arg Ala Ala Met Val Glu Tyr Ser Phe Ile Phe
1895            1900                1905

Leu Asp Glu Tyr His Cys Ala Thr Pro Glu Gln Leu Ala Ile Met
1910            1915                1920

Gly Lys Ile His Arg Phe Ser Glu Asn Leu Arg Val Val Ala Met
1925            1930                1935

Thr Ala Thr Pro Ala Gly Thr Val Thr Thr Gly Gln Lys His
1940            1945                1950

Pro Ile Glu Glu Phe Ile Ala Pro Glu Val Met Lys Gly Glu Asp
1955            1960                1965

Leu Gly Ser Glu Tyr Leu Asp Ile Ala Gly Leu Lys Ile Pro Val
1970            1975                1980

Glu Glu Met Lys Asn Asn Met Leu Val Phe Val Pro Thr Arg Asn
1985            1990                1995

Met Ala Val Glu Ala Ala Lys Lys Leu Lys Ala Lys Gly Tyr Asn
2000            2005                2010

Ser Gly Tyr Tyr Tyr Ser Gly Glu Asp Pro Ser Asn Leu Arg Val
2015            2020                2025

Val Thr Ser Gln Ser Pro Tyr Val Val Ala Thr Asn Ala Ile
2030            2035                2040

Glu Ser Gly Val Thr Leu Pro Asp Leu Asp Val Val Asp Thr
2045            2050                2055

Gly Leu Lys Cys Glu Lys Arg Ile Arg Leu Ser Pro Lys Met Pro
2060            2065                2070

Phe Ile Val Thr Gly Leu Lys Arg Met Ala Val Thr Ile Gly Glu
2075            2080                2085

Gln Ala Gln Arg Arg Gly Arg Val Gly Arg Val Lys Pro Gly Arg
2090            2095                2100

Tyr Tyr Arg Ser Gln Glu Thr Pro Val Gly Ser Lys Asp Tyr His
2105            2110                2115

Tyr Asp Leu Leu Gln Ala Gln Arg Tyr Gly Ile Glu Asp Gly Ile
2120            2125                2130

Asn Ile Thr Lys Ser Phe Arg Glu Met Asn Tyr Asp Trp Ser Leu
2135            2140                2145

Tyr Glu Glu Asp Ser Leu Met Ile Thr Gln Leu Glu Ile Leu Asn
2150            2155                2160

Asn Leu Leu Ile Ser Glu Glu Leu Pro Met Ala Val Lys Asn Ile
2165            2170                2175

Met Ala Arg Thr Asp His Pro Glu Pro Ile Gln Leu Ala Tyr Asn
2180            2185                2190

Ser Tyr Glu Thr Gln Val Pro Val Leu Phe Pro Lys Ile Arg Asn
2195            2200                2205

Gly Glu Val Thr Asp Thr Tyr Asp Asn Tyr Thr Phe Leu Asn Ala
2210            2215                2220

Arg Lys Leu Gly Asp Asp Val Pro Pro Tyr Val Tyr Ala Thr Glu
2225            2230                2235

Asp Glu Asp Leu Ala Val Glu Leu Leu Gly Leu Asp Trp Pro Asp
```

-continued

```
               2240                2245                2250
Pro Gly Asn Gln Gly Thr Val Glu Ala Gly Arg Ala Leu Lys Gln
               2255                2260                2265
Val Val Gly Leu Ser Thr Ala Glu Asn Ala Leu Leu Val Ala Leu
               2270                2275                2280
Phe Gly Tyr Val Gly Tyr Gln Ala Leu Ser Lys Arg His Ile Pro
               2285                2290                2295
Val Val Thr Asp Ile Tyr Ser Val Glu Asp His Arg Leu Glu Asp
               2300                2305                2310
Thr Thr His Leu Gln Tyr Ala Pro Asn Ala Ile Lys Thr Glu Gly
               2315                2320                2325
Lys Glu Thr Glu Leu Lys Glu Leu Ala Gln Gly Asp Val Gln Arg
               2330                2335                2340
Cys Val Glu Ala Val Thr Asn Tyr Ala Arg Glu Gly Ile Gln Phe
               2345                2350                2355
Met Lys Ser Gln Ala Leu Lys Val Arg Glu Thr Pro Thr Tyr Lys
               2360                2365                2370
Glu Thr Met Asn Thr Val Ala Asp Tyr Val Lys Lys Phe Ile Glu
               2375                2380                2385
Ala Leu Thr Asp Ser Lys Glu Asp Ile Ile Lys Tyr Gly Leu Trp
               2390                2395                2400
Gly Ala His Thr Ala Leu Tyr Lys Ser Ile Gly Ala Arg Leu Gly
               2405                2410                2415
His Glu Thr Ala Phe Ala Thr Leu Val Val Lys Trp Leu Ala Phe
               2420                2425                2430
Gly Gly Glu Ser Ile Ser Asp His Ile Lys Gln Ala Ala Thr Asp
               2435                2440                2445
Leu Val Val Tyr Tyr Ile Ile Asn Arg Pro Gln Phe Pro Gly Asp
               2450                2455                2460
Thr Glu Thr Gln Gln Glu Gly Arg Lys Phe Val Ala Ser Leu Leu
               2465                2470                2475
Val Ser Ala Leu Ala Thr Tyr Thr Tyr Lys Ser Trp Asn Tyr Asn
               2480                2485                2490
Asn Leu Ser Lys Ile Val Glu Pro Ala Leu Ala Thr Leu Pro Tyr
               2495                2500                2505
Ala Ala Lys Ala Leu Lys Leu Phe Ala Pro Thr Arg Leu Glu Ser
               2510                2515                2520
Val Val Ile Leu Ser Thr Ala Ile Tyr Lys Thr Tyr Leu Ser Ile
               2525                2530                2535
Arg Arg Gly Lys Ser Asp Gly Leu Leu Gly Thr Gly Val Ser Ala
               2540                2545                2550
Ala Met Glu Ile Met Ser Gln Asn Pro Val Ser Val Gly Ile Ala
               2555                2560                2565
Val Met Leu Gly Val Gly Ala Val Ala Ala His Asn Ala Ile Glu
               2570                2575                2580
Ala Ser Glu Gln Lys Arg Thr Leu Leu Met Lys Val Phe Val Lys
               2585                2590                2595
Asn Phe Leu Asp Gln Ala Ala Thr Asp Glu Leu Val Lys Glu Ser
               2600                2605                2610
Pro Glu Lys Ile Ile Met Ala Leu Phe Glu Ala Val Gln Thr Val
               2615                2620                2625
Gly Asn Pro Leu Arg Leu Val Tyr His Leu Tyr Gly Val Phe Tyr
               2630                2635                2640
```

-continued

Lys Gly Trp Glu Ala Lys Glu Leu Ala Gln Arg Thr Ala Gly Arg
2645                2650                2655

Asn Leu Phe Thr Leu Ile Met Phe Glu Ala Val Glu Leu Leu Gly
2660                2665                2670

Val Asp Ser Glu Gly Lys Ile Arg Gln Leu Ser Ser Asn Tyr Ile
2675                2680                2685

Leu Glu Leu Leu Tyr Lys Phe Arg Asp Asn Ile Lys Ser Ser Val
2690                2695                2700

Arg Glu Ile Ala Ile Ser Trp Ala Pro Ala Pro Phe Ser Cys Asp
2705                2710                2715

Trp Thr Pro Thr Asp Asp Arg Ile Gly Leu Pro His Asp Asn Tyr
2720                2725                2730

Leu Arg Val Glu Thr Lys Cys Pro Cys Gly Tyr Arg Met Lys Ala
2735                2740                2745

Val Lys Asn Cys Ala Gly Glu Leu Arg Leu Leu Glu Glu Gly Gly
2750                2755                2760

Ser Phe Leu Cys Arg Asn Lys Phe Gly Arg Gly Ser Gln Asn Tyr
2765                2770                2775

Arg Val Thr Lys Tyr Tyr Asp Asp Asn Leu Ser Glu Ile Lys Pro
2780                2785                2790

Val Ile Arg Met Glu Gly His Val Glu Leu Tyr Tyr Lys Gly Ala
2795                2800                2805

Thr Ile Lys Leu Asp Phe Asn Asn Ser Lys Thr Val Leu Ala Thr
2810                2815                2820

Asp Lys Trp Glu Val Asp His Ser Thr Leu Val Arg Ala Leu Lys
2825                2830                2835

Arg Tyr Thr Gly Ala Gly Tyr Arg Gly Ala Tyr Leu Gly Glu Lys
2840                2845                2850

Pro Asn His Lys His Leu Ile Gln Arg Asp Cys Ala Thr Leu Thr
2855                2860                2865

Lys Asp Lys Val Cys Phe Ile Lys Met Lys Arg Gly Cys Ala Phe
2870                2875                2880

Thr Tyr Asp Leu Ser Leu His Asn Leu Thr Arg Leu Ile Glu Leu
2885                2890                2895

Val His Lys Asn Asn Leu Glu Asp Arg Glu Ile Pro Ala Val Thr
2900                2905                2910

Val Thr Thr Trp Leu Ala Tyr Thr Phe Val Asn Glu Asp Ile Gly
2915                2920                2925

Thr Ile Lys Pro Thr Phe Gly Glu Lys Val Thr Pro Glu Lys Gln
2930                2935                2940

Glu Glu Val Val Leu Gln Pro Ala Val Val Asp Thr Thr Asp
2945                2950                2955

Val Ala Val Thr Val Val Gly Glu Thr Ser Thr Met Thr Thr Gly
2960                2965                2970

Glu Thr Pro Thr Thr Phe Thr Ser Leu Gly Ser Asp Ser Lys Val
2975                2980                2985

Arg Gln Val Leu Lys Leu Gly Val Asp Asp Gly Gln Tyr Pro Gly
2990                2995                3000

Pro Asn Gln Gln Arg Ala Ser Leu Leu Glu Ala Ile Gln Gly Val
3005                3010                3015

Asp Glu Arg Pro Ser Val Leu Ile Leu Gly Ser Asp Lys Ala Thr
3020                3025                3030

-continued

```
Ser Asn Arg Val Lys Thr Ala Lys Asn Val Lys Ile   Tyr Arg Ser
    3035                3040                3045

Arg Asp Pro Leu Glu Leu Arg Glu Met Met Lys Arg   Gly Lys Ile
    3050                3055                3060

Leu Val Val Ala Leu Ser Arg Val Asp Thr Ala Leu   Leu Lys Phe
    3065                3070                3075

Val Asp Tyr Lys Gly Thr Phe Leu Thr Arg Glu Thr   Leu Glu Ala
    3080                3085                3090

Leu Ser Leu Gly Lys Pro Lys Lys Arg Asp Ile Thr   Lys Ala Glu
    3095                3100                3105

Ala Gln Trp Leu Leu Arg Leu Glu Asp Gln Ile Glu   Glu Leu Pro
    3110                3115                3120

Asp Trp Phe Ala Ala Lys Glu Pro Ile Phe Leu Glu   Ala Asn Ile
    3125                3130                3135

Lys Arg Asp Lys Tyr His Leu Val Gly Asp Ile Ala   Thr Ile Lys
    3140                3145                3150

Glu Lys Ala Lys Gln Leu Gly Ala Thr Asp Ser Thr   Lys Ile Ser
    3155                3160                3165

Lys Glu Val Gly Ala Lys Val Tyr Ser Met Lys Leu   Ser Asn Trp
    3170                3175                3180

Val Ile Gln Glu Glu Asn Lys Gln Gly Ser Leu Ala   Pro Leu Phe
    3185                3190                3195

Glu Glu Leu Leu Gln Gln Cys Pro Pro Gly Gly Gln   Asn Lys Thr
    3200                3205                3210

Thr His Met Val Ser Ala Tyr Gln Leu Ala Gln Gly   Asn Trp Val
    3215                3220                3225

Pro Val Ser Cys His Val Phe Met Gly Thr Ile Pro   Ala Arg Arg
    3230                3235                3240

Thr Lys Thr His Pro Tyr Glu Ala Tyr Val Lys Leu   Arg Glu Leu
    3245                3250                3255

Val Asp Glu His Lys Met Lys Ala Leu Cys Gly Gly   Ser Gly Leu
    3260                3265                3270

Ser Lys His Asn Glu Trp Val Ile Gly Lys Val Lys   Tyr Gln Gly
    3275                3280                3285

Asn Leu Arg Thr Lys His Met Leu Asn Pro Gly Lys   Val Ala Glu
    3290                3295                3300

Gln Leu His Arg Glu Gly Tyr Arg His Asn Val Tyr   Asn Lys Thr
    3305                3310                3315

Ile Gly Ser Val Met Thr Ala Thr Gly Ile Arg Leu   Glu Lys Leu
    3320                3325                3330

Pro Val Val Arg Ala Gln Thr Asp Thr Thr Asn Phe   His Gln Ala
    3335                3340                3345

Ile Arg Asp Lys Ile Asp Lys Glu Glu Asn Leu Gln   Thr Pro Gly
    3350                3355                3360

Leu His Lys Lys Leu Met Glu Val Phe Asn Ala Leu   Lys Arg Pro
    3365                3370                3375

Glu Leu Glu Ala Ser Tyr Asp Ala Val Asp Trp Glu   Glu Leu Glu
    3380                3385                3390

Arg Gly Ile Asn Arg Lys Gly Ala Ala Gly Phe Phe   Glu Arg Lys
    3395                3400                3405

Asn Ile Gly Glu Val Leu Asp Ser Glu Lys Asn Lys   Val Glu Glu
    3410                3415                3420

Val Ile Asp Ser Leu Lys Lys Gly Arg Asn Ile Arg   Tyr Tyr Glu
```

```
                3425                3430                3435

Thr Ala Ile Pro Lys Asn Glu Lys Arg Asp Val Asn Asp Asp Trp
        3440                3445                3450

Thr Ala Gly Asp Phe Val Asp Glu Lys Lys Pro Arg Val Ile Gln
        3455                3460                3465

Tyr Pro Glu Ala Lys Thr Arg Leu Ala Ile Thr Lys Val Met Tyr
        3470                3475                3480

Lys Trp Val Lys Gln Lys Pro Val Val Ile Pro Gly Tyr Glu Gly
        3485                3490                3495

Lys Thr Pro Leu Phe Gln Ile Phe Asp Lys Val Lys Lys Glu Trp
        3500                3505                3510

Asp Gln Phe Gln Asn Pro Val Ala Val Ser Phe Asp Thr Lys Ala
        3515                3520                3525

Trp Asp Thr Gln Val Thr Thr Arg Asp Leu Glu Leu Ile Arg Asp
        3530                3535                3540

Ile Gln Lys Phe Tyr Phe Lys Lys Lys Trp His Lys Phe Ile Asp
        3545                3550                3555

Thr Leu Thr Lys His Met Ser Glu Val Pro Val Ile Ser Ala Asp
        3560                3565                3570

Gly Glu Val Tyr Ile Arg Lys Gly Gln Arg Gly Ser Gly Gln Pro
        3575                3580                3585

Asp Thr Ser Ala Gly Asn Ser Met Leu Asn Val Leu Thr Met Val
        3590                3595                3600

Tyr Ala Phe Cys Glu Ala Thr Gly Val Pro Tyr Lys Ser Phe Asp
        3605                3610                3615

Arg Val Ala Lys Ile His Val Cys Gly Asp Asp Gly Phe Leu Ile
        3620                3625                3630

Thr Glu Arg Ala Leu Gly Glu Lys Phe Ala Ser Lys Gly Val Gln
        3635                3640                3645

Ile Leu Tyr Glu Ala Gly Lys Pro Gln Lys Ile Thr Glu Gly Asp
        3650                3655                3660

Lys Met Lys Val Ala Tyr Gln Phe Asp Asp Ile Glu Phe Cys Ser
        3665                3670                3675

His Thr Pro Val Gln Val Arg Trp Ser Asp Asn Thr Ser Ser Tyr
        3680                3685                3690

Met Pro Gly Arg Asn Thr Thr Thr Ile Leu Ala Lys Met Ala Thr
        3695                3700                3705

Arg Leu Asp Ser Ser Gly Glu Arg Gly Thr Ile Ala Tyr Glu Lys
        3710                3715                3720

Ala Val Ala Phe Ser Phe Leu Leu Met Tyr Ser Trp Asn Pro Leu
        3725                3730                3735

Ile Arg Arg Ile Cys Leu Leu Val Leu Ser Thr Glu Leu Gln Val
        3740                3745                3750

Arg Pro Gly Lys Ser Thr Thr Tyr Tyr Tyr Glu Gly Asp Pro Ile
        3755                3760                3765

Ser Ala Tyr Lys Glu Val Ile Gly His Asn Leu Phe Asp Leu Lys
        3770                3775                3780

Arg Thr Ser Phe Glu Lys Leu Ala Lys Leu Asn Leu Ser Met Ser
        3785                3790                3795

Thr Leu Gly Val Trp Thr Arg His Thr Ser Lys Arg Leu Leu Gln
        3800                3805                3810

Asp Cys Val Asn Val Gly Thr Lys Glu Gly Asn Trp Leu Val Asn
        3815                3820                3825
```

```
Ala Asp Arg Leu Val Ser Ser Lys Thr Gly Asn Arg Tyr Ile Pro
    3830            3835            3840

Gly Glu Gly His Thr Leu Gln Gly Lys His Tyr Glu Glu Leu Ile
    3845            3850            3855

Leu Ala Arg Lys Pro Ile Gly Asn Phe Glu Gly Thr Asp Arg Tyr
    3860            3865            3870

Asn Leu Gly Pro Ile Val Asn Val Val Leu Arg Arg Leu Lys Ile
    3875            3880            3885

Met Met Met Ala Leu Ile Gly Arg Gly Val
    3890            3895

<210> SEQ ID NO 4
<211> LENGTH: 3897
<212> TYPE: PRT
<213> ORGANISM: CSFV

<400> SEQUENCE: 4

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys Ser Asp Asp Gly Ala Ser Gly Ser
                165                 170                 175

Lys Asp Lys Lys Pro Asp Arg Met Asn Lys Gly Lys Leu Lys Ile Ala
            180                 185                 190

Pro Arg Glu His Glu Lys Asp Ser Lys Thr Lys Pro Pro Asp Ala Thr
        195                 200                 205

Ile Val Val Glu Gly Val Lys Tyr Gln Ile Lys Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Thr Ile Leu Leu Tyr Gln Pro Val Ala Ala Glu Asn Ile Thr Gln
            260                 265                 270

Trp Asn Leu Ser Asp Asn Gly Thr Asn Gly Ile Gln Arg Ala Met Tyr
        275                 280                 285

Leu Arg Gly Val Asn Arg Ser Leu His Gly Ile Trp Pro Glu Lys Ile
```

```
              290                 295                 300
Cys Lys Gly Val Pro Thr His Leu Ala Thr Asp Thr Glu Leu Lys Glu
305                 310                 315                 320

Ile Arg Gly Met Met Asp Ala Ser Glu Arg Thr Asn Tyr Thr Cys Cys
                325                 330                 335

Arg Leu Gln Arg His Glu Trp Asn Lys Gly Trp Cys Asn Trp Tyr Asn
                340                 345                 350

Ile Asp Pro Trp Ile Gln Leu Met Asn Arg Thr Gln Thr Asn Leu Thr
                355                 360                 365

Glu Gly Pro Pro Asp Lys Glu Cys Ala Val Thr Cys Arg Tyr Asp Lys
370                 375                 380

Asn Thr Asp Val Asn Val Val Thr Gln Ala Arg Asn Arg Pro Thr Thr
385                 390                 395                 400

Leu Thr Gly Cys Lys Lys Gly Lys Asn Phe Ser Phe Ala Gly Thr Val
                405                 410                 415

Ile Glu Gly Pro Cys Asn Phe Asn Val Ser Val Glu Asp Ile Leu Tyr
                420                 425                 430

Gly Asp His Glu Cys Gly Ser Leu Leu Gln Asp Thr Ala Leu Tyr Leu
                435                 440                 445

Leu Asp Gly Met Thr Asn Thr Ile Glu Asn Ala Arg Gln Gly Ala Ala
                450                 455                 460

Arg Val Thr Ser Trp Leu Gly Arg Gln Leu Ser Thr Ala Gly Lys Lys
465                 470                 475                 480

Leu Glu Arg Arg Ser Lys Thr Trp Phe Gly Ala Tyr Ala Leu Ser Pro
                485                 490                 495

Tyr Cys Asn Val Thr Arg Lys Ile Gly Tyr Ile Trp Tyr Thr Asn Asn
                500                 505                 510

Cys Thr Pro Ala Cys Leu Pro Lys Asn Thr Lys Ile Ile Gly Pro Gly
                515                 520                 525

Lys Phe Asp Thr Asn Ala Glu Asp Gly Lys Ile Leu His Glu Met Gly
                530                 535                 540

Gly His Leu Ser Glu Phe Leu Leu Ser Leu Val Ile Leu Ser Asp
545                 550                 555                 560

Phe Ala Pro Glu Thr Ala Ser Thr Leu Tyr Leu Ile Leu His Tyr Ala
                565                 570                 575

Ile Pro Gln Ser His Glu Pro Glu Gly Cys Asp Thr Asn Gln Leu
                580                 585                 590

Asn Leu Thr Val Lys Leu Arg Thr Glu Asp Val Val Pro Ser Ser Val
                595                 600                 605

Trp Asn Ile Gly Lys Tyr Val Cys Val Arg Pro Asp Trp Pro Tyr
                610                 615                 620

Glu Thr Lys Val Ala Leu Leu Phe Glu Glu Ala Gly Gln Val Ile Lys
625                 630                 635                 640

Leu Val Leu Arg Ala Leu Arg Asp Leu Thr Arg Val Trp Asn Ser Ala
                645                 650                 655

Ser Thr Thr Ala Phe Leu Ile Cys Leu Ile Lys Val Leu Arg Gly Gln
                660                 665                 670

Val Val Gln Gly Ile Ile Trp Leu Leu Val Thr Gly Ala Gln Gly
                675                 680                 685

Arg Leu Ala Cys Lys Glu Asp Tyr Arg Tyr Ala Ile Ser Ser Thr Asn
                690                 695                 700

Glu Ile Gly Leu Leu Gly Ala Glu Gly Leu Thr Thr Thr Trp Lys Glu
705                 710                 715                 720
```

```
Tyr Ser His Gly Leu Gln Leu Asp Asp Gly Thr Val Lys Ala Val Cys
            725                 730                 735

Thr Ala Gly Ser Phe Lys Val Thr Ala Leu Asn Val Val Ser Arg Arg
            740                 745                 750

Tyr Leu Ala Ser Leu His Lys Arg Ala Leu Pro Thr Ser Val Thr Phe
            755                 760                 765

Glu Leu Leu Phe Asp Gly Thr Asn Pro Ala Ile Glu Glu Met Asp Asp
            770                 775                 780

Asp Phe Gly Phe Gly Leu Cys Pro Phe Asp Thr Ser Pro Val Ile Lys
785                 790                 795                 800

Gly Lys Tyr Asn Thr Thr Leu Leu Asn Gly Ser Ala Phe Tyr Leu Val
            805                 810                 815

Cys Pro Ile Gly Trp Thr Gly Val Val Glu Cys Thr Ala Val Ser Lys
            820                 825                 830

Asp Thr Leu Arg Thr Glu Val Val Lys Thr Phe Arg Arg Asp Lys Pro
            835                 840                 845

Phe Pro His Arg Val Asp Cys Val Thr Thr Ile Val Glu Lys Glu Asp
            850                 855                 860

Leu Phe His Cys Lys Leu Gly Gly Asn Trp Thr Cys Val Lys Gly Asp
865                 870                 875                 880

Pro Val Thr Tyr Lys Gly Gly Gln Val Lys Gln Cys Arg Trp Cys Gly
            885                 890                 895

Phe Glu Phe Lys Glu Pro Tyr Gly Leu Pro His Tyr Pro Ile Gly Lys
            900                 905                 910

Cys Ile Leu Thr Asn Glu Thr Gly Tyr Arg Val Val Asp Ser Thr Asp
            915                 920                 925

Cys Asn Arg Asp Gly Val Val Ile Ser Thr Glu Gly Glu His Glu Cys
            930                 935                 940

Leu Ile Gly Asn Thr Thr Val Lys Val His Ala Leu Asp Glu Arg Leu
945                 950                 955                 960

Gly Pro Met Pro Cys Arg Pro Lys Glu Ile Val Ser Ser Glu Gly Pro
            965                 970                 975

Val Arg Lys Thr Ser Cys Thr Phe Asn Tyr Thr Lys Thr Leu Arg Asn
            980                 985                 990

Lys Tyr Tyr Glu Pro Arg Asp Ser Tyr Phe Gln Gln Tyr Met Leu Lys
            995                 1000                1005

Gly Glu Tyr Gln Tyr Trp Phe Asn Leu Asp Val Thr Asp His His
            1010                1015                1020

Thr Asp Tyr Phe Ala Glu Phe Val Val Leu Val Val Val Ala Leu
            1025                1030                1035

Leu Gly Gly Arg Tyr Val Leu Trp Leu Ile Val Thr Tyr Ile Ile
            1040                1045                1050

Leu Thr Glu Gln Leu Ala Ala Gly Leu Gln Leu Gly Gln Gly Glu
            1055                1060                1065

Val Val Leu Ile Gly Asn Leu Ile Thr His Thr Asp Asn Glu Val
            1070                1075                1080

Val Val Tyr Phe Leu Leu Leu Tyr Leu Val Ile Arg Asp Glu Pro
            1085                1090                1095

Ile Lys Lys Trp Ile Leu Leu Leu Phe His Ala Met Thr Asn Asn
            1100                1105                1110

Pro Val Lys Thr Ile Thr Val Ala Leu Leu Met Ile Ser Gly Val
            1115                1120                1125
```

-continued

Ala Lys Gly Gly Lys Ile Asp Gly Gly Trp Gln Arg Gln Pro Val
1130            1135                1140

Thr Ser Phe Asp Ile Gln Leu Ala Leu Ala Val Val Val Val Val
1145            1150                1155

Val Met Leu Leu Ala Lys Arg Asp Pro Thr Thr Phe Pro Leu Val
1160            1165                1170

Ile Thr Val Ala Thr Leu Arg Thr Ala Lys Ile Thr Asn Gly Phe
1175            1180                1185

Ser Thr Asp Leu Val Ile Ala Thr Val Ser Ala Ala Leu Leu Thr
1190            1195                1200

Trp Thr Tyr Ile Ser Asp Tyr Tyr Lys Tyr Lys Thr Trp Leu Gln
1205            1210                1215

Tyr Leu Val Ser Thr Val Thr Gly Ile Phe Leu Ile Arg Val Leu
1220            1225                1230

Lys Gly Ile Gly Glu Leu Asp Leu His Ala Pro Thr Leu Pro Ser
1235            1240                1245

His Arg Pro Leu Phe Tyr Ile Leu Val Tyr Leu Ile Ser Thr Ala
1250            1255                1260

Val Val Thr Arg Trp Asn Leu Asp Val Ala Gly Leu Leu Leu Gln
1265            1270                1275

Cys Val Pro Thr Leu Leu Met Val Phe Thr Met Trp Ala Asp Ile
1280            1285                1290

Leu Thr Leu Ile Leu Ile Leu Pro Thr Tyr Glu Leu Thr Lys Leu
1295            1300                1305

Tyr Tyr Leu Lys Glu Val Lys Ile Gly Ala Glu Arg Gly Trp Leu
1310            1315                1320

Trp Lys Thr Asn Tyr Lys Arg Val Asn Asp Ile Tyr Glu Val Asp
1325            1330                1335

Gln Thr Ser Glu Gly Val Tyr Leu Phe Pro Ser Lys Gln Arg Thr
1340            1345                1350

Ser Ala Ile Thr Ser Thr Met Leu Pro Leu Ile Lys Ala Ile Leu
1355            1360                1365

Ile Ser Cys Ile Ser Asn Lys Trp Gln Leu Ile Tyr Leu Leu Tyr
1370            1375                1380

Leu Ile Phe Glu Val Ser Tyr Tyr Leu His Lys Lys Val Ile Asp
1385            1390                1395

Glu Ile Ala Gly Gly Thr Asn Phe Val Ser Arg Leu Val Ala Ala
1400            1405                1410

Leu Ile Glu Val Asn Trp Ala Phe Asp Asn Glu Glu Val Lys Gly
1415            1420                1425

Leu Lys Lys Phe Phe Leu Leu Ser Ser Arg Val Lys Glu Leu Ile
1430            1435                1440

Ile Lys His Lys Val Arg Asn Glu Val Val Val Arg Trp Phe Gly
1445            1450                1455

Asp Glu Glu Ile Tyr Gly Met Pro Lys Leu Ile Gly Leu Val Lys
1460            1465                1470

Ala Ala Thr Leu Ser Arg Asn Lys His Cys Met Leu Cys Thr Val
1475            1480                1485

Cys Glu Asp Arg Asp Trp Arg Gly Glu Thr Cys Pro Lys Cys Gly
1490            1495                1500

Arg Phe Gly Pro Pro Val Val Cys Gly Met Thr Leu Ala Asp Phe
1505            1510                1515

Glu Glu Lys His Tyr Lys Arg Ile Phe Ile Arg Glu Asp Gln Ser

```
                1520                1525                1530

Gly Gly  Pro Leu Arg Glu  Glu His Ala Gly Tyr  Leu Gln Tyr Lys
       1535                1540                1545

Ala Arg  Gly Gln Leu Phe  Leu Arg Asn Leu Pro  Val Leu Ala Thr
       1550                1555                1560

Lys Val  Lys Met Leu Leu  Val Gly Asn Leu Gly  Thr Glu Ile Gly
       1565                1570                1575

Asp Leu  Glu His Leu Gly  Trp Val Leu Arg Gly  Pro Ala Val Cys
       1580                1585                1590

Lys Lys  Val Thr Glu His  Glu Arg Cys Thr Thr  Ser Ile Met Asp
       1595                1600                1605

Lys Leu  Thr Ala Phe Phe  Gly Val Met Pro Arg  Gly Thr Thr Pro
       1610                1615                1620

Arg Ala  Pro Val Arg Phe  Pro Thr Ser Leu Leu  Lys Ile Arg Arg
       1625                1630                1635

Gly Leu  Glu Thr Gly Trp  Ala Tyr Thr His Gln  Gly Gly Ile Ser
       1640                1645                1650

Ser Val  Asp His Val Thr  Cys Gly Lys Asp Leu  Leu Val Cys Asp
       1655                1660                1665

Thr Met  Gly Arg Thr Arg  Val Val Cys Gln Ser  Asn Asn Lys Met
       1670                1675                1680

Thr Asp  Glu Ser Glu Tyr  Gly Val Lys Thr Asp  Ser Gly Cys Pro
       1685                1690                1695

Glu Gly  Ala Arg Cys Tyr  Val Phe Asn Pro Glu  Ala Val Asn Ile
       1700                1705                1710

Ser Gly  Thr Lys Gly Ala  Met Val His Leu Gln  Lys Thr Gly Gly
       1715                1720                1725

Glu Phe  Thr Cys Val Thr  Ala Ser Gly Thr Pro  Ala Phe Phe Asp
       1730                1735                1740

Leu Lys  Asn Leu Lys Gly  Trp Ser Gly Leu Pro  Ile Phe Glu Ala
       1745                1750                1755

Ser Ser  Gly Arg Val Val  Gly Arg Val Lys Val  Gly Lys Asn Glu
       1760                1765                1770

Asp Ser  Lys Pro Thr Lys  Leu Met Ser Gly Ile  Gln Thr Val Ser
       1775                1780                1785

Lys Ser  Ala Thr Asp Leu  Thr Glu Met Val Lys  Lys Ile Thr Thr
       1790                1795                1800

Met Asn  Arg Gly Glu Phe  Arg Gln Ile Thr Leu  Ala Thr Gly Ala
       1805                1810                1815

Gly Lys  Thr Thr Glu Leu  Pro Arg Ser Val Ile  Glu Glu Ile Gly
       1820                1825                1830

Arg His  Lys Arg Val Leu  Val Leu Ile Pro Leu  Arg Ala Ala Ala
       1835                1840                1845

Glu Ser  Val Tyr Gln Tyr  Met Arg Gln Lys His  Pro Ser Ile Ala
       1850                1855                1860

Phe Asn  Leu Arg Ile Gly  Glu Met Lys Glu Gly  Asp Met Ala Thr
       1865                1870                1875

Gly Ile  Thr Tyr Ala Ser  Tyr Gly Tyr Phe Cys  Gln Met Ser Gln
       1880                1885                1890

Pro Lys  Leu Arg Ala Ala  Met Val Glu Tyr Ser  Phe Ile Phe Leu
       1895                1900                1905

Asp Glu  Tyr His Cys Ala  Thr Pro Glu Gln Leu  Ala Ile Met Gly
       1910                1915                1920
```

-continued

```
Lys Ile His Arg Phe Ser Glu Asn Leu Arg Val Val Ala Met Thr
1925                1930                1935

Ala Thr Pro Ala Gly Thr Val Thr Thr Thr Gly Gln Lys His Pro
1940                1945                1950

Ile Glu Glu Phe Ile Ala Pro Glu Val Met Lys Gly Glu Asp Leu
1955                1960                1965

Gly Ser Glu Tyr Leu Asp Ile Ala Gly Leu Lys Ile Pro Val Glu
1970                1975                1980

Glu Met Lys Asn Asn Met Leu Val Phe Val Pro Thr Arg Asn Met
1985                1990                1995

Ala Val Glu Ala Ala Lys Lys Leu Lys Ala Lys Gly Tyr Asn Ser
2000                2005                2010

Gly Tyr Tyr Tyr Ser Gly Glu Asp Pro Ser Asn Leu Arg Val Val
2015                2020                2025

Thr Ser Gln Ser Pro Tyr Val Val Ala Thr Asn Ala Ile Glu
2030                2035                2040

Ser Gly Val Thr Leu Pro Asp Leu Asp Val Val Asp Thr Gly
2045                2050                2055

Leu Lys Cys Glu Lys Arg Ile Arg Leu Ser Pro Lys Met Pro Phe
2060                2065                2070

Ile Val Thr Gly Leu Lys Arg Met Ala Val Thr Ile Gly Glu Gln
2075                2080                2085

Ala Gln Arg Arg Gly Arg Val Gly Arg Val Lys Pro Gly Arg Tyr
2090                2095                2100

Tyr Arg Ser Gln Glu Thr Pro Val Gly Ser Lys Asp Tyr His Tyr
2105                2110                2115

Asp Leu Leu Gln Ala Gln Arg Tyr Gly Ile Glu Asp Gly Ile Asn
2120                2125                2130

Ile Thr Lys Ser Phe Arg Glu Met Asn Tyr Asp Trp Ser Leu Tyr
2135                2140                2145

Glu Glu Asp Ser Leu Met Ile Thr Gln Leu Glu Ile Leu Asn Asn
2150                2155                2160

Leu Leu Ile Ser Glu Glu Leu Pro Met Ala Val Lys Asn Ile Met
2165                2170                2175

Ala Arg Thr Asp His Pro Glu Pro Ile Gln Leu Ala Tyr Asn Ser
2180                2185                2190

Tyr Glu Thr Gln Val Pro Val Leu Phe Pro Lys Ile Arg Asn Gly
2195                2200                2205

Glu Val Thr Asp Thr Tyr Asp Asn Tyr Thr Phe Leu Asn Ala Arg
2210                2215                2220

Lys Leu Gly Asp Asp Val Pro Pro Tyr Val Tyr Ala Thr Glu Asp
2225                2230                2235

Glu Asp Leu Ala Val Glu Leu Leu Gly Leu Asp Trp Pro Asp Pro
2240                2245                2250

Gly Asn Gln Gly Thr Val Glu Ala Gly Arg Ala Leu Lys Gln Val
2255                2260                2265

Val Gly Leu Ser Thr Ala Glu Asn Ala Leu Leu Val Ala Leu Phe
2270                2275                2280

Gly Tyr Val Gly Tyr Gln Ala Leu Ser Lys Arg His Ile Pro Val
2285                2290                2295

Val Thr Asp Ile Tyr Ser Val Glu Asp His Arg Leu Glu Asp Thr
2300                2305                2310
```

-continued

| | | | | | | | | | | | |
|---|---|---|---|---|---|---|---|---|---|---|---|
| Thr | His | Leu | Gln | Tyr | Ala | Pro | Asn | Ala | Ile | Lys | Thr | Glu | Gly | Lys |
| 2315 | | | | | 2320 | | | | | 2325 | | | | |

Thr His Leu Gln Tyr Ala Pro Asn Ala Ile Lys Thr Glu Gly Lys
2315                2320                2325

Glu Thr Glu Leu Lys Glu Leu Ala Gln Gly Asp Val Gln Arg Cys
2330                2335                2340

Val Glu Ala Val Thr Asn Tyr Ala Arg Glu Gly Ile Gln Phe Met
2345                2350                2355

Lys Ser Gln Ala Leu Lys Val Arg Glu Thr Pro Thr Tyr Lys Glu
2360                2365                2370

Thr Met Asn Thr Val Ala Asp Tyr Val Lys Lys Phe Ile Glu Ala
2375                2380                2385

Leu Thr Asp Ser Lys Glu Asp Ile Ile Lys Tyr Gly Leu Trp Gly
2390                2395                2400

Ala His Thr Ala Leu Tyr Lys Ser Ile Gly Ala Arg Leu Gly His
2405                2410                2415

Glu Thr Ala Phe Ala Thr Leu Val Val Lys Trp Leu Ala Phe Gly
2420                2425                2430

Gly Glu Ser Ile Ser Asp His Ile Lys Gln Ala Ala Thr Asp Leu
2435                2440                2445

Val Val Tyr Tyr Ile Ile Asn Arg Pro Gln Phe Pro Gly Asp Thr
2450                2455                2460

Glu Thr Gln Gln Glu Gly Arg Lys Phe Val Ala Ser Leu Leu Val
2465                2470                2475

Ser Ala Leu Ala Thr Tyr Thr Tyr Lys Ser Trp Asn Tyr Asn Asn
2480                2485                2490

Leu Ser Lys Ile Val Glu Pro Ala Leu Ala Thr Leu Pro Tyr Ala
2495                2500                2505

Ala Lys Ala Leu Lys Leu Phe Ala Pro Thr Arg Leu Glu Ser Val
2510                2515                2520

Val Ile Leu Ser Thr Ala Ile Tyr Lys Thr Tyr Leu Ser Ile Arg
2525                2530                2535

Arg Gly Lys Ser Asp Gly Leu Leu Gly Thr Gly Val Ser Ala Ala
2540                2545                2550

Met Glu Ile Met Ser Gln Asn Pro Val Ser Val Gly Ile Ala Val
2555                2560                2565

Met Leu Gly Val Gly Ala Val Ala Ala His Asn Ala Ile Glu Ala
2570                2575                2580

Ser Glu Gln Lys Arg Thr Leu Leu Met Lys Val Phe Val Lys Asn
2585                2590                2595

Phe Leu Asp Gln Ala Ala Thr Asp Glu Leu Val Lys Glu Ser Pro
2600                2605                2610

Glu Lys Ile Ile Met Ala Leu Phe Glu Ala Val Gln Thr Val Gly
2615                2620                2625

Asn Pro Leu Arg Leu Val Tyr His Leu Tyr Gly Val Phe Tyr Lys
2630                2635                2640

Gly Trp Glu Ala Lys Glu Leu Ala Gln Arg Thr Ala Gly Arg Asn
2645                2650                2655

Leu Phe Thr Leu Ile Met Phe Glu Ala Val Glu Leu Leu Gly Val
2660                2665                2670

Asp Ser Glu Gly Lys Ile Arg Gln Leu Ser Ser Asn Tyr Ile Leu
2675                2680                2685

Glu Leu Leu Tyr Lys Phe Arg Asp Asn Ile Lys Ser Ser Val Arg
2690                2695                2700

Glu Ile Ala Ile Ser Trp Ala Pro Ala Pro Phe Ser Cys Asp Trp

-continued

```
            2705                2710                2715
Thr Pro Thr Asp Asp Arg Ile Gly Leu Pro His Asp Asn Tyr Leu
    2720                2725                2730

Arg Val Glu Thr Lys Cys Pro Cys Gly Tyr Arg Met Lys Ala Val
    2735                2740                2745

Lys Asn Cys Ala Gly Glu Leu Arg Leu Leu Glu Glu Gly Gly Ser
    2750                2755                2760

Phe Leu Cys Arg Asn Lys Phe Gly Arg Gly Ser Gln Asn Tyr Arg
    2765                2770                2775

Val Thr Lys Tyr Tyr Asp Asp Asn Leu Ser Glu Ile Lys Pro Val
    2780                2785                2790

Ile Arg Met Glu Gly His Val Glu Leu Tyr Tyr Lys Gly Ala Thr
    2795                2800                2805

Ile Lys Leu Asp Phe Asn Asn Ser Lys Thr Val Leu Ala Thr Asp
    2810                2815                2820

Lys Trp Glu Val Asp His Ser Thr Leu Val Arg Ala Leu Lys Arg
    2825                2830                2835

Tyr Thr Gly Ala Gly Tyr Arg Gly Ala Tyr Leu Gly Glu Lys Pro
    2840                2845                2850

Asn His Lys His Leu Ile Gln Arg Asp Cys Ala Thr Leu Thr Lys
    2855                2860                2865

Asp Lys Val Cys Phe Ile Lys Met Lys Arg Gly Cys Ala Phe Thr
    2870                2875                2880

Tyr Asp Leu Ser Leu His Asn Leu Thr Arg Leu Ile Glu Leu Val
    2885                2890                2895

His Lys Asn Asn Leu Glu Asp Arg Glu Ile Pro Ala Val Thr Val
    2900                2905                2910

Thr Thr Trp Leu Ala Tyr Thr Phe Val Asn Glu Asp Ile Gly Thr
    2915                2920                2925

Ile Lys Pro Thr Phe Gly Glu Lys Val Thr Pro Glu Lys Gln Glu
    2930                2935                2940

Glu Val Val Leu Gln Pro Ala Val Val Asp Thr Thr Asp Val
    2945                2950                2955

Ala Val Thr Val Val Gly Glu Thr Ser Thr Met Thr Thr Gly Glu
    2960                2965                2970

Thr Pro Thr Thr Phe Thr Ser Leu Gly Ser Asp Ser Lys Val Arg
    2975                2980                2985

Gln Val Leu Lys Leu Gly Val Asp Asp Gly Gln Tyr Pro Gly Pro
    2990                2995                3000

Asn Gln Gln Arg Ala Ser Leu Leu Glu Ala Ile Gln Gly Val Asp
    3005                3010                3015

Glu Arg Pro Ser Val Leu Ile Leu Gly Ser Asp Lys Ala Thr Ser
    3020                3025                3030

Asn Arg Val Lys Thr Ala Lys Asn Val Lys Ile Tyr Arg Ser Arg
    3035                3040                3045

Asp Pro Leu Glu Leu Arg Glu Met Met Lys Arg Gly Lys Ile Leu
    3050                3055                3060

Val Val Ala Leu Ser Arg Val Asp Thr Ala Leu Leu Lys Phe Val
    3065                3070                3075

Asp Tyr Lys Gly Thr Phe Leu Thr Arg Glu Thr Leu Glu Ala Leu
    3080                3085                3090

Ser Leu Gly Lys Pro Lys Lys Arg Asp Ile Thr Lys Ala Glu Ala
    3095                3100                3105
```

-continued

```
Gln Trp Leu Leu Arg Leu Glu Asp Gln Ile Glu Glu Leu Pro Asp
    3110                3115                3120

Trp Phe Ala Ala Lys Glu Pro Ile Phe Leu Glu Ala Asn Ile Lys
    3125                3130                3135

Arg Asp Lys Tyr His Leu Val Gly Asp Ile Ala Thr Ile Lys Glu
    3140                3145                3150

Lys Ala Lys Gln Leu Gly Ala Thr Asp Ser Thr Lys Ile Ser Lys
    3155                3160                3165

Glu Val Gly Ala Lys Val Tyr Ser Met Lys Leu Ser Asn Trp Val
    3170                3175                3180

Ile Gln Glu Glu Asn Lys Gln Gly Ser Leu Ala Pro Leu Phe Glu
    3185                3190                3195

Glu Leu Leu Gln Gln Cys Pro Pro Gly Gly Gln Asn Lys Thr Thr
    3200                3205                3210

His Met Val Ser Ala Tyr Gln Leu Ala Gln Gly Asn Trp Val Pro
    3215                3220                3225

Val Ser Cys His Val Phe Met Gly Thr Ile Pro Ala Arg Arg Thr
    3230                3235                3240

Lys Thr His Pro Tyr Glu Ala Tyr Val Lys Leu Arg Glu Leu Val
    3245                3250                3255

Asp Glu His Lys Met Lys Ala Leu Cys Gly Gly Ser Gly Leu Ser
    3260                3265                3270

Lys His Asn Glu Trp Val Ile Gly Lys Val Lys Tyr Gln Gly Asn
    3275                3280                3285

Leu Arg Thr Lys His Met Leu Asn Pro Gly Lys Val Ala Glu Gln
    3290                3295                3300

Leu His Arg Glu Gly Tyr Arg His Asn Val Tyr Asn Lys Thr Ile
    3305                3310                3315

Gly Ser Val Met Thr Ala Thr Gly Ile Arg Leu Glu Lys Leu Pro
    3320                3325                3330

Val Val Arg Ala Gln Thr Asp Thr Thr Asn Phe His Gln Ala Ile
    3335                3340                3345

Arg Asp Lys Ile Asp Lys Glu Glu Asn Leu Gln Thr Pro Gly Leu
    3350                3355                3360

His Lys Lys Leu Met Glu Val Phe Asn Ala Leu Lys Arg Pro Glu
    3365                3370                3375

Leu Glu Ala Ser Tyr Asp Ala Val Asp Trp Glu Glu Leu Glu Arg
    3380                3385                3390

Gly Ile Asn Arg Lys Gly Ala Ala Gly Phe Phe Glu Arg Lys Asn
    3395                3400                3405

Ile Gly Glu Val Leu Asp Ser Glu Lys Asn Lys Val Glu Glu Val
    3410                3415                3420

Ile Asp Ser Leu Lys Lys Gly Arg Asn Ile Arg Tyr Tyr Glu Thr
    3425                3430                3435

Ala Ile Pro Lys Asn Glu Lys Arg Asp Val Asn Asp Asp Trp Thr
    3440                3445                3450

Ala Gly Asp Phe Val Asp Glu Lys Lys Pro Arg Val Ile Gln Tyr
    3455                3460                3465

Pro Glu Ala Lys Thr Arg Leu Ala Ile Thr Lys Val Met Tyr Lys
    3470                3475                3480

Trp Val Lys Gln Lys Pro Val Val Ile Pro Gly Tyr Glu Gly Lys
    3485                3490                3495
```

```
Thr Pro Leu Phe Gln Ile Phe Asp Lys Val Lys Lys Glu Trp Asp
3500            3505            3510

Gln Phe Gln Asn Pro Val Ala Val Ser Phe Asp Thr Lys Ala Trp
3515            3520            3525

Asp Thr Gln Val Thr Thr Arg Asp Leu Glu Leu Ile Arg Asp Ile
3530            3535            3540

Gln Lys Phe Tyr Phe Lys Lys Trp His Lys Phe Ile Asp Thr
3545            3550            3555

Leu Thr Lys His Met Ser Glu Val Pro Val Ile Ser Ala Asp Gly
3560            3565            3570

Glu Val Tyr Ile Arg Lys Gly Gln Arg Gly Ser Gly Gln Pro Asp
3575            3580            3585

Thr Ser Ala Gly Asn Ser Met Leu Asn Val Leu Thr Met Val Tyr
3590            3595            3600

Ala Phe Cys Glu Ala Thr Gly Val Pro Tyr Lys Ser Phe Asp Arg
3605            3610            3615

Val Ala Lys Ile His Val Cys Gly Asp Asp Gly Phe Leu Ile Thr
3620            3625            3630

Glu Arg Ala Leu Gly Glu Lys Phe Ala Ser Lys Gly Val Gln Ile
3635            3640            3645

Leu Tyr Glu Ala Gly Lys Pro Gln Lys Ile Thr Glu Gly Asp Lys
3650            3655            3660

Met Lys Val Ala Tyr Gln Phe Asp Asp Ile Glu Phe Cys Ser His
3665            3670            3675

Thr Pro Val Gln Val Arg Trp Ser Asp Asn Thr Ser Ser Tyr Met
3680            3685            3690

Pro Gly Arg Asn Thr Thr Thr Ile Leu Ala Lys Met Ala Thr Arg
3695            3700            3705

Leu Asp Ser Ser Gly Glu Arg Gly Thr Ile Ala Tyr Glu Lys Ala
3710            3715            3720

Val Ala Phe Ser Phe Leu Leu Met Tyr Ser Trp Asn Pro Leu Ile
3725            3730            3735

Arg Arg Ile Cys Leu Leu Val Leu Ser Thr Glu Leu Gln Val Arg
3740            3745            3750

Pro Gly Lys Ser Thr Thr Tyr Tyr Tyr Glu Gly Asp Pro Ile Ser
3755            3760            3765

Ala Tyr Lys Glu Val Ile Gly His Asn Leu Phe Asp Leu Lys Arg
3770            3775            3780

Thr Ser Phe Glu Lys Leu Ala Lys Leu Asn Leu Ser Met Ser Thr
3785            3790            3795

Leu Gly Val Trp Thr Arg His Thr Ser Lys Arg Leu Leu Gln Asp
3800            3805            3810

Cys Val Asn Val Gly Thr Lys Glu Gly Asn Trp Leu Val Asn Ala
3815            3820            3825

Asp Arg Leu Val Ser Ser Lys Thr Gly Asn Arg Tyr Ile Pro Gly
3830            3835            3840

Glu Gly His Thr Leu Gln Gly Lys His Tyr Glu Glu Leu Ile Leu
3845            3850            3855

Ala Arg Lys Pro Ile Gly Asn Phe Glu Gly Thr Asp Arg Tyr Asn
3860            3865            3870

Leu Gly Pro Ile Val Asn Val Val Leu Arg Arg Leu Lys Ile Met
3875            3880            3885

Met Met Ala Leu Ile Gly Arg Gly Val
```

<210> SEQ ID NO 5
<211> LENGTH: 3732
<212> TYPE: PRT
<213> ORGANISM: CSFV

<400> SEQUENCE: 5

```
Met Gly Ser Asp Asp Gly Ala Ser Gly Ser Lys Glu Lys Lys Pro Asp
1               5                   10                  15

Arg Ile Asn Lys Gly Lys Leu Lys Ile Thr Pro Lys Glu His Glu Lys
            20                  25                  30

Asp Ser Arg Thr Lys Pro Pro Asp Ala Thr Ile Val Val Glu Gly Val
        35                  40                  45

Lys Tyr Gln Val Lys Lys Gly Lys Val Lys Gly Lys Asn Thr Gln
    50                  55                  60

Asp Gly Leu Tyr His Asn Lys Asn Lys Pro Glu Ser Arg Lys Lys
65              70                  75                  80

Leu Glu Lys Ala Leu Leu Ala Trp Ala Val Ile Thr Ile Leu Leu Tyr
                85                  90                  95

Gln Pro Val Ala Ala Glu Asn Ile Thr Gln Trp Asn Leu Ser Asp Asn
            100                 105                 110

Gly Thr Asn Gly Ile Gln Arg Ala Met Tyr Leu Arg Gly Val Asn Arg
        115                 120                 125

Ser Leu His Gly Ile Trp Pro Glu Lys Ile Cys Lys Gly Val Pro Thr
    130                 135                 140

His Leu Ala Thr Asp Thr Glu Leu Lys Glu Ile Arg Gly Met Met Asp
145             150                 155                 160

Ala Ser Glu Arg Thr Asn Tyr Thr Cys Cys Arg Leu Gln Arg His Glu
                165                 170                 175

Trp Asn Lys His Gly Trp Cys Asn Trp Tyr Asn Ile Asp Pro Trp Ile
            180                 185                 190

Gln Leu Met Asn Arg Thr Gln Thr Asn Leu Thr Glu Gly Pro Pro Asp
        195                 200                 205

Lys Glu Cys Ala Val Thr Cys Arg Tyr Asp Lys Asn Thr Asp Val Asn
    210                 215                 220

Val Val Thr Gln Ala Arg Asn Arg Pro Thr Thr Leu Thr Gly Cys Lys
225             230                 235                 240

Lys Gly Lys Asn Phe Ser Phe Ala Gly Thr Val Ile Glu Gly Pro Cys
                245                 250                 255

Asn Phe Asn Val Ser Val Glu Asp Ile Leu Tyr Gly Asp His Glu Cys
            260                 265                 270

Gly Ser Leu Leu Gln Asp Thr Ala Leu Tyr Leu Leu Asp Gly Met Thr
        275                 280                 285

Asn Thr Ile Glu Asn Ala Arg Gln Gly Ala Ala Arg Val Thr Ser Trp
    290                 295                 300

Leu Gly Arg Gln Leu Ser Thr Ala Gly Lys Lys Leu Glu Arg Arg Ser
305             310                 315                 320

Lys Thr Trp Phe Gly Ala Tyr Ala Leu Ser Pro Tyr Cys Asn Val Thr
                325                 330                 335

Arg Lys Ile Gly Tyr Ile Trp Tyr Thr Asn Asn Cys Thr Pro Ala Cys
            340                 345                 350

Leu Pro Lys Asn Thr Lys Ile Ile Gly Pro Gly Lys Phe Asp Thr Asn
        355                 360                 365
```

-continued

Ala Glu Asp Gly Lys Ile Leu His Glu Met Gly Gly His Leu Ser Glu
    370                 375                 380

Phe Leu Leu Leu Ser Leu Val Ile Leu Ser Asp Phe Ala Pro Glu Thr
385                 390                 395                 400

Ala Ser Thr Leu Tyr Leu Ile Leu His Tyr Ala Ile Pro Gln Ser His
                405                 410                 415

Glu Glu Pro Glu Gly Cys Asp Thr Asn Gln Leu Asn Leu Thr Val Lys
            420                 425                 430

Leu Arg Thr Glu Asp Val Val Pro Ser Ser Val Trp Asn Ile Gly Lys
        435                 440                 445

Tyr Val Cys Val Arg Pro Asp Trp Trp Pro Tyr Glu Thr Lys Val Ala
    450                 455                 460

Leu Leu Phe Glu Glu Ala Gly Gln Val Ile Lys Leu Val Leu Arg Ala
465                 470                 475                 480

Leu Arg Asp Leu Thr Arg Val Trp Asn Ser Ala Ser Thr Thr Ala Phe
                485                 490                 495

Leu Ile Cys Leu Ile Lys Val Leu Arg Gly Gln Val Val Gln Gly Ile
            500                 505                 510

Ile Trp Leu Leu Leu Val Thr Gly Ala Gln Gly Arg Leu Ala Cys Lys
        515                 520                 525

Glu Asp Tyr Arg Tyr Ala Ile Ser Ser Thr Asn Glu Ile Gly Leu Leu
    530                 535                 540

Gly Ala Glu Gly Leu Thr Thr Thr Trp Lys Glu Tyr Ser His Gly Leu
545                 550                 555                 560

Gln Leu Asp Asp Gly Thr Val Lys Ala Val Cys Thr Ala Gly Ser Phe
                565                 570                 575

Lys Val Thr Ala Leu Asn Val Val Ser Arg Arg Tyr Leu Ala Ser Leu
            580                 585                 590

His Lys Arg Ala Leu Pro Thr Ser Val Thr Phe Glu Leu Leu Phe Asp
        595                 600                 605

Gly Thr Asn Pro Ala Ile Glu Glu Met Asp Asp Asp Phe Gly Phe Gly
    610                 615                 620

Leu Cys Pro Phe Asp Thr Ser Pro Val Ile Lys Gly Lys Tyr Asn Thr
625                 630                 635                 640

Thr Leu Leu Asn Gly Ser Ala Phe Tyr Leu Val Cys Pro Ile Gly Trp
                645                 650                 655

Thr Gly Val Val Glu Cys Thr Ala Val Ser Lys Asp Thr Leu Arg Thr
            660                 665                 670

Glu Val Val Lys Thr Phe Arg Arg Asp Lys Pro Phe Pro His Arg Val
        675                 680                 685

Asp Cys Val Thr Thr Ile Val Glu Lys Glu Asp Leu Phe His Cys Lys
    690                 695                 700

Leu Gly Gly Asn Trp Thr Cys Val Lys Gly Asp Pro Val Thr Tyr Lys
705                 710                 715                 720

Gly Gly Gln Val Lys Gln Cys Arg Trp Cys Gly Phe Glu Phe Lys Glu
                725                 730                 735

Pro Tyr Gly Leu Pro His Tyr Pro Ile Gly Lys Cys Ile Leu Thr Asn
            740                 745                 750

Glu Thr Gly Tyr Arg Val Asp Ser Thr Asp Cys Asn Arg Asp Gly
        755                 760                 765

Val Val Ile Ser Thr Glu Gly Glu His Glu Cys Leu Ile Gly Asn Thr
    770                 775                 780

Thr Val Lys Val His Ala Leu Asp Glu Arg Leu Gly Pro Met Pro Cys

-continued

```
            785                 790                 795                 800
        Arg Pro Lys Glu Ile Val Ser Ser Glu Gly Pro Val Arg Lys Thr Ser
                        805                 810                 815
        Cys Thr Phe Asn Tyr Thr Lys Thr Leu Arg Asn Lys Tyr Tyr Glu Pro
                        820                 825                 830
        Arg Asp Ser Tyr Phe Gln Gln Tyr Met Leu Lys Gly Glu Tyr Gln Tyr
                        835                 840                 845
        Trp Phe Asn Leu Asp Val Thr Asp His His Thr Asp Tyr Phe Ala Glu
            850                 855                 860
        Phe Val Val Leu Val Val Val Ala Leu Leu Gly Gly Arg Tyr Val Leu
            865                 870                 875                 880
        Trp Leu Ile Val Thr Tyr Ile Ile Leu Thr Glu Gln Leu Ala Ala Gly
                        885                 890                 895
        Leu Gln Leu Gly Gln Gly Glu Val Val Leu Ile Gly Asn Leu Ile Thr
                        900                 905                 910
        His Thr Asp Asn Glu Val Val Val Tyr Phe Leu Leu Leu Tyr Leu Val
                        915                 920                 925
        Ile Arg Asp Glu Pro Ile Lys Lys Trp Ile Leu Leu Leu Phe His Ala
                        930                 935                 940
        Met Thr Asn Asn Pro Val Lys Thr Ile Thr Val Ala Leu Leu Met Ile
            945                 950                 955                 960
        Ser Gly Val Ala Lys Gly Gly Lys Ile Asp Gly Gly Trp Gln Arg Gln
                        965                 970                 975
        Pro Val Thr Ser Phe Asp Ile Gln Leu Ala Leu Ala Val Val Val Val
                        980                 985                 990
        Val Val Met Leu Leu Ala Lys Arg Asp Pro Thr Thr Phe Pro Leu Val
                        995                1000                1005
        Ile Thr Val Ala Thr Leu Arg Thr Ala Lys Ile Thr Asn Gly Phe
                       1010                1015                1020
        Ser Thr Asp Leu Val Ile Ala Thr Val Ser Ala Ala Leu Leu Thr
                       1025                1030                1035
        Trp Thr Tyr Ile Ser Asp Tyr Tyr Lys Tyr Lys Thr Trp Leu Gln
                       1040                1045                1050
        Tyr Leu Val Ser Thr Val Thr Gly Ile Phe Leu Ile Arg Val Leu
                       1055                1060                1065
        Lys Gly Ile Gly Glu Leu Asp Leu His Ala Pro Thr Leu Pro Ser
                       1070                1075                1080
        His Arg Pro Leu Phe Tyr Ile Leu Val Tyr Leu Ile Ser Thr Ala
                       1085                1090                1095
        Val Val Thr Arg Trp Asn Leu Asp Val Ala Gly Leu Leu Leu Gln
                       1100                1105                1110
        Cys Val Pro Thr Leu Leu Met Val Phe Thr Met Trp Ala Asp Ile
                       1115                1120                1125
        Leu Thr Leu Ile Leu Ile Leu Pro Thr Tyr Glu Leu Thr Lys Leu
                       1130                1135                1140
        Tyr Tyr Leu Lys Glu Val Lys Ile Gly Ala Glu Arg Gly Trp Leu
                       1145                1150                1155
        Trp Lys Thr Asn Tyr Lys Arg Val Asn Asp Ile Tyr Glu Val Asp
                       1160                1165                1170
        Gln Thr Ser Glu Gly Val Tyr Leu Phe Pro Ser Lys Gln Arg Thr
                       1175                1180                1185
        Ser Ala Ile Thr Ser Thr Met Leu Pro Leu Ile Lys Ala Ile Leu
                       1190                1195                1200
```

```
Ile Ser Cys Ile Ser Asn Lys Trp Gln Leu Ile Tyr Leu Leu Tyr
1205                1210                1215

Leu Ile Phe Glu Val Ser Tyr Tyr Leu His Lys Lys Val Ile Asp
1220                1225                1230

Glu Ile Ala Gly Gly Thr Asn Phe Val Ser Arg Leu Val Ala Ala
1235                1240                1245

Leu Ile Glu Val Asn Trp Ala Phe Asp Asn Glu Glu Val Lys Gly
1250                1255                1260

Leu Lys Lys Phe Phe Leu Leu Ser Ser Arg Val Lys Glu Leu Ile
1265                1270                1275

Ile Lys His Lys Val Arg Asn Glu Val Val Val Arg Trp Phe Gly
1280                1285                1290

Asp Glu Glu Ile Tyr Gly Met Pro Lys Leu Ile Gly Leu Val Lys
1295                1300                1305

Ala Ala Thr Leu Ser Arg Asn Lys His Cys Met Leu Cys Thr Val
1310                1315                1320

Cys Glu Asp Arg Asp Trp Arg Gly Glu Thr Cys Pro Lys Cys Gly
1325                1330                1335

Arg Phe Gly Pro Pro Val Val Cys Gly Met Thr Leu Ala Asp Phe
1340                1345                1350

Glu Glu Lys His Tyr Lys Arg Ile Phe Ile Arg Glu Asp Gln Ser
1355                1360                1365

Gly Gly Pro Leu Arg Glu Glu His Ala Gly Tyr Leu Gln Tyr Lys
1370                1375                1380

Ala Arg Gly Gln Leu Phe Leu Arg Asn Leu Pro Val Leu Ala Thr
1385                1390                1395

Lys Val Lys Met Leu Leu Val Gly Asn Leu Gly Thr Glu Ile Gly
1400                1405                1410

Asp Leu Glu His Leu Gly Trp Val Leu Arg Gly Pro Ala Val Cys
1415                1420                1425

Lys Lys Val Thr Glu His Glu Arg Cys Thr Thr Ser Ile Met Asp
1430                1435                1440

Lys Leu Thr Ala Phe Phe Gly Val Met Pro Arg Gly Thr Thr Pro
1445                1450                1455

Arg Ala Pro Val Arg Phe Pro Thr Ser Leu Leu Lys Ile Arg Arg
1460                1465                1470

Gly Leu Glu Thr Gly Trp Ala Tyr Thr His Gln Gly Gly Ile Ser
1475                1480                1485

Ser Val Asp His Val Thr Cys Gly Lys Asp Leu Leu Val Cys Asp
1490                1495                1500

Thr Met Gly Arg Thr Arg Val Val Cys Gln Ser Asn Asn Lys Met
1505                1510                1515

Thr Asp Glu Ser Glu Tyr Gly Val Lys Thr Asp Ser Gly Cys Pro
1520                1525                1530

Glu Gly Ala Arg Cys Tyr Val Phe Asn Pro Glu Ala Val Asn Ile
1535                1540                1545

Ser Gly Thr Lys Gly Ala Met Val His Leu Gln Lys Thr Gly Gly
1550                1555                1560

Glu Phe Thr Cys Val Thr Ala Ser Gly Thr Pro Ala Phe Phe Asp
1565                1570                1575

Leu Lys Asn Leu Lys Gly Trp Ser Gly Leu Pro Ile Phe Glu Ala
1580                1585                1590
```

```
Ser Ser Gly Arg Val Val Gly Arg Val Lys Val Gly Lys Asn Glu
    1595                1600                1605

Asp Ser Lys Pro Thr Lys Leu Met Ser Gly Ile Gln Thr Val Ser
    1610                1615                1620

Lys Ser Ala Thr Asp Leu Thr Glu Met Val Lys Lys Ile Thr Thr
    1625                1630                1635

Met Asn Arg Gly Glu Phe Arg Gln Ile Thr Leu Ala Thr Gly Ala
    1640                1645                1650

Gly Lys Thr Thr Glu Leu Pro Arg Ser Val Ile Glu Glu Ile Gly
    1655                1660                1665

Arg His Lys Arg Val Leu Val Leu Ile Pro Leu Arg Ala Ala Ala
    1670                1675                1680

Glu Ser Val Tyr Gln Tyr Met Arg Gln Lys His Pro Ser Ile Ala
    1685                1690                1695

Phe Asn Leu Arg Ile Gly Glu Met Lys Glu Gly Asp Met Ala Thr
    1700                1705                1710

Gly Ile Thr Tyr Ala Ser Tyr Gly Tyr Phe Cys Gln Met Ser Gln
    1715                1720                1725

Pro Lys Leu Arg Ala Ala Met Val Glu Tyr Ser Phe Ile Phe Leu
    1730                1735                1740

Asp Glu Tyr His Cys Ala Thr Pro Glu Gln Leu Ala Ile Met Gly
    1745                1750                1755

Lys Ile His Arg Phe Ser Glu Asn Leu Arg Val Val Ala Met Thr
    1760                1765                1770

Ala Thr Pro Ala Gly Thr Val Thr Thr Thr Gly Gln Lys His Pro
    1775                1780                1785

Ile Glu Glu Phe Ile Ala Pro Glu Val Met Lys Gly Glu Asp Leu
    1790                1795                1800

Gly Ser Glu Tyr Leu Asp Ile Ala Gly Leu Lys Ile Pro Val Glu
    1805                1810                1815

Glu Met Lys Asn Asn Met Leu Val Phe Val Pro Thr Arg Asn Met
    1820                1825                1830

Ala Val Glu Ala Ala Lys Lys Leu Lys Ala Lys Gly Tyr Asn Ser
    1835                1840                1845

Gly Tyr Tyr Tyr Ser Gly Glu Asp Pro Ser Asn Leu Arg Val Val
    1850                1855                1860

Thr Ser Gln Ser Pro Tyr Val Val Ala Thr Asn Ala Ile Glu
    1865                1870                1875

Ser Gly Val Thr Leu Pro Asp Leu Asp Val Val Asp Thr Gly
    1880                1885                1890

Leu Lys Cys Glu Lys Arg Ile Arg Leu Ser Pro Lys Met Pro Phe
    1895                1900                1905

Ile Val Thr Gly Leu Lys Arg Met Ala Val Thr Ile Gly Glu Gln
    1910                1915                1920

Ala Gln Arg Arg Gly Arg Val Gly Arg Val Lys Pro Gly Arg Tyr
    1925                1930                1935

Tyr Arg Ser Gln Glu Thr Pro Val Gly Ser Lys Asp Tyr His Tyr
    1940                1945                1950

Asp Leu Leu Gln Ala Gln Arg Tyr Gly Ile Glu Asp Gly Ile Asn
    1955                1960                1965

Ile Thr Lys Ser Phe Arg Glu Met Asn Tyr Asp Trp Ser Leu Tyr
    1970                1975                1980

Glu Glu Asp Ser Leu Met Ile Thr Gln Leu Glu Ile Leu Asn Asn
```

-continued

```
            1985                1990                1995
Leu Leu Ile Ser Glu Glu Leu Pro Met Ala Val Lys Asn Ile Met
        2000                2005                2010

Ala Arg Thr Asp His Pro Glu Pro Ile Gln Leu Ala Tyr Asn Ser
        2015                2020                2025

Tyr Glu Thr Gln Val Pro Val Leu Phe Pro Lys Ile Arg Asn Gly
        2030                2035                2040

Glu Val Thr Asp Thr Tyr Asp Asn Tyr Thr Phe Leu Asn Ala Arg
        2045                2050                2055

Lys Leu Gly Asp Asp Val Pro Pro Tyr Val Tyr Ala Thr Glu Asp
        2060                2065                2070

Glu Asp Leu Ala Val Glu Leu Leu Gly Leu Asp Trp Pro Asp Pro
        2075                2080                2085

Gly Asn Gln Gly Thr Val Glu Ala Gly Arg Ala Leu Lys Gln Val
        2090                2095                2100

Val Gly Leu Ser Thr Ala Glu Asn Ala Leu Leu Val Ala Leu Phe
        2105                2110                2115

Gly Tyr Val Gly Tyr Gln Ala Leu Ser Lys Arg His Ile Pro Val
        2120                2125                2130

Val Thr Asp Ile Tyr Ser Val Glu Asp His Arg Leu Glu Asp Thr
        2135                2140                2145

Thr His Leu Gln Tyr Ala Pro Asn Ala Ile Lys Thr Glu Gly Lys
        2150                2155                2160

Glu Thr Glu Leu Lys Glu Leu Ala Gln Gly Asp Val Gln Arg Cys
        2165                2170                2175

Val Glu Ala Val Thr Asn Tyr Ala Arg Glu Gly Ile Gln Phe Met
        2180                2185                2190

Lys Ser Gln Ala Leu Lys Val Arg Glu Thr Pro Thr Tyr Lys Glu
        2195                2200                2205

Thr Met Asn Thr Val Ala Asp Tyr Val Lys Lys Phe Ile Glu Ala
        2210                2215                2220

Leu Thr Asp Ser Lys Glu Asp Ile Ile Lys Tyr Gly Leu Trp Gly
        2225                2230                2235

Ala His Thr Ala Leu Tyr Lys Ser Ile Gly Ala Arg Leu Gly His
        2240                2245                2250

Glu Thr Ala Phe Ala Thr Leu Val Val Lys Trp Leu Ala Phe Gly
        2255                2260                2265

Gly Glu Ser Ile Ser Asp His Ile Lys Gln Ala Ala Thr Asp Leu
        2270                2275                2280

Val Val Tyr Tyr Ile Ile Asn Arg Pro Gln Phe Pro Gly Asp Thr
        2285                2290                2295

Glu Thr Gln Gln Glu Gly Arg Lys Phe Val Ala Ser Leu Leu Val
        2300                2305                2310

Ser Ala Leu Ala Thr Tyr Thr Tyr Lys Ser Trp Asn Tyr Asn Asn
        2315                2320                2325

Leu Ser Lys Ile Val Glu Pro Ala Leu Ala Thr Leu Pro Tyr Ala
        2330                2335                2340

Ala Lys Ala Leu Lys Leu Phe Ala Pro Thr Arg Leu Glu Ser Val
        2345                2350                2355

Val Ile Leu Ser Thr Ala Ile Tyr Lys Thr Tyr Leu Ser Ile Arg
        2360                2365                2370

Arg Gly Lys Ser Asp Gly Leu Leu Gly Thr Gly Val Ser Ala Ala
        2375                2380                2385
```

```
Met Glu Ile Met Ser Gln Asn Pro Val Ser Val Gly Ile Ala Val
2390                 2395                2400

Met Leu Gly Val Gly Ala Val Ala Ala His Asn Ala Ile Glu Ala
2405                 2410                2415

Ser Glu Gln Lys Arg Thr Leu Leu Met Lys Val Phe Val Lys Asn
2420                 2425                2430

Phe Leu Asp Gln Ala Ala Thr Asp Glu Leu Val Lys Glu Ser Pro
2435                 2440                2445

Glu Lys Ile Ile Met Ala Leu Phe Glu Ala Val Gln Thr Val Gly
2450                 2455                2460

Asn Pro Leu Arg Leu Val Tyr His Leu Tyr Gly Val Phe Tyr Lys
2465                 2470                2475

Gly Trp Glu Ala Lys Glu Leu Ala Gln Arg Thr Ala Gly Arg Asn
2480                 2485                2490

Leu Phe Thr Leu Ile Met Phe Glu Ala Val Glu Leu Leu Gly Val
2495                 2500                2505

Asp Ser Glu Gly Lys Ile Arg Gln Leu Ser Ser Asn Tyr Ile Leu
2510                 2515                2520

Glu Leu Leu Tyr Lys Phe Arg Asp Asn Ile Lys Ser Ser Val Arg
2525                 2530                2535

Glu Ile Ala Ile Ser Trp Ala Pro Ala Pro Phe Ser Cys Asp Trp
2540                 2545                2550

Thr Pro Thr Asp Asp Arg Ile Gly Leu Pro His Asp Asn Tyr Leu
2555                 2560                2565

Arg Val Glu Thr Lys Cys Pro Cys Gly Tyr Arg Met Lys Ala Val
2570                 2575                2580

Lys Asn Cys Ala Gly Glu Leu Arg Leu Leu Glu Glu Gly Gly Ser
2585                 2590                2595

Phe Leu Cys Arg Asn Lys Phe Gly Arg Gly Ser Gln Asn Tyr Arg
2600                 2605                2610

Val Thr Lys Tyr Tyr Asp Asp Asn Leu Ser Glu Ile Lys Pro Val
2615                 2620                2625

Ile Arg Met Glu Gly His Val Glu Leu Tyr Tyr Lys Gly Ala Thr
2630                 2635                2640

Ile Lys Leu Asp Phe Asn Asn Ser Lys Thr Val Leu Ala Thr Asp
2645                 2650                2655

Lys Trp Glu Val Asp His Ser Thr Leu Val Arg Ala Leu Lys Arg
2660                 2665                2670

Tyr Thr Gly Ala Gly Tyr Arg Gly Ala Tyr Leu Gly Glu Lys Pro
2675                 2680                2685

Asn His Lys His Leu Ile Gln Arg Asp Cys Ala Thr Leu Thr Lys
2690                 2695                2700

Asp Lys Val Cys Phe Ile Lys Met Lys Arg Gly Cys Ala Phe Thr
2705                 2710                2715

Tyr Asp Leu Ser Leu His Asn Leu Thr Arg Leu Ile Glu Leu Val
2720                 2725                2730

His Lys Asn Asn Leu Glu Asp Arg Glu Ile Pro Ala Val Thr Val
2735                 2740                2745

Thr Thr Trp Leu Ala Tyr Thr Phe Val Asn Glu Asp Ile Gly Thr
2750                 2755                2760

Ile Lys Pro Thr Phe Gly Glu Lys Val Thr Pro Glu Lys Gln Glu
2765                 2770                2775
```

```
Glu Val Val Leu Gln Pro Ala Val Val Asp Thr Thr Asp Val
2780                2785                2790

Ala Val Thr Val Val Gly Glu Thr Ser Thr Met Thr Thr Gly Glu
2795                2800                2805

Thr Pro Thr Thr Phe Thr Ser Leu Gly Ser Asp Ser Lys Val Arg
2810                2815                2820

Gln Val Leu Lys Leu Gly Val Asp Asp Gly Gln Tyr Pro Gly Pro
2825                2830                2835

Asn Gln Gln Arg Ala Ser Leu Leu Glu Ala Ile Gln Gly Val Asp
2840                2845                2850

Glu Arg Pro Ser Val Leu Ile Leu Gly Ser Asp Lys Ala Thr Ser
2855                2860                2865

Asn Arg Val Lys Thr Ala Lys Asn Val Lys Ile Tyr Arg Ser Arg
2870                2875                2880

Asp Pro Leu Glu Leu Arg Glu Met Met Lys Arg Gly Lys Ile Leu
2885                2890                2895

Val Val Ala Leu Ser Arg Val Asp Thr Ala Leu Leu Lys Phe Val
2900                2905                2910

Asp Tyr Lys Gly Thr Phe Leu Thr Arg Glu Thr Leu Glu Ala Leu
2915                2920                2925

Ser Leu Gly Lys Pro Lys Lys Arg Asp Ile Thr Lys Ala Glu Ala
2930                2935                2940

Gln Trp Leu Leu Arg Leu Glu Asp Gln Ile Glu Glu Leu Pro Asp
2945                2950                2955

Trp Phe Ala Ala Lys Glu Pro Ile Phe Leu Glu Ala Asn Ile Lys
2960                2965                2970

Arg Asp Lys Tyr His Leu Val Gly Asp Ile Ala Thr Ile Lys Glu
2975                2980                2985

Lys Ala Lys Gln Leu Gly Ala Thr Asp Ser Thr Lys Ile Ser Lys
2990                2995                3000

Glu Val Gly Ala Lys Val Tyr Ser Met Lys Leu Ser Asn Trp Val
3005                3010                3015

Ile Gln Glu Glu Asn Lys Gln Gly Ser Leu Ala Pro Leu Phe Glu
3020                3025                3030

Glu Leu Leu Gln Gln Cys Pro Pro Gly Gly Gln Asn Lys Thr Thr
3035                3040                3045

His Met Val Ser Ala Tyr Gln Leu Ala Gln Gly Asn Trp Val Pro
3050                3055                3060

Val Ser Cys His Val Phe Met Gly Thr Ile Pro Ala Arg Arg Thr
3065                3070                3075

Lys Thr His Pro Tyr Glu Ala Tyr Val Lys Leu Arg Glu Leu Val
3080                3085                3090

Asp Glu His Lys Met Lys Ala Leu Cys Gly Gly Ser Gly Leu Ser
3095                3100                3105

Lys His Asn Glu Trp Val Ile Gly Lys Val Lys Tyr Gln Gly Asn
3110                3115                3120

Leu Arg Thr Lys His Met Leu Asn Pro Gly Lys Val Ala Glu Gln
3125                3130                3135

Leu His Arg Glu Gly Tyr Arg His Asn Val Tyr Asn Lys Thr Ile
3140                3145                3150

Gly Ser Val Met Thr Ala Thr Gly Ile Arg Leu Glu Lys Leu Pro
3155                3160                3165

Val Val Arg Ala Gln Thr Asp Thr Thr Asn Phe His Gln Ala Ile
```

-continued

```
            3170                3175                3180
Arg Asp Lys Ile Asp Lys Glu Glu Asn Leu Gln Thr Pro Gly Leu
            3185                3190                3195
His Lys Lys Leu Met Glu Val Phe Asn Ala Leu Lys Arg Pro Glu
            3200                3205                3210
Leu Glu Ala Ser Tyr Asp Ala Val Asp Trp Glu Glu Leu Glu Arg
            3215                3220                3225
Gly Ile Asn Arg Lys Gly Ala Ala Gly Phe Phe Glu Arg Lys Asn
            3230                3235                3240
Ile Gly Glu Val Leu Asp Ser Glu Lys Asn Lys Val Glu Glu Val
            3245                3250                3255
Ile Asp Ser Leu Lys Lys Gly Arg Asn Ile Arg Tyr Tyr Glu Thr
            3260                3265                3270
Ala Ile Pro Lys Asn Glu Lys Arg Asp Val Asn Asp Asp Trp Thr
            3275                3280                3285
Ala Gly Asp Phe Val Asp Glu Lys Lys Pro Arg Val Ile Gln Tyr
            3290                3295                3300
Pro Glu Ala Lys Thr Arg Leu Ala Ile Thr Lys Val Met Tyr Lys
            3305                3310                3315
Trp Val Lys Gln Lys Pro Val Val Ile Pro Gly Tyr Glu Gly Lys
            3320                3325                3330
Thr Pro Leu Phe Gln Ile Phe Asp Lys Val Lys Lys Glu Trp Asp
            3335                3340                3345
Gln Phe Gln Asn Pro Val Ala Val Ser Phe Asp Thr Lys Ala Trp
            3350                3355                3360
Asp Thr Gln Val Thr Thr Arg Asp Leu Glu Leu Ile Arg Asp Ile
            3365                3370                3375
Gln Lys Phe Tyr Phe Lys Lys Lys Trp His Lys Phe Ile Asp Thr
            3380                3385                3390
Leu Thr Lys His Met Ser Glu Val Pro Val Ile Ser Ala Asp Gly
            3395                3400                3405
Glu Val Tyr Ile Arg Lys Gly Gln Arg Gly Ser Gly Gln Pro Asp
            3410                3415                3420
Thr Ser Ala Gly Asn Ser Met Leu Asn Val Leu Thr Met Val Tyr
            3425                3430                3435
Ala Phe Cys Glu Ala Thr Gly Val Pro Tyr Lys Ser Phe Asp Arg
            3440                3445                3450
Val Ala Lys Ile His Val Cys Gly Asp Asp Gly Phe Leu Ile Thr
            3455                3460                3465
Glu Arg Ala Leu Gly Glu Lys Phe Ala Ser Lys Gly Val Gln Ile
            3470                3475                3480
Leu Tyr Glu Ala Gly Lys Pro Gln Lys Ile Thr Glu Gly Asp Lys
            3485                3490                3495
Met Lys Val Ala Tyr Gln Phe Asp Asp Ile Glu Phe Cys Ser His
            3500                3505                3510
Thr Pro Val Gln Val Arg Trp Ser Asp Asn Thr Ser Ser Tyr Met
            3515                3520                3525
Pro Gly Arg Asn Thr Thr Thr Ile Leu Ala Lys Met Ala Thr Arg
            3530                3535                3540
Leu Asp Ser Ser Gly Glu Arg Gly Thr Ile Ala Tyr Glu Lys Ala
            3545                3550                3555
Val Ala Phe Ser Phe Leu Leu Met Tyr Ser Trp Asn Pro Leu Ile
            3560                3565                3570
```

-continued

```
Arg Arg Ile Cys Leu Leu Val Leu Ser Thr Glu Leu Gln Val Arg
    3575                3580                3585

Pro Gly Lys Ser Thr Thr Tyr Tyr Glu Gly Asp Pro Ile Ser
    3590                3595                3600

Ala Tyr Lys Glu Val Ile Gly His Asn Leu Phe Asp Leu Lys Arg
    3605                3610                3615

Thr Ser Phe Glu Lys Leu Ala Lys Leu Asn Leu Ser Met Ser Thr
    3620                3625                3630

Leu Gly Val Trp Thr Arg His Thr Ser Lys Arg Leu Leu Gln Asp
    3635                3640                3645

Cys Val Asn Val Gly Thr Lys Glu Gly Asn Trp Leu Val Asn Ala
    3650                3655                3660

Asp Arg Leu Val Ser Ser Lys Thr Gly Asn Arg Tyr Ile Pro Gly
    3665                3670                3675

Glu Gly His Thr Leu Gln Gly Lys His Tyr Glu Glu Leu Ile Leu
    3680                3685                3690

Ala Arg Lys Pro Ile Gly Asn Phe Glu Gly Thr Asp Arg Tyr Asn
    3695                3700                3705

Leu Gly Pro Ile Val Asn Val Val Leu Arg Arg Leu Lys Ile Met
    3710                3715                3720

Met Met Ala Leu Ile Gly Arg Gly Val
    3725                3730

<210> SEQ ID NO 6
<211> LENGTH: 3731
<212> TYPE: PRT
<213> ORGANISM: CSFV

<400> SEQUENCE: 6

Met Gly Ser Asp Asp Gly Ala Ser Gly Ser Lys Glu Lys Lys Pro Asp
1               5                   10                  15

Arg Ile Asn Lys Gly Lys Leu Lys Ile Thr Pro Lys Glu His Glu Lys
            20                  25                  30

Asp Ser Arg Thr Lys Pro Pro Asp Ala Thr Ile Val Val Glu Gly Val
        35                  40                  45

Lys Tyr Gln Val Lys Lys Gly Lys Val Leu Gly Lys Asn Thr Gln
    50                  55                  60

Asp Gly Leu Tyr His Asn Lys Asn Lys Pro Glu Ser Arg Lys Lys
65                  70                  75                  80

Leu Glu Lys Ala Leu Leu Ala Trp Ala Val Ile Thr Ile Leu Leu Tyr
                85                  90                  95

Gln Pro Val Ala Ala Glu Asn Ile Thr Gln Trp Asn Leu Ser Asp Asn
            100                 105                 110

Gly Thr Asn Gly Ile Gln Arg Ala Met Tyr Leu Arg Gly Val Asn Arg
        115                 120                 125

Ser Leu His Gly Ile Trp Pro Glu Lys Ile Cys Lys Gly Val Pro Thr
    130                 135                 140

His Leu Ala Thr Asp Thr Glu Leu Lys Glu Ile Arg Gly Met Met Asp
145                 150                 155                 160

Ala Ser Glu Arg Thr Asn Tyr Thr Cys Cys Arg Leu Gln Arg His Glu
                165                 170                 175

Trp Asn Lys Gly Trp Cys Asn Trp Tyr Asn Ile Asp Pro Trp Ile Gln
            180                 185                 190

Leu Met Asn Arg Thr Gln Thr Asn Leu Thr Glu Gly Pro Pro Asp Lys
```

```
                195                 200                 205
Glu Cys Ala Val Thr Cys Arg Tyr Asp Lys Asn Thr Asp Val Asn Val
210                 215                 220

Val Thr Gln Ala Arg Asn Arg Pro Thr Thr Leu Thr Gly Cys Lys Lys
225                 230                 235                 240

Gly Lys Asn Phe Ser Phe Ala Gly Thr Val Ile Glu Gly Pro Cys Asn
                245                 250                 255

Phe Asn Val Ser Val Glu Asp Ile Leu Tyr Gly Asp His Glu Cys Gly
            260                 265                 270

Ser Leu Leu Gln Asp Thr Ala Leu Tyr Leu Leu Asp Gly Met Thr Asn
        275                 280                 285

Thr Ile Glu Asn Ala Arg Gln Gly Ala Ala Arg Val Thr Ser Trp Leu
    290                 295                 300

Gly Arg Gln Leu Ser Thr Ala Gly Lys Lys Leu Glu Arg Arg Ser Lys
305                 310                 315                 320

Thr Trp Phe Gly Ala Tyr Ala Leu Ser Pro Tyr Cys Asn Val Thr Arg
                325                 330                 335

Lys Ile Gly Tyr Ile Trp Tyr Thr Asn Asn Cys Thr Pro Ala Cys Leu
            340                 345                 350

Pro Lys Asn Thr Lys Ile Ile Gly Pro Gly Lys Phe Asp Thr Asn Ala
        355                 360                 365

Glu Asp Gly Lys Ile Leu His Glu Met Gly Gly His Leu Ser Glu Phe
    370                 375                 380

Leu Leu Leu Ser Leu Val Ile Leu Ser Asp Phe Ala Pro Glu Thr Ala
385                 390                 395                 400

Ser Thr Leu Tyr Leu Ile Leu His Tyr Ala Ile Pro Gln Ser His Glu
                405                 410                 415

Glu Pro Glu Gly Cys Asp Thr Asn Gln Leu Asn Leu Thr Val Lys Leu
            420                 425                 430

Arg Thr Glu Asp Val Val Pro Ser Ser Val Trp Asn Ile Gly Lys Tyr
        435                 440                 445

Val Cys Val Arg Pro Asp Trp Trp Pro Tyr Glu Thr Lys Val Ala Leu
    450                 455                 460

Leu Phe Glu Glu Ala Gly Gln Val Ile Lys Leu Val Leu Arg Ala Leu
465                 470                 475                 480

Arg Asp Leu Thr Arg Val Trp Asn Ser Ala Ser Thr Thr Ala Phe Leu
                485                 490                 495

Ile Cys Leu Ile Lys Val Leu Arg Gly Gln Val Val Gln Gly Ile Ile
            500                 505                 510

Trp Leu Leu Leu Val Thr Gly Ala Gln Gly Arg Leu Ala Cys Lys Glu
        515                 520                 525

Asp Tyr Arg Tyr Ala Ile Ser Ser Thr Asn Glu Ile Gly Leu Leu Gly
    530                 535                 540

Ala Glu Gly Leu Thr Thr Thr Trp Lys Glu Tyr Ser His Gly Leu Gln
545                 550                 555                 560

Leu Asp Asp Gly Thr Val Lys Ala Val Cys Thr Ala Gly Ser Phe Lys
                565                 570                 575

Val Thr Ala Leu Asn Val Val Ser Arg Arg Tyr Leu Ala Ser Leu His
            580                 585                 590

Lys Arg Ala Leu Pro Thr Ser Val Thr Phe Glu Leu Leu Phe Asp Gly
        595                 600                 605

Thr Asn Pro Ala Ile Glu Glu Met Asp Asp Phe Gly Phe Gly Leu
    610                 615                 620
```

-continued

```
Cys Pro Phe Asp Thr Ser Pro Val Ile Lys Gly Lys Tyr Asn Thr Thr
625                 630                 635                 640

Leu Leu Asn Gly Ser Ala Phe Tyr Leu Val Cys Pro Ile Gly Trp Thr
            645                 650                 655

Gly Val Val Glu Cys Thr Ala Val Ser Lys Asp Thr Leu Arg Thr Glu
                660                 665                 670

Val Val Lys Thr Phe Arg Arg Asp Lys Pro Phe Pro His Arg Val Asp
            675                 680                 685

Cys Val Thr Thr Ile Val Glu Lys Glu Asp Leu Phe His Cys Lys Leu
690                 695                 700

Gly Gly Asn Trp Thr Cys Val Lys Gly Asp Pro Val Tyr Lys Gly
705                 710                 715                 720

Gly Gln Val Lys Gln Cys Arg Trp Cys Gly Phe Glu Phe Lys Glu Pro
                725                 730                 735

Tyr Gly Leu Pro His Tyr Pro Ile Gly Lys Cys Ile Leu Thr Asn Glu
            740                 745                 750

Thr Gly Tyr Arg Val Val Asp Ser Thr Asp Cys Asn Arg Asp Gly Val
                755                 760                 765

Val Ile Ser Thr Glu Gly Glu His Glu Cys Leu Ile Gly Asn Thr Thr
770                 775                 780

Val Lys Val His Ala Leu Asp Glu Arg Leu Gly Pro Met Pro Cys Arg
785                 790                 795                 800

Pro Lys Glu Ile Val Ser Ser Glu Gly Pro Val Arg Lys Thr Ser Cys
                805                 810                 815

Thr Phe Asn Tyr Thr Lys Thr Leu Arg Asn Lys Tyr Tyr Glu Pro Arg
            820                 825                 830

Asp Ser Tyr Phe Gln Gln Tyr Met Leu Lys Gly Glu Tyr Gln Tyr Trp
            835                 840                 845

Phe Asn Leu Asp Val Thr Asp His His Thr Asp Tyr Phe Ala Glu Phe
850                 855                 860

Val Val Leu Val Val Val Ala Leu Leu Gly Gly Arg Tyr Val Leu Trp
865                 870                 875                 880

Leu Ile Val Thr Tyr Ile Ile Leu Thr Glu Gln Leu Ala Ala Gly Leu
            885                 890                 895

Gln Leu Gly Gln Gly Glu Val Val Leu Ile Gly Asn Leu Ile Thr His
        900                 905                 910

Thr Asp Asn Glu Val Val Val Tyr Phe Leu Leu Leu Tyr Leu Val Ile
            915                 920                 925

Arg Asp Glu Pro Ile Lys Lys Trp Ile Leu Leu Leu Phe His Ala Met
        930                 935                 940

Thr Asn Asn Pro Val Lys Thr Ile Thr Val Ala Leu Leu Met Ile Ser
945                 950                 955                 960

Gly Val Ala Lys Gly Gly Lys Ile Asp Gly Gly Trp Gln Arg Gln Pro
                965                 970                 975

Val Thr Ser Phe Asp Ile Gln Leu Ala Leu Ala Val Val Val Val Val
                980                 985                 990

Val Met Leu Leu Ala Lys Arg Asp Pro Thr Thr Phe Pro Leu Val Ile
        995                 1000                1005

Thr Val Ala Thr Leu Arg Thr Ala Lys Ile Thr Asn Gly Phe Ser
        1010                1015                1020

Thr Asp Leu Val Ile Ala Thr Val Ser Ala Ala Leu Leu Thr Trp
        1025                1030                1035
```

-continued

```
Thr Tyr Ile Ser Asp Tyr Tyr Lys Tyr Lys Thr Trp Leu Gln Tyr
1040                1045                1050

Leu Val Ser Thr Val Thr Gly Ile Phe Leu Ile Arg Val Leu Lys
1055                1060                1065

Gly Ile Gly Glu Leu Asp Leu His Ala Pro Thr Leu Pro Ser His
1070                1075                1080

Arg Pro Leu Phe Tyr Ile Leu Val Tyr Leu Ile Ser Thr Ala Val
1085                1090                1095

Val Thr Arg Trp Asn Leu Asp Val Ala Gly Leu Leu Leu Gln Cys
1100                1105                1110

Val Pro Thr Leu Leu Met Val Phe Thr Met Trp Ala Asp Ile Leu
1115                1120                1125

Thr Leu Ile Leu Ile Leu Pro Thr Tyr Glu Leu Thr Lys Leu Tyr
1130                1135                1140

Tyr Leu Lys Glu Val Lys Ile Gly Ala Glu Arg Gly Trp Leu Trp
1145                1150                1155

Lys Thr Asn Tyr Lys Arg Val Asn Asp Ile Tyr Glu Val Asp Gln
1160                1165                1170

Thr Ser Glu Gly Val Tyr Leu Phe Pro Ser Lys Gln Arg Thr Ser
1175                1180                1185

Ala Ile Thr Ser Thr Met Leu Pro Leu Ile Lys Ala Ile Leu Ile
1190                1195                1200

Ser Cys Ile Ser Asn Lys Trp Gln Leu Ile Tyr Leu Leu Tyr Leu
1205                1210                1215

Ile Phe Glu Val Ser Tyr Tyr Leu His Lys Lys Val Ile Asp Glu
1220                1225                1230

Ile Ala Gly Gly Thr Asn Phe Val Ser Arg Leu Val Ala Ala Leu
1235                1240                1245

Ile Glu Val Asn Trp Ala Phe Asp Asn Glu Glu Val Lys Gly Leu
1250                1255                1260

Lys Lys Phe Phe Leu Leu Ser Ser Arg Val Lys Glu Leu Ile Ile
1265                1270                1275

Lys His Lys Val Arg Asn Glu Val Val Val Arg Trp Phe Gly Asp
1280                1285                1290

Glu Glu Ile Tyr Gly Met Pro Lys Leu Ile Gly Leu Val Lys Ala
1295                1300                1305

Ala Thr Leu Ser Arg Asn Lys His Cys Met Leu Cys Thr Val Cys
1310                1315                1320

Glu Asp Arg Asp Trp Arg Gly Glu Thr Cys Pro Lys Cys Gly Arg
1325                1330                1335

Phe Gly Pro Pro Val Val Cys Gly Met Thr Leu Ala Asp Phe Glu
1340                1345                1350

Glu Lys His Tyr Lys Arg Ile Phe Ile Arg Glu Asp Gln Ser Gly
1355                1360                1365

Gly Pro Leu Arg Glu Glu His Ala Gly Tyr Leu Gln Tyr Lys Ala
1370                1375                1380

Arg Gly Gln Leu Phe Leu Arg Asn Leu Pro Val Leu Ala Thr Lys
1385                1390                1395

Val Lys Met Leu Leu Val Gly Asn Leu Gly Thr Glu Ile Gly Asp
1400                1405                1410

Leu Glu His Leu Gly Trp Val Leu Arg Gly Pro Ala Val Cys Lys
1415                1420                1425

Lys Val Thr Glu His Glu Arg Cys Thr Thr Ser Ile Met Asp Lys
```

-continued

```
            1430                1435                1440
Leu Thr Ala Phe Phe Gly Val Met Pro Arg Gly Thr Thr Pro Arg
            1445                1450                1455
Ala Pro Val Arg Phe Pro Thr Ser Leu Leu Lys Ile Arg Arg Gly
            1460                1465                1470
Leu Glu Thr Gly Trp Ala Tyr Thr His Gln Gly Gly Ile Ser Ser
            1475                1480                1485
Val Asp His Val Thr Cys Gly Lys Asp Leu Leu Val Cys Asp Thr
            1490                1495                1500
Met Gly Arg Thr Arg Val Val Cys Gln Ser Asn Asn Lys Met Thr
            1505                1510                1515
Asp Glu Ser Glu Tyr Gly Val Lys Thr Asp Ser Gly Cys Pro Glu
            1520                1525                1530
Gly Ala Arg Cys Tyr Val Phe Asn Pro Glu Ala Val Asn Ile Ser
            1535                1540                1545
Gly Thr Lys Gly Ala Met Val His Leu Gln Lys Thr Gly Gly Glu
            1550                1555                1560
Phe Thr Cys Val Thr Ala Ser Gly Thr Pro Ala Phe Phe Asp Leu
            1565                1570                1575
Lys Asn Leu Lys Gly Trp Ser Gly Leu Pro Ile Phe Glu Ala Ser
            1580                1585                1590
Ser Gly Arg Val Val Gly Arg Val Lys Val Gly Lys Asn Glu Asp
            1595                1600                1605
Ser Lys Pro Thr Lys Leu Met Ser Gly Ile Gln Thr Val Ser Lys
            1610                1615                1620
Ser Ala Thr Asp Leu Thr Glu Met Val Lys Lys Ile Thr Thr Met
            1625                1630                1635
Asn Arg Gly Glu Phe Arg Gln Ile Thr Leu Ala Thr Gly Ala Gly
            1640                1645                1650
Lys Thr Thr Glu Leu Pro Arg Ser Val Ile Glu Glu Ile Gly Arg
            1655                1660                1665
His Lys Arg Val Leu Val Leu Ile Pro Leu Arg Ala Ala Ala Glu
            1670                1675                1680
Ser Val Tyr Gln Tyr Met Arg Gln Lys His Pro Ser Ile Ala Phe
            1685                1690                1695
Asn Leu Arg Ile Gly Glu Met Lys Glu Gly Asp Met Ala Thr Gly
            1700                1705                1710
Ile Thr Tyr Ala Ser Tyr Gly Tyr Phe Cys Gln Met Ser Gln Pro
            1715                1720                1725
Lys Leu Arg Ala Ala Met Val Glu Tyr Ser Phe Ile Phe Leu Asp
            1730                1735                1740
Glu Tyr His Cys Ala Thr Pro Glu Gln Leu Ala Ile Met Gly Lys
            1745                1750                1755
Ile His Arg Phe Ser Glu Asn Leu Arg Val Val Ala Met Thr Ala
            1760                1765                1770
Thr Pro Ala Gly Thr Val Thr Thr Thr Gly Gln Lys His Pro Ile
            1775                1780                1785
Glu Glu Phe Ile Ala Pro Glu Val Met Lys Gly Glu Asp Leu Gly
            1790                1795                1800
Ser Glu Tyr Leu Asp Ile Ala Gly Leu Lys Ile Pro Val Glu Glu
            1805                1810                1815
Met Lys Asn Asn Met Leu Val Phe Val Pro Thr Arg Asn Met Ala
            1820                1825                1830
```

```
Val Glu Ala Ala Lys Lys Leu Lys Ala Lys Gly Tyr Asn Ser Gly
1835                1840                1845

Tyr Tyr Tyr Ser Gly Glu Asp Pro Ser Asn Leu Arg Val Val Thr
1850                1855                1860

Ser Gln Ser Pro Tyr Val Val Ala Thr Asn Ala Ile Glu Ser
1865                1870                1875

Gly Val Thr Leu Pro Asp Leu Asp Val Val Asp Thr Gly Leu
1880                1885                1890

Lys Cys Glu Lys Arg Ile Arg Leu Ser Pro Lys Met Pro Phe Ile
1895                1900                1905

Val Thr Gly Leu Lys Arg Met Ala Val Thr Ile Gly Glu Gln Ala
1910                1915                1920

Gln Arg Arg Gly Arg Val Gly Arg Val Lys Pro Gly Arg Tyr Tyr
1925                1930                1935

Arg Ser Gln Glu Thr Pro Val Gly Ser Lys Asp Tyr His Tyr Asp
1940                1945                1950

Leu Leu Gln Ala Gln Arg Tyr Gly Ile Glu Asp Gly Ile Asn Ile
1955                1960                1965

Thr Lys Ser Phe Arg Glu Met Asn Tyr Asp Trp Ser Leu Tyr Glu
1970                1975                1980

Glu Asp Ser Leu Met Ile Thr Gln Leu Glu Ile Leu Asn Asn Leu
1985                1990                1995

Leu Ile Ser Glu Glu Leu Pro Met Ala Val Lys Asn Ile Met Ala
2000                2005                2010

Arg Thr Asp His Pro Glu Pro Ile Gln Leu Ala Tyr Asn Ser Tyr
2015                2020                2025

Glu Thr Gln Val Pro Val Leu Phe Pro Lys Ile Arg Asn Gly Glu
2030                2035                2040

Val Thr Asp Thr Tyr Asp Asn Tyr Thr Phe Leu Asn Ala Arg Lys
2045                2050                2055

Leu Gly Asp Asp Val Pro Pro Tyr Val Tyr Ala Thr Glu Asp Glu
2060                2065                2070

Asp Leu Ala Val Glu Leu Leu Gly Leu Asp Trp Pro Asp Pro Gly
2075                2080                2085

Asn Gln Gly Thr Val Glu Ala Gly Arg Ala Leu Lys Gln Val Val
2090                2095                2100

Gly Leu Ser Thr Ala Glu Asn Ala Leu Leu Val Ala Leu Phe Gly
2105                2110                2115

Tyr Val Gly Tyr Gln Ala Leu Ser Lys Arg His Ile Pro Val Val
2120                2125                2130

Thr Asp Ile Tyr Ser Val Glu Asp His Arg Leu Glu Asp Thr Thr
2135                2140                2145

His Leu Gln Tyr Ala Pro Asn Ala Ile Lys Thr Glu Gly Lys Glu
2150                2155                2160

Thr Glu Leu Lys Glu Leu Ala Gln Gly Asp Val Gln Arg Cys Val
2165                2170                2175

Glu Ala Val Thr Asn Tyr Ala Arg Glu Gly Ile Gln Phe Met Lys
2180                2185                2190

Ser Gln Ala Leu Lys Val Arg Glu Thr Pro Thr Tyr Lys Glu Thr
2195                2200                2205

Met Asn Thr Val Ala Asp Tyr Val Lys Lys Phe Ile Glu Ala Leu
2210                2215                2220
```

-continued

```
Thr Asp Ser Lys Glu Asp Ile Ile Lys Tyr Gly Leu Trp Gly Ala
2225                2230                2235

His Thr Ala Leu Tyr Lys Ser Ile Gly Ala Arg Leu Gly His Glu
2240                2245                2250

Thr Ala Phe Ala Thr Leu Val Val Lys Trp Leu Ala Phe Gly Gly
2255                2260                2265

Glu Ser Ile Ser Asp His Ile Lys Gln Ala Ala Thr Asp Leu Val
2270                2275                2280

Val Tyr Tyr Ile Ile Asn Arg Pro Gln Phe Pro Gly Asp Thr Glu
2285                2290                2295

Thr Gln Gln Glu Gly Arg Lys Phe Val Ala Ser Leu Leu Val Ser
2300                2305                2310

Ala Leu Ala Thr Tyr Thr Tyr Lys Ser Trp Asn Tyr Asn Asn Leu
2315                2320                2325

Ser Lys Ile Val Glu Pro Ala Leu Ala Thr Leu Pro Tyr Ala Ala
2330                2335                2340

Lys Ala Leu Lys Leu Phe Ala Pro Thr Arg Leu Glu Ser Val Val
2345                2350                2355

Ile Leu Ser Thr Ala Ile Tyr Lys Thr Tyr Leu Ser Ile Arg Arg
2360                2365                2370

Gly Lys Ser Asp Gly Leu Leu Gly Thr Gly Val Ser Ala Ala Met
2375                2380                2385

Glu Ile Met Ser Gln Asn Pro Val Ser Val Gly Ile Ala Val Met
2390                2395                2400

Leu Gly Val Gly Ala Val Ala Ala His Asn Ala Ile Glu Ala Ser
2405                2410                2415

Glu Gln Lys Arg Thr Leu Leu Met Lys Val Phe Val Lys Asn Phe
2420                2425                2430

Leu Asp Gln Ala Ala Thr Asp Glu Leu Val Lys Glu Ser Pro Glu
2435                2440                2445

Lys Ile Ile Met Ala Leu Phe Glu Ala Val Gln Thr Val Gly Asn
2450                2455                2460

Pro Leu Arg Leu Val Tyr His Leu Tyr Gly Val Phe Tyr Lys Gly
2465                2470                2475

Trp Glu Ala Lys Glu Leu Ala Gln Arg Thr Ala Gly Arg Asn Leu
2480                2485                2490

Phe Thr Leu Ile Met Phe Glu Ala Val Glu Leu Leu Gly Val Asp
2495                2500                2505

Ser Glu Gly Lys Ile Arg Gln Leu Ser Ser Asn Tyr Ile Leu Glu
2510                2515                2520

Leu Leu Tyr Lys Phe Arg Asp Asn Ile Lys Ser Ser Val Arg Glu
2525                2530                2535

Ile Ala Ile Ser Trp Ala Pro Ala Pro Phe Ser Cys Asp Trp Thr
2540                2545                2550

Pro Thr Asp Asp Arg Ile Gly Leu Pro His Asp Asn Tyr Leu Arg
2555                2560                2565

Val Glu Thr Lys Cys Pro Cys Gly Tyr Arg Met Lys Ala Val Lys
2570                2575                2580

Asn Cys Ala Gly Glu Leu Arg Leu Leu Glu Glu Gly Gly Ser Phe
2585                2590                2595

Leu Cys Arg Asn Lys Phe Gly Arg Gly Ser Gln Asn Tyr Arg Val
2600                2605                2610

Thr Lys Tyr Tyr Asp Asp Asn Leu Ser Glu Ile Lys Pro Val Ile
```

```
                2615                2620                2625

Arg Met Glu Gly His Val Glu Leu Tyr Tyr Lys Gly Ala Thr Ile
        2630            2635                2640

Lys Leu Asp Phe Asn Asn Ser Lys Thr Val Leu Ala Thr Asp Lys
        2645            2650                2655

Trp Glu Val Asp His Ser Thr Leu Val Arg Ala Leu Lys Arg Tyr
        2660            2665                2670

Thr Gly Ala Gly Tyr Arg Gly Ala Tyr Leu Gly Glu Lys Pro Asn
        2675            2680                2685

His Lys His Leu Ile Gln Arg Asp Cys Ala Thr Leu Thr Lys Asp
        2690            2695                2700

Lys Val Cys Phe Ile Lys Met Lys Arg Gly Cys Ala Phe Thr Tyr
        2705            2710                2715

Asp Leu Ser Leu His Asn Leu Thr Arg Leu Ile Glu Leu Val His
        2720            2725                2730

Lys Asn Asn Leu Glu Asp Arg Glu Ile Pro Ala Val Thr Val Thr
        2735            2740                2745

Thr Trp Leu Ala Tyr Thr Phe Val Asn Glu Asp Ile Gly Thr Ile
        2750            2755                2760

Lys Pro Thr Phe Gly Glu Lys Val Thr Pro Glu Lys Gln Glu Glu
        2765            2770                2775

Val Val Leu Gln Pro Ala Val Val Asp Thr Thr Asp Val Ala
        2780            2785                2790

Val Thr Val Val Gly Glu Thr Ser Thr Met Thr Thr Gly Glu Thr
        2795            2800                2805

Pro Thr Thr Phe Thr Ser Leu Gly Ser Asp Ser Lys Val Arg Gln
        2810            2815                2820

Val Leu Lys Leu Gly Val Asp Asp Gly Gln Tyr Pro Gly Pro Asn
        2825            2830                2835

Gln Gln Arg Ala Ser Leu Leu Glu Ala Ile Gln Gly Val Asp Glu
        2840            2845                2850

Arg Pro Ser Val Leu Ile Leu Gly Ser Asp Lys Ala Thr Ser Asn
        2855            2860                2865

Arg Val Lys Thr Ala Lys Asn Val Lys Ile Tyr Arg Ser Arg Asp
        2870            2875                2880

Pro Leu Glu Leu Arg Glu Met Met Lys Arg Gly Lys Ile Leu Val
        2885            2890                2895

Val Ala Leu Ser Arg Val Asp Thr Ala Leu Leu Lys Phe Val Asp
        2900            2905                2910

Tyr Lys Gly Thr Phe Leu Thr Arg Glu Thr Leu Glu Ala Leu Ser
        2915            2920                2925

Leu Gly Lys Pro Lys Lys Arg Asp Ile Thr Lys Ala Glu Ala Gln
        2930            2935                2940

Trp Leu Leu Arg Leu Glu Asp Gln Ile Glu Glu Leu Pro Asp Trp
        2945            2950                2955

Phe Ala Ala Lys Glu Pro Ile Phe Leu Glu Ala Asn Ile Lys Arg
        2960            2965                2970

Asp Lys Tyr His Leu Val Gly Asp Ile Ala Thr Ile Lys Glu Lys
        2975            2980                2985

Ala Lys Gln Leu Gly Ala Thr Asp Ser Thr Lys Ile Ser Lys Glu
        2990            2995                3000

Val Gly Ala Lys Val Tyr Ser Met Lys Leu Ser Asn Trp Val Ile
        3005            3010                3015
```

-continued

```
Gln Glu  Glu Asn Lys Gln Gly  Ser Leu Ala Pro  Leu Phe Glu Glu
    3020             3025             3030

Leu Leu  Gln Gln Cys Pro Pro  Gly Gly Gln Asn  Lys Thr Thr His
    3035             3040             3045

Met Val  Ser Ala Tyr Gln Leu  Ala Gln Gly Asn  Trp Val Pro Val
    3050             3055             3060

Ser Cys  His Val Phe Met Gly  Thr Ile Pro Ala  Arg Arg Thr Lys
    3065             3070             3075

Thr His  Pro Tyr Glu Ala Tyr  Val Lys Leu Arg  Glu Leu Val Asp
    3080             3085             3090

Glu His  Lys Met Lys Ala Leu  Cys Gly Gly Ser  Gly Leu Ser Lys
    3095             3100             3105

His Asn  Glu Trp Val Ile Gly  Lys Val Lys Tyr  Gln Gly Asn Leu
    3110             3115             3120

Arg Thr  Lys His Met Leu Asn  Pro Gly Lys Val  Ala Glu Gln Leu
    3125             3130             3135

His Arg  Glu Gly Tyr Arg His  Asn Val Tyr Asn  Lys Thr Ile Gly
    3140             3145             3150

Ser Val  Met Thr Ala Thr Gly  Ile Arg Leu Glu  Lys Leu Pro Val
    3155             3160             3165

Val Arg  Ala Gln Thr Asp Thr  Thr Asn Phe His  Gln Ala Ile Arg
    3170             3175             3180

Asp Lys  Ile Asp Lys Glu Glu  Asn Leu Gln Thr  Pro Gly Leu His
    3185             3190             3195

Lys Lys  Leu Met Glu Val Phe  Asn Ala Leu Lys  Arg Pro Glu Leu
    3200             3205             3210

Glu Ala  Ser Tyr Asp Ala Val  Asp Trp Glu Glu  Leu Glu Arg Gly
    3215             3220             3225

Ile Asn  Arg Lys Gly Ala Ala  Gly Phe Phe Glu  Arg Lys Asn Ile
    3230             3235             3240

Gly Glu  Val Leu Asp Ser Glu  Lys Asn Lys Val  Glu Glu Val Ile
    3245             3250             3255

Asp Ser  Leu Lys Lys Gly Arg  Asn Ile Arg Tyr  Tyr Glu Thr Ala
    3260             3265             3270

Ile Pro  Lys Asn Glu Lys Arg  Asp Val Asn Asp  Asp Trp Thr Ala
    3275             3280             3285

Gly Asp  Phe Val Asp Glu Lys  Lys Pro Arg Val  Ile Gln Tyr Pro
    3290             3295             3300

Glu Ala  Lys Thr Arg Leu Ala  Ile Thr Lys Val  Met Tyr Lys Trp
    3305             3310             3315

Val Lys  Gln Lys Pro Val Val  Ile Pro Gly Tyr  Glu Gly Lys Thr
    3320             3325             3330

Pro Leu  Phe Gln Ile Phe Asp  Lys Val Lys Lys  Glu Trp Asp Gln
    3335             3340             3345

Phe Gln  Asn Pro Val Ala Val  Ser Phe Asp Thr  Lys Ala Trp Asp
    3350             3355             3360

Thr Gln  Val Thr Thr Arg Asp  Leu Glu Leu Ile  Arg Asp Ile Gln
    3365             3370             3375

Lys Phe  Tyr Phe Lys Lys Lys  Trp His Lys Phe  Ile Asp Thr Leu
    3380             3385             3390

Thr Lys  His Met Ser Glu Val  Pro Val Ile Ser  Ala Asp Gly Glu
    3395             3400             3405
```

Val Tyr Ile Arg Lys Gly Gln Arg Gly Ser Gly Gln Pro Asp Thr
3410                3415                3420

Ser Ala Gly Asn Ser Met Leu Asn Val Leu Thr Met Val Tyr Ala
3425                3430                3435

Phe Cys Glu Ala Thr Gly Val Pro Tyr Lys Ser Phe Asp Arg Val
3440                3445                3450

Ala Lys Ile His Val Cys Gly Asp Asp Gly Phe Leu Ile Thr Glu
3455                3460                3465

Arg Ala Leu Gly Glu Lys Phe Ala Ser Lys Gly Val Gln Ile Leu
3470                3475                3480

Tyr Glu Ala Gly Lys Pro Gln Lys Ile Thr Glu Gly Asp Lys Met
3485                3490                3495

Lys Val Ala Tyr Gln Phe Asp Asp Ile Glu Phe Cys Ser His Thr
3500                3505                3510

Pro Val Gln Val Arg Trp Ser Asp Asn Thr Ser Ser Tyr Met Pro
3515                3520                3525

Gly Arg Asn Thr Thr Thr Ile Leu Ala Lys Met Ala Thr Arg Leu
3530                3535                3540

Asp Ser Ser Gly Glu Arg Gly Thr Ile Ala Tyr Glu Lys Ala Val
3545                3550                3555

Ala Phe Ser Phe Leu Leu Met Tyr Ser Trp Asn Pro Leu Ile Arg
3560                3565                3570

Arg Ile Cys Leu Leu Val Leu Ser Thr Glu Leu Gln Val Arg Pro
3575                3580                3585

Gly Lys Ser Thr Thr Tyr Tyr Tyr Glu Gly Asp Pro Ile Ser Ala
3590                3595                3600

Tyr Lys Glu Val Ile Gly His Asn Leu Phe Asp Leu Lys Arg Thr
3605                3610                3615

Ser Phe Glu Lys Leu Ala Lys Leu Asn Leu Ser Met Ser Thr Leu
3620                3625                3630

Gly Val Trp Thr Arg His Thr Ser Lys Arg Leu Leu Gln Asp Cys
3635                3640                3645

Val Asn Val Gly Thr Lys Glu Gly Asn Trp Leu Val Asn Ala Asp
3650                3655                3660

Arg Leu Val Ser Ser Lys Thr Gly Asn Arg Tyr Ile Pro Gly Glu
3665                3670                3675

Gly His Thr Leu Gln Gly Lys His Tyr Glu Glu Leu Ile Leu Ala
3680                3685                3690

Arg Lys Pro Ile Gly Asn Phe Glu Gly Thr Asp Arg Tyr Asn Leu
3695                3700                3705

Gly Pro Ile Val Asn Val Val Leu Arg Arg Leu Lys Ile Met Met
3710                3715                3720

Met Ala Leu Ile Gly Arg Gly Val
3725                3730

<210> SEQ ID NO 7
<211> LENGTH: 3898
<212> TYPE: PRT
<213> ORGANISM: CSFV

<400> SEQUENCE: 7

Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Arg Pro Leu
            20                  25                  30

```
Phe Gly Asp Pro Ser Glu Val His Pro Gln Ser Thr Leu Lys Leu Pro
         35                  40                  45

His Asp Arg Gly Arg Gly Asn Ile Lys Thr Thr Leu Lys Asn Leu Pro
 50                  55                  60

Arg Lys Gly Asp Cys Arg Ser Gly Asn His Leu Gly Pro Val Ser Gly
 65                  70                  75                  80

Ile Tyr Val Lys Pro Gly Pro Val Phe Tyr Gln Asp Tyr Met Gly Pro
                 85                  90                  95

Val Tyr His Arg Ala Pro Leu Glu Phe Phe Asp Glu Val Gln Phe Cys
             100                 105                 110

Glu Val Thr Lys Arg Ile Gly Arg Val Thr Gly Ser Asp Gly Lys Leu
         115                 120                 125

Tyr His Thr Tyr Val Cys Ile Asp Gly Cys Ile Leu Leu Lys Leu Ala
     130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Gly Ala Ser Gly Ser
                165                 170                 175

Lys Glu Lys Lys Pro Asp Arg Ile Asn Lys Gly Lys Leu Lys Ile Ala
                180                 185                 190

Pro Lys Glu His Glu Lys Asp Ser Arg Thr Arg Pro Pro Asp Ala Thr
            195                 200                 205

Ile Val Val Glu Gly Val Lys Tyr Gln Val Lys Lys Gly Lys Val
        210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Asn Arg Ser Leu His Gly Ile Trp Pro Gly Lys Ile
    290                 295                 300

Cys Lys Gly Val Pro Thr His Leu Ala Thr Asp Val Glu Leu Lys Glu
305                 310                 315                 320

Ile Gln Gly Met Met Asp Ala Ser Glu Gly Thr Asn Tyr Thr Cys Cys
                325                 330                 335

Lys Leu Gln Arg His Glu Trp Asn Lys His Gly Trp Cys Asn Trp His
            340                 345                 350

Asn Ile Asp Pro Trp Ile Gln Leu Met Asn Arg Thr Gln Ala Asp Leu
        355                 360                 365

Ala Glu Gly Pro Pro Val Lys Glu Cys Ala Val Thr Cys Arg Tyr Asp
    370                 375                 380

Lys Asp Ala Asp Ile Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Ser Pro Cys Asn Phe Asn Val Ser Val Glu Asp Thr Leu
            420                 425                 430

Tyr Gly Asp His Glu Ser Cys Ser Leu Leu Gln Asp Ala Ala Leu Tyr
        435                 440                 445
```

-continued

```
Leu Val Asp Gly Met Thr Asn Thr Ile Glu Asn Ala Arg Gln Gly Ala
450                 455                 460
Ala Arg Val Thr Ser Trp Leu Gly Arg Gln Leu Arg Ile Ala Gly Lys
465                 470                 475                 480
Arg Leu Glu Gly Arg Ser Lys Thr Trp Phe Gly Ala Tyr Ala Leu Ser
            485                 490                 495
Pro Tyr Cys Asn Val Thr Ser Lys Ile Gly Tyr Ile Trp Tyr Thr Asn
            500                 505                 510
Asn Cys Thr Pro Ala Cys Leu Pro Lys Asn Thr Lys Ile Ile Gly Pro
        515                 520                 525
Gly Lys Phe Asp Thr Asn Ala Glu Asp Gly Lys Ile Leu His Glu Met
530                 535                 540
Gly Gly His Leu Ser Glu Phe Leu Leu Leu Ser Leu Val Val Leu Ser
545                 550                 555                 560
Asp Phe Ala Pro Glu Thr Ala Ser Ala Leu Tyr Leu Ile Phe His Tyr
                565                 570                 575
Val Ile Pro Gln Pro His Asp Glu Pro Glu Gly Cys Asp Thr Asn Gln
            580                 585                 590
Leu Asn Leu Thr Val Glu Leu Arg Thr Glu Asp Val Ile Pro Ser Ser
        595                 600                 605
Val Trp Asn Val Gly Lys Tyr Val Cys Val Arg Pro Asp Trp Trp Pro
610                 615                 620
Tyr Glu Thr Glu Val Ala Leu Leu Phe Glu Glu Val Gly Gln Val Val
625                 630                 635                 640
Lys Leu Ala Leu Arg Ala Leu Arg Asp Leu Thr Arg Val Trp Asn Ser
                645                 650                 655
Ala Ser Thr Ile Ala Phe Leu Ile Cys Leu Ile Lys Val Leu Arg Gly
            660                 665                 670
Gln Ile Val Gln Gly Val Val Trp Leu Leu Leu Val Thr Gly Ala Gln
        675                 680                 685
Gly Arg Leu Ala Cys Lys Glu Asp Tyr Arg Tyr Ala Ile Ser Ser Thr
690                 695                 700
Asp Glu Ile Gly Leu Leu Gly Ala Gly Gly Leu Thr Thr Thr Trp Lys
705                 710                 715                 720
Glu Tyr Asn His Asp Leu Gln Leu Asn Asp Gly Thr Val Lys Ala Ser
                725                 730                 735
Cys Val Ala Gly Ser Phe Lys Val Thr Ala Leu Asn Val Val Ser Arg
            740                 745                 750
Arg Tyr Leu Ala Ser Leu His Lys Lys Ala Leu Pro Thr Ser Val Thr
        755                 760                 765
Phe Glu Leu Leu Phe Asp Gly Thr Asn Pro Ser Thr Glu Glu Met Gly
770                 775                 780
Asp Asp Phe Arg Ser Gly Leu Cys Pro Phe Asp Thr Ser Pro Val Val
785                 790                 795                 800
Lys Gly Lys Tyr Asn Thr Thr Leu Leu Asn Gly Ser Ala Phe Tyr Leu
                805                 810                 815
Val Cys Pro Ile Gly Trp Thr Gly Val Ile Glu Cys Thr Ala Val Ser
            820                 825                 830
Pro Thr Thr Leu Arg Thr Glu Val Lys Thr Phe Arg Arg Asp Lys
        835                 840                 845
Pro Phe Pro His Arg Met Asp Cys Val Thr Thr Val Glu Asn Glu
850                 855                 860
Asp Leu Phe Tyr Cys Lys Leu Gly Gly Asn Trp Thr Cys Val Lys Gly
```

```
865                 870                 875                 880
Glu Pro Val Val Tyr Thr Gly Gly Leu Val Lys Gln Cys Arg Trp Cys
                    885                 890                 895
Gly Phe Asp Phe Asp Gly Pro Asp Gly Leu Pro His Tyr Pro Ile Gly
                    900                 905                 910
Lys Cys Ile Leu Ala Asn Glu Thr Gly Tyr Arg Ile Val Asp Ser Thr
                    915                 920                 925
Asp Cys Asn Arg Asp Gly Val Val Ile Ser Thr Glu Gly Ser His Glu
                    930                 935                 940
Cys Leu Ile Gly Asn Thr Thr Val Lys Val His Ala Ser Asp Glu Arg
945                 950                 955                 960
Leu Gly Pro Met Pro Cys Arg Pro Lys Glu Ile Val Ser Ser Ala Gly
                    965                 970                 975
Pro Val Lys Lys Thr Ser Cys Thr Phe Asn Tyr Thr Lys Thr Leu Lys
                    980                 985                 990
Asn Arg Tyr Tyr Glu Pro Arg Asp Ser Tyr Phe Gln Gln Tyr Met Leu
                    995                 1000                1005
Lys Gly Glu Tyr Gln Tyr Trp Phe Asp Leu Asp Ala Thr Asp Arg
1010                    1015                1020
His Ser Asp Tyr Phe Ala Glu Phe Val Leu Val Val Val Ala
1025                    1030                1035
Leu Leu Gly Gly Arg Tyr Val Leu Trp Leu Ile Val Thr Tyr Val
1040                    1045                1050
Val Leu Thr Glu Gln Leu Ala Ala Gly Leu Pro Leu Gly Gln Gly
1055                    1060                1065
Glu Val Val Leu Ile Gly Asn Leu Ile Thr His Thr Asp Ile Glu
1070                    1075                1080
Val Val Val Tyr Phe Leu Leu Leu Tyr Leu Val Met Arg Asp Glu
1085                    1090                1095
Pro Ile Lys Lys Trp Ile Leu Leu Leu Phe His Ala Met Thr Asn
1100                    1105                1110
Asn Pro Val Lys Thr Ile Thr Val Ala Leu Leu Met Val Ser Gly
1115                    1120                1125
Val Ala Lys Gly Gly Lys Ile Asp Gly Gly Trp Gln Arg Leu Pro
1130                    1135                1140
Gly Thr Ser Phe Asp Ile Gln Leu Ala Leu Thr Val Ile Val Val
1145                    1150                1155
Ala Val Met Leu Leu Ala Lys Arg Asp Pro Thr Thr Val Pro Leu
1160                    1165                1170
Val Ile Thr Val Ala Thr Leu Arg Thr Ala Lys Met Thr Asn Gly
1175                    1180                1185
Leu Ser Thr Asp Ile Ala Ile Ala Thr Val Ser Ala Ala Leu Leu
1190                    1195                1200
Thr Trp Thr Tyr Ile Ser Asp Tyr Tyr Arg Tyr Lys Thr Trp Leu
1205                    1210                1215
Gln Tyr Leu Ile Ser Thr Val Thr Gly Ile Phe Leu Ile Arg Val
1220                    1225                1230
Leu Lys Gly Ile Gly Glu Leu Asp Leu His Thr Pro Thr Leu Pro
1235                    1240                1245
Ser His Arg Pro Leu Phe Phe Ile Leu Val Tyr Leu Ile Ser Thr
1250                    1255                1260
Ala Val Val Thr Arg Trp Asn Leu Asp Ile Ala Gly Leu Leu Leu
1265                    1270                1275
```

-continued

```
Gln Cys Val Pro Thr Leu Leu Met Val Phe Thr Met Trp Ala Asp
    1280            1285            1290

Ile Leu Thr Leu Ile Leu Ile Leu Pro Thr Tyr Glu Leu Thr Lys
    1295            1300            1305

Leu Tyr Tyr Leu Lys Glu Val Lys Ile Gly Ala Glu Lys Gly Trp
    1310            1315            1320

Leu Trp Lys Thr Asn Phe Lys Arg Val Asn Asp Ile Tyr Glu Val
    1325            1330            1335

Asp Gln Ala Gly Glu Gly Val Tyr Leu Phe Pro Ser Lys Gln Lys
    1340            1345            1350

Thr Ser Ser Met Thr Gly Thr Met Leu Pro Leu Ile Lys Ala Ile
    1355            1360            1365

Leu Ile Ser Cys Val Ser Asn Lys Trp Gln Phe Ile Tyr Leu Leu
    1370            1375            1380

Tyr Leu Ile Phe Glu Val Ser Tyr Tyr Leu His Lys Lys Ile Ile
    1385            1390            1395

Asp Glu Ile Ala Gly Gly Thr Asn Phe Ile Ser Arg Leu Val Ala
    1400            1405            1410

Ala Leu Ile Glu Val Asn Trp Ala Phe Asp Asn Glu Glu Val Arg
    1415            1420            1425

Gly Leu Lys Lys Phe Phe Leu Leu Ser Ser Arg Val Lys Glu Leu
    1430            1435            1440

Ile Ile Lys His Lys Val Arg Asn Glu Val Met Val Arg Trp Phe
    1445            1450            1455

Gly Asp Glu Glu Val Tyr Gly Met Pro Lys Leu Val Gly Leu Val
    1460            1465            1470

Lys Ala Ala Thr Leu Ser Lys Asn Lys His Cys Ile Leu Cys Thr
    1475            1480            1485

Val Cys Glu Asp Arg Glu Trp Arg Gly Glu Thr Cys Pro Lys Cys
    1490            1495            1500

Gly Arg Phe Gly Pro Pro Met Thr Cys Gly Met Thr Leu Ala Asp
    1505            1510            1515

Phe Glu Glu Lys His Tyr Lys Arg Ile Phe Phe Arg Glu Asp Gln
    1520            1525            1530

Ser Glu Gly Pro Val Arg Glu Glu Tyr Ala Gly Tyr Leu Gln Tyr
    1535            1540            1545

Arg Ala Arg Gly Gln Leu Phe Leu Arg Asn Leu Pro Val Leu Ala
    1550            1555            1560

Thr Lys Val Lys Met Leu Leu Val Gly Asn Leu Gly Thr Glu Val
    1565            1570            1575

Gly Asp Leu Glu His Leu Gly Trp Val Leu Arg Gly Pro Ala Val
    1580            1585            1590

Cys Lys Lys Val Thr Glu His Glu Lys Cys Thr Thr Ser Met Met
    1595            1600            1605

Asp Lys Leu Thr Ala Phe Phe Gly Val Met Pro Arg Gly Thr Thr
    1610            1615            1620

Pro Arg Ala Pro Val Arg Phe Pro Thr Ser Leu Leu Lys Ile Arg
    1625            1630            1635

Arg Gly Leu Glu Thr Gly Trp Ala Tyr Thr His Gln Gly Gly Ile
    1640            1645            1650

Ser Ser Val Asp His Val Thr Cys Gly Lys Asp Leu Leu Val Cys
    1655            1660            1665
```

```
Asp Thr Met Gly Arg Thr Arg Val Val Cys Gln Ser Asn Asn Lys
    1670            1675                1680
Met Thr Asp Glu Ser Glu Tyr Gly Val Lys Thr Asp Ser Gly Cys
1685                1690                1695
Pro Glu Gly Ala Arg Cys Tyr Val Phe Asn Pro Glu Ala Val Asn
    1700            1705                1710
Ile Ser Gly Thr Lys Gly Ala Met Val His Leu Gln Lys Thr Gly
    1715            1720                1725
Gly Glu Phe Thr Cys Val Thr Ala Ser Gly Thr Pro Ala Phe Phe
    1730            1735                1740
Asp Leu Lys Asn Leu Lys Gly Trp Ser Gly Leu Pro Ile Phe Glu
    1745            1750                1755
Ala Ser Ser Gly Arg Val Val Gly Arg Val Lys Val Gly Lys Asn
    1760            1765                1770
Glu Asp Ser Lys Pro Thr Lys Leu Met Ser Gly Ile Gln Thr Val
    1775            1780                1785
Ser Lys Ser Thr Thr Asp Leu Thr Glu Met Val Lys Lys Ile Thr
    1790            1795                1800
Thr Met Ser Arg Gly Glu Phe Arg Gln Ile Thr Leu Ala Thr Gly
    1805            1810                1815
Ala Gly Lys Thr Thr Glu Leu Pro Arg Ser Val Ile Glu Glu Ile
    1820            1825                1830
Gly Arg His Lys Arg Val Leu Val Leu Ile Pro Leu Arg Ala Ala
    1835            1840                1845
Ala Glu Ser Val Tyr Gln Tyr Met Arg Gln Lys His Pro Ser Ile
    1850            1855                1860
Ala Phe Asn Leu Arg Ile Gly Glu Met Lys Glu Gly Asp Met Ala
    1865            1870                1875
Thr Gly Ile Thr Tyr Ala Ser Tyr Gly Tyr Phe Cys Gln Met Pro
    1880            1885                1890
Gln Pro Lys Leu Arg Ala Ala Met Val Glu Tyr Ser Phe Ile Phe
    1895            1900                1905
Leu Asp Glu Tyr His Cys Ala Thr Pro Glu Gln Leu Ala Ile Met
    1910            1915                1920
Gly Lys Ile His Arg Phe Ser Glu Asn Leu Arg Val Val Ala Met
    1925            1930                1935
Thr Ala Thr Pro Val Gly Thr Val Thr Thr Thr Gly Gln Lys His
    1940            1945                1950
Pro Ile Glu Glu Phe Ile Ala Pro Asp Val Met Lys Gly Glu Asp
    1955            1960                1965
Leu Gly Ser Glu Tyr Leu Asp Ile Ala Gly Leu Lys Ile Pro Val
    1970            1975                1980
Glu Glu Met Lys Ser Asn Met Leu Val Phe Val Pro Thr Arg Asn
    1985            1990                1995
Met Ala Val Glu Thr Ala Lys Lys Leu Lys Ala Lys Gly Tyr Asn
2000                2005                2010
Ser Gly Tyr Tyr Tyr Ser Gly Glu Asp Pro Ser Asn Leu Arg Val
    2015            2020                2025
Val Thr Ser Gln Ser Pro Tyr Val Val Val Ala Thr Asn Ala Ile
    2030            2035                2040
Glu Pro Gly Val Thr Leu Pro Asp Leu Asp Val Val Val Asp Thr
    2045            2050                2055
Gly Leu Lys Cys Glu Lys Arg Ile Arg Leu Ser Pro Lys Met Pro
```

-continued

```
            2060                2065                2070
Phe Ile Val Thr Gly Leu Lys Arg Met Ala Val Thr Ile Gly Glu
            2075                2080                2085
Gln Ala Gln Arg Arg Gly Arg Val Gly Arg Val Lys Pro Gly Arg
            2090                2095                2100
Tyr Tyr Arg Ser Gln Glu Thr Pro Val Gly Ser Lys Asp Tyr His
            2105                2110                2115
Tyr Asp Leu Leu Gln Ala Gln Arg Tyr Gly Ile Glu Asp Gly Ile
            2120                2125                2130
Asn Ile Thr Lys Ser Phe Arg Glu Met Asn Tyr Asp Trp Ser Leu
            2135                2140                2145
Tyr Glu Glu Asp Ser Leu Met Ile Thr Gln Leu Glu Ile Leu Asn
            2150                2155                2160
Asn Leu Leu Ile Ser Asp Glu Leu Pro Met Ala Val Lys Asn Ile
            2165                2170                2175
Met Ala Arg Thr Asp His Pro Glu Pro Ile Gln Leu Ala Tyr Asn
            2180                2185                2190
Ser Tyr Glu Thr Gln Val Pro Val Leu Phe Pro Lys Ile Lys Asn
            2195                2200                2205
Gly Glu Val Thr Asp Ser Tyr Asp Asn Tyr Thr Phe Leu Asn Ala
            2210                2215                2220
Arg Lys Leu Gly Asp Asp Val Pro Pro Tyr Val Tyr Ala Thr Glu
            2225                2230                2235
Asp Glu Asp Leu Ala Val Glu Leu Leu Gly Leu Asp Trp Pro Asp
            2240                2245                2250
Pro Gly Asn Leu Gly Thr Val Glu Thr Gly Arg Ala Leu Lys Gln
            2255                2260                2265
Val Val Gly Leu Ser Thr Ala Glu Asn Ala Leu Leu Val Ala Leu
            2270                2275                2280
Phe Gly Tyr Val Gly Tyr Gln Ala Leu Ser Lys Arg His Ile Pro
            2285                2290                2295
Val Val Thr Asp Ile Tyr Ser Ile Glu Asp His Arg Leu Glu Asp
            2300                2305                2310
Thr Thr His Leu Gln Tyr Ala Pro Asn Ala Ile Lys Thr Glu Gly
            2315                2320                2325
Lys Glu Thr Glu Leu Lys Glu Leu Ala Gln Gly Asp Val Gln Arg
            2330                2335                2340
Cys Val Glu Ala Met Thr Asn Tyr Ala Arg Glu Gly Ile Gln Phe
            2345                2350                2355
Met Lys Ser Gln Ala Leu Lys Val Lys Glu Thr Pro Thr Tyr Lys
            2360                2365                2370
Glu Thr Met Asp Thr Val Thr Asp Tyr Val Lys Lys Phe Met Glu
            2375                2380                2385
Ala Leu Ala Asp Ser Lys Glu Asp Ile Ile Lys Tyr Gly Leu Trp
            2390                2395                2400
Gly Thr His Thr Ala Leu Tyr Lys Ser Ile Ser Ala Arg Leu Gly
            2405                2410                2415
Gly Glu Thr Ala Phe Ala Thr Leu Val Val Lys Trp Leu Ala Phe
            2420                2425                2430
Gly Gly Glu Ser Ile Ala Asp His Val Lys Gln Ala Ala Thr Asp
            2435                2440                2445
Leu Val Val Tyr Tyr Ile Ile Asn Arg Pro Gln Phe Pro Gly Asp
            2450                2455                2460
```

```
Thr Glu Thr Gln Gln Asp Gly Arg Lys Phe Val Ala Ser Leu Leu
    2465                2470                2475

Ala Ser Ala Leu Ala Thr Tyr Thr Tyr Lys Ser Trp Asn Tyr Asn
    2480                2485                2490

Asn Leu Ser Lys Ile Val Glu Pro Ala Leu Ala Thr Leu Pro Tyr
    2495                2500                2505

Ala Ala Thr Ala Leu Lys Leu Phe Ala Pro Thr Arg Leu Glu Ser
    2510                2515                2520

Val Val Ile Leu Ser Thr Ala Ile Tyr Lys Thr Tyr Leu Ser Ile
    2525                2530                2535

Arg Arg Gly Lys Ser Asp Gly Leu Leu Gly Thr Gly Val Ser Ala
    2540                2545                2550

Ala Met Glu Ile Met Ser Gln Asn Pro Val Ser Val Gly Ile Ala
    2555                2560                2565

Val Met Leu Gly Val Gly Ala Val Ala Ala His Asn Ala Ile Glu
    2570                2575                2580

Ala Ser Glu Gln Lys Arg Thr Leu Leu Met Lys Val Phe Val Lys
    2585                2590                2595

Asn Phe Leu Asp Gln Ala Ala Thr Asp Glu Leu Val Lys Glu Ser
    2600                2605                2610

Pro Glu Lys Ile Ile Met Ala Leu Phe Glu Ala Val Gln Thr Val
    2615                2620                2625

Gly Asn Pro Leu Arg Leu Val Tyr His Leu Tyr Gly Val Phe Tyr
    2630                2635                2640

Lys Gly Trp Arg Pro Lys Glu Leu Ala Gln Arg Thr Ala Gly Arg
    2645                2650                2655

Asn Leu Phe Thr Leu Ile Met Phe Glu Ala Val Glu Leu Leu Gly
    2660                2665                2670

Val Asp Ser Glu Gly Lys Val Arg Gln Leu Ser Ser Asn Tyr Ile
    2675                2680                2685

Leu Glu Leu Leu Tyr Lys Phe Arg Asp Ser Ile Lys Ser Ser Val
    2690                2695                2700

Arg Glu Met Ala Ile Ser Trp Ala Pro Ala Pro Phe Ser Cys Asp
    2705                2710                2715

Trp Thr Pro Thr Asp Asp Arg Ile Gly Leu Pro Gln Asp Asn Phe
    2720                2725                2730

His Gln Val Glu Thr Lys Cys Pro Cys Gly Tyr Lys Met Lys Ala
    2735                2740                2745

Val Lys Asn Cys Ala Gly Glu Leu Arg Leu Leu Glu Glu Glu Gly
    2750                2755                2760

Ser Phe Leu Cys Arg Asn Lys Phe Gly Arg Gly Ser Arg Asn Tyr
    2765                2770                2775

Arg Val Thr Lys Tyr Tyr Asp Asp Asn Leu Leu Glu Ile Lys Pro
    2780                2785                2790

Val Ile Arg Met Glu Gly His Val Glu Leu Tyr Tyr Lys Gly Ala
    2795                2800                2805

Thr Ile Lys Leu Asp Phe Asn Asn Ser Lys Thr Ile Leu Ala Thr
    2810                2815                2820

Asp Lys Trp Glu Val Asp His Ser Thr Leu Val Arg Val Leu Lys
    2825                2830                2835

Arg His Thr Gly Ala Gly Tyr His Gly Ala Tyr Leu Gly Glu Lys
    2840                2845                2850
```

```
Pro Asn His Lys His Leu Ile Glu Arg Asp Cys Ala Thr Ile Thr
2855                2860                2865

Lys Asp Lys Val Cys Phe Leu Lys Met Lys Arg Gly Cys Ala Phe
2870                2875                2880

Thr Tyr Asp Leu Ser Leu His Asn Leu Ala Arg Leu Ile Glu Leu
2885                2890                2895

Val His Lys Asn Asn Leu Glu Asp Lys Glu Ile Pro Ala Ala Thr
2900                2905                2910

Val Thr Thr Trp Leu Ala Tyr Thr Phe Val Asn Glu Asp Ile Gly
2915                2920                2925

Thr Ile Lys Pro Ala Phe Gly Glu Lys Val Thr Leu Glu Met Gln
2930                2935                2940

Glu Glu Ile Thr Leu Gln Pro Ala Val Val Asp Thr Thr Asp
2945                2950                2955

Val Ala Val Thr Val Val Gly Glu Ala Pro Thr Met Thr Thr Gly
2960                2965                2970

Glu Thr Pro Thr Val Phe Thr Ser Ser Gly Ser Gly Leu Lys Asn
2975                2980                2985

Gln Gln Val Leu Lys Leu Gly Val Gly Glu Gly Gln Tyr Pro Gly
2990                2995                3000

Thr Asn Pro Gln Arg Ala Ser Leu His Glu Ala Ile Gln Gly Ala
3005                3010                3015

Asp Glu Arg Pro Ser Val Leu Ile Leu Gly Ser Asp Lys Ala Thr
3020                3025                3030

Ser Asn Arg Val Lys Thr Ala Lys Asn Val Lys Val Tyr Arg Gly
3035                3040                3045

Arg Asp Pro Leu Glu Val Arg Asp Met Met Arg Arg Gly Lys Ile
3050                3055                3060

Leu Val Val Ala Leu Ser Arg Val Asp Asn Ala Leu Leu Lys Phe
3065                3070                3075

Val Asp Tyr Lys Gly Thr Phe Leu Thr Arg Glu Ala Leu Glu Ala
3080                3085                3090

Leu Ser Leu Gly Arg Pro Lys Lys Lys Asn Ile Thr Lys Ala Glu
3095                3100                3105

Ala Gln Cys Leu Leu Cys Pro Glu Asp Gln Met Glu Glu Leu Pro
3110                3115                3120

Asp Trp Phe Ala Ala Gly Glu Pro Ile Phe Leu Glu Ala Asn Ile
3125                3130                3135

Lys His Asp Arg Leu His Leu Val Gly Asp Ile Ala Thr Ile Lys
3140                3145                3150

Glu Lys Ala Lys Gln Leu Gly Ala Thr Asp Ser Thr Lys Ile Ser
3155                3160                3165

Lys Glu Val Gly Ala Lys Val Tyr Ser Met Lys Leu Ser Asn Trp
3170                3175                3180

Val Met Gln Glu Glu Asn Lys Gln Gly Asn Leu Thr Pro Leu Phe
3185                3190                3195

Glu Glu Leu Leu Gln Gln Cys Pro Pro Gly Gly Gln Asn Lys Thr
3200                3205                3210

Ala His Met Val Ser Ala Tyr Gln Leu Ala Gln Gly Asn Trp Met
3215                3220                3225

Pro Thr Ser Cys His Val Phe Met Gly Thr Ile Ser Ala Arg Arg
3230                3235                3240

Thr Lys Thr His Pro Tyr Glu Ala Tyr Val Lys Leu Arg Glu Leu
```

-continued

```
            3245                3250                3255
Val Glu Glu His Lys Met Lys Thr Leu Cys Pro Gly Ser Ser Leu
    3260                3265                3270
Gly Lys His Asn Asp Trp Ile Ile Gly Lys Ile Lys Tyr Gln Gly
    3275                3280                3285
Asn Leu Arg Thr Lys His Met Leu Asn Pro Gly Lys Val Ala Glu
    3290                3295                3300
Gln Leu Cys Arg Glu Gly His Arg His Asn Val Tyr Asn Lys Thr
    3305                3310                3315
Ile Ser Ser Val Met Thr Ala Thr Gly Ile Arg Leu Glu Lys Leu
    3320                3325                3330
Pro Val Val Arg Ala Gln Thr Asp Pro Thr Asn Phe His Gln Ala
    3335                3340                3345
Ile Arg Asp Lys Ile Asp Lys Glu Glu Asn Leu Gln Thr Pro Gly
    3350                3355                3360
Leu His Lys Lys Leu Met Glu Val Phe Asn Ala Leu Lys Arg Pro
    3365                3370                3375
Glu Leu Glu Ser Ser Tyr Asp Ala Val Glu Trp Glu Glu Leu Glu
    3380                3385                3390
Arg Gly Ile Asn Arg Lys Gly Ala Ala Gly Phe Phe Glu Arg Lys
    3395                3400                3405
Asn Ile Gly Glu Ile Leu Asp Ser Glu Lys Asn Lys Val Glu Glu
    3410                3415                3420
Ile Ile Asp Asn Leu Lys Lys Gly Arg Asn Ile Lys Tyr Tyr Glu
    3425                3430                3435
Thr Ala Ile Pro Lys Asn Glu Lys Arg Val Val Asn Asp Asp Trp
    3440                3445                3450
Thr Ala Gly Asp Phe Val Asp Glu Lys Lys Pro Arg Val Ile Gln
    3455                3460                3465
Tyr Pro Glu Ala Lys Thr Arg Leu Ala Ile Thr Lys Val Met Tyr
    3470                3475                3480
Lys Trp Val Lys Gln Lys Pro Val Val Ile Pro Gly Tyr Glu Gly
    3485                3490                3495
Lys Thr Pro Leu Phe Gln Ile Phe Asp Lys Val Lys Lys Glu Trp
    3500                3505                3510
Asp Gln Phe Gln Asn Pro Val Ala Val Ser Phe Asp Thr Lys Ala
    3515                3520                3525
Trp Asp Thr Gln Val Thr Thr Lys Asp Leu Glu Leu Ile Arg Asp
    3530                3535                3540
Ile Gln Lys Tyr Tyr Phe Lys Lys Trp His Lys Phe Ile Asp
    3545                3550                3555
Thr Leu Thr Thr His Met Ser Glu Val Pro Val Ile Ser Ala Asp
    3560                3565                3570
Gly Glu Val Tyr Ile Arg Lys Gly Gln Arg Gly Ser Gly Gln Pro
    3575                3580                3585
Asp Thr Ser Ala Gly Asn Ser Met Leu Asn Val Leu Thr Met Val
    3590                3595                3600
Tyr Ala Phe Cys Glu Ala Thr Gly Val Pro Tyr Lys Ser Phe Asp
    3605                3610                3615
Arg Val Ala Lys Ile His Val Cys Gly Asp Asp Gly Phe Leu Ile
    3620                3625                3630
Thr Glu Arg Ala Leu Gly Glu Lys Phe Ala Ser Lys Gly Val Gln
    3635                3640                3645
```

```
Ile Leu Tyr Glu Ala Gly Lys Pro Gln Lys Ile Thr Glu Gly Asp
    3650                3655                3660

Lys Met Lys Val Ala Tyr Gln Phe Asp Asp Ile Glu Phe Cys Ser
    3665                3670                3675

His Thr Pro Ile Gln Val Arg Trp Ser Asp Asn Thr Ser Ser Tyr
    3680                3685                3690

Met Pro Gly Arg Asn Thr Thr Ile Leu Ala Lys Met Ala Thr
    3695                3700                3705

Arg Leu Asp Ser Ser Gly Glu Arg Gly Thr Ile Ala Tyr Glu Lys
    3710                3715                3720

Ala Val Ala Phe Ser Phe Leu Leu Met Tyr Ser Trp Asn Pro Leu
    3725                3730                3735

Ile Arg Arg Ile Cys Leu Leu Val Leu Ser Thr Glu Leu Gln Val
    3740                3745                3750

Lys Pro Gly Lys Ser Thr Thr Tyr Tyr Glu Gly Asp Pro Ile
    3755                3760                3765

Ser Ala Tyr Lys Glu Val Ile Gly His Asn Leu Phe Asp Leu Lys
    3770                3775                3780

Arg Thr Ser Phe Glu Lys Leu Ala Lys Leu Asn Leu Ser Met Ser
    3785                3790                3795

Val Leu Gly Ala Trp Thr Arg His Thr Ser Lys Arg Leu Leu Gln
    3800                3805                3810

Asp Cys Val Asn Ile Gly Val Lys Glu Gly Asn Trp Leu Val Asn
    3815                3820                3825

Ala Asp Arg Leu Val Ser Ser Lys Thr Gly Asn Arg Tyr Ile Pro
    3830                3835                3840

Gly Glu Gly His Thr Leu Gln Gly Arg His Tyr Glu Glu Leu Val
    3845                3850                3855

Leu Ala Arg Lys Gln Ile Asn Asn Phe Gln Gly Thr Asp Arg Tyr
    3860                3865                3870

Asn Leu Gly Pro Ile Val Asn Met Val Leu Arg Arg Leu Arg Val
    3875                3880                3885

Met Met Met Thr Leu Ile Gly Arg Gly Ala
    3890                3895

<210> SEQ ID NO 8
<211> LENGTH: 3898
<212> TYPE: PRT
<213> ORGANISM: CSFV

<400> SEQUENCE: 8

Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Arg Pro Leu
                20                  25                  30

Phe Gly Asp Pro Ser Glu Val His Pro Gln Ser Thr Leu Lys Leu Pro
            35                  40                  45

His Asp Arg Gly Arg Gly Asn Ile Lys Thr Thr Leu Lys Asn Leu Pro
        50                  55                  60

Arg Lys Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Val Gln Phe Cys
```

```
                100               105               110
Glu Val Thr Lys Arg Ile Gly Arg Val Thr Gly Ser Asp Gly Lys Leu
            115               120               125

Tyr His Thr Tyr Val Cys Ile Asp Gly Cys Ile Leu Leu Lys Leu Ala
            130               135           140

Lys Arg Gly Glu Pro Arg Thr Leu Lys Trp Ile Arg Asn Phe Thr Asp
145             150               155               160

Cys Pro Leu Trp Val Thr Ser Cys Ser Asp Asp Gly Ala Ser Gly Ser
                165               170               175

Lys Glu Lys Lys Pro Asp Arg Ile Asn Lys Gly Lys Leu Lys Ile Ala
            180               185               190

Pro Lys Glu His Glu Lys Asp Ser Arg Thr Arg Pro Pro Asp Ala Thr
            195               200               205

Ile Val Val Glu Gly Val Lys Tyr Gln Val Lys Lys Gly Lys Val
            210               215               220

Lys Gly Lys Asn Thr Gln Asp Gly Leu Tyr His Asn Lys Asn Lys Pro
225             230               235               240

Pro Glu Ser Arg Lys Lys Leu Glu Lys Ala Leu Leu Ala Trp Ala Val
                245               250               255

Ile Ala Ile Met Leu Tyr Gln Pro Val Glu Ala Glu Asn Ile Thr Gln
            260               265               270

Trp Asn Leu Ser Asp Asn Gly Thr Asn Gly Ile Gln His Ala Met Tyr
            275               280               285

Leu Arg Gly Val Asn Arg Ser Leu His Gly Ile Trp Pro Gly Lys Ile
            290               295               300

Cys Lys Gly Val Pro Thr His Leu Ala Thr Asp Val Glu Leu Lys Glu
305             310               315               320

Ile Gln Gly Met Met Asp Ala Ser Glu Gly Thr Asn Tyr Thr Cys Cys
                325               330               335

Lys Leu Gln Arg His Glu Trp Asn Lys His Gly Trp Cys Asn Trp His
            340               345               350

Asn Ile Asp Pro Trp Ile Gln Leu Met Asn Arg Thr Gln Ala Asp Leu
            355               360               365

Ala Glu Gly Pro Pro Val Lys Glu Cys Ala Val Thr Cys Arg Tyr Asp
            370               375               380

Lys Asp Ala Asp Ile Asn Val Val Thr Gln Ala Arg Asn Arg Pro Thr
385             390               395               400

Thr Leu Thr Gly Cys Lys Lys Gly Lys Asn Phe Ser Phe Ala Gly Thr
                405               410               415

Val Ile Glu Ser Pro Cys Asn Phe Asn Val Ser Val Glu Asp Thr Leu
            420               425               430

Tyr Gly Asp His Glu Ser Cys Ser Leu Leu Gln Asp Ala Ala Leu Tyr
            435               440               445

Leu Val Asp Gly Met Thr Asn Thr Ile Glu Asn Ala Arg Gln Gly Ala
450             455               460

Ala Arg Val Thr Ser Trp Leu Gly Arg Gln Leu Arg Ile Ala Gly Lys
465             470               475               480

Arg Leu Glu Gly Arg Ser Lys Trp Phe Gly Ala Tyr Ala Leu Ser
                485               490               495

Pro Tyr Cys Asn Val Thr Ser Lys Ile Gly Tyr Ile Trp Tyr Thr Asn
            500               505               510

Asn Cys Thr Pro Ala Cys Leu Pro Lys Asn Thr Lys Ile Ile Gly Pro
            515               520               525
```

-continued

```
Gly Lys Phe Asp Thr Asn Ala Glu Asp Gly Lys Ile Leu His Glu Met
            530                 535                 540
Gly Gly His Leu Ser Glu Phe Leu Leu Leu Ser Leu Val Val Leu Ser
545                 550                 555                 560
Asp Phe Ala Pro Glu Thr Ala Ser Ala Leu Tyr Leu Ile Phe His Tyr
                565                 570                 575
Val Ile Pro Gln Pro His Asp Glu Pro Glu Gly Cys Asp Thr Asn Gln
            580                 585                 590
Leu Asn Leu Thr Val Glu Leu Arg Thr Glu Asp Val Ile Pro Ser Ser
            595                 600                 605
Val Trp Asn Val Gly Lys Tyr Val Cys Val Arg Pro Asp Trp Trp Pro
610                 615                 620
Tyr Glu Thr Glu Val Ala Leu Leu Phe Glu Glu Val Gly Gln Val Val
625                 630                 635                 640
Lys Leu Ala Leu Arg Ala Leu Arg Asp Leu Thr Arg Val Trp Asn Ser
                645                 650                 655
Ala Ser Thr Ile Ala Phe Leu Ile Cys Leu Ile Lys Val Leu Arg Gly
                660                 665                 670
Gln Ile Val Gln Gly Val Val Trp Leu Leu Leu Val Thr Gly Ala Gln
            675                 680                 685
Gly Arg Leu Ala Cys Lys Glu Asp Tyr Arg Tyr Ala Ile Ser Ser Thr
690                 695                 700
Asp Glu Ile Gly Leu Leu Gly Ala Gly Gly Leu Thr Thr Thr Trp Lys
705                 710                 715                 720
Glu Tyr Asn His Asp Leu Gln Leu Asn Asp Gly Thr Val Lys Ala Ser
                725                 730                 735
Cys Val Ala Gly Ser Phe Lys Val Thr Ala Leu Asn Val Ser Arg
                740                 745                 750
Arg Tyr Leu Ala Ser Leu His Lys Lys Ala Leu Pro Thr Ser Val Thr
            755                 760                 765
Phe Glu Leu Leu Phe Asp Gly Thr Asn Pro Ser Thr Glu Glu Met Gly
            770                 775                 780
Asp Asp Phe Arg Ser Gly Leu Cys Pro Phe Asp Thr Ser Pro Val Val
785                 790                 795                 800
Lys Gly Lys Tyr Asn Thr Thr Leu Leu Asn Gly Ser Ala Phe Tyr Leu
                805                 810                 815
Val Cys Pro Ile Gly Trp Thr Gly Val Ile Glu Cys Thr Ala Val Ser
                820                 825                 830
Lys Asp Thr Leu Arg Thr Glu Val Lys Thr Phe Arg Arg Asp Lys
            835                 840                 845
Pro Phe Pro His Arg Met Asp Cys Val Thr Thr Val Glu Asn Glu
850                 855                 860
Asp Leu Phe Tyr Cys Lys Leu Gly Gly Asn Trp Thr Cys Val Lys Gly
865                 870                 875                 880
Glu Pro Val Val Tyr Thr Gly Gly Leu Val Lys Gln Cys Arg Trp Cys
                885                 890                 895
Gly Phe Asp Phe Asp Gly Pro Asp Gly Leu Pro His Tyr Pro Ile Gly
                900                 905                 910
Lys Cys Ile Leu Ala Asn Glu Thr Gly Tyr Arg Ile Val Asp Ser Thr
            915                 920                 925
Asp Cys Asn Arg Asp Gly Val Val Ile Ser Thr Glu Gly Ser His Glu
930                 935                 940
```

```
Cys Leu Ile Gly Asn Thr Thr Val Lys Val His Ala Ser Asp Glu Arg
945                 950                 955                 960

Leu Gly Pro Met Pro Cys Arg Pro Lys Glu Ile Val Ser Ser Ala Gly
                965                 970                 975

Pro Val Lys Lys Thr Ser Cys Thr Phe Asn Tyr Thr Lys Thr Leu Lys
            980                 985                 990

Asn Arg Tyr Tyr Glu Pro Arg Asp Ser Tyr Phe Gln Gln Tyr Met Leu
        995                 1000                1005

Lys Gly Glu Tyr Gln Tyr Trp Phe Asp Leu Asp Ala Thr Asp Arg
    1010                1015                1020

His Ser Asp Tyr Phe Ala Glu Phe Val Val Leu Val Val Val Ala
    1025                1030                1035

Leu Leu Gly Gly Arg Tyr Val Leu Trp Leu Ile Val Thr Tyr Val
    1040                1045                1050

Val Leu Thr Glu Gln Leu Ala Ala Gly Leu Pro Leu Gly Gln Gly
    1055                1060                1065

Glu Val Val Leu Ile Gly Asn Leu Ile Thr His Thr Asp Ile Glu
    1070                1075                1080

Val Val Val Tyr Phe Leu Leu Leu Tyr Leu Val Met Arg Asp Glu
    1085                1090                1095

Pro Ile Lys Lys Trp Ile Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Lys Gly Gly Lys Ile Asp Gly Gly Trp Gln Arg Leu Pro
    1130                1135                1140

Gly Thr Ser Phe Asp Ile Gln Leu Ala Leu Thr Val Ile Val Val
    1145                1150                1155

Ala Val Met Leu Leu Ala Lys Arg Asp Pro Thr Thr Val Pro Leu
    1160                1165                1170

Val Ile Thr Val Ala Thr Leu Arg Thr Ala Lys Met Thr Asn Gly
    1175                1180                1185

Leu Ser Thr Asp Ile Ala Ile Ala Thr Val Ser Ala Ala Leu Leu
    1190                1195                1200

Thr Trp Thr Tyr Ile Ser Asp Tyr Tyr Arg Tyr Lys Thr Trp Leu
    1205                1210                1215

Gln Tyr Leu Ile Ser Thr Val Thr Gly Ile Phe Leu Ile Arg Val
    1220                1225                1230

Leu Lys Gly Ile Gly Glu Leu Asp Leu His Thr Pro Thr Leu Pro
    1235                1240                1245

Ser His Arg Pro Leu Phe Phe Ile Leu Val Tyr Leu Ile Ser Thr
    1250                1255                1260

Ala Val Val Thr Arg Trp Asn Leu Asp Ile Ala Gly Leu Leu Leu
    1265                1270                1275

Gln Cys Val Pro Thr Leu Leu Met Val Phe Thr Met Trp Ala Asp
    1280                1285                1290

Ile Leu Thr Leu Ile Leu Ile Leu Pro Thr Tyr Glu Leu Thr Lys
    1295                1300                1305

Leu Tyr Tyr Leu Lys Glu Val Lys Ile Gly Ala Glu Lys Gly Trp
    1310                1315                1320

Leu Trp Lys Thr Asn Phe Lys Arg Val Asn Asp Ile Tyr Glu Val
    1325                1330                1335

Asp Gln Ala Gly Glu Gly Val Tyr Leu Phe Pro Ser Lys Gln Lys
```

|  | 1340 |  |  |  | 1345 |  |  |  | 1350 |  |  |
|---|---|---|---|---|---|---|---|---|---|---|---|
| Thr | Ser | Ser | Met | Thr | Gly | Thr | Met | Leu | Pro | Leu | Ile | Lys | Ala | Ile |
|  | 1355 |  |  |  | 1360 |  |  |  | 1365 |  |  |
| Leu | Ile | Ser | Cys | Val | Ser | Asn | Lys | Trp | Gln | Phe | Ile | Tyr | Leu | Leu |
|  | 1370 |  |  |  | 1375 |  |  |  | 1380 |  |  |
| Tyr | Leu | Ile | Phe | Glu | Val | Ser | Tyr | Tyr | Leu | His | Lys | Lys | Ile | Ile |
|  | 1385 |  |  |  | 1390 |  |  |  | 1395 |  |  |
| Asp | Glu | Ile | Ala | Gly | Gly | Thr | Asn | Phe | Ile | Ser | Arg | Leu | Val | Ala |
|  | 1400 |  |  |  | 1405 |  |  |  | 1410 |  |  |
| Ala | Leu | Ile | Glu | Val | Asn | Trp | Ala | Phe | Asp | Asn | Glu | Glu | Val | Arg |
|  | 1415 |  |  |  | 1420 |  |  |  | 1425 |  |  |
| Gly | Leu | Lys | Lys | Phe | Phe | Leu | Leu | Ser | Ser | Arg | Val | Lys | Glu | Leu |
|  | 1430 |  |  |  | 1435 |  |  |  | 1440 |  |  |
| Ile | Ile | Lys | His | Lys | Val | Arg | Asn | Glu | Val | Met | Val | Arg | Trp | Phe |
|  | 1445 |  |  |  | 1450 |  |  |  | 1455 |  |  |
| Gly | Asp | Glu | Glu | Val | Tyr | Gly | Met | Pro | Lys | Leu | Val | Gly | Leu | Val |
|  | 1460 |  |  |  | 1465 |  |  |  | 1470 |  |  |
| Lys | Ala | Ala | Thr | Leu | Ser | Lys | Asn | Lys | His | Cys | Ile | Leu | Cys | Thr |
|  | 1475 |  |  |  | 1480 |  |  |  | 1485 |  |  |
| Val | Cys | Glu | Asp | Arg | Glu | Trp | Arg | Gly | Glu | Thr | Cys | Pro | Lys | Cys |
|  | 1490 |  |  |  | 1495 |  |  |  | 1500 |  |  |
| Gly | Arg | Phe | Gly | Pro | Pro | Met | Thr | Cys | Gly | Met | Thr | Leu | Ala | Asp |
|  | 1505 |  |  |  | 1510 |  |  |  | 1515 |  |  |
| Phe | Glu | Glu | Lys | His | Tyr | Lys | Arg | Ile | Phe | Phe | Arg | Glu | Asp | Gln |
|  | 1520 |  |  |  | 1525 |  |  |  | 1530 |  |  |
| Ser | Glu | Gly | Pro | Val | Arg | Glu | Glu | Tyr | Ala | Gly | Tyr | Leu | Gln | Tyr |
|  | 1535 |  |  |  | 1540 |  |  |  | 1545 |  |  |
| Arg | Ala | Arg | Gly | Gln | Leu | Phe | Leu | Arg | Asn | Leu | Pro | Val | Leu | Ala |
|  | 1550 |  |  |  | 1555 |  |  |  | 1560 |  |  |
| Thr | Lys | Val | Lys | Met | Leu | Leu | Val | Gly | Asn | Leu | Gly | Thr | Glu | Val |
|  | 1565 |  |  |  | 1570 |  |  |  | 1575 |  |  |
| Gly | Asp | Leu | Glu | His | Leu | Gly | Trp | Val | Leu | Arg | Gly | Pro | Ala | Val |
|  | 1580 |  |  |  | 1585 |  |  |  | 1590 |  |  |
| Cys | Lys | Lys | Val | Thr | Glu | His | Glu | Lys | Cys | Thr | Thr | Ser | Met | Met |
|  | 1595 |  |  |  | 1600 |  |  |  | 1605 |  |  |
| Asp | Lys | Leu | Thr | Ala | Phe | Phe | Gly | Val | Met | Pro | Arg | Gly | Thr | Thr |
|  | 1610 |  |  |  | 1615 |  |  |  | 1620 |  |  |
| Pro | Arg | Ala | Pro | Val | Arg | Phe | Pro | Thr | Ser | Leu | Leu | Lys | Ile | Arg |
|  | 1625 |  |  |  | 1630 |  |  |  | 1635 |  |  |
| Arg | Gly | Leu | Glu | Thr | Gly | Trp | Ala | Tyr | Thr | His | Gln | Gly | Gly | Ile |
|  | 1640 |  |  |  | 1645 |  |  |  | 1650 |  |  |
| Ser | Ser | Val | Asp | His | Val | Thr | Cys | Gly | Lys | Asp | Leu | Leu | Val | Cys |
|  | 1655 |  |  |  | 1660 |  |  |  | 1665 |  |  |
| Asp | Thr | Met | Gly | Arg | Thr | Arg | Val | Val | Cys | Gln | Ser | Asn | Asn | Lys |
|  | 1670 |  |  |  | 1675 |  |  |  | 1680 |  |  |
| Met | Thr | Asp | Glu | Ser | Glu | Tyr | Gly | Val | Lys | Thr | Asp | Ser | Gly | Cys |
|  | 1685 |  |  |  | 1690 |  |  |  | 1695 |  |  |
| Pro | Glu | Gly | Ala | Arg | Cys | Tyr | Val | Phe | Asn | Pro | Glu | Ala | Val | Asn |
|  | 1700 |  |  |  | 1705 |  |  |  | 1710 |  |  |
| Ile | Ser | Gly | Thr | Lys | Gly | Ala | Met | Val | His | Leu | Gln | Lys | Thr | Gly |
|  | 1715 |  |  |  | 1720 |  |  |  | 1725 |  |  |
| Gly | Glu | Phe | Thr | Cys | Val | Thr | Ala | Ser | Gly | Thr | Pro | Ala | Phe | Phe |
|  | 1730 |  |  |  | 1735 |  |  |  | 1740 |  |  |

```
Asp Leu Lys Asn Leu Lys Gly Trp Ser Gly Leu Pro Ile Phe Glu
    1745            1750                1755

Ala Ser Ser Gly Arg Val Val Gly Arg Val Lys Val Gly Lys Asn
    1760            1765                1770

Glu Asp Ser Lys Pro Thr Lys Leu Met Ser Gly Ile Gln Thr Val
    1775            1780                1785

Ser Lys Ser Thr Thr Asp Leu Thr Glu Met Val Lys Lys Ile Thr
    1790            1795                1800

Thr Met Ser Arg Gly Glu Phe Arg Gln Ile Thr Leu Ala Thr Gly
    1805            1810                1815

Ala Gly Lys Thr Thr Glu Leu Pro Arg Ser Val Ile Glu Glu Ile
    1820            1825                1830

Gly Arg His Lys Arg Val Leu Val Leu Ile Pro Leu Arg Ala Ala
    1835            1840                1845

Ala Glu Ser Val Tyr Gln Tyr Met Arg Gln Lys His Pro Ser Ile
    1850            1855                1860

Ala Phe Asn Leu Arg Ile Gly Glu Met Lys Glu Gly Asp Met Ala
    1865            1870                1875

Thr Gly Ile Thr Tyr Ala Ser Tyr Gly Tyr Phe Cys Gln Met Pro
    1880            1885                1890

Gln Pro Lys Leu Arg Ala Ala Met Val Glu Tyr Ser Phe Ile Phe
    1895            1900                1905

Leu Asp Glu Tyr His Cys Ala Thr Pro Glu Gln Leu Ala Ile Met
    1910            1915                1920

Gly Lys Ile His Arg Phe Ser Glu Asn Leu Arg Val Val Ala Met
    1925            1930                1935

Thr Ala Thr Pro Val Gly Thr Val Thr Thr Thr Gly Gln Lys His
    1940            1945                1950

Pro Ile Glu Glu Phe Ile Ala Pro Asp Val Met Lys Gly Glu Asp
    1955            1960                1965

Leu Gly Ser Glu Tyr Leu Asp Ile Ala Gly Leu Lys Ile Pro Val
    1970            1975                1980

Glu Glu Met Lys Ser Asn Met Leu Val Phe Val Pro Thr Arg Asn
    1985            1990                1995

Met Ala Val Glu Thr Ala Lys Lys Leu Lys Ala Lys Gly Tyr Asn
    2000            2005                2010

Ser Gly Tyr Tyr Tyr Ser Gly Glu Asp Pro Ser Asn Leu Arg Val
    2015            2020                2025

Val Thr Ser Gln Ser Pro Tyr Val Val Val Ala Thr Asn Ala Ile
    2030            2035                2040

Glu Pro Gly Val Thr Leu Pro Asp Leu Asp Val Val Val Asp Thr
    2045            2050                2055

Gly Leu Lys Cys Glu Lys Arg Ile Arg Leu Ser Pro Lys Met Pro
    2060            2065                2070

Phe Ile Val Thr Gly Leu Lys Arg Met Ala Val Thr Ile Gly Glu
    2075            2080                2085

Gln Ala Gln Arg Arg Gly Arg Val Gly Arg Val Lys Pro Gly Arg
    2090            2095                2100

Tyr Tyr Arg Ser Gln Glu Thr Pro Val Gly Ser Lys Asp Tyr His
    2105            2110                2115

Tyr Asp Leu Leu Gln Ala Gln Arg Tyr Gly Ile Glu Asp Gly Ile
    2120            2125                2130
```

```
Asn Ile Thr Lys Ser Phe Arg Glu Met Asn Tyr Asp Trp Ser Leu
    2135                2140                2145

Tyr Glu Glu Asp Ser Leu Met Ile Thr Gln Leu Glu Ile Leu Asn
    2150                2155                2160

Asn Leu Leu Ile Ser Asp Glu Leu Pro Met Ala Val Lys Asn Ile
    2165                2170                2175

Met Ala Arg Thr Asp His Pro Glu Pro Ile Gln Leu Ala Tyr Asn
    2180                2185                2190

Ser Tyr Glu Thr Gln Val Pro Val Leu Phe Pro Lys Ile Lys Asn
    2195                2200                2205

Gly Glu Val Thr Asp Ser Tyr Asp Asn Tyr Thr Phe Leu Asn Ala
    2210                2215                2220

Arg Lys Leu Gly Asp Val Pro Pro Tyr Val Tyr Ala Thr Glu
    2225                2230                2235

Asp Glu Asp Leu Ala Val Glu Leu Leu Gly Leu Asp Trp Pro Asp
    2240                2245                2250

Pro Gly Asn Leu Gly Thr Val Glu Thr Gly Arg Ala Leu Lys Gln
    2255                2260                2265

Val Val Gly Leu Ser Thr Ala Glu Asn Ala Leu Leu Val Ala Leu
    2270                2275                2280

Phe Gly Tyr Val Gly Tyr Gln Ala Leu Ser Lys Arg His Ile Pro
    2285                2290                2295

Val Val Thr Asp Ile Tyr Ser Ile Glu Asp His Arg Leu Glu Asp
    2300                2305                2310

Thr Thr His Leu Gln Tyr Ala Pro Asn Ala Ile Lys Thr Glu Gly
    2315                2320                2325

Lys Glu Thr Glu Leu Lys Glu Leu Ala Gln Gly Asp Val Gln Arg
    2330                2335                2340

Cys Val Glu Ala Met Thr Asn Tyr Ala Arg Glu Gly Ile Gln Phe
    2345                2350                2355

Met Lys Ser Gln Ala Leu Lys Val Lys Glu Thr Pro Thr Tyr Lys
    2360                2365                2370

Glu Thr Met Asp Thr Val Thr Asp Tyr Val Lys Lys Phe Met Glu
    2375                2380                2385

Ala Leu Ala Asp Ser Lys Glu Asp Ile Ile Lys Tyr Gly Leu Trp
    2390                2395                2400

Gly Thr His Thr Ala Leu Tyr Lys Ser Ile Ser Ala Arg Leu Gly
    2405                2410                2415

Gly Glu Thr Ala Phe Ala Thr Leu Val Val Lys Trp Leu Ala Phe
    2420                2425                2430

Gly Gly Glu Ser Ile Ala Asp His Val Lys Gln Ala Ala Thr Asp
    2435                2440                2445

Leu Val Val Tyr Tyr Ile Ile Asn Arg Pro Gln Phe Pro Gly Asp
    2450                2455                2460

Thr Glu Thr Gln Gln Asp Gly Arg Lys Phe Val Ala Ser Leu Leu
    2465                2470                2475

Ala Ser Ala Leu Ala Thr Tyr Thr Tyr Lys Ser Trp Asn Tyr Asn
    2480                2485                2490

Asn Leu Ser Lys Ile Val Glu Pro Ala Leu Ala Thr Leu Pro Tyr
    2495                2500                2505

Ala Ala Thr Ala Leu Lys Leu Phe Ala Pro Thr Arg Leu Glu Ser
    2510                2515                2520

Val Val Ile Leu Ser Thr Ala Ile Tyr Lys Thr Tyr Leu Ser Ile
```

-continued

```
             2525                2530                2535

Arg Arg Gly Lys Ser Asp Gly Leu Leu Gly Thr Gly Val Ser Ala
    2540                2545                2550

Ala Met Glu Ile Met Ser Gln Asn Pro Val Ser Val Gly Ile Ala
    2555                2560                2565

Val Met Leu Gly Val Gly Ala Val Ala Ala His Asn Ala Ile Glu
    2570                2575                2580

Ala Ser Glu Gln Lys Arg Thr Leu Leu Met Lys Val Phe Val Lys
    2585                2590                2595

Asn Phe Leu Asp Gln Ala Ala Thr Asp Glu Leu Val Lys Glu Ser
    2600                2605                2610

Pro Glu Lys Ile Ile Met Ala Leu Phe Glu Ala Val Gln Thr Val
    2615                2620                2625

Gly Asn Pro Leu Arg Leu Val Tyr His Leu Tyr Gly Val Phe Tyr
    2630                2635                2640

Lys Gly Trp Arg Pro Lys Glu Leu Ala Gln Arg Thr Ala Gly Arg
    2645                2650                2655

Asn Leu Phe Thr Leu Ile Met Phe Glu Ala Val Glu Leu Leu Gly
    2660                2665                2670

Val Asp Ser Glu Gly Lys Val Arg Gln Leu Ser Ser Asn Tyr Ile
    2675                2680                2685

Leu Glu Leu Leu Tyr Lys Phe Arg Asp Ser Ile Lys Ser Ser Val
    2690                2695                2700

Arg Glu Met Ala Ile Ser Trp Ala Pro Ala Pro Phe Ser Cys Asp
    2705                2710                2715

Trp Thr Pro Thr Asp Asp Arg Ile Gly Leu Pro Gln Asp Asn Phe
    2720                2725                2730

His Gln Val Glu Thr Lys Cys Pro Cys Gly Tyr Lys Met Lys Ala
    2735                2740                2745

Val Lys Asn Cys Ala Gly Glu Leu Arg Leu Leu Glu Glu Glu Gly
    2750                2755                2760

Ser Phe Leu Cys Arg Asn Lys Phe Gly Arg Gly Ser Arg Asn Tyr
    2765                2770                2775

Arg Val Thr Lys Tyr Tyr Asp Asp Asn Leu Leu Glu Ile Lys Pro
    2780                2785                2790

Val Ile Arg Met Glu Gly His Val Glu Leu Tyr Tyr Lys Gly Ala
    2795                2800                2805

Thr Ile Lys Leu Asp Phe Asn Asn Ser Lys Thr Ile Leu Ala Thr
    2810                2815                2820

Asp Lys Trp Glu Val Asp His Ser Thr Leu Val Arg Val Leu Lys
    2825                2830                2835

Arg His Thr Gly Ala Gly Tyr His Gly Ala Tyr Leu Gly Glu Lys
    2840                2845                2850

Pro Asn His Lys His Leu Ile Glu Arg Asp Cys Ala Thr Ile Thr
    2855                2860                2865

Lys Asp Lys Val Cys Phe Leu Lys Met Lys Arg Gly Cys Ala Phe
    2870                2875                2880

Thr Tyr Asp Leu Ser Leu His Asn Leu Ala Arg Leu Ile Glu Leu
    2885                2890                2895

Val His Lys Asn Asn Leu Glu Asp Lys Glu Ile Pro Ala Ala Thr
    2900                2905                2910

Val Thr Thr Trp Leu Ala Tyr Thr Phe Val Asn Glu Asp Ile Gly
    2915                2920                2925
```

```
Thr Ile Lys Pro Ala Phe Gly Glu Lys Val Thr Leu Glu Met Gln
    2930            2935            2940

Glu Glu Ile Thr Leu Gln Pro Ala Val Val Asp Thr Thr Asp
    2945            2950            2955

Val Ala Val Thr Val Val Gly Glu Ala Pro Thr Met Thr Thr Gly
    2960            2965            2970

Glu Thr Pro Thr Val Phe Thr Ser Ser Gly Ser Gly Leu Lys Asn
    2975            2980            2985

Gln Gln Val Leu Lys Leu Gly Val Gly Glu Gly Gln Tyr Pro Gly
    2990            2995            3000

Thr Asn Pro Gln Arg Ala Ser Leu His Glu Ala Ile Gln Gly Ala
    3005            3010            3015

Asp Glu Arg Pro Ser Val Leu Ile Leu Gly Ser Asp Lys Ala Thr
    3020            3025            3030

Ser Asn Arg Val Lys Thr Ala Lys Asn Val Lys Val Tyr Arg Gly
    3035            3040            3045

Arg Asp Pro Leu Glu Val Arg Asp Met Met Arg Arg Gly Lys Ile
    3050            3055            3060

Leu Val Val Ala Leu Ser Arg Val Asp Asn Ala Leu Leu Lys Phe
    3065            3070            3075

Val Asp Tyr Lys Gly Thr Phe Leu Thr Arg Glu Ala Leu Glu Ala
    3080            3085            3090

Leu Ser Leu Gly Arg Pro Lys Lys Lys Asn Ile Thr Lys Ala Glu
    3095            3100            3105

Ala Gln Cys Leu Leu Cys Pro Glu Asp Gln Met Glu Glu Leu Pro
    3110            3115            3120

Asp Trp Phe Ala Ala Gly Glu Pro Ile Phe Leu Glu Ala Asn Ile
    3125            3130            3135

Lys His Asp Arg Leu His Leu Val Gly Asp Ile Ala Thr Ile Lys
    3140            3145            3150

Glu Lys Ala Lys Gln Leu Gly Ala Thr Asp Ser Thr Lys Ile Ser
    3155            3160            3165

Lys Glu Val Gly Ala Lys Val Tyr Ser Met Lys Leu Ser Asn Trp
    3170            3175            3180

Val Met Gln Glu Glu Asn Lys Gln Gly Asn Leu Thr Pro Leu Phe
    3185            3190            3195

Glu Glu Leu Leu Gln Gln Cys Pro Pro Gly Gly Gln Asn Lys Thr
    3200            3205            3210

Ala His Met Val Ser Ala Tyr Gln Leu Ala Gln Gly Asn Trp Met
    3215            3220            3225

Pro Thr Ser Cys His Val Phe Met Gly Thr Ile Ser Ala Arg Arg
    3230            3235            3240

Thr Lys Thr His Pro Tyr Glu Ala Tyr Val Lys Leu Arg Glu Leu
    3245            3250            3255

Val Glu Glu His Lys Met Lys Thr Leu Cys Pro Gly Ser Ser Leu
    3260            3265            3270

Gly Lys His Asn Asp Trp Ile Ile Gly Lys Ile Lys Tyr Gln Gly
    3275            3280            3285

Asn Leu Arg Thr Lys His Met Leu Asn Pro Gly Lys Val Ala Glu
    3290            3295            3300

Gln Leu Cys Arg Glu Gly His Arg His Asn Val Tyr Asn Lys Thr
    3305            3310            3315
```

-continued

Ile Ser Ser Val Met Thr Ala Thr Gly Ile Arg Leu Glu Lys Leu
3320            3325            3330

Pro Val Val Arg Ala Gln Thr Asp Pro Thr Asn Phe His Gln Ala
3335            3340            3345

Ile Arg Asp Lys Ile Asp Lys Glu Glu Asn Leu Gln Thr Pro Gly
3350            3355            3360

Leu His Lys Lys Leu Met Glu Val Phe Asn Ala Leu Lys Arg Pro
3365            3370            3375

Glu Leu Glu Ser Ser Tyr Asp Ala Val Glu Trp Glu Glu Leu Glu
3380            3385            3390

Arg Gly Ile Asn Arg Lys Gly Ala Ala Gly Phe Phe Glu Arg Lys
3395            3400            3405

Asn Ile Gly Glu Ile Leu Asp Ser Glu Lys Asn Lys Val Glu Glu
3410            3415            3420

Ile Ile Asp Asn Leu Lys Lys Gly Arg Asn Ile Lys Tyr Tyr Glu
3425            3430            3435

Thr Ala Ile Pro Lys Asn Glu Lys Arg Val Val Asn Asp Asp Trp
3440            3445            3450

Thr Ala Gly Asp Phe Val Asp Glu Lys Lys Pro Arg Val Ile Gln
3455            3460            3465

Tyr Pro Glu Ala Lys Thr Arg Leu Ala Ile Thr Lys Val Met Tyr
3470            3475            3480

Lys Trp Val Lys Gln Lys Pro Val Val Ile Pro Gly Tyr Glu Gly
3485            3490            3495

Lys Thr Pro Leu Phe Gln Ile Phe Asp Lys Val Lys Lys Glu Trp
3500            3505            3510

Asp Gln Phe Gln Asn Pro Val Ala Val Ser Phe Asp Thr Lys Ala
3515            3520            3525

Trp Asp Thr Gln Val Thr Thr Lys Asp Leu Glu Leu Ile Arg Asp
3530            3535            3540

Ile Gln Lys Tyr Tyr Phe Lys Lys Lys Trp His Lys Phe Ile Asp
3545            3550            3555

Thr Leu Thr Thr His Met Ser Glu Val Pro Val Ile Ser Ala Asp
3560            3565            3570

Gly Glu Val Tyr Ile Arg Lys Gly Gln Arg Gly Ser Gly Gln Pro
3575            3580            3585

Asp Thr Ser Ala Gly Asn Ser Met Leu Asn Val Leu Thr Met Val
3590            3595            3600

Tyr Ala Phe Cys Glu Ala Thr Gly Val Pro Tyr Lys Ser Phe Asp
3605            3610            3615

Arg Val Ala Lys Ile His Val Cys Gly Asp Asp Gly Phe Leu Ile
3620            3625            3630

Thr Glu Arg Ala Leu Gly Glu Lys Phe Ala Ser Lys Gly Val Gln
3635            3640            3645

Ile Leu Tyr Glu Ala Gly Lys Pro Gln Lys Ile Thr Glu Gly Asp
3650            3655            3660

Lys Met Lys Val Ala Tyr Gln Phe Asp Asp Ile Glu Phe Cys Ser
3665            3670            3675

His Thr Pro Ile Gln Val Arg Trp Ser Asp Asn Thr Ser Ser Tyr
3680            3685            3690

Met Pro Gly Arg Asn Thr Thr Thr Ile Leu Ala Lys Met Ala Thr
3695            3700            3705

Arg Leu Asp Ser Ser Gly Glu Arg Gly Thr Ile Ala Tyr Glu Lys

```
                     3710                3715                3720

Ala Val Ala Phe Ser Phe Leu Leu Met Tyr Ser Trp Asn Pro Leu
    3725                3730                3735

Ile Arg Arg Ile Cys Leu Leu Val Leu Ser Thr Glu Leu Gln Val
    3740                3745                3750

Lys Pro Gly Lys Ser Thr Thr Tyr Tyr Tyr Glu Gly Asp Pro Ile
    3755                3760                3765

Ser Ala Tyr Lys Glu Val Ile Gly His Asn Leu Phe Asp Leu Lys
    3770                3775                3780

Arg Thr Ser Phe Glu Lys Leu Ala Lys Leu Asn Leu Ser Met Ser
    3785                3790                3795

Val Leu Gly Ala Trp Thr Arg His Thr Ser Lys Arg Leu Leu Gln
    3800                3805                3810

Asp Cys Val Asn Ile Gly Val Lys Glu Gly Asn Trp Leu Val Asn
    3815                3820                3825

Ala Asp Arg Leu Val Ser Ser Lys Thr Gly Asn Arg Tyr Ile Pro
    3830                3835                3840

Gly Glu Gly His Thr Leu Gln Gly Arg His Tyr Glu Glu Leu Val
    3845                3850                3855

Leu Ala Arg Lys Gln Ile Asn Asn Phe Gln Gly Thr Asp Arg Tyr
    3860                3865                3870

Asn Leu Gly Pro Ile Val Asn Met Val Leu Arg Arg Leu Arg Val
    3875                3880                3885

Met Met Met Thr Leu Ile Gly Arg Gly Ala
    3890                3895

<210> SEQ ID NO 9
<211> LENGTH: 3897
<212> TYPE: PRT
<213> ORGANISM: CSFV

<400> SEQUENCE: 9

Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Arg Pro Leu
                20                  25                  30

Phe Gly Asp Pro Ser Glu Val His Pro Gln Ser Thr Leu Lys Leu Pro
            35                  40                  45

His Asp Arg Gly Arg Gly Asn Ile Lys Thr Thr Leu Lys Asn Leu Pro
        50                  55                  60

Arg Lys Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Val Gln Phe Cys
            100                 105                 110

Glu Val Thr Lys Arg Ile Gly Arg Val Thr Gly Ser Asp Gly Lys Leu
        115                 120                 125

Tyr His Thr Tyr Val Cys Ile Asp Gly Cys Ile Leu Leu Lys Leu Ala
    130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Asp Gly Ala Ser Gly Ser
                165                 170                 175
```

```
Lys Glu Lys Lys Pro Asp Arg Ile Asn Lys Gly Lys Leu Lys Ile Ala
            180                 185                 190

Pro Lys Glu His Glu Lys Asp Ser Arg Thr Arg Pro Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Asn Arg Ser Leu His Gly Ile Trp Pro Gly Lys Ile
    290                 295                 300

Cys Lys Gly Val Pro Thr His Leu Ala Thr Asp Val Glu Leu Lys Glu
305                 310                 315                 320

Ile Gln Gly Met Met Asp Ala Ser Glu Gly Thr Asn Tyr Thr Cys Cys
                325                 330                 335

Lys Leu Gln Arg His Glu Trp Asn Lys Gly Trp Cys Asn Trp His Asn
            340                 345                 350

Ile Asp Pro Trp Ile Gln Leu Met Asn Arg Thr Gln Ala Asp Leu Ala
        355                 360                 365

Glu Gly Pro Pro Val Lys Glu Cys Ala Val Thr Cys Arg Tyr Asp Lys
    370                 375                 380

Asp Ala Asp Ile Asn Val Val Thr Gln Ala Arg Asn Arg Pro Thr Thr
385                 390                 395                 400

Leu Thr Gly Cys Lys Lys Gly Lys Asn Phe Ser Phe Ala Gly Thr Val
                405                 410                 415

Ile Glu Ser Pro Cys Asn Phe Asn Val Ser Val Glu Asp Thr Leu Tyr
            420                 425                 430

Gly Asp His Glu Ser Cys Ser Leu Leu Gln Asp Ala Ala Leu Tyr Leu
        435                 440                 445

Val Asp Gly Met Thr Asn Thr Ile Glu Asn Ala Arg Gln Gly Ala Ala
    450                 455                 460

Arg Val Thr Ser Trp Leu Gly Arg Gln Leu Arg Ile Ala Gly Lys Arg
465                 470                 475                 480

Leu Glu Gly Arg Ser Lys Thr Trp Phe Gly Ala Tyr Ala Leu Ser Pro
                485                 490                 495

Tyr Cys Asn Val Thr Ser Lys Ile Gly Tyr Ile Trp Tyr Thr Asn Asn
            500                 505                 510

Cys Thr Pro Ala Cys Leu Pro Lys Asn Thr Lys Ile Ile Gly Pro Gly
        515                 520                 525

Lys Phe Asp Thr Asn Ala Glu Asp Gly Lys Ile Leu His Glu Met Gly
    530                 535                 540

Gly His Leu Ser Glu Phe Leu Leu Leu Ser Leu Val Val Leu Ser Asp
545                 550                 555                 560

Phe Ala Pro Glu Thr Ala Ser Ala Leu Tyr Leu Ile Phe His Tyr Val
                565                 570                 575

Ile Pro Gln Pro His Asp Glu Pro Glu Gly Cys Asp Thr Asn Gln Leu
            580                 585                 590

Asn Leu Thr Val Glu Leu Arg Thr Glu Asp Val Ile Pro Ser Ser Val
```

```
                595                 600                 605
Trp Asn Val Gly Lys Tyr Val Cys Val Arg Pro Asp Trp Trp Pro Tyr
610                 615                 620
Glu Thr Glu Val Ala Leu Leu Phe Glu Glu Val Gly Gln Val Val Lys
625                 630                 635                 640
Leu Ala Leu Arg Ala Leu Arg Asp Leu Thr Arg Val Trp Asn Ser Ala
                645                 650                 655
Ser Thr Ile Ala Phe Leu Ile Cys Leu Ile Lys Val Leu Arg Gly Gln
                660                 665                 670
Ile Val Gln Gly Val Val Trp Leu Leu Leu Val Thr Gly Ala Gln Gly
                675                 680                 685
Arg Leu Ala Cys Lys Glu Asp Tyr Arg Tyr Ala Ile Ser Ser Thr Asp
                690                 695                 700
Glu Ile Gly Leu Leu Gly Ala Gly Gly Leu Thr Thr Thr Trp Lys Glu
705                 710                 715                 720
Tyr Asn His Asp Leu Gln Leu Asn Asp Gly Thr Val Lys Ala Ser Cys
                725                 730                 735
Val Ala Gly Ser Phe Lys Val Thr Ala Leu Asn Val Val Ser Arg Arg
                740                 745                 750
Tyr Leu Ala Ser Leu His Lys Lys Ala Leu Pro Thr Ser Val Thr Phe
                755                 760                 765
Glu Leu Leu Phe Asp Gly Thr Asn Pro Ser Thr Glu Glu Met Gly Asp
770                 775                 780
Asp Phe Arg Ser Gly Leu Cys Pro Phe Asp Thr Ser Pro Val Val Lys
785                 790                 795                 800
Gly Lys Tyr Asn Thr Thr Leu Leu Asn Gly Ser Ala Phe Tyr Leu Val
                805                 810                 815
Cys Pro Ile Gly Trp Thr Gly Val Ile Glu Cys Thr Ala Val Ser Lys
                820                 825                 830
Asp Thr Leu Arg Thr Glu Val Val Lys Thr Phe Arg Arg Asp Lys Pro
                835                 840                 845
Phe Pro His Arg Met Asp Cys Val Thr Thr Thr Val Glu Asn Glu Asp
850                 855                 860
Leu Phe Tyr Cys Lys Leu Gly Gly Asn Trp Thr Cys Val Lys Gly Glu
865                 870                 875                 880
Pro Val Val Tyr Thr Gly Gly Leu Val Lys Gln Cys Arg Trp Cys Gly
                885                 890                 895
Phe Asp Phe Asp Gly Pro Asp Gly Leu Pro His Tyr Pro Ile Gly Lys
                900                 905                 910
Cys Ile Leu Ala Asn Glu Thr Gly Tyr Arg Ile Val Asp Ser Thr Asp
                915                 920                 925
Cys Asn Arg Asp Gly Val Val Ile Ser Thr Glu Gly Ser His Glu Cys
                930                 935                 940
Leu Ile Gly Asn Thr Thr Val Lys Val His Ala Ser Asp Glu Arg Leu
945                 950                 955                 960
Gly Pro Met Pro Cys Arg Pro Lys Glu Ile Val Ser Ser Ala Gly Pro
                965                 970                 975
Val Lys Lys Thr Ser Cys Thr Phe Asn Tyr Thr Lys Thr Leu Lys Asn
                980                 985                 990
Arg Tyr Tyr Glu Pro Arg Asp Ser  Tyr Phe Gln Gln Tyr  Met Leu Lys
                995                1000                1005
Gly Glu  Tyr Gln Tyr Trp Phe  Asp Leu Asp Ala Thr  Asp Arg His
1010                1015                1020
```

-continued

Ser Asp Tyr Phe Ala Glu Phe Val Val Leu Val Val Val Ala Leu
    1025                1030                1035

Leu Gly Gly Arg Tyr Val Leu Trp Leu Ile Val Thr Tyr Val Val
    1040                1045                1050

Leu Thr Glu Gln Leu Ala Ala Gly Leu Pro Leu Gly Gln Gly Glu
    1055                1060                1065

Val Val Leu Ile Gly Asn Leu Ile Thr His Thr Asp Ile Glu Val
    1070                1075                1080

Val Val Tyr Phe Leu Leu Leu Tyr Leu Val Met Arg Asp Glu Pro
    1085                1090                1095

Ile Lys Lys Trp Ile Leu Leu Leu Phe His Ala Met Thr Asn Asn
    1100                1105                1110

Pro Val Lys Thr Ile Thr Val Ala Leu Leu Met Val Ser Gly Val
    1115                1120                1125

Ala Lys Gly Gly Lys Ile Asp Gly Gly Trp Gln Arg Leu Pro Gly
    1130                1135                1140

Thr Ser Phe Asp Ile Gln Leu Ala Leu Thr Val Ile Val Val Ala
    1145                1150                1155

Val Met Leu Leu Ala Lys Arg Asp Pro Thr Thr Val Pro Leu Val
    1160                1165                1170

Ile Thr Val Ala Thr Leu Arg Thr Ala Lys Met Thr Asn Gly Leu
    1175                1180                1185

Ser Thr Asp Ile Ala Ile Ala Thr Val Ser Ala Ala Leu Leu Thr
    1190                1195                1200

Trp Thr Tyr Ile Ser Asp Tyr Tyr Arg Tyr Lys Thr Trp Leu Gln
    1205                1210                1215

Tyr Leu Ile Ser Thr Val Thr Gly Ile Phe Leu Ile Arg Val Leu
    1220                1225                1230

Lys Gly Ile Gly Glu Leu Asp Leu His Thr Pro Thr Leu Pro Ser
    1235                1240                1245

His Arg Pro Leu Phe Phe Ile Leu Val Tyr Leu Ile Ser Thr Ala
    1250                1255                1260

Val Val Thr Arg Trp Asn Leu Asp Ile Ala Gly Leu Leu Leu Gln
    1265                1270                1275

Cys Val Pro Thr Leu Leu Met Val Phe Thr Met Trp Ala Asp Ile
    1280                1285                1290

Leu Thr Leu Ile Leu Ile Leu Pro Thr Tyr Glu Leu Thr Lys Leu
    1295                1300                1305

Tyr Tyr Leu Lys Glu Val Lys Ile Gly Ala Glu Lys Gly Trp Leu
    1310                1315                1320

Trp Lys Thr Asn Phe Lys Arg Val Asn Asp Ile Tyr Glu Val Asp
    1325                1330                1335

Gln Ala Gly Glu Gly Val Tyr Leu Phe Pro Ser Lys Gln Lys Thr
    1340                1345                1350

Ser Ser Met Thr Gly Thr Met Leu Pro Leu Ile Lys Ala Ile Leu
    1355                1360                1365

Ile Ser Cys Val Ser Asn Lys Trp Gln Phe Ile Tyr Leu Leu Tyr
    1370                1375                1380

Leu Ile Phe Glu Val Ser Tyr Tyr Leu His Lys Lys Ile Ile Asp
    1385                1390                1395

Glu Ile Ala Gly Gly Thr Asn Phe Ile Ser Arg Leu Val Ala Ala
    1400                1405                1410

-continued

Leu Ile Glu Val Asn Trp Ala Phe Asp Asn Glu Glu Val Arg Gly
1415                1420                1425

Leu Lys Lys Phe Phe Leu Leu Ser Ser Arg Val Lys Glu Leu Ile
1430                1435                1440

Ile Lys His Lys Val Arg Asn Glu Val Met Val Arg Trp Phe Gly
1445                1450                1455

Asp Glu Glu Val Tyr Gly Met Pro Lys Leu Val Gly Leu Val Lys
1460                1465                1470

Ala Ala Thr Leu Ser Lys Asn Lys His Cys Ile Leu Cys Thr Val
1475                1480                1485

Cys Glu Asp Arg Glu Trp Arg Gly Glu Thr Cys Pro Lys Cys Gly
1490                1495                1500

Arg Phe Gly Pro Pro Met Thr Cys Gly Met Thr Leu Ala Asp Phe
1505                1510                1515

Glu Glu Lys His Tyr Lys Arg Ile Phe Phe Arg Glu Asp Gln Ser
1520                1525                1530

Glu Gly Pro Val Arg Glu Glu Tyr Ala Gly Tyr Leu Gln Tyr Arg
1535                1540                1545

Ala Arg Gly Gln Leu Phe Leu Arg Asn Leu Pro Val Leu Ala Thr
1550                1555                1560

Lys Val Lys Met Leu Leu Val Gly Asn Leu Gly Thr Glu Val Gly
1565                1570                1575

Asp Leu Glu His Leu Gly Trp Val Leu Arg Gly Pro Ala Val Cys
1580                1585                1590

Lys Lys Val Thr Glu His Glu Lys Cys Thr Thr Ser Met Met Asp
1595                1600                1605

Lys Leu Thr Ala Phe Phe Gly Val Met Pro Arg Gly Thr Thr Pro
1610                1615                1620

Arg Ala Pro Val Arg Phe Pro Thr Ser Leu Leu Lys Ile Arg Arg
1625                1630                1635

Gly Leu Glu Thr Gly Trp Ala Tyr Thr His Gln Gly Gly Ile Ser
1640                1645                1650

Ser Val Asp His Val Thr Cys Gly Lys Asp Leu Leu Val Cys Asp
1655                1660                1665

Thr Met Gly Arg Thr Arg Val Val Cys Gln Ser Asn Asn Lys Met
1670                1675                1680

Thr Asp Glu Ser Glu Tyr Gly Val Lys Thr Asp Ser Gly Cys Pro
1685                1690                1695

Glu Gly Ala Arg Cys Tyr Val Phe Asn Pro Glu Ala Val Asn Ile
1700                1705                1710

Ser Gly Thr Lys Gly Ala Met Val His Leu Gln Lys Thr Gly Gly
1715                1720                1725

Glu Phe Thr Cys Val Thr Ala Ser Gly Thr Pro Ala Phe Phe Asp
1730                1735                1740

Leu Lys Asn Leu Lys Gly Trp Ser Gly Leu Pro Ile Phe Glu Ala
1745                1750                1755

Ser Ser Gly Arg Val Val Gly Arg Val Lys Val Gly Lys Asn Glu
1760                1765                1770

Asp Ser Lys Pro Thr Lys Leu Met Ser Gly Ile Gln Thr Val Ser
1775                1780                1785

Lys Ser Thr Thr Asp Leu Thr Glu Met Val Lys Lys Ile Thr Thr
1790                1795                1800

Met Ser Arg Gly Glu Phe Arg Gln Ile Thr Leu Ala Thr Gly Ala

```
            1805                1810                1815
Gly Lys Thr Thr Glu Leu Pro Arg Ser Val Ile Glu Glu Ile Gly
            1820                1825                1830
Arg His Lys Arg Val Leu Val Leu Ile Pro Leu Arg Ala Ala Ala
            1835                1840                1845
Glu Ser Val Tyr Gln Tyr Met Arg Gln Lys His Pro Ser Ile Ala
            1850                1855                1860
Phe Asn Leu Arg Ile Gly Glu Met Lys Glu Gly Asp Met Ala Thr
            1865                1870                1875
Gly Ile Thr Tyr Ala Ser Tyr Gly Tyr Phe Cys Gln Met Pro Gln
            1880                1885                1890
Pro Lys Leu Arg Ala Ala Met Val Glu Tyr Ser Phe Ile Phe Leu
            1895                1900                1905
Asp Glu Tyr His Cys Ala Thr Pro Glu Gln Leu Ala Ile Met Gly
            1910                1915                1920
Lys Ile His Arg Phe Ser Glu Asn Leu Arg Val Val Ala Met Thr
            1925                1930                1935
Ala Thr Pro Val Gly Thr Val Thr Thr Thr Gly Gln Lys His Pro
            1940                1945                1950
Ile Glu Glu Phe Ile Ala Pro Asp Val Met Lys Gly Glu Asp Leu
            1955                1960                1965
Gly Ser Glu Tyr Leu Asp Ile Ala Gly Leu Lys Ile Pro Val Glu
            1970                1975                1980
Glu Met Lys Ser Asn Met Leu Val Phe Val Pro Thr Arg Asn Met
            1985                1990                1995
Ala Val Glu Thr Ala Lys Lys Leu Lys Ala Lys Gly Tyr Asn Ser
            2000                2005                2010
Gly Tyr Tyr Tyr Ser Gly Glu Asp Pro Ser Asn Leu Arg Val Val
            2015                2020                2025
Thr Ser Gln Ser Pro Tyr Val Val Ala Thr Asn Ala Ile Glu
            2030                2035                2040
Pro Gly Val Thr Leu Pro Asp Leu Asp Val Val Val Asp Thr Gly
            2045                2050                2055
Leu Lys Cys Glu Lys Arg Ile Arg Leu Ser Pro Lys Met Pro Phe
            2060                2065                2070
Ile Val Thr Gly Leu Lys Arg Met Ala Val Thr Ile Gly Glu Gln
            2075                2080                2085
Ala Gln Arg Arg Gly Arg Val Gly Arg Val Lys Pro Gly Arg Tyr
            2090                2095                2100
Tyr Arg Ser Gln Glu Thr Pro Val Gly Ser Lys Asp Tyr His Tyr
            2105                2110                2115
Asp Leu Leu Gln Ala Gln Arg Tyr Gly Ile Glu Asp Gly Ile Asn
            2120                2125                2130
Ile Thr Lys Ser Phe Arg Glu Met Asn Tyr Asp Trp Ser Leu Tyr
            2135                2140                2145
Glu Glu Asp Ser Leu Met Ile Thr Gln Leu Glu Ile Leu Asn Asn
            2150                2155                2160
Leu Leu Ile Ser Asp Glu Leu Pro Met Ala Val Lys Asn Ile Met
            2165                2170                2175
Ala Arg Thr Asp His Pro Glu Pro Ile Gln Leu Ala Tyr Asn Ser
            2180                2185                2190
Tyr Glu Thr Gln Val Pro Val Leu Phe Pro Lys Ile Lys Asn Gly
            2195                2200                2205
```

-continued

Glu Val Thr Asp Ser Tyr Asp Asn Tyr Thr Phe Leu Asn Ala Arg
        2210                2215                2220

Lys Leu Gly Asp Asp Val Pro Pro Tyr Val Tyr Ala Thr Glu Asp
    2225                2230                2235

Glu Asp Leu Ala Val Glu Leu Leu Gly Leu Asp Trp Pro Asp Pro
    2240                2245                2250

Gly Asn Leu Gly Thr Val Glu Thr Gly Arg Ala Leu Lys Gln Val
    2255                2260                2265

Val Gly Leu Ser Thr Ala Glu Asn Ala Leu Leu Val Ala Leu Phe
2270                2275                2280

Gly Tyr Val Gly Tyr Gln Ala Leu Ser Lys Arg His Ile Pro Val
2285                2290                2295

Val Thr Asp Ile Tyr Ser Ile Glu Asp His Arg Leu Glu Asp Thr
2300                2305                2310

Thr His Leu Gln Tyr Ala Pro Asn Ala Ile Lys Thr Glu Gly Lys
2315                2320                2325

Glu Thr Glu Leu Lys Glu Leu Ala Gln Gly Asp Val Gln Arg Cys
    2330                2335                2340

Val Glu Ala Met Thr Asn Tyr Ala Arg Glu Gly Ile Gln Phe Met
2345                2350                2355

Lys Ser Gln Ala Leu Lys Val Lys Glu Thr Pro Thr Tyr Lys Glu
2360                2365                2370

Thr Met Asp Thr Val Thr Asp Tyr Val Lys Lys Phe Met Glu Ala
2375                2380                2385

Leu Ala Asp Ser Lys Glu Asp Ile Ile Lys Tyr Gly Leu Trp Gly
    2390                2395                2400

Thr His Thr Ala Leu Tyr Lys Ser Ile Ser Ala Arg Leu Gly Gly
2405                2410                2415

Glu Thr Ala Phe Ala Thr Leu Val Val Lys Trp Leu Ala Phe Gly
    2420                2425                2430

Gly Glu Ser Ile Ala Asp His Val Lys Gln Ala Ala Thr Asp Leu
2435                2440                2445

Val Val Tyr Tyr Ile Ile Asn Arg Pro Gln Phe Pro Gly Asp Thr
2450                2455                2460

Glu Thr Gln Gln Asp Gly Arg Lys Phe Val Ala Ser Leu Leu Ala
    2465                2470                2475

Ser Ala Leu Ala Thr Tyr Thr Lys Ser Trp Asn Tyr Asn Asn
2480                2485                2490

Leu Ser Lys Ile Val Glu Pro Ala Leu Ala Thr Leu Pro Tyr Ala
    2495                2500                2505

Ala Thr Ala Leu Lys Leu Phe Ala Pro Thr Arg Leu Glu Ser Val
2510                2515                2520

Val Ile Leu Ser Thr Ala Ile Tyr Lys Thr Tyr Leu Ser Ile Arg
2525                2530                2535

Arg Gly Lys Ser Asp Gly Leu Gly Thr Gly Val Ser Ala Ala
    2540                2545                2550

Met Glu Ile Met Ser Gln Asn Pro Val Ser Val Gly Ile Ala Val
2555                2560                2565

Met Leu Gly Val Gly Ala Val Ala Ala His Asn Ala Ile Glu Ala
2570                2575                2580

Ser Glu Gln Lys Arg Thr Leu Leu Met Lys Val Phe Val Lys Asn
2585                2590                2595

-continued

Phe Leu Asp Gln Ala Ala Thr Asp Glu Leu Val Lys Glu Ser Pro
2600                2605                2610

Glu Lys Ile Ile Met Ala Leu Phe Glu Ala Val Gln Thr Val Gly
2615                2620                2625

Asn Pro Leu Arg Leu Val Tyr His Leu Tyr Gly Val Phe Tyr Lys
2630                2635                2640

Gly Trp Arg Pro Lys Glu Leu Ala Gln Arg Thr Ala Gly Arg Asn
2645                2650                2655

Leu Phe Thr Leu Ile Met Phe Glu Ala Val Glu Leu Leu Gly Val
2660                2665                2670

Asp Ser Glu Gly Lys Val Arg Gln Leu Ser Ser Asn Tyr Ile Leu
2675                2680                2685

Glu Leu Leu Tyr Lys Phe Arg Asp Ser Ile Lys Ser Ser Val Arg
2690                2695                2700

Glu Met Ala Ile Ser Trp Ala Pro Ala Pro Phe Ser Cys Asp Trp
2705                2710                2715

Thr Pro Thr Asp Asp Arg Ile Gly Leu Pro Gln Asp Asn Phe His
2720                2725                2730

Gln Val Glu Thr Lys Cys Pro Cys Gly Tyr Lys Met Lys Ala Val
2735                2740                2745

Lys Asn Cys Ala Gly Glu Leu Arg Leu Leu Glu Glu Glu Gly Ser
2750                2755                2760

Phe Leu Cys Arg Asn Lys Phe Gly Arg Gly Ser Arg Asn Tyr Arg
2765                2770                2775

Val Thr Lys Tyr Tyr Asp Asp Asn Leu Leu Glu Ile Lys Pro Val
2780                2785                2790

Ile Arg Met Glu Gly His Val Glu Leu Tyr Tyr Lys Gly Ala Thr
2795                2800                2805

Ile Lys Leu Asp Phe Asn Asn Ser Lys Thr Ile Leu Ala Thr Asp
2810                2815                2820

Lys Trp Glu Val Asp His Ser Thr Leu Val Arg Val Leu Lys Arg
2825                2830                2835

His Thr Gly Ala Gly Tyr His Gly Ala Tyr Leu Gly Glu Lys Pro
2840                2845                2850

Asn His Lys His Leu Ile Glu Arg Asp Cys Ala Thr Ile Thr Lys
2855                2860                2865

Asp Lys Val Cys Phe Leu Lys Met Lys Arg Gly Cys Ala Phe Thr
2870                2875                2880

Tyr Asp Leu Ser Leu His Asn Leu Ala Arg Leu Ile Glu Leu Val
2885                2890                2895

His Lys Asn Asn Leu Glu Asp Lys Glu Ile Pro Ala Ala Thr Val
2900                2905                2910

Thr Thr Trp Leu Ala Tyr Thr Phe Val Asn Glu Asp Ile Gly Thr
2915                2920                2925

Ile Lys Pro Ala Phe Gly Glu Lys Val Thr Leu Glu Met Gln Glu
2930                2935                2940

Glu Ile Thr Leu Gln Pro Ala Val Val Val Asp Thr Thr Asp Val
2945                2950                2955

Ala Val Thr Val Val Gly Glu Ala Pro Thr Met Thr Thr Gly Glu
2960                2965                2970

Thr Pro Thr Val Phe Thr Ser Ser Gly Ser Gly Leu Lys Asn Gln
2975                2980                2985

Gln Val Leu Lys Leu Gly Val Gly Glu Gly Gln Tyr Pro Gly Thr

```
                    2990                2995                3000
Asn Pro Gln Arg Ala Ser Leu His Glu Ala Ile Gln Gly Ala Asp
        3005                3010                3015

Glu Arg Pro Ser Val Leu Ile Leu Gly Ser Asp Lys Ala Thr Ser
        3020                3025                3030

Asn Arg Val Lys Thr Ala Lys Asn Val Lys Val Tyr Arg Gly Arg
        3035                3040                3045

Asp Pro Leu Glu Val Arg Asp Met Met Arg Arg Gly Lys Ile Leu
        3050                3055                3060

Val Val Ala Leu Ser Arg Val Asp Asn Ala Leu Leu Lys Phe Val
        3065                3070                3075

Asp Tyr Lys Gly Thr Phe Leu Thr Arg Glu Ala Leu Glu Ala Leu
        3080                3085                3090

Ser Leu Gly Arg Pro Lys Lys Asn Ile Thr Lys Ala Glu Ala
        3095                3100                3105

Gln Cys Leu Leu Cys Pro Glu Asp Gln Met Glu Leu Pro Asp
        3110                3115                3120

Trp Phe Ala Ala Gly Glu Pro Ile Phe Leu Glu Ala Asn Ile Lys
        3125                3130                3135

His Asp Arg Leu His Leu Val Gly Asp Ile Ala Thr Ile Lys Glu
        3140                3145                3150

Lys Ala Lys Gln Leu Gly Ala Thr Asp Ser Thr Lys Ile Ser Lys
        3155                3160                3165

Glu Val Gly Ala Lys Val Tyr Ser Met Lys Leu Ser Asn Trp Val
        3170                3175                3180

Met Gln Glu Glu Asn Lys Gln Gly Asn Leu Thr Pro Leu Phe Glu
        3185                3190                3195

Glu Leu Leu Gln Gln Cys Pro Pro Gly Gly Gln Asn Lys Thr Ala
        3200                3205                3210

His Met Val Ser Ala Tyr Gln Leu Ala Gln Gly Asn Trp Met Pro
        3215                3220                3225

Thr Ser Cys His Val Phe Met Gly Thr Ile Ser Ala Arg Arg Thr
        3230                3235                3240

Lys Thr His Pro Tyr Glu Ala Tyr Val Lys Leu Arg Glu Leu Val
        3245                3250                3255

Glu Glu His Lys Met Lys Thr Leu Cys Pro Gly Ser Ser Leu Gly
        3260                3265                3270

Lys His Asn Asp Trp Ile Ile Gly Lys Ile Lys Tyr Gln Gly Asn
        3275                3280                3285

Leu Arg Thr Lys His Met Leu Asn Pro Gly Lys Val Ala Glu Gln
        3290                3295                3300

Leu Cys Arg Glu Gly His Arg His Asn Val Tyr Asn Lys Thr Ile
        3305                3310                3315

Ser Ser Val Met Thr Ala Thr Gly Ile Arg Leu Glu Lys Leu Pro
        3320                3325                3330

Val Val Arg Ala Gln Thr Asp Pro Thr Asn Phe His Gln Ala Ile
        3335                3340                3345

Arg Asp Lys Ile Asp Lys Glu Glu Asn Leu Gln Thr Pro Gly Leu
        3350                3355                3360

His Lys Lys Leu Met Glu Val Phe Asn Ala Leu Lys Arg Pro Glu
        3365                3370                3375

Leu Glu Ser Ser Tyr Asp Ala Val Glu Trp Glu Glu Leu Glu Arg
        3380                3385                3390
```

-continued

Gly Ile Asn Arg Lys Gly Ala Ala Gly Phe Phe Glu Arg Lys Asn
3395                3400                3405

Ile Gly Glu Ile Leu Asp Ser Glu Lys Asn Lys Val Glu Glu Ile
3410                3415                3420

Ile Asp Asn Leu Lys Lys Gly Arg Asn Ile Lys Tyr Tyr Glu Thr
3425                3430                3435

Ala Ile Pro Lys Asn Glu Lys Arg Val Val Asn Asp Asp Trp Thr
3440                3445                3450

Ala Gly Asp Phe Val Asp Glu Lys Lys Pro Arg Val Ile Gln Tyr
3455                3460                3465

Pro Glu Ala Lys Thr Arg Leu Ala Ile Thr Lys Val Met Tyr Lys
3470                3475                3480

Trp Val Lys Gln Lys Pro Val Ile Pro Gly Tyr Glu Gly Lys
3485                3490                3495

Thr Pro Leu Phe Gln Ile Phe Asp Lys Val Lys Lys Glu Trp Asp
3500                3505                3510

Gln Phe Gln Asn Pro Val Ala Val Ser Phe Asp Thr Lys Ala Trp
3515                3520                3525

Asp Thr Gln Val Thr Thr Lys Asp Leu Glu Leu Ile Arg Asp Ile
3530                3535                3540

Gln Lys Tyr Tyr Phe Lys Lys Lys Trp His Lys Phe Ile Asp Thr
3545                3550                3555

Leu Thr Thr His Met Ser Glu Val Pro Val Ile Ser Ala Asp Gly
3560                3565                3570

Glu Val Tyr Ile Arg Lys Gly Gln Arg Gly Ser Gly Gln Pro Asp
3575                3580                3585

Thr Ser Ala Gly Asn Ser Met Leu Asn Val Leu Thr Met Val Tyr
3590                3595                3600

Ala Phe Cys Glu Ala Thr Gly Val Pro Tyr Lys Ser Phe Asp Arg
3605                3610                3615

Val Ala Lys Ile His Val Cys Gly Asp Asp Gly Phe Leu Ile Thr
3620                3625                3630

Glu Arg Ala Leu Gly Glu Lys Phe Ala Ser Lys Gly Val Gln Ile
3635                3640                3645

Leu Tyr Glu Ala Gly Lys Pro Gln Lys Ile Thr Glu Gly Asp Lys
3650                3655                3660

Met Lys Val Ala Tyr Gln Phe Asp Asp Ile Glu Phe Cys Ser His
3665                3670                3675

Thr Pro Ile Gln Val Arg Trp Ser Asp Asn Thr Ser Ser Tyr Met
3680                3685                3690

Pro Gly Arg Asn Thr Thr Thr Ile Leu Ala Lys Met Ala Thr Arg
3695                3700                3705

Leu Asp Ser Ser Gly Glu Arg Gly Thr Ile Ala Tyr Glu Lys Ala
3710                3715                3720

Val Ala Phe Ser Phe Leu Leu Met Tyr Ser Trp Asn Pro Leu Ile
3725                3730                3735

Arg Arg Ile Cys Leu Leu Val Leu Ser Thr Glu Leu Gln Val Lys
3740                3745                3750

Pro Gly Lys Ser Thr Thr Tyr Tyr Tyr Glu Gly Asp Pro Ile Ser
3755                3760                3765

Ala Tyr Lys Glu Val Ile Gly His Asn Leu Phe Asp Leu Lys Arg
3770                3775                3780

Thr Ser Phe Glu Lys Leu Ala Lys Leu Asn Leu Ser Met Ser Val
    3785                3790                3795

Leu Gly Ala Trp Thr Arg His Thr Ser Lys Arg Leu Leu Gln Asp
    3800                3805                3810

Cys Val Asn Ile Gly Val Lys Glu Gly Asn Trp Leu Val Asn Ala
    3815                3820                3825

Asp Arg Leu Val Ser Ser Lys Thr Gly Asn Arg Tyr Ile Pro Gly
    3830                3835                3840

Glu Gly His Thr Leu Gln Gly Arg His Tyr Glu Glu Leu Val Leu
    3845                3850                3855

Ala Arg Lys Gln Ile Asn Asn Phe Gln Gly Thr Asp Arg Tyr Asn
    3860                3865                3870

Leu Gly Pro Ile Val Asn Met Val Leu Arg Arg Leu Arg Val Met
    3875                3880                3885

Met Met Thr Leu Ile Gly Arg Gly Ala
    3890                3895

<210> SEQ ID NO 10
<211> LENGTH: 3732
<212> TYPE: PRT
<213> ORGANISM: CSFV

<400> SEQUENCE: 10

Met Gly Ser Asp Asp Gly Ala Ser Gly Ser Lys Glu Lys Pro Asp
1               5                   10                  15

Arg Ile Asn Lys Gly Lys Leu Lys Ile Ala Pro Lys Glu His Glu Lys
                20                  25                  30

Asp Ser Arg Thr Arg Pro Pro Asp Ala Thr Ile Val Val Glu Gly Val
            35                  40                  45

Lys Tyr Gln Val Lys Lys Lys Gly Lys Val Lys Gly Lys Asn Thr Gln
50                  55                  60

Asp Gly Leu Tyr His Asn Lys Asn Lys Pro Pro Glu Ser Arg Lys Lys
65                  70                  75                  80

Leu Glu Lys Ala Leu Leu Ala Trp Ala Val Ile Ala Ile Met Leu Tyr
                85                  90                  95

Gln Pro Val Glu Ala Glu Asn Ile Thr Gln Trp Asn Leu Ser Asp Asn
            100                 105                 110

Gly Thr Asn Gly Ile Gln His Ala Met Tyr Leu Arg Gly Val Asn Arg
        115                 120                 125

Ser Leu His Gly Ile Trp Pro Gly Lys Ile Cys Lys Gly Val Pro Thr
    130                 135                 140

His Leu Ala Thr Asp Val Glu Leu Lys Glu Ile Gln Gly Met Met Asp
145                 150                 155                 160

Ala Ser Glu Gly Thr Asn Tyr Thr Cys Cys Lys Leu Gln Arg His Glu
                165                 170                 175

Trp Asn Lys His Gly Trp Cys Asn Trp His Asn Ile Asp Pro Trp Ile
            180                 185                 190

Gln Leu Met Asn Arg Thr Gln Ala Asp Leu Ala Glu Gly Pro Pro Val
        195                 200                 205

Lys Glu Cys Ala Val Thr Cys Arg Tyr Asp Lys Asp Ala Asp Ile Asn
    210                 215                 220

Val Val Thr Gln Ala Arg Asn Arg Pro Thr Thr Leu Thr Gly Cys Lys
225                 230                 235                 240

Lys Gly Lys Asn Phe Ser Phe Ala Gly Thr Val Ile Glu Ser Pro Cys
                245                 250                 255

```
Asn Phe Asn Val Ser Val Glu Asp Thr Leu Tyr Gly Asp His Glu Ser
            260                 265                 270

Cys Ser Leu Leu Gln Asp Ala Ala Leu Tyr Leu Val Asp Gly Met Thr
            275                 280                 285

Asn Thr Ile Glu Asn Ala Arg Gln Gly Ala Ala Arg Val Thr Ser Trp
            290                 295                 300

Leu Gly Arg Gln Leu Arg Ile Ala Gly Lys Arg Leu Glu Gly Arg Ser
305                 310                 315                 320

Lys Thr Trp Phe Gly Ala Tyr Ala Leu Ser Pro Tyr Cys Asn Val Thr
                325                 330                 335

Ser Lys Ile Gly Tyr Ile Trp Tyr Thr Asn Asn Cys Thr Pro Ala Cys
            340                 345                 350

Leu Pro Lys Asn Thr Lys Ile Ile Gly Pro Gly Lys Phe Asp Thr Asn
            355                 360                 365

Ala Glu Asp Gly Lys Ile Leu His Glu Met Gly Gly His Leu Ser Glu
            370                 375                 380

Phe Leu Leu Leu Ser Leu Val Val Leu Ser Asp Phe Ala Pro Glu Thr
385                 390                 395                 400

Ala Ser Ala Leu Tyr Leu Ile Phe His Tyr Val Ile Pro Gln Pro His
                405                 410                 415

Asp Glu Pro Glu Gly Cys Asp Thr Asn Gln Leu Asn Leu Thr Val Glu
            420                 425                 430

Leu Arg Thr Glu Asp Val Ile Pro Ser Ser Val Trp Asn Val Gly Lys
            435                 440                 445

Tyr Val Cys Val Arg Pro Asp Trp Trp Pro Tyr Glu Thr Glu Val Ala
            450                 455                 460

Leu Leu Phe Glu Glu Val Gly Gln Val Val Lys Leu Ala Leu Arg Ala
465                 470                 475                 480

Leu Arg Asp Leu Thr Arg Val Trp Asn Ser Ala Ser Thr Ile Ala Phe
                485                 490                 495

Leu Ile Cys Leu Ile Lys Val Leu Arg Gly Gln Ile Val Gln Gly Val
            500                 505                 510

Val Trp Leu Leu Leu Val Thr Gly Ala Gln Gly Arg Leu Ala Cys Lys
            515                 520                 525

Glu Asp Tyr Arg Tyr Ala Ile Ser Ser Thr Asp Glu Ile Gly Leu Leu
            530                 535                 540

Gly Ala Gly Gly Leu Thr Thr Trp Lys Glu Tyr Asn His Asp Leu
545                 550                 555                 560

Gln Leu Asn Asp Gly Thr Val Lys Ala Ser Cys Val Ala Gly Ser Phe
                565                 570                 575

Lys Val Thr Ala Leu Asn Val Val Ser Arg Arg Tyr Leu Ala Ser Leu
            580                 585                 590

His Lys Lys Ala Leu Pro Thr Ser Val Thr Phe Glu Leu Leu Phe Asp
            595                 600                 605

Gly Thr Asn Pro Ser Thr Glu Glu Met Gly Asp Asp Phe Arg Ser Gly
            610                 615                 620

Leu Cys Pro Phe Asp Thr Ser Pro Val Val Lys Gly Lys Tyr Asn Thr
625                 630                 635                 640

Thr Leu Leu Asn Gly Ser Ala Phe Tyr Leu Val Cys Pro Ile Gly Trp
                645                 650                 655

Thr Gly Val Ile Glu Cys Thr Ala Val Ser Lys Asp Thr Leu Arg Thr
            660                 665                 670
```

```
Glu Val Val Lys Thr Phe Arg Arg Asp Lys Pro Phe Pro His Arg Met
            675                 680                 685

Asp Cys Val Thr Thr Thr Val Glu Asn Glu Asp Leu Phe Tyr Cys Lys
690                 695                 700

Leu Gly Gly Asn Trp Thr Cys Val Lys Gly Glu Pro Val Val Tyr Thr
705                 710                 715                 720

Gly Gly Leu Val Lys Gln Cys Arg Trp Cys Gly Phe Asp Phe Asp Gly
                725                 730                 735

Pro Asp Gly Leu Pro His Tyr Pro Ile Gly Lys Cys Ile Leu Ala Asn
            740                 745                 750

Glu Thr Gly Tyr Arg Ile Val Asp Ser Thr Asp Cys Asn Arg Asp Gly
        755                 760                 765

Val Val Ile Ser Thr Glu Gly Ser His Glu Cys Leu Ile Gly Asn Thr
    770                 775                 780

Thr Val Lys Val His Ala Ser Asp Glu Arg Leu Gly Pro Met Pro Cys
785                 790                 795                 800

Arg Pro Lys Glu Ile Val Ser Ser Ala Gly Pro Val Lys Lys Thr Ser
                805                 810                 815

Cys Thr Phe Asn Tyr Thr Lys Thr Leu Lys Asn Arg Tyr Tyr Glu Pro
                820                 825                 830

Arg Asp Ser Tyr Phe Gln Gln Tyr Met Leu Lys Gly Glu Tyr Gln Tyr
            835                 840                 845

Trp Phe Asp Leu Asp Ala Thr Asp Arg His Ser Asp Tyr Phe Ala Glu
        850                 855                 860

Phe Val Val Leu Val Val Ala Leu Leu Gly Gly Arg Tyr Val Leu
865                 870                 875                 880

Trp Leu Ile Val Thr Tyr Val Leu Thr Glu Gln Leu Ala Ala Gly
                885                 890                 895

Leu Pro Leu Gly Gln Gly Glu Val Val Leu Ile Gly Asn Leu Ile Thr
            900                 905                 910

His Thr Asp Ile Glu Val Val Tyr Phe Leu Leu Leu Tyr Leu Val
        915                 920                 925

Met Arg Asp Glu Pro Ile Lys Lys Trp Ile Leu Leu Leu Phe His Ala
    930                 935                 940

Met Thr Asn Asn Pro Val Lys Thr Ile Thr Val Ala Leu Leu Met Val
945                 950                 955                 960

Ser Gly Val Ala Lys Gly Gly Lys Ile Asp Gly Gly Trp Gln Arg Leu
                965                 970                 975

Pro Gly Thr Ser Phe Asp Ile Gln Leu Ala Leu Thr Ile Val Val
            980                 985                 990

Ala Val Met Leu Leu Ala Lys Arg  Asp Pro Thr Thr Val  Pro Leu Val
        995                 1000                1005

Ile Thr  Val Ala Thr Leu Arg  Thr Ala Lys Met  Thr Asn Gly Leu
    1010                1015                1020

Ser Thr  Asp Ile Ala Ile Ala  Thr Val Ser Ala Ala  Leu Leu Thr
    1025                1030                1035

Trp Thr  Tyr Ile Ser Asp Tyr  Tyr Arg Tyr Lys Thr  Trp Leu Gln
    1040                1045                1050

Tyr Leu  Ile Ser Thr Val Thr  Gly Ile Phe Leu Ile  Arg Val Leu
    1055                1060                1065

Lys Gly  Ile Gly Glu Leu Asp  Leu His Thr Pro Thr  Leu Pro Ser
    1070                1075                1080

His Arg  Pro Leu Phe Phe Ile  Leu Val Tyr Leu Ile  Ser Thr Ala
```

```
             1085                1090                1095

Val Val Thr Arg Trp Asn Leu Asp Ile Ala Gly Leu Leu Leu Gln
    1100                1105                1110

Cys Val Pro Thr Leu Leu Met Val Phe Thr Met Trp Ala Asp Ile
    1115                1120                1125

Leu Thr Leu Ile Leu Ile Leu Pro Thr Tyr Glu Leu Thr Lys Leu
    1130                1135                1140

Tyr Tyr Leu Lys Glu Val Lys Ile Gly Ala Glu Lys Gly Trp Leu
    1145                1150                1155

Trp Lys Thr Asn Phe Lys Arg Val Asn Asp Ile Tyr Glu Val Asp
    1160                1165                1170

Gln Ala Gly Glu Gly Val Tyr Leu Phe Pro Ser Lys Gln Lys Thr
    1175                1180                1185

Ser Ser Met Thr Gly Thr Met Leu Pro Leu Ile Lys Ala Ile Leu
    1190                1195                1200

Ile Ser Cys Val Ser Asn Lys Trp Gln Phe Ile Tyr Leu Leu Tyr
    1205                1210                1215

Leu Ile Phe Glu Val Ser Tyr Tyr Leu His Lys Lys Ile Ile Asp
    1220                1225                1230

Glu Ile Ala Gly Gly Thr Asn Phe Ile Ser Arg Leu Val Ala Ala
    1235                1240                1245

Leu Ile Glu Val Asn Trp Ala Phe Asp Asn Glu Glu Val Arg Gly
    1250                1255                1260

Leu Lys Lys Phe Phe Leu Leu Ser Ser Arg Val Lys Glu Leu Ile
    1265                1270                1275

Ile Lys His Lys Val Arg Asn Glu Val Met Val Arg Trp Phe Gly
    1280                1285                1290

Asp Glu Glu Val Tyr Gly Met Pro Lys Leu Val Gly Leu Val Lys
    1295                1300                1305

Ala Ala Thr Leu Ser Lys Asn Lys His Cys Ile Leu Cys Thr Val
    1310                1315                1320

Cys Glu Asp Arg Glu Trp Arg Gly Glu Thr Cys Pro Lys Cys Gly
    1325                1330                1335

Arg Phe Gly Pro Pro Met Thr Cys Gly Met Thr Leu Ala Asp Phe
    1340                1345                1350

Glu Glu Lys His Tyr Lys Arg Ile Phe Phe Arg Glu Asp Gln Ser
    1355                1360                1365

Glu Gly Pro Val Arg Glu Glu Tyr Ala Gly Tyr Leu Gln Tyr Arg
    1370                1375                1380

Ala Arg Gly Gln Leu Phe Leu Arg Asn Leu Pro Val Leu Ala Thr
    1385                1390                1395

Lys Val Lys Met Leu Leu Val Gly Asn Leu Gly Thr Glu Val Gly
    1400                1405                1410

Asp Leu Glu His Leu Gly Trp Val Leu Arg Gly Pro Ala Val Cys
    1415                1420                1425

Lys Lys Val Thr Glu His Glu Lys Cys Thr Thr Ser Met Met Asp
    1430                1435                1440

Lys Leu Thr Ala Phe Phe Gly Val Met Pro Arg Gly Thr Thr Pro
    1445                1450                1455

Arg Ala Pro Val Arg Phe Pro Thr Ser Leu Leu Lys Ile Arg Arg
    1460                1465                1470

Gly Leu Glu Thr Gly Trp Ala Tyr Thr His Gln Gly Gly Ile Ser
    1475                1480                1485
```

```
Ser Val Asp His Val Thr Cys Gly Lys Asp Leu Leu Val Cys Asp
    1490            1495                1500

Thr Met Gly Arg Thr Arg Val Val Cys Gln Ser Asn Asn Lys Met
    1505            1510                1515

Thr Asp Glu Ser Glu Tyr Gly Val Lys Thr Asp Ser Gly Cys Pro
    1520            1525                1530

Glu Gly Ala Arg Cys Tyr Val Phe Asn Pro Glu Ala Val Asn Ile
    1535            1540                1545

Ser Gly Thr Lys Gly Ala Met Val His Leu Gln Lys Thr Gly Gly
    1550            1555                1560

Glu Phe Thr Cys Val Thr Ala Ser Gly Thr Pro Ala Phe Phe Asp
    1565            1570                1575

Leu Lys Asn Leu Lys Gly Trp Ser Gly Leu Pro Ile Phe Glu Ala
    1580            1585                1590

Ser Ser Gly Arg Val Val Gly Arg Val Lys Val Gly Lys Asn Glu
    1595            1600                1605

Asp Ser Lys Pro Thr Lys Leu Met Ser Gly Ile Gln Thr Val Ser
    1610            1615                1620

Lys Ser Thr Thr Asp Leu Thr Glu Met Val Lys Lys Ile Thr Thr
    1625            1630                1635

Met Ser Arg Gly Glu Phe Arg Gln Ile Thr Leu Ala Thr Gly Ala
    1640            1645                1650

Gly Lys Thr Thr Glu Leu Pro Arg Ser Val Ile Glu Glu Ile Gly
    1655            1660                1665

Arg His Lys Arg Val Leu Val Leu Ile Pro Leu Arg Ala Ala Ala
    1670            1675                1680

Glu Ser Val Tyr Gln Tyr Met Arg Gln Lys His Pro Ser Ile Ala
    1685            1690                1695

Phe Asn Leu Arg Ile Gly Glu Met Lys Glu Gly Asp Met Ala Thr
    1700            1705                1710

Gly Ile Thr Tyr Ala Ser Tyr Gly Tyr Phe Cys Gln Met Pro Gln
    1715            1720                1725

Pro Lys Leu Arg Ala Ala Met Val Glu Tyr Ser Phe Ile Phe Leu
    1730            1735                1740

Asp Glu Tyr His Cys Ala Thr Pro Glu Gln Leu Ala Ile Met Gly
    1745            1750                1755

Lys Ile His Arg Phe Ser Glu Asn Leu Arg Val Val Ala Met Thr
    1760            1765                1770

Ala Thr Pro Val Gly Thr Val Thr Thr Thr Gly Gln Lys His Pro
    1775            1780                1785

Ile Glu Glu Phe Ile Ala Pro Asp Val Met Lys Gly Glu Asp Leu
    1790            1795                1800

Gly Ser Glu Tyr Leu Asp Ile Ala Gly Leu Lys Ile Pro Val Glu
    1805            1810                1815

Glu Met Lys Ser Asn Met Leu Val Phe Val Pro Thr Arg Asn Met
    1820            1825                1830

Ala Val Glu Thr Ala Lys Lys Leu Lys Ala Lys Gly Tyr Asn Ser
    1835            1840                1845

Gly Tyr Tyr Tyr Ser Gly Glu Asp Pro Ser Asn Leu Arg Val Val
    1850            1855                1860

Thr Ser Gln Ser Pro Tyr Val Val Val Ala Thr Asn Ala Ile Glu
    1865            1870                1875
```

```
Pro Gly Val Thr Leu Pro Asp Leu Asp Val Val Asp Thr Gly
    1880            1885            1890

Leu Lys Cys Glu Lys Arg Ile Arg Leu Ser Pro Lys Met Pro Phe
    1895            1900            1905

Ile Val Thr Gly Leu Lys Arg Met Ala Val Thr Ile Gly Glu Gln
    1910            1915            1920

Ala Gln Arg Arg Gly Arg Val Gly Arg Val Lys Pro Gly Arg Tyr
    1925            1930            1935

Tyr Arg Ser Gln Glu Thr Pro Val Gly Ser Lys Asp Tyr His Tyr
    1940            1945            1950

Asp Leu Leu Gln Ala Gln Arg Tyr Gly Ile Glu Asp Gly Ile Asn
    1955            1960            1965

Ile Thr Lys Ser Phe Arg Glu Met Asn Tyr Asp Trp Ser Leu Tyr
    1970            1975            1980

Glu Glu Asp Ser Leu Met Ile Thr Gln Leu Glu Ile Leu Asn Asn
    1985            1990            1995

Leu Leu Ile Ser Asp Glu Leu Pro Met Ala Val Lys Asn Ile Met
    2000            2005            2010

Ala Arg Thr Asp His Pro Glu Pro Ile Gln Leu Ala Tyr Asn Ser
    2015            2020            2025

Tyr Glu Thr Gln Val Pro Val Leu Phe Pro Lys Ile Lys Asn Gly
    2030            2035            2040

Glu Val Thr Asp Ser Tyr Asp Asn Tyr Thr Phe Leu Asn Ala Arg
    2045            2050            2055

Lys Leu Gly Asp Asp Val Pro Pro Tyr Val Tyr Ala Thr Glu Asp
    2060            2065            2070

Glu Asp Leu Ala Val Glu Leu Leu Gly Leu Asp Trp Pro Asp Pro
    2075            2080            2085

Gly Asn Leu Gly Thr Val Glu Thr Gly Arg Ala Leu Lys Gln Val
    2090            2095            2100

Val Gly Leu Ser Thr Ala Glu Asn Ala Leu Leu Val Ala Leu Phe
    2105            2110            2115

Gly Tyr Val Gly Tyr Gln Ala Leu Ser Lys Arg His Ile Pro Val
    2120            2125            2130

Val Thr Asp Ile Tyr Ser Ile Glu Asp His Arg Leu Glu Asp Thr
    2135            2140            2145

Thr His Leu Gln Tyr Ala Pro Asn Ala Ile Lys Thr Glu Gly Lys
    2150            2155            2160

Glu Thr Glu Leu Lys Glu Leu Ala Gln Gly Asp Val Gln Arg Cys
    2165            2170            2175

Val Glu Ala Met Thr Asn Tyr Ala Arg Glu Gly Ile Gln Phe Met
    2180            2185            2190

Lys Ser Gln Ala Leu Lys Val Lys Glu Thr Pro Thr Tyr Lys Glu
    2195            2200            2205

Thr Met Asp Thr Val Thr Asp Tyr Val Lys Lys Phe Met Glu Ala
    2210            2215            2220

Leu Ala Asp Ser Lys Glu Asp Ile Ile Lys Tyr Gly Leu Trp Gly
    2225            2230            2235

Thr His Thr Ala Leu Tyr Lys Ser Ile Ser Ala Arg Leu Gly Gly
    2240            2245            2250

Glu Thr Ala Phe Ala Thr Leu Val Val Lys Trp Leu Ala Phe Gly
    2255            2260            2265

Gly Glu Ser Ile Ala Asp His Val Lys Gln Ala Ala Thr Asp Leu
```

```
                2270              2275              2280
Val Val Tyr Tyr Ile Ile Asn Arg Pro Gln Phe Pro Gly Asp Thr
    2285              2290              2295
Glu Thr Gln Gln Asp Gly Arg Lys Phe Val Ala Ser Leu Leu Ala
    2300              2305              2310
Ser Ala Leu Ala Thr Tyr Thr Tyr Lys Ser Trp Asn Tyr Asn Asn
    2315              2320              2325
Leu Ser Lys Ile Val Glu Pro Ala Leu Ala Thr Leu Pro Tyr Ala
    2330              2335              2340
Ala Thr Ala Leu Lys Leu Phe Ala Pro Thr Arg Leu Glu Ser Val
    2345              2350              2355
Val Ile Leu Ser Thr Ala Ile Tyr Lys Thr Tyr Leu Ser Ile Arg
    2360              2365              2370
Arg Gly Lys Ser Asp Gly Leu Leu Gly Thr Gly Val Ser Ala Ala
    2375              2380              2385
Met Glu Ile Met Ser Gln Asn Pro Val Ser Val Gly Ile Ala Val
    2390              2395              2400
Met Leu Gly Val Gly Ala Val Ala Ala His Asn Ala Ile Glu Ala
    2405              2410              2415
Ser Glu Gln Lys Arg Thr Leu Leu Met Lys Val Phe Val Lys Asn
    2420              2425              2430
Phe Leu Asp Gln Ala Ala Thr Asp Glu Leu Val Lys Glu Ser Pro
    2435              2440              2445
Glu Lys Ile Ile Met Ala Leu Phe Glu Ala Val Gln Thr Val Gly
    2450              2455              2460
Asn Pro Leu Arg Leu Val Tyr His Leu Tyr Gly Val Phe Tyr Lys
    2465              2470              2475
Gly Trp Arg Pro Lys Glu Leu Ala Gln Arg Thr Ala Gly Arg Asn
    2480              2485              2490
Leu Phe Thr Leu Ile Met Phe Glu Ala Val Glu Leu Leu Gly Val
    2495              2500              2505
Asp Ser Glu Gly Lys Val Arg Gln Leu Ser Ser Asn Tyr Ile Leu
    2510              2515              2520
Glu Leu Leu Tyr Lys Phe Arg Asp Ser Ile Lys Ser Ser Val Arg
    2525              2530              2535
Glu Met Ala Ile Ser Trp Ala Pro Ala Pro Phe Ser Cys Asp Trp
    2540              2545              2550
Thr Pro Thr Asp Asp Arg Ile Gly Leu Pro Gln Asp Asn Phe His
    2555              2560              2565
Gln Val Glu Thr Lys Cys Pro Cys Gly Tyr Lys Met Lys Ala Val
    2570              2575              2580
Lys Asn Cys Ala Gly Glu Leu Arg Leu Leu Glu Glu Gly Ser
    2585              2590              2595
Phe Leu Cys Arg Asn Lys Phe Gly Arg Gly Ser Arg Asn Tyr Arg
    2600              2605              2610
Val Thr Lys Tyr Tyr Asp Asp Asn Leu Leu Glu Ile Lys Pro Val
    2615              2620              2625
Ile Arg Met Glu Gly His Val Glu Leu Tyr Tyr Lys Gly Ala Thr
    2630              2635              2640
Ile Lys Leu Asp Phe Asn Asn Ser Lys Thr Ile Leu Ala Thr Asp
    2645              2650              2655
Lys Trp Glu Val Asp His Ser Thr Leu Val Arg Val Leu Lys Arg
    2660              2665              2670
```

```
His Thr Gly Ala Gly Tyr His Gly Ala Tyr Leu Gly Glu Lys Pro
2675                    2680                2685

Asn His Lys His Leu Ile Glu Arg Asp Cys Ala Thr Ile Thr Lys
2690                    2695                2700

Asp Lys Val Cys Phe Leu Lys Met Lys Arg Gly Cys Ala Phe Thr
2705                    2710                2715

Tyr Asp Leu Ser Leu His Asn Leu Ala Arg Leu Ile Glu Leu Val
2720                    2725                2730

His Lys Asn Asn Leu Glu Asp Lys Glu Ile Pro Ala Ala Thr Val
2735                    2740                2745

Thr Thr Trp Leu Ala Tyr Thr Phe Val Asn Glu Asp Ile Gly Thr
2750                    2755                2760

Ile Lys Pro Ala Phe Gly Glu Lys Val Thr Leu Glu Met Gln Glu
2765                    2770                2775

Glu Ile Thr Leu Gln Pro Ala Val Val Asp Thr Thr Asp Val
2780                    2785                2790

Ala Val Thr Val Val Gly Glu Ala Pro Thr Met Thr Thr Gly Glu
2795                    2800                2805

Thr Pro Thr Val Phe Thr Ser Ser Gly Ser Gly Leu Lys Asn Gln
2810                    2815                2820

Gln Val Leu Lys Leu Gly Val Gly Glu Gly Gln Tyr Pro Gly Thr
2825                    2830                2835

Asn Pro Gln Arg Ala Ser Leu His Glu Ala Ile Gln Gly Ala Asp
2840                    2845                2850

Glu Arg Pro Ser Val Leu Ile Leu Gly Ser Asp Lys Ala Thr Ser
2855                    2860                2865

Asn Arg Val Lys Thr Ala Lys Asn Val Lys Val Tyr Arg Gly Arg
2870                    2875                2880

Asp Pro Leu Glu Val Arg Asp Met Met Arg Arg Gly Lys Ile Leu
2885                    2890                2895

Val Val Ala Leu Ser Arg Val Asp Asn Ala Leu Leu Lys Phe Val
2900                    2905                2910

Asp Tyr Lys Gly Thr Phe Leu Thr Arg Glu Ala Leu Glu Ala Leu
2915                    2920                2925

Ser Leu Gly Arg Pro Lys Lys Lys Asn Ile Thr Lys Ala Glu Ala
2930                    2935                2940

Gln Cys Leu Leu Cys Pro Glu Asp Gln Met Glu Glu Leu Pro Asp
2945                    2950                2955

Trp Phe Ala Ala Gly Glu Pro Ile Phe Leu Glu Ala Asn Ile Lys
2960                    2965                2970

His Asp Arg Leu His Leu Val Gly Asp Ile Ala Thr Ile Lys Glu
2975                    2980                2985

Lys Ala Lys Gln Leu Gly Ala Thr Asp Ser Thr Lys Ile Ser Lys
2990                    2995                3000

Glu Val Gly Ala Lys Val Tyr Ser Met Lys Leu Ser Asn Trp Val
3005                    3010                3015

Met Gln Glu Glu Asn Lys Gln Gly Asn Leu Thr Pro Leu Phe Glu
3020                    3025                3030

Glu Leu Leu Gln Gln Cys Pro Pro Gly Gly Gln Asn Lys Thr Ala
3035                    3040                3045

His Met Val Ser Ala Tyr Gln Leu Ala Gln Gly Asn Trp Met Pro
3050                    3055                3060
```

```
Thr Ser Cys His Val Phe Met Gly Thr Ile Ser Ala Arg Arg Thr
    3065                3070            3075

Lys Thr His Pro Tyr Glu Ala Tyr Val Lys Leu Arg Glu Leu Val
    3080                3085            3090

Glu Glu His Lys Met Lys Thr Leu Cys Pro Gly Ser Ser Leu Gly
    3095                3100            3105

Lys His Asn Asp Trp Ile Ile Gly Lys Ile Lys Tyr Gln Gly Asn
    3110                3115            3120

Leu Arg Thr Lys His Met Leu Asn Pro Gly Lys Val Ala Glu Gln
    3125                3130            3135

Leu Cys Arg Glu Gly His Arg His Asn Val Tyr Asn Lys Thr Ile
    3140                3145            3150

Ser Ser Val Met Thr Ala Thr Gly Ile Arg Leu Glu Lys Leu Pro
    3155                3160            3165

Val Val Arg Ala Gln Thr Asp Pro Thr Asn Phe His Gln Ala Ile
    3170                3175            3180

Arg Asp Lys Ile Asp Lys Glu Glu Asn Leu Gln Thr Pro Gly Leu
    3185                3190            3195

His Lys Lys Leu Met Glu Val Phe Asn Ala Leu Lys Arg Pro Glu
    3200                3205            3210

Leu Glu Ser Ser Tyr Asp Ala Val Glu Trp Glu Glu Leu Glu Arg
    3215                3220            3225

Gly Ile Asn Arg Lys Gly Ala Ala Gly Phe Phe Glu Arg Lys Asn
    3230                3235            3240

Ile Gly Glu Ile Leu Asp Ser Glu Lys Asn Lys Val Glu Glu Ile
    3245                3250            3255

Ile Asp Asn Leu Lys Lys Gly Arg Asn Ile Lys Tyr Tyr Glu Thr
    3260                3265            3270

Ala Ile Pro Lys Asn Glu Lys Arg Val Val Asn Asp Asp Trp Thr
    3275                3280            3285

Ala Gly Asp Phe Val Asp Glu Lys Lys Pro Arg Val Ile Gln Tyr
    3290                3295            3300

Pro Glu Ala Lys Thr Arg Leu Ala Ile Thr Lys Val Met Tyr Lys
    3305                3310            3315

Trp Val Lys Gln Lys Pro Val Val Ile Pro Gly Tyr Glu Gly Lys
    3320                3325            3330

Thr Pro Leu Phe Gln Ile Phe Asp Lys Val Lys Lys Glu Trp Asp
    3335                3340            3345

Gln Phe Gln Asn Pro Val Ala Val Ser Phe Asp Thr Lys Ala Trp
    3350                3355            3360

Asp Thr Gln Val Thr Thr Lys Asp Leu Glu Leu Ile Arg Asp Ile
    3365                3370            3375

Gln Lys Tyr Tyr Phe Lys Lys Lys Trp His Lys Phe Ile Asp Thr
    3380                3385            3390

Leu Thr Thr His Met Ser Glu Val Pro Val Ile Ser Ala Asp Gly
    3395                3400            3405

Glu Val Tyr Ile Arg Lys Gly Gln Arg Gly Ser Gly Gln Pro Asp
    3410                3415            3420

Thr Ser Ala Gly Asn Ser Met Leu Asn Val Leu Thr Met Val Tyr
    3425                3430            3435

Ala Phe Cys Glu Ala Thr Gly Val Pro Tyr Lys Ser Phe Asp Arg
    3440                3445            3450

Val Ala Lys Ile His Val Cys Gly Asp Asp Gly Phe Leu Ile Thr
```

```
                  3455                  3460                  3465
Glu Arg Ala Leu Gly Glu Lys Phe Ala Ser Lys Gly Val Gln Ile
        3470                  3475                  3480
Leu Tyr Glu Ala Gly Lys Pro Gln Lys Ile Thr Glu Gly Asp Lys
    3485                  3490                  3495
Met Lys Val Ala Tyr Gln Phe Asp Asp Ile Glu Phe Cys Ser His
3500                  3505                  3510
Thr Pro Ile Gln Val Arg Trp Ser Asp Asn Thr Ser Ser Tyr Met
        3515                  3520                  3525
Pro Gly Arg Asn Thr Thr Thr Ile Leu Ala Lys Met Ala Thr Arg
    3530                  3535                  3540
Leu Asp Ser Ser Gly Glu Arg Gly Thr Ile Ala Tyr Glu Lys Ala
3545                  3550                  3555
Val Ala Phe Ser Phe Leu Leu Met Tyr Ser Trp Asn Pro Leu Ile
        3560                  3565                  3570
Arg Arg Ile Cys Leu Leu Val Leu Ser Thr Glu Leu Gln Val Lys
    3575                  3580                  3585
Pro Gly Lys Ser Thr Thr Tyr Tyr Tyr Glu Gly Asp Pro Ile Ser
3590                  3595                  3600
Ala Tyr Lys Glu Val Ile Gly His Asn Leu Phe Asp Leu Lys Arg
        3605                  3610                  3615
Thr Ser Phe Glu Lys Leu Ala Lys Leu Asn Leu Ser Met Ser Val
    3620                  3625                  3630
Leu Gly Ala Trp Thr Arg His Thr Ser Lys Arg Leu Leu Gln Asp
3635                  3640                  3645
Cys Val Asn Ile Gly Val Lys Glu Gly Asn Trp Leu Val Asn Ala
        3650                  3655                  3660
Asp Arg Leu Val Ser Ser Lys Thr Gly Asn Arg Tyr Ile Pro Gly
    3665                  3670                  3675
Glu Gly His Thr Leu Gln Gly Arg His Tyr Glu Glu Leu Val Leu
3680                  3685                  3690
Ala Arg Lys Gln Ile Asn Asn Phe Gln Gly Thr Asp Arg Tyr Asn
        3695                  3700                  3705
Leu Gly Pro Ile Val Asn Met Val Leu Arg Arg Leu Arg Val Met
    3710                  3715                  3720
Met Met Thr Leu Ile Gly Arg Gly Ala
3725                  3730

<210> SEQ ID NO 11
<211> LENGTH: 3731
<212> TYPE: PRT
<213> ORGANISM: CSFV

<400> SEQUENCE: 11

Met Gly Ser Asp Asp Gly Ala Ser Gly Ser Lys Glu Lys Lys Pro Asp
1               5                   10                  15
Arg Ile Asn Lys Gly Lys Leu Lys Ile Ala Pro Lys Glu His Glu Lys
                20                  25                  30
Asp Ser Arg Thr Arg Pro Pro Asp Ala Thr Ile Val Val Glu Gly Val
            35                  40                  45
Lys Tyr Gln Val Lys Lys Lys Gly Lys Val Lys Gly Lys Asn Thr Gln
        50                  55                  60
Asp Gly Leu Tyr His Asn Lys Asn Lys Pro Pro Glu Ser Arg Lys Lys
65                  70                  75                  80
```

```
Leu Glu Lys Ala Leu Leu Ala Trp Ala Val Ile Ala Ile Met Leu Tyr
            85                  90                  95

Gln Pro Val Glu Ala Glu Asn Ile Thr Gln Trp Asn Leu Ser Asp Asn
           100                 105                 110

Gly Thr Asn Gly Ile Gln His Ala Met Tyr Leu Arg Gly Val Asn Arg
           115                 120                 125

Ser Leu His Gly Ile Trp Pro Gly Lys Ile Cys Lys Gly Val Pro Thr
       130                 135                 140

His Leu Ala Thr Asp Val Glu Leu Lys Glu Ile Gln Gly Met Met Asp
145                 150                 155                 160

Ala Ser Glu Gly Thr Asn Tyr Thr Cys Cys Lys Leu Gln Arg His Glu
                165                 170                 175

Trp Asn Lys Gly Trp Cys Asn Trp His Asn Ile Asp Pro Trp Ile Gln
            180                 185                 190

Leu Met Asn Arg Thr Gln Ala Asp Leu Ala Glu Gly Pro Pro Val Lys
        195                 200                 205

Glu Cys Ala Val Thr Cys Arg Tyr Asp Lys Asp Ala Asp Ile Asn Val
    210                 215                 220

Val Thr Gln Ala Arg Asn Arg Pro Thr Thr Leu Thr Gly Cys Lys Lys
225                 230                 235                 240

Gly Lys Asn Phe Ser Phe Ala Gly Thr Val Ile Glu Ser Pro Cys Asn
                245                 250                 255

Phe Asn Val Ser Val Glu Asp Thr Leu Tyr Gly Asp His Glu Ser Cys
            260                 265                 270

Ser Leu Leu Gln Asp Ala Ala Leu Tyr Leu Val Asp Gly Met Thr Asn
        275                 280                 285

Thr Ile Glu Asn Ala Arg Gln Gly Ala Ala Arg Val Thr Ser Trp Leu
    290                 295                 300

Gly Arg Gln Leu Arg Ile Ala Gly Lys Arg Leu Glu Gly Arg Ser Lys
305                 310                 315                 320

Thr Trp Phe Gly Ala Tyr Ala Leu Ser Pro Tyr Cys Asn Val Thr Ser
                325                 330                 335

Lys Ile Gly Tyr Ile Trp Tyr Thr Asn Asn Cys Thr Pro Ala Cys Leu
            340                 345                 350

Pro Lys Asn Thr Lys Ile Ile Gly Pro Gly Lys Phe Asp Thr Asn Ala
        355                 360                 365

Glu Asp Gly Lys Ile Leu His Glu Met Gly Gly His Leu Ser Glu Phe
    370                 375                 380

Leu Leu Leu Ser Leu Val Val Leu Ser Asp Phe Ala Pro Glu Thr Ala
385                 390                 395                 400

Ser Ala Leu Tyr Leu Ile Phe His Tyr Val Ile Pro Gln Pro His Asp
                405                 410                 415

Glu Pro Glu Gly Cys Asp Thr Asn Gln Leu Asn Leu Thr Val Glu Leu
            420                 425                 430

Arg Thr Glu Asp Val Ile Pro Ser Ser Val Trp Asn Val Gly Lys Tyr
        435                 440                 445

Val Cys Val Arg Pro Asp Trp Trp Pro Tyr Glu Thr Glu Val Ala Leu
    450                 455                 460

Leu Phe Glu Glu Val Gly Gln Val Val Lys Leu Ala Leu Arg Ala Leu
465                 470                 475                 480

Arg Asp Leu Thr Arg Val Trp Asn Ser Ala Ser Thr Ile Ala Phe Leu
                485                 490                 495

Ile Cys Leu Ile Lys Val Leu Arg Gly Gln Ile Val Gln Gly Val Val
```

```
                500             505              510
Trp Leu Leu Val Thr Gly Ala Gln Gly Arg Leu Ala Cys Lys Glu
            515             520             525
Asp Tyr Arg Tyr Ala Ile Ser Ser Thr Asp Glu Ile Gly Leu Leu Gly
            530             535             540
Ala Gly Gly Leu Thr Thr Thr Trp Lys Glu Tyr Asn His Asp Leu Gln
545             550             555             560
Leu Asn Asp Gly Thr Val Lys Ala Ser Cys Val Ala Gly Ser Phe Lys
                565             570             575
Val Thr Ala Leu Asn Val Val Ser Arg Arg Tyr Leu Ala Ser Leu His
            580             585             590
Lys Lys Ala Leu Pro Thr Ser Val Thr Phe Glu Leu Leu Phe Asp Gly
            595             600             605
Thr Asn Pro Ser Thr Glu Glu Met Gly Asp Asp Phe Arg Ser Gly Leu
            610             615             620
Cys Pro Phe Asp Thr Ser Pro Val Val Lys Gly Lys Tyr Asn Thr Thr
625             630             635             640
Leu Leu Asn Gly Ser Ala Phe Tyr Leu Val Cys Pro Ile Gly Trp Thr
                645             650             655
Gly Val Ile Glu Cys Thr Ala Val Ser Lys Asp Thr Leu Arg Thr Glu
            660             665             670
Val Val Lys Thr Phe Arg Arg Asp Lys Pro Phe Pro His Arg Met Asp
            675             680             685
Cys Val Thr Thr Thr Val Glu Asn Glu Asp Leu Phe Tyr Cys Lys Leu
            690             695             700
Gly Gly Asn Trp Thr Cys Val Lys Gly Glu Pro Val Val Tyr Thr Gly
705             710             715             720
Gly Leu Val Lys Gln Cys Arg Trp Cys Gly Phe Asp Phe Asp Gly Pro
                725             730             735
Asp Gly Leu Pro His Tyr Pro Ile Gly Lys Cys Ile Leu Ala Asn Glu
            740             745             750
Thr Gly Tyr Arg Ile Val Asp Ser Thr Asp Cys Asn Arg Asp Gly Val
            755             760             765
Val Ile Ser Thr Glu Gly Ser His Glu Cys Leu Ile Gly Asn Thr Thr
            770             775             780
Val Lys Val His Ala Ser Asp Glu Arg Leu Gly Pro Met Pro Cys Arg
785             790             795             800
Pro Lys Glu Ile Val Ser Ser Ala Gly Pro Val Lys Lys Thr Ser Cys
                805             810             815
Thr Phe Asn Tyr Thr Lys Thr Leu Lys Asn Arg Tyr Tyr Glu Pro Arg
            820             825             830
Asp Ser Tyr Phe Gln Gln Tyr Met Leu Lys Gly Glu Tyr Gln Tyr Trp
            835             840             845
Phe Asp Leu Asp Ala Thr Asp Arg His Ser Asp Tyr Phe Ala Glu Phe
            850             855             860
Val Val Leu Val Val Ala Leu Leu Gly Arg Tyr Val Leu Trp
865             870             875             880
Leu Ile Val Thr Tyr Val Val Leu Thr Glu Gln Leu Ala Ala Gly Leu
                885             890             895
Pro Leu Gly Gln Gly Glu Val Leu Ile Gly Asn Leu Ile Thr His
            900             905             910
Thr Asp Ile Glu Val Val Val Tyr Phe Leu Leu Leu Tyr Leu Val Met
            915             920             925
```

-continued

```
Arg Asp Glu Pro Ile Lys Lys Trp Ile Leu Leu Phe His Ala Met
930             935             940

Thr Asn Asn Pro Val Lys Thr Ile Thr Val Ala Leu Leu Met Val Ser
945             950             955             960

Gly Val Ala Lys Gly Gly Lys Ile Asp Gly Gly Trp Gln Arg Leu Pro
                965             970             975

Gly Thr Ser Phe Asp Ile Gln Leu Ala Leu Thr Val Ile Val Val Ala
                980             985             990

Val Met Leu Leu Ala Lys Arg Asp Pro Thr Thr Val Pro Leu Val Ile
        995             1000            1005

Thr Val Ala Thr Leu Arg Thr Ala Lys Met Thr Asn Gly Leu Ser
    1010            1015            1020

Thr Asp Ile Ala Ile Ala Thr Val Ser Ala Ala Leu Leu Thr Trp
    1025            1030            1035

Thr Tyr Ile Ser Asp Tyr Tyr Arg Tyr Lys Thr Trp Leu Gln Tyr
    1040            1045            1050

Leu Ile Ser Thr Val Thr Gly Ile Phe Leu Ile Arg Val Leu Lys
    1055            1060            1065

Gly Ile Gly Glu Leu Asp Leu His Thr Pro Thr Leu Pro Ser His
    1070            1075            1080

Arg Pro Leu Phe Phe Ile Leu Val Tyr Leu Ile Ser Thr Ala Val
    1085            1090            1095

Val Thr Arg Trp Asn Leu Asp Ile Ala Gly Leu Leu Leu Gln Cys
    1100            1105            1110

Val Pro Thr Leu Leu Met Val Phe Thr Met Trp Ala Asp Ile Leu
    1115            1120            1125

Thr Leu Ile Leu Ile Leu Pro Thr Tyr Glu Leu Thr Lys Leu Tyr
    1130            1135            1140

Tyr Leu Lys Glu Val Lys Ile Gly Ala Glu Lys Gly Trp Leu Trp
    1145            1150            1155

Lys Thr Asn Phe Lys Arg Val Asn Asp Ile Tyr Glu Val Asp Gln
    1160            1165            1170

Ala Gly Glu Gly Val Tyr Leu Phe Pro Ser Lys Gln Lys Thr Ser
    1175            1180            1185

Ser Met Thr Gly Thr Met Leu Pro Leu Ile Lys Ala Ile Leu Ile
    1190            1195            1200

Ser Cys Val Ser Asn Lys Trp Gln Phe Ile Tyr Leu Leu Tyr Leu
    1205            1210            1215

Ile Phe Glu Val Ser Tyr Tyr Leu His Lys Lys Ile Ile Asp Glu
    1220            1225            1230

Ile Ala Gly Gly Thr Asn Phe Ile Ser Arg Leu Val Ala Ala Leu
    1235            1240            1245

Ile Glu Val Asn Trp Ala Phe Asp Asn Glu Glu Val Arg Gly Leu
    1250            1255            1260

Lys Lys Phe Phe Leu Leu Ser Ser Arg Val Lys Glu Leu Ile Ile
    1265            1270            1275

Lys His Lys Val Arg Asn Glu Val Met Val Arg Trp Phe Gly Asp
    1280            1285            1290

Glu Glu Val Tyr Gly Met Pro Lys Leu Val Gly Leu Val Lys Ala
    1295            1300            1305

Ala Thr Leu Ser Lys Asn Lys His Cys Ile Leu Cys Thr Val Cys
    1310            1315            1320
```

```
Glu Asp Arg Glu Trp Arg Gly Glu Thr Cys Pro Lys Cys Gly Arg
1325                1330                1335

Phe Gly Pro Pro Met Thr Cys Gly Met Thr Leu Ala Asp Phe Glu
1340                1345                1350

Glu Lys His Tyr Lys Arg Ile Phe Phe Arg Glu Asp Gln Ser Glu
1355                1360                1365

Gly Pro Val Arg Glu Glu Tyr Ala Gly Tyr Leu Gln Tyr Arg Ala
1370                1375                1380

Arg Gly Gln Leu Phe Leu Arg Asn Leu Pro Val Leu Ala Thr Lys
1385                1390                1395

Val Lys Met Leu Leu Val Gly Asn Leu Gly Thr Glu Val Gly Asp
1400                1405                1410

Leu Glu His Leu Gly Trp Val Leu Arg Gly Pro Ala Val Cys Lys
1415                1420                1425

Lys Val Thr Glu His Glu Lys Cys Thr Thr Ser Met Met Asp Lys
1430                1435                1440

Leu Thr Ala Phe Phe Gly Val Met Pro Arg Gly Thr Thr Pro Arg
1445                1450                1455

Ala Pro Val Arg Phe Pro Thr Ser Leu Leu Lys Ile Arg Arg Gly
1460                1465                1470

Leu Glu Thr Gly Trp Ala Tyr Thr His Gln Gly Ile Ser Ser
1475                1480                1485

Val Asp His Val Thr Cys Gly Lys Asp Leu Leu Val Cys Asp Thr
1490                1495                1500

Met Gly Arg Thr Arg Val Val Cys Gln Ser Asn Asn Lys Met Thr
1505                1510                1515

Asp Glu Ser Glu Tyr Gly Val Lys Thr Asp Ser Gly Cys Pro Glu
1520                1525                1530

Gly Ala Arg Cys Tyr Val Phe Asn Pro Glu Ala Val Asn Ile Ser
1535                1540                1545

Gly Thr Lys Gly Ala Met Val His Leu Gln Lys Thr Gly Gly Glu
1550                1555                1560

Phe Thr Cys Val Thr Ala Ser Gly Thr Pro Ala Phe Phe Asp Leu
1565                1570                1575

Lys Asn Leu Lys Gly Trp Ser Gly Leu Pro Ile Phe Glu Ala Ser
1580                1585                1590

Ser Gly Arg Val Val Gly Arg Val Lys Val Gly Lys Asn Glu Asp
1595                1600                1605

Ser Lys Pro Thr Lys Leu Met Ser Gly Ile Gln Thr Val Ser Lys
1610                1615                1620

Ser Thr Thr Asp Leu Thr Glu Met Val Lys Lys Ile Thr Thr Met
1625                1630                1635

Ser Arg Gly Glu Phe Arg Gln Ile Thr Leu Ala Thr Gly Ala Gly
1640                1645                1650

Lys Thr Thr Glu Leu Pro Arg Ser Val Ile Glu Glu Ile Gly Arg
1655                1660                1665

His Lys Arg Val Leu Val Leu Ile Pro Leu Arg Ala Ala Ala Glu
1670                1675                1680

Ser Val Tyr Gln Tyr Met Arg Gln Lys His Pro Ser Ile Ala Phe
1685                1690                1695

Asn Leu Arg Ile Gly Glu Met Lys Glu Gly Asp Met Ala Thr Gly
1700                1705                1710

Ile Thr Tyr Ala Ser Tyr Gly Tyr Phe Cys Gln Met Pro Gln Pro
```

-continued

```
            1715                1720                1725

Lys Leu Arg Ala Ala Met Val Glu Tyr Ser Phe Ile Phe Leu Asp
            1730                1735                1740

Glu Tyr His Cys Ala Thr Pro Glu Gln Leu Ala Ile Met Gly Lys
            1745                1750                1755

Ile His Arg Phe Ser Glu Asn Leu Arg Val Val Ala Met Thr Ala
            1760                1765                1770

Thr Pro Val Gly Thr Val Thr Thr Gly Gln Lys His Pro Ile
            1775                1780                1785

Glu Glu Phe Ile Ala Pro Asp Val Met Lys Gly Glu Asp Leu Gly
            1790                1795                1800

Ser Glu Tyr Leu Asp Ile Ala Gly Leu Lys Ile Pro Val Glu Glu
            1805                1810                1815

Met Lys Ser Asn Met Leu Val Phe Val Pro Thr Arg Asn Met Ala
            1820                1825                1830

Val Glu Thr Ala Lys Lys Leu Lys Ala Lys Gly Tyr Asn Ser Gly
            1835                1840                1845

Tyr Tyr Tyr Ser Gly Glu Asp Pro Ser Asn Leu Arg Val Val Thr
            1850                1855                1860

Ser Gln Ser Pro Tyr Val Val Ala Thr Asn Ala Ile Glu Pro
            1865                1870                1875

Gly Val Thr Leu Pro Asp Leu Asp Val Val Val Asp Thr Gly Leu
            1880                1885                1890

Lys Cys Glu Lys Arg Ile Arg Leu Ser Pro Lys Met Pro Phe Ile
            1895                1900                1905

Val Thr Gly Leu Lys Arg Met Ala Val Thr Ile Gly Glu Gln Ala
            1910                1915                1920

Gln Arg Arg Gly Arg Val Gly Arg Val Lys Pro Gly Arg Tyr Tyr
            1925                1930                1935

Arg Ser Gln Glu Thr Pro Val Gly Ser Lys Asp Tyr His Tyr Asp
            1940                1945                1950

Leu Leu Gln Ala Gln Arg Tyr Gly Ile Glu Asp Gly Ile Asn Ile
            1955                1960                1965

Thr Lys Ser Phe Arg Glu Met Asn Tyr Asp Trp Ser Leu Tyr Glu
            1970                1975                1980

Glu Asp Ser Leu Met Ile Thr Gln Leu Glu Ile Leu Asn Asn Leu
            1985                1990                1995

Leu Ile Ser Asp Glu Leu Pro Met Ala Val Lys Asn Ile Met Ala
            2000                2005                2010

Arg Thr Asp His Pro Glu Pro Ile Gln Leu Ala Tyr Asn Ser Tyr
            2015                2020                2025

Glu Thr Gln Val Pro Val Leu Phe Pro Lys Ile Lys Asn Gly Glu
            2030                2035                2040

Val Thr Asp Ser Tyr Asp Asn Tyr Thr Phe Leu Asn Ala Arg Lys
            2045                2050                2055

Leu Gly Asp Asp Val Pro Pro Tyr Val Tyr Ala Thr Glu Asp Glu
            2060                2065                2070

Asp Leu Ala Val Glu Leu Leu Gly Leu Asp Trp Pro Asp Pro Gly
            2075                2080                2085

Asn Leu Gly Thr Val Glu Thr Gly Arg Ala Leu Lys Gln Val Val
            2090                2095                2100

Gly Leu Ser Thr Ala Glu Asn Ala Leu Leu Val Ala Leu Phe Gly
            2105                2110                2115
```

```
Tyr Val Gly Tyr Gln Ala Leu Ser Lys Arg His Ile Pro Val Val
2120                2125                2130

Thr Asp Ile Tyr Ser Ile Glu Asp His Arg Leu Glu Asp Thr Thr
2135                2140                2145

His Leu Gln Tyr Ala Pro Asn Ala Ile Lys Thr Glu Gly Lys Glu
2150                2155                2160

Thr Glu Leu Lys Glu Leu Ala Gln Gly Asp Val Gln Arg Cys Val
2165                2170                2175

Glu Ala Met Thr Asn Tyr Ala Arg Glu Gly Ile Gln Phe Met Lys
2180                2185                2190

Ser Gln Ala Leu Lys Val Lys Glu Thr Pro Thr Tyr Lys Glu Thr
2195                2200                2205

Met Asp Thr Val Thr Asp Tyr Val Lys Lys Phe Met Glu Ala Leu
2210                2215                2220

Ala Asp Ser Lys Glu Asp Ile Ile Lys Tyr Gly Leu Trp Gly Thr
2225                2230                2235

His Thr Ala Leu Tyr Lys Ser Ile Ser Ala Arg Leu Gly Gly Glu
2240                2245                2250

Thr Ala Phe Ala Thr Leu Val Val Lys Trp Leu Ala Phe Gly Gly
2255                2260                2265

Glu Ser Ile Ala Asp His Val Lys Gln Ala Ala Thr Asp Leu Val
2270                2275                2280

Val Tyr Tyr Ile Ile Asn Arg Pro Gln Phe Pro Gly Asp Thr Glu
2285                2290                2295

Thr Gln Gln Asp Gly Arg Lys Phe Val Ala Ser Leu Leu Ala Ser
2300                2305                2310

Ala Leu Ala Thr Tyr Thr Tyr Lys Ser Trp Asn Tyr Asn Asn Leu
2315                2320                2325

Ser Lys Ile Val Glu Pro Leu Ala Thr Leu Pro Tyr Ala Ala
2330                2335                2340

Thr Ala Leu Lys Leu Phe Ala Pro Thr Arg Leu Glu Ser Val Val
2345                2350                2355

Ile Leu Ser Thr Ala Ile Tyr Lys Thr Tyr Leu Ser Ile Arg Arg
2360                2365                2370

Gly Lys Ser Asp Gly Leu Leu Gly Thr Gly Val Ser Ala Ala Met
2375                2380                2385

Glu Ile Met Ser Gln Asn Pro Val Ser Val Gly Ile Ala Val Met
2390                2395                2400

Leu Gly Val Gly Ala Val Ala Ala His Asn Ala Ile Glu Ala Ser
2405                2410                2415

Glu Gln Lys Arg Thr Leu Leu Met Lys Val Phe Val Lys Asn Phe
2420                2425                2430

Leu Asp Gln Ala Ala Thr Asp Glu Leu Val Lys Glu Ser Pro Glu
2435                2440                2445

Lys Ile Ile Met Ala Leu Phe Glu Ala Val Gln Thr Val Gly Asn
2450                2455                2460

Pro Leu Arg Leu Val Tyr His Leu Tyr Gly Val Phe Tyr Lys Gly
2465                2470                2475

Trp Arg Pro Lys Glu Leu Ala Gln Arg Thr Ala Gly Arg Asn Leu
2480                2485                2490

Phe Thr Leu Ile Met Phe Glu Ala Val Glu Leu Leu Gly Val Asp
2495                2500                2505
```

| | | | | | | | | | | |
|---|---|---|---|---|---|---|---|---|---|---|
| Ser | Glu | Gly | Lys | Val | Arg | Gln | Leu | Ser | Ser | Asn | Tyr | Ile | Leu | Glu |
| 2510 | | | | | 2515 | | | | | 2520 | | | | |
| Leu | Leu | Tyr | Lys | Phe | Arg | Asp | Ser | Ile | Lys | Ser | Ser | Val | Arg | Glu |
| 2525 | | | | | 2530 | | | | | 2535 | | | | |
| Met | Ala | Ile | Ser | Trp | Ala | Pro | Ala | Pro | Phe | Ser | Cys | Asp | Trp | Thr |
| 2540 | | | | | 2545 | | | | | 2550 | | | | |
| Pro | Thr | Asp | Asp | Arg | Ile | Gly | Leu | Pro | Gln | Asp | Asn | Phe | His | Gln |
| 2555 | | | | | 2560 | | | | | 2565 | | | | |
| Val | Glu | Thr | Lys | Cys | Pro | Cys | Gly | Tyr | Lys | Met | Lys | Ala | Val | Lys |
| 2570 | | | | | 2575 | | | | | 2580 | | | | |
| Asn | Cys | Ala | Gly | Glu | Leu | Arg | Leu | Leu | Glu | Glu | Gly | Ser | Phe |
| 2585 | | | | | 2590 | | | | | 2595 | | | | |
| Leu | Cys | Arg | Asn | Lys | Phe | Gly | Arg | Gly | Ser | Arg | Asn | Tyr | Arg | Val |
| 2600 | | | | | 2605 | | | | | 2610 | | | | |
| Thr | Lys | Tyr | Tyr | Asp | Asp | Asn | Leu | Leu | Glu | Ile | Lys | Pro | Val | Ile |
| 2615 | | | | | 2620 | | | | | 2625 | | | | |
| Arg | Met | Glu | Gly | His | Val | Glu | Leu | Tyr | Tyr | Lys | Gly | Ala | Thr | Ile |
| 2630 | | | | | 2635 | | | | | 2640 | | | | |
| Lys | Leu | Asp | Phe | Asn | Asn | Ser | Lys | Thr | Ile | Leu | Ala | Thr | Asp | Lys |
| 2645 | | | | | 2650 | | | | | 2655 | | | | |
| Trp | Glu | Val | Asp | His | Ser | Thr | Leu | Val | Arg | Val | Leu | Lys | Arg | His |
| 2660 | | | | | 2665 | | | | | 2670 | | | | |
| Thr | Gly | Ala | Gly | Tyr | His | Gly | Ala | Tyr | Leu | Gly | Glu | Lys | Pro | Asn |
| 2675 | | | | | 2680 | | | | | 2685 | | | | |
| His | Lys | His | Leu | Ile | Glu | Arg | Asp | Cys | Ala | Thr | Ile | Thr | Lys | Asp |
| 2690 | | | | | 2695 | | | | | 2700 | | | | |
| Lys | Val | Cys | Phe | Leu | Lys | Met | Lys | Arg | Gly | Cys | Ala | Phe | Thr | Tyr |
| 2705 | | | | | 2710 | | | | | 2715 | | | | |
| Asp | Leu | Ser | Leu | His | Asn | Leu | Ala | Arg | Leu | Ile | Glu | Leu | Val | His |
| 2720 | | | | | 2725 | | | | | 2730 | | | | |
| Lys | Asn | Asn | Leu | Glu | Asp | Lys | Glu | Ile | Pro | Ala | Ala | Thr | Val | Thr |
| 2735 | | | | | 2740 | | | | | 2745 | | | | |
| Thr | Trp | Leu | Ala | Tyr | Thr | Phe | Val | Asn | Glu | Asp | Ile | Gly | Thr | Ile |
| 2750 | | | | | 2755 | | | | | 2760 | | | | |
| Lys | Pro | Ala | Phe | Gly | Glu | Lys | Val | Thr | Leu | Glu | Met | Gln | Glu | Glu |
| 2765 | | | | | 2770 | | | | | 2775 | | | | |
| Ile | Thr | Leu | Gln | Pro | Ala | Val | Val | Val | Asp | Thr | Thr | Asp | Val | Ala |
| 2780 | | | | | 2785 | | | | | 2790 | | | | |
| Val | Thr | Val | Val | Gly | Glu | Ala | Pro | Thr | Met | Thr | Thr | Gly | Glu | Thr |
| 2795 | | | | | 2800 | | | | | 2805 | | | | |
| Pro | Thr | Val | Phe | Thr | Ser | Ser | Gly | Ser | Gly | Leu | Lys | Asn | Gln | Gln |
| 2810 | | | | | 2815 | | | | | 2820 | | | | |
| Val | Leu | Lys | Leu | Gly | Val | Gly | Glu | Gly | Gln | Tyr | Pro | Gly | Thr | Asn |
| 2825 | | | | | 2830 | | | | | 2835 | | | | |
| Pro | Gln | Arg | Ala | Ser | Leu | His | Glu | Ala | Ile | Gln | Gly | Ala | Asp | Glu |
| 2840 | | | | | 2845 | | | | | 2850 | | | | |
| Arg | Pro | Ser | Val | Leu | Ile | Leu | Gly | Ser | Asp | Lys | Ala | Thr | Ser | Asn |
| 2855 | | | | | 2860 | | | | | 2865 | | | | |
| Arg | Val | Lys | Thr | Ala | Lys | Asn | Val | Lys | Val | Tyr | Arg | Gly | Arg | Asp |
| 2870 | | | | | 2875 | | | | | 2880 | | | | |
| Pro | Leu | Glu | Val | Arg | Asp | Met | Met | Arg | Arg | Gly | Lys | Ile | Leu | Val |
| 2885 | | | | | 2890 | | | | | 2895 | | | | |
| Val | Ala | Leu | Ser | Arg | Val | Asp | Asn | Ala | Leu | Leu | Lys | Phe | Val | Asp |

```
                    2900                2905                2910
Tyr Lys Gly Thr Phe Leu Thr Arg Glu Ala Leu Glu Ala Leu Ser
    2915                2920                2925
Leu Gly Arg Pro Lys Lys Lys Asn Ile Thr Lys Ala Glu Ala Gln
    2930                2935                2940
Cys Leu Leu Cys Pro Glu Asp Gln Met Glu Glu Leu Pro Asp Trp
    2945                2950                2955
Phe Ala Ala Gly Glu Pro Ile Phe Leu Glu Ala Asn Ile Lys His
    2960                2965                2970
Asp Arg Leu His Leu Val Gly Asp Ile Ala Thr Ile Lys Glu Lys
    2975                2980                2985
Ala Lys Gln Leu Gly Ala Thr Asp Ser Thr Lys Ile Ser Lys Glu
    2990                2995                3000
Val Gly Ala Lys Val Tyr Ser Met Lys Leu Ser Asn Trp Val Met
    3005                3010                3015
Gln Glu Glu Asn Lys Gln Gly Asn Leu Thr Pro Leu Phe Glu Glu
    3020                3025                3030
Leu Leu Gln Gln Cys Pro Pro Gly Gly Gln Asn Lys Thr Ala His
    3035                3040                3045
Met Val Ser Ala Tyr Gln Leu Ala Gln Gly Asn Trp Met Pro Thr
    3050                3055                3060
Ser Cys His Val Phe Met Gly Thr Ile Ser Ala Arg Arg Thr Lys
    3065                3070                3075
Thr His Pro Tyr Glu Ala Tyr Val Lys Leu Arg Glu Leu Val Glu
    3080                3085                3090
Glu His Lys Met Lys Thr Leu Cys Pro Gly Ser Ser Leu Gly Lys
    3095                3100                3105
His Asn Asp Trp Ile Ile Gly Lys Ile Lys Tyr Gln Gly Asn Leu
    3110                3115                3120
Arg Thr Lys His Met Leu Asn Pro Gly Lys Val Ala Glu Gln Leu
    3125                3130                3135
Cys Arg Glu Gly His Arg His Asn Val Tyr Asn Lys Thr Ile Ser
    3140                3145                3150
Ser Val Met Thr Ala Thr Gly Ile Arg Leu Glu Lys Leu Pro Val
    3155                3160                3165
Val Arg Ala Gln Thr Asp Pro Thr Asn Phe His Gln Ala Ile Arg
    3170                3175                3180
Asp Lys Ile Asp Lys Glu Glu Asn Leu Gln Thr Pro Gly Leu His
    3185                3190                3195
Lys Lys Leu Met Glu Val Phe Asn Ala Leu Lys Arg Pro Glu Leu
    3200                3205                3210
Glu Ser Ser Tyr Asp Ala Val Glu Trp Glu Glu Leu Glu Arg Gly
    3215                3220                3225
Ile Asn Arg Lys Gly Ala Ala Gly Phe Phe Glu Arg Lys Asn Ile
    3230                3235                3240
Gly Glu Ile Leu Asp Ser Glu Lys Asn Lys Val Glu Glu Ile Ile
    3245                3250                3255
Asp Asn Leu Lys Lys Gly Arg Asn Ile Lys Tyr Tyr Glu Thr Ala
    3260                3265                3270
Ile Pro Lys Asn Glu Lys Arg Val Val Asn Asp Asp Trp Thr Ala
    3275                3280                3285
Gly Asp Phe Val Asp Glu Lys Lys Pro Arg Val Ile Gln Tyr Pro
    3290                3295                3300
```

```
Glu Ala Lys Thr Arg Leu Ala Ile Thr Lys Val Met Tyr Lys Trp
3305                3310                3315

Val Lys Gln Lys Pro Val Val Ile Pro Gly Tyr Glu Gly Lys Thr
3320                3325                3330

Pro Leu Phe Gln Ile Phe Asp Lys Val Lys Lys Glu Trp Asp Gln
3335                3340                3345

Phe Gln Asn Pro Val Ala Val Ser Phe Asp Thr Lys Ala Trp Asp
3350                3355                3360

Thr Gln Val Thr Thr Lys Asp Leu Glu Leu Ile Arg Asp Ile Gln
3365                3370                3375

Lys Tyr Tyr Phe Lys Lys Trp His Lys Phe Ile Asp Thr Leu
3380                3385                3390

Thr Thr His Met Ser Glu Val Pro Val Ile Ser Ala Asp Gly Glu
3395                3400                3405

Val Tyr Ile Arg Lys Gly Gln Arg Gly Ser Gly Gln Pro Asp Thr
3410                3415                3420

Ser Ala Gly Asn Ser Met Leu Asn Val Leu Thr Met Val Tyr Ala
3425                3430                3435

Phe Cys Glu Ala Thr Gly Val Pro Tyr Lys Ser Phe Asp Arg Val
3440                3445                3450

Ala Lys Ile His Val Cys Gly Asp Asp Gly Phe Leu Ile Thr Glu
3455                3460                3465

Arg Ala Leu Gly Glu Lys Phe Ala Ser Lys Gly Val Gln Ile Leu
3470                3475                3480

Tyr Glu Ala Gly Lys Pro Gln Lys Ile Thr Glu Gly Asp Lys Met
3485                3490                3495

Lys Val Ala Tyr Gln Phe Asp Asp Ile Glu Phe Cys Ser His Thr
3500                3505                3510

Pro Ile Gln Val Arg Trp Ser Asp Asn Thr Ser Ser Tyr Met Pro
3515                3520                3525

Gly Arg Asn Thr Thr Thr Ile Leu Ala Lys Met Ala Thr Arg Leu
3530                3535                3540

Asp Ser Ser Gly Glu Arg Gly Thr Ile Ala Tyr Glu Lys Ala Val
3545                3550                3555

Ala Phe Ser Phe Leu Leu Met Tyr Ser Trp Asn Pro Leu Ile Arg
3560                3565                3570

Arg Ile Cys Leu Leu Val Leu Ser Thr Glu Leu Gln Val Lys Pro
3575                3580                3585

Gly Lys Ser Thr Thr Tyr Tyr Tyr Glu Gly Asp Pro Ile Ser Ala
3590                3595                3600

Tyr Lys Glu Val Ile Gly His Asn Leu Phe Asp Leu Lys Arg Thr
3605                3610                3615

Ser Phe Glu Lys Leu Ala Lys Leu Asn Leu Ser Met Ser Val Leu
3620                3625                3630

Gly Ala Trp Thr Arg His Thr Ser Lys Arg Leu Leu Gln Asp Cys
3635                3640                3645

Val Asn Ile Gly Val Lys Glu Gly Asn Trp Leu Val Asn Ala Asp
3650                3655                3660

Arg Leu Val Ser Ser Lys Thr Gly Asn Arg Tyr Ile Pro Gly Glu
3665                3670                3675

Gly His Thr Leu Gln Gly Arg His Tyr Glu Glu Leu Val Leu Ala
3680                3685                3690
```

```
Arg Lys Gln Ile Asn Asn Phe Gln Gly Thr Asp Arg Tyr Asn Leu
    3695                3700                3705

Gly Pro Ile Val Asn Met Val Leu Arg Arg Leu Arg Val Met Met
    3710                3715                3720

Met Thr Leu Ile Gly Arg Gly Ala
    3725            3730

<210> SEQ ID NO 12
<211> LENGTH: 3898
<212> TYPE: PRT
<213> ORGANISM: CSFV

<400> SEQUENCE: 12

Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Lys Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Val Gln Phe Cys
            100                 105                 110

Glu Val Thr Lys Arg Ile Gly Arg Val Thr Gly Ser Asp Gly Lys Leu
        115                 120                 125

Tyr His Thr Tyr Val Cys Ile Asp Gly Cys Ile Leu Leu Lys Leu Ala
    130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Asp Gly Ala Ser Gly Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Arg Pro Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Asn Arg Ser Leu His Gly Ile Trp Pro Gly Lys Ile
    290                 295                 300

Cys Lys Gly Val Pro Thr His Leu Ala Thr Asp Val Glu Leu Lys Glu
305                 310                 315                 320

Ile Gln Gly Met Met Asp Ala Ser Glu Gly Thr Asn Tyr Thr Cys Cys
                325                 330                 335
```

```
Lys Leu Gln Arg His Glu Trp Asn Lys His Gly Trp Cys Asn Trp His
            340                 345                 350
Asn Ile Asp Pro Trp Ile Gln Leu Met Asn Arg Thr Gln Ala Asp Leu
            355                 360                 365
Ala Glu Gly Pro Pro Val Lys Glu Cys Ala Val Thr Cys Arg Tyr Asp
        370                 375                 380
Lys Asp Ala Asp Ile Asn Val Val Thr Gln Ala Arg Asn Arg Pro Thr
385                 390                 395                 400
Thr Leu Thr Gly Cys Lys Lys Gly Lys Asn Phe Ser Phe Ala Gly Thr
            405                 410                 415
Val Ile Glu Ser Pro Cys Asn Phe Asn Val Ser Val Glu Asp Thr Leu
            420                 425                 430
Tyr Gly Asp His Glu Cys Gly Ser Leu Leu Gln Asp Ala Ala Leu Tyr
        435                 440                 445
Leu Val Asp Gly Met Thr Asn Thr Ile Glu Asn Ala Arg Gln Gly Ala
        450                 455                 460
Ala Arg Val Thr Ser Trp Leu Gly Arg Gln Leu Arg Thr Ala Gly Lys
465                 470                 475                 480
Arg Leu Glu Gly Arg Ser Lys Thr Trp Phe Gly Ala Tyr Ala Leu Ser
            485                 490                 495
Pro Tyr Cys Asn Val Thr Ser Lys Ile Gly Tyr Ile Trp Tyr Thr Asn
            500                 505                 510
Asn Cys Thr Pro Ala Cys Leu Pro Lys Asn Thr Lys Ile Ile Gly Pro
        515                 520                 525
Gly Lys Phe Asp Thr Asn Ala Glu Asp Gly Lys Ile Leu His Glu Met
        530                 535                 540
Gly Gly His Leu Ser Glu Phe Leu Leu Leu Ser Leu Val Val Leu Ser
545                 550                 555                 560
Asp Phe Ala Pro Glu Thr Ala Ser Ala Leu Tyr Leu Ile Leu His Tyr
            565                 570                 575
Val Ile Pro Gln Pro His Asp Glu Pro Glu Gly Cys Asp Thr Asn Gln
            580                 585                 590
Leu Asn Leu Thr Val Glu Leu Arg Thr Glu Asp Val Ile Pro Ser Ser
        595                 600                 605
Val Trp Asn Val Gly Lys Tyr Val Cys Val Arg Pro Asp Trp Trp Pro
        610                 615                 620
Tyr Glu Thr Glu Val Ala Leu Leu Phe Glu Glu Val Gly Gln Val Val
625                 630                 635                 640
Lys Leu Ala Leu Arg Ala Leu Arg Asp Leu Thr Arg Val Trp Asn Ser
            645                 650                 655
Ala Ser Thr Ile Ala Phe Leu Ile Cys Leu Ile Lys Val Leu Arg Gly
            660                 665                 670
Gln Ile Val Gln Gly Val Val Trp Leu Leu Leu Val Thr Gly Ala Gln
        675                 680                 685
Gly Arg Leu Ala Cys Lys Glu Asp Tyr Arg Tyr Ala Ile Ser Ser Thr
        690                 695                 700
Asp Glu Ile Gly Leu Leu Gly Ala Gly Gly Leu Thr Thr Thr Trp Lys
705                 710                 715                 720
Glu Tyr Asn His Asp Leu Gln Leu Asn Asp Gly Thr Val Lys Ala Ser
            725                 730                 735
Cys Val Ala Gly Ser Phe Lys Val Thr Ala Leu Asn Val Val Ser Arg
            740                 745                 750
```

-continued

Arg Tyr Leu Ala Ser Leu His Lys Lys Ala Leu Pro Thr Ser Val Thr
        755                 760                 765

Phe Glu Leu Leu Phe Asp Gly Thr Asn Pro Ser Thr Glu Glu Met Gly
770                 775                 780

Asp Asp Phe Arg Ser Gly Leu Cys Pro Phe Asp Thr Ser Pro Val Val
785                 790                 795                 800

Lys Gly Lys Tyr Asn Thr Thr Leu Leu Asn Gly Ser Ala Phe Tyr Leu
            805                 810                 815

Val Cys Pro Ile Gly Trp Thr Gly Val Ile Glu Cys Thr Ala Val Ser
                820                 825                 830

Pro Thr Thr Leu Arg Thr Glu Val Val Lys Thr Phe Arg Arg Asp Lys
        835                 840                 845

Pro Phe Pro His Arg Met Asp Cys Val Thr Thr Val Glu Asn Glu
850                 855                 860

Asp Leu Phe Tyr Cys Lys Leu Gly Gly Asn Trp Thr Cys Val Lys Gly
865                 870                 875                 880

Glu Pro Val Val Tyr Thr Gly Gly Leu Val Lys Gln Cys Arg Trp Cys
            885                 890                 895

Gly Phe Asp Phe Asp Gly Pro Asp Gly Leu Pro His Tyr Pro Ile Gly
                900                 905                 910

Lys Cys Ile Leu Ala Asn Glu Thr Gly Tyr Arg Ile Val Asp Ser Thr
        915                 920                 925

Asp Cys Asn Arg Asp Gly Val Val Ile Ser Thr Glu Gly Ser His Glu
        930                 935                 940

Cys Leu Ile Gly Asn Thr Thr Val Lys Val His Ala Ser Asp Glu Arg
945                 950                 955                 960

Leu Gly Pro Met Pro Cys Arg Pro Lys Glu Ile Val Ser Ser Ala Gly
            965                 970                 975

Pro Val Lys Lys Thr Ser Cys Thr Phe Asn Tyr Thr Lys Thr Leu Lys
                980                 985                 990

Asn Arg Tyr Tyr Glu Pro Arg Asp Ser Tyr Phe Gln Gln Tyr Met Leu
        995                 1000                1005

Lys Gly Glu Tyr Gln Tyr Trp Phe Asp Leu Asp Ala Thr Asp Arg
    1010                1015                1020

His Ser Asp Tyr Phe Ala Glu Phe Val Val Leu Val Val Val Ala
    1025                1030                1035

Leu Leu Gly Gly Arg Tyr Val Leu Trp Leu Ile Val Thr Tyr Val
    1040                1045                1050

Val Leu Thr Glu Gln Leu Ala Ala Gly Leu Pro Leu Gly Gln Gly
    1055                1060                1065

Glu Val Val Leu Ile Gly Asn Leu Ile Thr His Thr Asp Ile Glu
    1070                1075                1080

Val Val Val Tyr Phe Leu Leu Leu Tyr Leu Val Met Arg Asp Glu
    1085                1090                1095

Pro Ile Lys Lys Trp Ile Leu Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Lys Gly Gly Lys Ile Asp Gly Gly Trp Gln Arg Leu Pro
    1130                1135                1140

Gly Thr Ser Phe Asp Ile Gln Leu Ala Leu Thr Val Ile Val Val
    1145                1150                1155

Ala Val Met Leu Leu Ala Lys Arg Asp Pro Thr Thr Val Pro Leu

-continued

```
                1160                1165                1170
Val Ile Thr Val Ala Pro Leu Arg Thr Ala Lys Met Thr Asn Gly
                1175                1180                1185

Leu Ser Thr Asp Ile Ala Ile Ala Thr Val Ser Ala Ala Leu Leu
                1190                1195                1200

Thr Trp Thr Tyr Ile Ser Asp Tyr Tyr Arg Tyr Lys Thr Trp Leu
                1205                1210                1215

Gln Tyr Leu Ile Ser Thr Val Thr Gly Ile Phe Leu Ile Arg Val
                1220                1225                1230

Leu Lys Gly Ile Gly Glu Leu Asp Leu His Thr Pro Thr Leu Pro
                1235                1240                1245

Ser His Arg Pro Leu Phe Phe Ile Leu Val Tyr Leu Ile Ser Thr
                1250                1255                1260

Ala Val Val Thr Arg Trp Asn Leu Asp Ile Ala Gly Leu Leu Leu
                1265                1270                1275

Gln Cys Val Pro Thr Leu Leu Met Val Phe Thr Met Trp Ala Asp
                1280                1285                1290

Ile Leu Thr Leu Ile Leu Ile Leu Pro Thr Tyr Glu Leu Thr Lys
                1295                1300                1305

Leu Tyr Tyr Leu Lys Glu Val Arg Ile Gly Ala Glu Lys Gly Trp
                1310                1315                1320

Leu Trp Lys Thr Asn Phe Lys Arg Val Asn Asp Ile Tyr Glu Val
                1325                1330                1335

Asp Gln Ala Gly Glu Gly Val Tyr Leu Phe Pro Ser Lys Gln Lys
                1340                1345                1350

Thr Ser Ser Met Thr Gly Thr Met Leu Pro Leu Ile Lys Ala Ile
                1355                1360                1365

Leu Ile Ser Cys Val Ser Asn Lys Trp Gln Phe Ile Tyr Leu Leu
                1370                1375                1380

Tyr Leu Ile Phe Glu Val Ser Tyr Tyr Leu His Lys Lys Ile Ile
                1385                1390                1395

Asp Glu Ile Ala Gly Gly Thr Asn Phe Ile Ser Arg Leu Val Ala
                1400                1405                1410

Ala Leu Ile Glu Val Asn Trp Ala Phe Asp Asn Glu Glu Val Arg
                1415                1420                1425

Gly Leu Lys Lys Phe Phe Leu Leu Ser Ser Arg Val Lys Glu Leu
                1430                1435                1440

Ile Ile Lys His Lys Val Arg Asn Glu Val Met Val Arg Trp Phe
                1445                1450                1455

Gly Asp Glu Glu Val Tyr Gly Met Pro Lys Leu Val Gly Leu Val
                1460                1465                1470

Lys Ala Ala Thr Leu Ser Lys Asn Lys His Cys Ile Leu Cys Thr
                1475                1480                1485

Val Cys Glu Asp Arg Glu Trp Arg Gly Glu Thr Cys Pro Lys Cys
                1490                1495                1500

Gly Arg Phe Gly Pro Pro Met Thr Cys Gly Met Thr Leu Ala Asp
                1505                1510                1515

Phe Glu Glu Lys His Tyr Lys Arg Ile Phe Phe Arg Glu Asp Gln
                1520                1525                1530

Ser Glu Gly Pro Val Arg Glu Glu Tyr Ala Gly Tyr Leu Gln Tyr
                1535                1540                1545

Arg Ala Arg Gly Gln Leu Phe Leu Arg Asn Leu Pro Val Leu Ala
                1550                1555                1560
```

```
Thr Lys Val Lys Met Leu Leu Val Gly Asn Leu Gly Thr Glu Val
1565                1570                1575

Gly Asp Leu Glu His Leu Gly Trp Val Leu Arg Gly Pro Ala Val
1580                1585                1590

Cys Lys Lys Val Thr Glu His Glu Lys Cys Thr Thr Ser Met Met
1595                1600                1605

Asp Lys Leu Thr Ala Phe Phe Gly Val Met Pro Arg Gly Thr Thr
1610                1615                1620

Pro Arg Ala Pro Val Arg Phe Pro Thr Ser Leu Leu Lys Ile Arg
1625                1630                1635

Arg Gly Leu Glu Thr Gly Trp Ala Tyr Thr His Gln Gly Gly Ile
1640                1645                1650

Ser Ser Val Asp His Val Thr Cys Gly Lys Asp Leu Leu Val Cys
1655                1660                1665

Asp Thr Met Gly Arg Thr Arg Val Val Cys Gln Ser Asn Asn Lys
1670                1675                1680

Met Thr Asp Glu Ser Glu Tyr Gly Val Lys Thr Asp Ser Gly Cys
1685                1690                1695

Pro Glu Gly Ala Arg Cys Tyr Val Phe Asn Pro Glu Ala Val Asn
1700                1705                1710

Ile Ser Gly Thr Lys Gly Ala Met Val His Leu Gln Lys Thr Gly
1715                1720                1725

Gly Glu Phe Thr Cys Val Thr Ala Ser Gly Thr Pro Ala Phe Phe
1730                1735                1740

Asp Leu Lys Asn Leu Lys Gly Trp Ser Gly Leu Pro Ile Phe Glu
1745                1750                1755

Ala Ser Ser Gly Arg Val Val Gly Arg Val Lys Val Gly Lys Asn
1760                1765                1770

Glu Asp Ser Lys Pro Thr Lys Leu Met Ser Gly Ile Gln Thr Val
1775                1780                1785

Ser Lys Ser Thr Thr Asp Leu Thr Glu Met Val Lys Lys Ile Thr
1790                1795                1800

Thr Met Ser Arg Gly Glu Phe Arg Gln Ile Thr Leu Ala Thr Gly
1805                1810                1815

Ala Gly Lys Thr Thr Glu Leu Pro Arg Ser Val Ile Glu Glu Ile
1820                1825                1830

Gly Arg His Lys Arg Val Leu Val Leu Ile Pro Leu Arg Ala Ala
1835                1840                1845

Ala Glu Ser Val Tyr Gln Tyr Met Arg Gln Lys His Pro Ser Ile
1850                1855                1860

Ala Phe Asn Leu Arg Ile Gly Glu Met Lys Glu Gly Asp Met Ala
1865                1870                1875

Thr Gly Ile Thr Tyr Ala Ser Tyr Gly Tyr Phe Cys Gln Met Pro
1880                1885                1890

Gln Pro Lys Leu Arg Ala Ala Met Val Glu Tyr Ser Phe Ile Phe
1895                1900                1905

Leu Asp Glu Tyr His Cys Ala Thr Pro Glu Gln Leu Ala Ile Met
1910                1915                1920

Gly Lys Ile His Arg Phe Ser Glu Asn Leu Arg Val Val Ala Met
1925                1930                1935

Thr Ala Thr Pro Val Gly Thr Val Thr Thr Thr Gly Gln Lys His
1940                1945                1950
```

```
Pro Ile Glu Glu Phe Ile Ala Pro Asp Val Met Lys Gly Lys Asp
1955                1960                1965

Leu Gly Ser Glu Tyr Leu Asp Ile Ala Gly Leu Lys Ile Pro Val
1970                1975                1980

Glu Glu Met Lys Ser Asn Met Leu Val Phe Val Pro Thr Arg Asn
1985                1990                1995

Met Ala Val Glu Thr Ala Lys Lys Leu Lys Ala Lys Gly Tyr Asn
2000                2005                2010

Ser Gly Tyr Tyr Tyr Ser Gly Glu Asp Pro Ser Asn Leu Arg Val
2015                2020                2025

Val Thr Ser Gln Ser Pro Tyr Val Val Ala Thr Asn Ala Ile
2030                2035                2040

Glu Ser Gly Val Thr Leu Pro Asp Leu Asp Val Val Asp Thr
2045                2050                2055

Gly Leu Lys Cys Glu Lys Arg Ile Arg Leu Ser Pro Lys Met Pro
2060                2065                2070

Phe Ile Val Thr Gly Leu Lys Arg Met Ala Val Thr Ile Gly Glu
2075                2080                2085

Gln Ala Gln Arg Arg Gly Arg Val Gly Arg Val Lys Pro Gly Arg
2090                2095                2100

Tyr Tyr Arg Ser Gln Glu Thr Pro Val Gly Ser Lys Asp Tyr His
2105                2110                2115

Tyr Asp Leu Leu Gln Ala Gln Arg Tyr Gly Ile Glu Asp Gly Ile
2120                2125                2130

Asn Ile Thr Lys Ser Phe Arg Glu Met Asn Tyr Asp Trp Ser Leu
2135                2140                2145

Tyr Glu Glu Asp Ser Leu Met Ile Thr Gln Leu Glu Ile Leu Asn
2150                2155                2160

Asn Leu Leu Ile Ser Asp Glu Leu Pro Met Ala Val Lys Asn Ile
2165                2170                2175

Met Ala Arg Thr Asp His Pro Glu Pro Ile Gln Leu Ala Tyr Asn
2180                2185                2190

Ser Tyr Glu Thr Gln Val Pro Val Leu Phe Pro Lys Ile Lys Asn
2195                2200                2205

Gly Glu Val Thr Asp Ser Tyr Asp Asn Tyr Thr Phe Leu Asn Ala
2210                2215                2220

Arg Lys Leu Gly Asp Asp Val Pro Pro Tyr Val Tyr Ala Thr Glu
2225                2230                2235

Asp Glu Asp Leu Ala Val Glu Leu Leu Gly Leu Asp Trp Pro Asp
2240                2245                2250

Pro Gly Asn Gln Gly Thr Val Glu Thr Gly Arg Ala Leu Lys Gln
2255                2260                2265

Val Val Gly Leu Ser Thr Ala Glu Asn Ala Leu Leu Val Ala Leu
2270                2275                2280

Phe Gly Tyr Val Gly Tyr Gln Ala Leu Ser Lys Arg His Ile Pro
2285                2290                2295

Val Val Thr Asp Ile Tyr Ser Ile Glu Asp His Arg Leu Glu Asp
2300                2305                2310

Thr Thr His Leu Gln Tyr Ala Pro Asn Ala Ile Lys Thr Glu Gly
2315                2320                2325

Lys Glu Thr Glu Leu Lys Glu Leu Ala Gln Gly Asp Val Gln Arg
2330                2335                2340

Cys Val Glu Ala Met Thr Asn Tyr Ala Arg Glu Gly Ile Gln Phe
```

2345                2350                2355
Met Lys Ser Gln Ala Leu Lys Val Lys Glu Thr Pro Thr Tyr Lys
        2360                2365                2370
Glu Thr Met Asp Thr Val Thr Asp Tyr Val Lys Lys Phe Met Glu
        2375                2380                2385
Ala Leu Ala Asp Ser Lys Glu Asp Ile Ile Lys Tyr Gly Leu Trp
        2390                2395                2400
Gly Thr His Thr Ala Leu Tyr Lys Ser Ile Ser Ala Arg Leu Gly
        2405                2410                2415
Gly Glu Thr Ala Phe Ala Thr Leu Val Val Lys Trp Leu Ala Phe
        2420                2425                2430
Gly Gly Glu Ser Ile Ala Asp His Val Lys Gln Ala Ala Thr Asp
        2435                2440                2445
Leu Val Val Tyr Tyr Ile Ile Asn Arg Pro Gln Phe Pro Gly Asp
        2450                2455                2460
Thr Glu Thr Gln Gln Asp Gly Arg Lys Phe Val Ala Ser Leu Leu
        2465                2470                2475
Ala Ser Ala Leu Ala Thr Tyr Thr Tyr Lys Ser Trp Asn Tyr Asn
        2480                2485                2490
Asn Leu Ser Lys Ile Val Glu Pro Ala Leu Ala Thr Leu Pro Tyr
        2495                2500                2505
Ala Ala Thr Ala Leu Lys Leu Phe Ala Pro Thr Arg Leu Glu Ser
        2510                2515                2520
Val Val Ile Leu Ser Thr Ala Ile Tyr Lys Thr Tyr Leu Ser Ile
        2525                2530                2535
Arg Arg Gly Lys Ser Asp Gly Leu Leu Gly Thr Gly Val Ser Ala
        2540                2545                2550
Ala Met Glu Ile Met Ser Gln Asn Pro Val Ser Val Gly Ile Ala
        2555                2560                2565
Val Met Leu Gly Val Gly Ala Val Ala Ala His Asn Ala Ile Glu
        2570                2575                2580
Ala Ser Glu Gln Lys Arg Thr Leu Leu Met Lys Val Phe Val Lys
        2585                2590                2595
Asn Phe Leu Asp Gln Ala Ala Thr Asp Glu Leu Val Lys Glu Ser
        2600                2605                2610
Pro Glu Lys Ile Ile Met Ala Leu Phe Glu Ala Val Gln Thr Val
        2615                2620                2625
Gly Asn Pro Leu Arg Leu Val Tyr His Leu Tyr Gly Val Phe Tyr
        2630                2635                2640
Lys Gly Trp Glu Ala Lys Glu Leu Ala Gln Arg Thr Ala Gly Arg
        2645                2650                2655
Asn Leu Phe Thr Leu Ile Met Phe Glu Ala Val Glu Leu Leu Gly
        2660                2665                2670
Val Asp Ser Glu Gly Lys Val Arg Gln Leu Ser Asn Tyr Ile
        2675                2680                2685
Leu Glu Leu Leu Tyr Lys Phe Arg Asp Ser Ile Lys Ser Ser Val
        2690                2695                2700
Arg Glu Met Ala Ile Ser Trp Ala Pro Ala Pro Phe Ser Cys Asp
        2705                2710                2715
Trp Thr Pro Thr Asp Asp Arg Ile Gly Leu Pro Gln Asp Asn Phe
        2720                2725                2730
His Gln Val Glu Thr Lys Cys Pro Cys Gly Tyr Lys Met Lys Ala
        2735                2740                2745

```
Val Lys Asn Cys Ala Gly Glu Leu Arg Leu Leu Glu Glu Glu Gly
    2750                2755                2760

Ser Phe Leu Cys Arg Asn Lys Phe Gly Arg Gly Ser Arg Asn Tyr
2765                2770                2775

Arg Val Thr Lys Tyr Tyr Asp Asp Asn Leu Leu Glu Ile Lys Pro
    2780                2785                2790

Val Ile Arg Met Glu Gly His Val Glu Leu Tyr Tyr Lys Gly Ala
2795                2800                2805

Thr Ile Lys Leu Asp Phe Asn Asn Ser Lys Thr Ile Leu Ala Thr
    2810                2815                2820

Asp Lys Trp Glu Val Asp His Ser Thr Leu Val Arg Val Leu Lys
2825                2830                2835

Arg His Thr Gly Ala Gly Tyr His Gly Ala Tyr Leu Gly Glu Lys
    2840                2845                2850

Pro Asn His Lys His Leu Ile Glu Arg Asp Cys Ala Thr Ile Thr
2855                2860                2865

Lys Asp Lys Val Cys Phe Leu Lys Met Lys Arg Gly Cys Ala Phe
    2870                2875                2880

Thr Tyr Asp Leu Ser Leu His Asn Leu Thr Arg Leu Ile Glu Leu
2885                2890                2895

Val His Lys Asn Asn Leu Glu Asp Lys Glu Ile Pro Ala Ala Thr
    2900                2905                2910

Val Thr Thr Trp Leu Ala Tyr Thr Phe Val Asn Glu Asp Ile Gly
2915                2920                2925

Thr Ile Lys Pro Ala Phe Gly Glu Lys Val Thr Leu Glu Met Gln
    2930                2935                2940

Glu Glu Ile Thr Leu Gln Pro Ala Val Val Val Asp Thr Thr Asp
2945                2950                2955

Val Ala Val Thr Val Val Gly Glu Ala Pro Thr Met Thr Thr Gly
    2960                2965                2970

Glu Thr Pro Thr Val Phe Thr Ser Ser Gly Ser Gly Leu Lys Ser
2975                2980                2985

Gln Gln Val Leu Lys Leu Gly Val Gly Glu Gly Gln Tyr Pro Gly
    2990                2995                3000

Thr Asn Pro Gln Arg Ala Ser Leu His Glu Ala Ile Gln Gly Ala
3005                3010                3015

Asp Glu Arg Pro Ser Val Leu Ile Leu Gly Ser Asp Lys Ala Thr
    3020                3025                3030

Ser Asn Arg Val Lys Thr Ala Lys Asn Val Lys Val Tyr Arg Gly
3035                3040                3045

Arg Asp Pro Leu Glu Val Arg Asp Met Met Arg Arg Gly Lys Ile
    3050                3055                3060

Leu Val Val Ala Leu Ser Arg Val Asp Asn Ala Leu Leu Lys Phe
3065                3070                3075

Val Asp Tyr Lys Gly Thr Phe Leu Thr Arg Glu Ala Leu Glu Ala
    3080                3085                3090

Leu Ser Leu Gly Arg Pro Lys Lys Lys Asn Ile Thr Lys Ala Glu
3095                3100                3105

Ala Gln Trp Leu Leu Cys Pro Glu Asp Gln Met Glu Glu Leu Pro
    3110                3115                3120

Asp Trp Phe Ala Ala Gly Glu Pro Ile Phe Leu Glu Ala Asn Ile
3125                3130                3135
```

```
Lys His Asp Arg Tyr His Leu Val Gly Asp Ile Ala     Thr Ile Lys
    3140                3145                        3150

Glu Lys Ala Lys Gln Leu Gly Ala Thr Asp Ser Thr     Lys Ile Ser
    3155                3160                        3165

Lys Glu Val Gly Ala Lys Val Tyr Ser Met Lys Leu     Ser Asn Trp
    3170                3175                        3180

Val Met Gln Glu Glu Asn Lys Gln Gly Asn Leu Thr     Pro Leu Phe
    3185                3190                        3195

Glu Glu Leu Leu Gln Gln Cys Pro Pro Gly Gly Gln     Asn Lys Thr
    3200                3205                        3210

Ala His Met Val Ser Ala Tyr Gln Leu Ala Gln Gly     Asn Trp Met
    3215                3220                        3225

Pro Thr Ser Cys His Val Phe Met Gly Thr Val Ser     Ala Arg Arg
    3230                3235                        3240

Thr Lys Thr His Pro Tyr Glu Ala Tyr Val Lys Leu     Arg Glu Leu
    3245                3250                        3255

Val Glu Glu His Lys Met Lys Thr Leu Cys Pro Gly     Ser Ser Leu
    3260                3265                        3270

Gly Arg His Asn Asp Trp Ile Ile Gly Lys Ile Lys     Tyr Gln Gly
    3275                3280                        3285

Asn Leu Arg Thr Lys His Met Leu Asn Pro Gly Lys     Val Ala Glu
    3290                3295                        3300

Gln Leu Cys Arg Glu Gly His Arg His Asn Val Tyr     Asn Lys Thr
    3305                3310                        3315

Ile Ser Ser Val Met Thr Ala Thr Gly Ile Arg Leu     Glu Lys Leu
    3320                3325                        3330

Pro Val Val Arg Ala Gln Thr Asp Pro Thr Asn Phe     His Gln Ala
    3335                3340                        3345

Ile Arg Asp Lys Ile Asp Lys Glu Glu Asn Leu Gln     Thr Pro Gly
    3350                3355                        3360

Leu His Lys Lys Leu Met Glu Val Phe Asn Ala Leu     Lys Arg Pro
    3365                3370                        3375

Glu Leu Glu Ser Ser Tyr Asp Ala Val Glu Trp Glu     Glu Leu Glu
    3380                3385                        3390

Arg Gly Ile Asn Arg Lys Gly Ala Ala Gly Phe Phe     Glu Arg Lys
    3395                3400                        3405

Asn Ile Gly Glu Ile Leu Asp Ser Glu Lys Asn Lys     Val Glu Glu
    3410                3415                        3420

Ile Ile Asp Asn Leu Lys Lys Gly Arg Asn Ile Lys     Tyr Tyr Glu
    3425                3430                        3435

Thr Ala Ile Pro Lys Asn Glu Lys Arg Asp Val Asn     Asp Asp Trp
    3440                3445                        3450

Thr Ala Gly Asp Phe Val Asp Glu Lys Lys Pro Arg     Val Ile Gln
    3455                3460                        3465

Tyr Pro Glu Ala Lys Thr Arg Leu Ala Ile Thr Lys     Val Met Tyr
    3470                3475                        3480

Lys Trp Val Lys Gln Lys Pro Val Val Ile Pro Gly     Tyr Glu Gly
    3485                3490                        3495

Lys Thr Pro Leu Phe Gln Ile Phe Asp Lys Val Lys     Lys Glu Trp
    3500                3505                        3510

Asp Gln Phe Gln Asn Pro Val Ala Val Ser Phe Asp     Thr Lys Ala
    3515                3520                        3525

Trp Asp Thr Gln Val Thr Thr Lys Asp Leu Glu Leu     Ile Arg Asp
```

-continued

```
            3530                3535                3540

Ile Gln Lys Tyr Tyr Phe Lys Lys Lys Trp His Lys Phe Ile Asp
    3545                3550                3555

Thr Leu Thr Thr His Met Ser Glu Val Pro Val Ile Ser Ala Asp
    3560                3565                3570

Gly Glu Val Tyr Ile Arg Lys Gly Gln Arg Gly Ser Gly Gln Pro
    3575                3580                3585

Asp Thr Ser Ala Gly Asn Ser Met Leu Asn Val Leu Thr Met Val
    3590                3595                3600

Tyr Ala Phe Cys Glu Ala Thr Gly Val Pro Tyr Lys Ser Phe Asp
    3605                3610                3615

Arg Val Ala Lys Ile His Val Cys Gly Asp Asp Gly Phe Leu Ile
    3620                3625                3630

Thr Glu Arg Ala Leu Gly Glu Lys Phe Ala Ser Lys Gly Val Gln
    3635                3640                3645

Ile Leu Tyr Glu Ala Gly Lys Pro Gln Lys Ile Thr Glu Gly Asp
    3650                3655                3660

Lys Met Lys Val Ala Tyr Gln Phe Asp Asp Ile Glu Phe Cys Ser
    3665                3670                3675

His Thr Pro Ile Gln Val Arg Trp Ser Asp Asn Thr Ser Ser Tyr
    3680                3685                3690

Met Pro Gly Arg Asn Thr Thr Thr Ile Leu Ala Lys Met Ala Thr
    3695                3700                3705

Arg Leu Asp Ser Ser Gly Glu Arg Gly Thr Ile Ala Tyr Glu Lys
    3710                3715                3720

Ala Val Ala Phe Ser Phe Leu Leu Met Tyr Ser Trp Asn Pro Leu
    3725                3730                3735

Ile Arg Arg Ile Cys Leu Leu Val Leu Ser Thr Glu Leu Gln Val
    3740                3745                3750

Lys Pro Gly Lys Ser Thr Thr Tyr Tyr Tyr Glu Gly Asp Pro Ile
    3755                3760                3765

Ser Ala Tyr Lys Glu Val Ile Gly His Asn Leu Phe Asp Leu Lys
    3770                3775                3780

Arg Thr Ser Phe Glu Lys Leu Ala Lys Leu Asn Leu Ser Met Ser
    3785                3790                3795

Val Leu Gly Ala Trp Thr Arg His Thr Ser Lys Arg Leu Leu Gln
    3800                3805                3810

Asp Cys Val Asn Ile Gly Val Lys Glu Gly Asn Trp Leu Val Asn
    3815                3820                3825

Ala Asp Arg Leu Val Ser Ser Lys Thr Gly Asn Arg Tyr Ile Pro
    3830                3835                3840

Gly Glu Gly His Thr Leu Gln Gly Arg His Tyr Glu Glu Leu Val
    3845                3850                3855

Leu Ala Arg Lys Gln Ile Asn Asn Phe Gln Gly Thr Asp Arg Tyr
    3860                3865                3870

Asn Leu Gly Pro Ile Val Asn Met Val Leu Arg Arg Leu Arg Val
    3875                3880                3885

Met Met Met Thr Leu Ile Gly Arg Gly Ala
    3890                3895

<210> SEQ ID NO 13
<211> LENGTH: 3898
<212> TYPE: PRT
<213> ORGANISM: CSFV
```

<400> SEQUENCE: 13

```
Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Lys Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Val Gln Phe Cys
            100                 105                 110

Glu Val Thr Lys Arg Ile Gly Arg Val Thr Gly Ser Asp Gly Lys Leu
        115                 120                 125

Tyr His Thr Tyr Val Cys Ile Asp Gly Cys Ile Leu Leu Lys Leu Ala
    130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Asp Gly Ala Ser Gly Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Arg Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Asn Arg Ser Leu His Gly Ile Trp Pro Gly Lys Ile
    290                 295                 300

Cys Lys Gly Val Pro Thr His Leu Ala Thr Asp Val Glu Leu Lys Glu
305                 310                 315                 320

Ile Gln Gly Met Met Asp Ala Ser Glu Gly Thr Asn Tyr Thr Cys Cys
                325                 330                 335

Lys Leu Gln Arg His Glu Trp Asn Lys His Gly Trp Cys Asn Trp His
            340                 345                 350

Asn Ile Asp Pro Trp Ile Gln Leu Met Asn Arg Thr Gln Ala Asp Leu
        355                 360                 365

Ala Glu Gly Pro Pro Val Lys Glu Cys Ala Val Thr Cys Arg Tyr Asp
    370                 375                 380

Lys Asp Ala Asp Ile Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
```

```
            405                 410                 415
Val Ile Glu Ser Pro Cys Asn Phe Asn Val Ser Val Glu Asp Thr Leu
            420                 425                 430

Tyr Gly Asp His Glu Cys Gly Ser Leu Leu Gln Asp Ala Ala Leu Tyr
            435                 440                 445

Leu Val Asp Gly Met Thr Asn Thr Ile Glu Asn Ala Arg Gln Gly Ala
            450                 455                 460

Ala Arg Val Thr Ser Trp Leu Gly Arg Gln Leu Arg Thr Ala Gly Lys
465                 470                 475                 480

Arg Leu Glu Gly Arg Ser Lys Thr Trp Phe Gly Ala Tyr Ala Leu Ser
                    485                 490                 495

Pro Tyr Cys Asn Val Thr Ser Lys Ile Gly Tyr Ile Trp Tyr Thr Asn
            500                 505                 510

Asn Cys Thr Pro Ala Cys Leu Pro Lys Asn Thr Lys Ile Ile Gly Pro
            515                 520                 525

Gly Lys Phe Asp Thr Asn Ala Glu Asp Gly Lys Ile Leu His Glu Met
            530                 535                 540

Gly Gly His Leu Ser Glu Phe Leu Leu Leu Ser Leu Val Val Leu Ser
545                 550                 555                 560

Asp Phe Ala Pro Glu Thr Ala Ser Ala Leu Tyr Leu Ile Leu His Tyr
                    565                 570                 575

Val Ile Pro Gln Pro His Asp Glu Pro Glu Gly Cys Asp Thr Asn Gln
            580                 585                 590

Leu Asn Leu Thr Val Glu Leu Arg Thr Glu Asp Val Ile Pro Ser Ser
            595                 600                 605

Val Trp Asn Val Gly Lys Tyr Val Cys Val Arg Pro Asp Trp Trp Pro
            610                 615                 620

Tyr Glu Thr Glu Val Ala Leu Leu Phe Glu Glu Val Gly Gln Val Val
625                 630                 635                 640

Lys Leu Ala Leu Arg Ala Leu Arg Asp Leu Thr Arg Val Trp Asn Ser
                    645                 650                 655

Ala Ser Thr Ile Ala Phe Leu Ile Cys Leu Ile Lys Val Leu Arg Gly
            660                 665                 670

Gln Ile Val Gln Gly Val Val Trp Leu Leu Leu Val Thr Gly Ala Gln
            675                 680                 685

Gly Arg Leu Ala Cys Lys Glu Asp Tyr Arg Tyr Ala Ile Ser Ser Thr
            690                 695                 700

Asp Glu Ile Gly Leu Leu Gly Ala Gly Gly Leu Thr Thr Thr Trp Lys
705                 710                 715                 720

Glu Tyr Asn His Asp Leu Gln Leu Asn Asp Gly Thr Val Lys Ala Ser
                    725                 730                 735

Cys Val Ala Gly Ser Phe Lys Val Thr Ala Leu Asn Val Val Ser Arg
            740                 745                 750

Arg Tyr Leu Ala Ser Leu His Lys Lys Ala Leu Pro Thr Ser Val Thr
            755                 760                 765

Phe Glu Leu Leu Phe Asp Gly Thr Asn Pro Ser Thr Glu Glu Met Gly
            770                 775                 780

Asp Asp Phe Arg Ser Gly Leu Cys Pro Phe Asp Thr Ser Pro Val Val
785                 790                 795                 800

Lys Gly Lys Tyr Asn Thr Thr Leu Leu Asn Gly Ser Ala Phe Tyr Leu
                    805                 810                 815

Val Cys Pro Ile Gly Trp Thr Gly Val Ile Glu Cys Thr Ala Val Ser
            820                 825                 830
```

```
Lys Asp Thr Leu Arg Thr Glu Val Val Lys Thr Phe Arg Arg Asp Lys
        835                 840                 845

Pro Phe Pro His Arg Met Asp Cys Val Thr Thr Val Glu Asn Glu
850                 855                 860

Asp Leu Phe Tyr Cys Lys Leu Gly Gly Asn Trp Thr Cys Val Lys Gly
865                 870                 875                 880

Glu Pro Val Val Tyr Thr Gly Gly Leu Val Lys Gln Cys Arg Trp Cys
                885                 890                 895

Gly Phe Asp Phe Asp Gly Pro Asp Gly Leu Pro His Tyr Pro Ile Gly
            900                 905                 910

Lys Cys Ile Leu Ala Asn Glu Thr Gly Tyr Arg Ile Val Asp Ser Thr
            915                 920                 925

Asp Cys Asn Arg Asp Gly Val Val Ile Ser Thr Glu Gly Ser His Glu
930                 935                 940

Cys Leu Ile Gly Asn Thr Thr Val Lys Val His Ala Ser Asp Glu Arg
945                 950                 955                 960

Leu Gly Pro Met Pro Cys Arg Pro Lys Glu Ile Val Ser Ser Ala Gly
                965                 970                 975

Pro Val Lys Lys Thr Ser Cys Thr Phe Asn Tyr Thr Lys Thr Leu Lys
                980                 985                 990

Asn Arg Tyr Tyr Glu Pro Arg Asp Ser Tyr Phe Gln Gln Tyr Met Leu
            995                 1000                1005

Lys Gly Glu Tyr Gln Tyr Trp Phe Asp Leu Asp Ala Thr Asp Arg
    1010                1015                1020

His Ser Asp Tyr Phe Ala Glu Phe Val Val Leu Val Val Val Ala
    1025                1030                1035

Leu Leu Gly Gly Arg Tyr Val Leu Trp Leu Ile Val Thr Tyr Val
    1040                1045                1050

Val Leu Thr Glu Gln Leu Ala Ala Gly Leu Pro Leu Gly Gln Gly
    1055                1060                1065

Glu Val Val Leu Ile Gly Asn Leu Ile Thr His Thr Asp Ile Glu
    1070                1075                1080

Val Val Val Tyr Phe Leu Leu Leu Tyr Leu Val Met Arg Asp Glu
    1085                1090                1095

Pro Ile Lys Lys Trp Ile Leu Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Lys Gly Gly Lys Ile Asp Gly Gly Trp Gln Arg Leu Pro
    1130                1135                1140

Gly Thr Ser Phe Asp Ile Gln Leu Ala Leu Thr Val Ile Val Val
    1145                1150                1155

Ala Val Met Leu Leu Ala Lys Arg Asp Pro Thr Thr Val Pro Leu
    1160                1165                1170

Val Ile Thr Val Ala Pro Leu Arg Thr Ala Lys Met Thr Asn Gly
    1175                1180                1185

Leu Ser Thr Asp Ile Ala Ile Ala Thr Val Ser Ala Ala Leu Leu
    1190                1195                1200

Thr Trp Thr Tyr Ile Ser Asp Tyr Tyr Arg Tyr Lys Thr Trp Leu
    1205                1210                1215

Gln Tyr Leu Ile Ser Thr Val Thr Gly Ile Phe Leu Ile Arg Val
    1220                1225                1230
```

```
Leu Lys Gly Ile Gly Glu Leu Asp Leu His Thr Pro Thr Leu Pro
1235                1240                1245

Ser His Arg Pro Leu Phe Phe Ile Leu Val Tyr Leu Ile Ser Thr
1250                1255                1260

Ala Val Val Thr Arg Trp Asn Leu Asp Ile Ala Gly Leu Leu Leu
1265                1270                1275

Gln Cys Val Pro Thr Leu Leu Met Val Phe Thr Met Trp Ala Asp
1280                1285                1290

Ile Leu Thr Leu Ile Leu Leu Pro Thr Tyr Glu Leu Thr Lys
1295                1300                1305

Leu Tyr Tyr Leu Lys Glu Val Arg Ile Gly Ala Glu Lys Gly Trp
1310                1315                1320

Leu Trp Lys Thr Asn Phe Lys Arg Val Asn Asp Ile Tyr Glu Val
1325                1330                1335

Asp Gln Ala Gly Glu Gly Val Tyr Leu Phe Pro Ser Lys Gln Lys
1340                1345                1350

Thr Ser Ser Met Thr Gly Thr Met Leu Pro Leu Ile Lys Ala Ile
1355                1360                1365

Leu Ile Ser Cys Val Ser Asn Lys Trp Gln Phe Ile Tyr Leu Leu
1370                1375                1380

Tyr Leu Ile Phe Glu Val Ser Tyr Tyr Leu His Lys Lys Ile Ile
1385                1390                1395

Asp Glu Ile Ala Gly Gly Thr Asn Phe Ile Ser Arg Leu Val Ala
1400                1405                1410

Ala Leu Ile Glu Val Asn Trp Ala Phe Asp Asn Glu Glu Val Arg
1415                1420                1425

Gly Leu Lys Lys Phe Phe Leu Leu Ser Ser Arg Val Lys Glu Leu
1430                1435                1440

Ile Ile Lys His Lys Val Arg Asn Glu Val Met Val Arg Trp Phe
1445                1450                1455

Gly Asp Glu Glu Val Tyr Gly Met Pro Lys Leu Val Gly Leu Val
1460                1465                1470

Lys Ala Ala Thr Leu Ser Lys Asn Lys His Cys Ile Leu Cys Thr
1475                1480                1485

Val Cys Glu Asp Arg Glu Trp Arg Gly Glu Thr Cys Pro Lys Cys
1490                1495                1500

Gly Arg Phe Gly Pro Pro Met Thr Cys Gly Met Thr Leu Ala Asp
1505                1510                1515

Phe Glu Glu Lys His Tyr Lys Arg Ile Phe Phe Arg Glu Asp Gln
1520                1525                1530

Ser Glu Gly Pro Val Arg Glu Glu Tyr Ala Gly Tyr Leu Gln Tyr
1535                1540                1545

Arg Ala Arg Gly Gln Leu Phe Leu Arg Asn Leu Pro Val Leu Ala
1550                1555                1560

Thr Lys Val Lys Met Leu Leu Val Gly Asn Leu Gly Thr Glu Val
1565                1570                1575

Gly Asp Leu Glu His Leu Gly Trp Val Leu Arg Gly Pro Ala Val
1580                1585                1590

Cys Lys Lys Val Thr Glu His Glu Lys Cys Thr Thr Ser Met Met
1595                1600                1605

Asp Lys Leu Thr Ala Phe Phe Gly Val Met Pro Arg Gly Thr Thr
1610                1615                1620

Pro Arg Ala Pro Val Arg Phe Pro Thr Ser Leu Leu Lys Ile Arg
```

```
          1625                1630                1635

Arg  Gly  Leu  Glu  Thr  Gly  Trp  Ala  Tyr  Thr  His  Gln  Gly  Gly  Ile
          1640                1645                1650

Ser  Ser  Val  Asp  His  Val  Thr  Cys  Gly  Lys  Asp  Leu  Leu  Val  Cys
          1655                1660                1665

Asp  Thr  Met  Gly  Arg  Thr  Arg  Val  Val  Cys  Gln  Ser  Asn  Asn  Lys
          1670                1675                1680

Met  Thr  Asp  Glu  Ser  Glu  Tyr  Gly  Val  Lys  Thr  Asp  Ser  Gly  Cys
          1685                1690                1695

Pro  Glu  Gly  Ala  Arg  Cys  Tyr  Val  Phe  Asn  Pro  Glu  Ala  Val  Asn
          1700                1705                1710

Ile  Ser  Gly  Thr  Lys  Gly  Ala  Met  Val  His  Leu  Gln  Lys  Thr  Gly
          1715                1720                1725

Gly  Glu  Phe  Thr  Cys  Val  Thr  Ala  Ser  Gly  Thr  Pro  Ala  Phe  Phe
          1730                1735                1740

Asp  Leu  Lys  Asn  Leu  Lys  Gly  Trp  Ser  Gly  Leu  Pro  Ile  Phe  Glu
          1745                1750                1755

Ala  Ser  Ser  Gly  Arg  Val  Val  Gly  Arg  Val  Lys  Val  Gly  Lys  Asn
          1760                1765                1770

Glu  Asp  Ser  Lys  Pro  Thr  Lys  Leu  Met  Ser  Gly  Ile  Gln  Thr  Val
          1775                1780                1785

Ser  Lys  Ser  Thr  Thr  Asp  Leu  Thr  Glu  Met  Val  Lys  Lys  Ile  Thr
          1790                1795                1800

Thr  Met  Ser  Arg  Gly  Glu  Phe  Arg  Gln  Ile  Thr  Leu  Ala  Thr  Gly
          1805                1810                1815

Ala  Gly  Lys  Thr  Thr  Glu  Leu  Pro  Arg  Ser  Val  Ile  Glu  Glu  Ile
          1820                1825                1830

Gly  Arg  His  Lys  Arg  Val  Leu  Val  Leu  Ile  Pro  Leu  Arg  Ala  Ala
          1835                1840                1845

Ala  Glu  Ser  Val  Tyr  Gln  Tyr  Met  Arg  Gln  Lys  His  Pro  Ser  Ile
          1850                1855                1860

Ala  Phe  Asn  Leu  Arg  Ile  Gly  Glu  Met  Lys  Glu  Gly  Asp  Met  Ala
          1865                1870                1875

Thr  Gly  Ile  Thr  Tyr  Ala  Ser  Tyr  Gly  Tyr  Phe  Cys  Gln  Met  Pro
          1880                1885                1890

Gln  Pro  Lys  Leu  Arg  Ala  Ala  Met  Val  Glu  Tyr  Ser  Phe  Ile  Phe
          1895                1900                1905

Leu  Asp  Glu  Tyr  His  Cys  Ala  Thr  Pro  Glu  Gln  Leu  Ala  Ile  Met
          1910                1915                1920

Gly  Lys  Ile  His  Arg  Phe  Ser  Glu  Asn  Leu  Arg  Val  Val  Ala  Met
          1925                1930                1935

Thr  Ala  Thr  Pro  Val  Gly  Thr  Val  Thr  Thr  Gly  Gln  Lys  His
          1940                1945                1950

Pro  Ile  Glu  Glu  Phe  Ile  Ala  Pro  Asp  Val  Met  Lys  Gly  Lys  Asp
          1955                1960                1965

Leu  Gly  Ser  Glu  Tyr  Leu  Asp  Ile  Ala  Gly  Leu  Lys  Ile  Pro  Val
          1970                1975                1980

Glu  Glu  Met  Lys  Ser  Asn  Met  Leu  Val  Phe  Val  Pro  Thr  Arg  Asn
          1985                1990                1995

Met  Ala  Val  Glu  Thr  Ala  Lys  Lys  Leu  Lys  Ala  Lys  Gly  Tyr  Asn
          2000                2005                2010

Ser  Gly  Tyr  Tyr  Tyr  Ser  Gly  Glu  Asp  Pro  Ser  Asn  Leu  Arg  Val
          2015                2020                2025
```

```
Val Thr Ser Gln Ser Pro Tyr Val Val Ala Thr Asn Ala Ile
    2030            2035            2040

Glu Ser Gly Val Thr Leu Pro Asp Leu Asp Val Val Asp Thr
    2045            2050            2055

Gly Leu Lys Cys Glu Lys Arg Ile Arg Leu Ser Pro Lys Met Pro
    2060            2065            2070

Phe Ile Val Thr Gly Leu Lys Arg Met Ala Val Thr Ile Gly Glu
    2075            2080            2085

Gln Ala Gln Arg Arg Gly Arg Val Gly Arg Val Lys Pro Gly Arg
    2090            2095            2100

Tyr Tyr Arg Ser Gln Glu Thr Pro Val Gly Ser Lys Asp Tyr His
    2105            2110            2115

Tyr Asp Leu Leu Gln Ala Gln Arg Tyr Gly Ile Glu Asp Gly Ile
    2120            2125            2130

Asn Ile Thr Lys Ser Phe Arg Glu Met Asn Tyr Asp Trp Ser Leu
    2135            2140            2145

Tyr Glu Glu Asp Ser Leu Met Ile Thr Gln Leu Glu Ile Leu Asn
    2150            2155            2160

Asn Leu Leu Ile Ser Asp Glu Leu Pro Met Ala Val Lys Asn Ile
    2165            2170            2175

Met Ala Arg Thr Asp His Pro Glu Pro Ile Gln Leu Ala Tyr Asn
    2180            2185            2190

Ser Tyr Glu Thr Gln Val Pro Val Leu Phe Pro Lys Ile Lys Asn
    2195            2200            2205

Gly Glu Val Thr Asp Ser Tyr Asp Asn Tyr Thr Phe Leu Asn Ala
    2210            2215            2220

Arg Lys Leu Gly Asp Asp Val Pro Pro Tyr Val Tyr Ala Thr Glu
    2225            2230            2235

Asp Glu Asp Leu Ala Val Glu Leu Leu Gly Leu Asp Trp Pro Asp
    2240            2245            2250

Pro Gly Asn Gln Gly Thr Val Glu Thr Gly Arg Ala Leu Lys Gln
    2255            2260            2265

Val Val Gly Leu Ser Thr Ala Glu Asn Ala Leu Leu Val Ala Leu
    2270            2275            2280

Phe Gly Tyr Val Gly Tyr Gln Ala Leu Ser Lys Arg His Ile Pro
    2285            2290            2295

Val Val Thr Asp Ile Tyr Ser Ile Glu Asp His Arg Leu Glu Asp
    2300            2305            2310

Thr Thr His Leu Gln Tyr Ala Pro Asn Ala Ile Lys Thr Glu Gly
    2315            2320            2325

Lys Glu Thr Glu Leu Lys Glu Leu Ala Gln Gly Asp Val Gln Arg
    2330            2335            2340

Cys Val Glu Ala Met Thr Asn Tyr Ala Arg Glu Gly Ile Gln Phe
    2345            2350            2355

Met Lys Ser Gln Ala Leu Lys Val Lys Glu Thr Pro Thr Tyr Lys
    2360            2365            2370

Glu Thr Met Asp Thr Val Thr Asp Tyr Val Lys Lys Phe Met Glu
    2375            2380            2385

Ala Leu Ala Asp Ser Lys Glu Asp Ile Ile Lys Tyr Gly Leu Trp
    2390            2395            2400

Gly Thr His Thr Ala Leu Tyr Lys Ser Ile Ser Ala Arg Leu Gly
    2405            2410            2415
```

-continued

| | | | | | | | | | | | |
|---|---|---|---|---|---|---|---|---|---|---|---|
|Gly|Glu|Thr|Ala|Phe|Ala|Thr|Leu|Val|Val|Lys|Trp|Leu|Ala|Phe|
| 2420 | | | | | 2425 | | | | | 2430 | | | | |

Gly Gly Glu Ser Ile Ala Asp His Val Lys Gln Ala Ala Thr Asp
 2435                2440               2445

Leu Val Val Tyr Tyr Ile Ile Asn Arg Pro Gln Phe Pro Gly Asp
 2450                2455               2460

Thr Glu Thr Gln Gln Asp Gly Arg Lys Phe Val Ala Ser Leu Leu
 2465                2470               2475

Ala Ser Ala Leu Ala Thr Tyr Thr Tyr Lys Ser Trp Asn Tyr Asn
 2480                2485               2490

Asn Leu Ser Lys Ile Val Glu Pro Ala Leu Ala Thr Leu Pro Tyr
 2495                2500               2505

Ala Ala Thr Ala Leu Lys Leu Phe Ala Pro Thr Arg Leu Glu Ser
 2510                2515               2520

Val Val Ile Leu Ser Thr Ala Ile Tyr Lys Thr Tyr Leu Ser Ile
 2525                2530               2535

Arg Arg Gly Lys Ser Asp Gly Leu Leu Gly Thr Gly Val Ser Ala
 2540                2545               2550

Ala Met Glu Ile Met Ser Gln Asn Pro Val Ser Val Gly Ile Ala
 2555                2560               2565

Val Met Leu Gly Val Gly Ala Val Ala Ala His Asn Ala Ile Glu
 2570                2575               2580

Ala Ser Glu Gln Lys Arg Thr Leu Leu Met Lys Val Phe Val Lys
 2585                2590               2595

Asn Phe Leu Asp Gln Ala Ala Thr Asp Glu Leu Val Lys Glu Ser
 2600                2605               2610

Pro Glu Lys Ile Ile Met Ala Leu Phe Glu Ala Val Gln Thr Val
 2615                2620               2625

Gly Asn Pro Leu Arg Leu Val Tyr His Leu Tyr Gly Val Phe Tyr
 2630                2635               2640

Lys Gly Trp Glu Ala Lys Glu Leu Ala Gln Arg Thr Ala Gly Arg
 2645                2650               2655

Asn Leu Phe Thr Leu Ile Met Phe Glu Ala Val Glu Leu Leu Gly
 2660                2665               2670

Val Asp Ser Glu Gly Lys Val Arg Gln Leu Ser Ser Asn Tyr Ile
 2675                2680               2685

Leu Glu Leu Leu Tyr Lys Phe Arg Asp Ser Ile Lys Ser Ser Val
 2690                2695               2700

Arg Glu Met Ala Ile Ser Trp Ala Pro Ala Pro Phe Ser Cys Asp
 2705                2710               2715

Trp Thr Pro Thr Asp Asp Arg Ile Gly Leu Pro Gln Asp Asn Phe
 2720                2725               2730

His Gln Val Glu Thr Lys Cys Pro Cys Gly Tyr Lys Met Lys Ala
 2735                2740               2745

Val Lys Asn Cys Ala Gly Glu Leu Arg Leu Leu Glu Glu Glu Gly
 2750                2755               2760

Ser Phe Leu Cys Arg Asn Lys Phe Gly Arg Gly Ser Arg Asn Tyr
 2765                2770               2775

Arg Val Thr Lys Tyr Tyr Asp Asp Asn Leu Leu Glu Ile Lys Pro
 2780                2785               2790

Val Ile Arg Met Glu Gly His Val Glu Leu Tyr Tyr Lys Gly Ala
 2795                2800               2805

Thr Ile Lys Leu Asp Phe Asn Asn Ser Lys Thr Ile Leu Ala Thr

```
                    2810            2815                  2820

Asp Lys Trp Glu Val Asp His Ser Thr Leu Val Arg Val Leu Lys
    2825            2830                2835

Arg His Thr Gly Ala Gly Tyr His Gly Ala Tyr Leu Gly Glu Lys
    2840            2845                2850

Pro Asn His Lys His Leu Ile Glu Arg Asp Cys Ala Thr Ile Thr
    2855            2860                2865

Lys Asp Lys Val Cys Phe Leu Lys Met Lys Arg Gly Cys Ala Phe
    2870            2875                2880

Thr Tyr Asp Leu Ser Leu His Asn Leu Thr Arg Leu Ile Glu Leu
    2885            2890                2895

Val His Lys Asn Asn Leu Glu Asp Lys Glu Ile Pro Ala Ala Thr
    2900            2905                2910

Val Thr Thr Trp Leu Ala Tyr Thr Phe Val Asn Glu Asp Ile Gly
    2915            2920                2925

Thr Ile Lys Pro Ala Phe Gly Glu Lys Val Thr Leu Glu Met Gln
    2930            2935                2940

Glu Glu Ile Thr Leu Gln Pro Ala Val Val Asp Thr Thr Asp
    2945            2950                2955

Val Ala Val Thr Val Val Gly Glu Ala Pro Thr Met Thr Thr Gly
    2960            2965                2970

Glu Thr Pro Thr Val Phe Thr Ser Ser Gly Ser Gly Leu Lys Ser
    2975            2980                2985

Gln Gln Val Leu Lys Leu Gly Val Gly Glu Gly Gln Tyr Pro Gly
    2990            2995                3000

Thr Asn Pro Gln Arg Ala Ser Leu His Glu Ala Ile Gln Gly Ala
    3005            3010                3015

Asp Glu Arg Pro Ser Val Leu Ile Leu Gly Ser Asp Lys Ala Thr
    3020            3025                3030

Ser Asn Arg Val Lys Thr Ala Lys Asn Val Lys Val Tyr Arg Gly
    3035            3040                3045

Arg Asp Pro Leu Glu Val Arg Asp Met Met Arg Arg Gly Lys Ile
    3050            3055                3060

Leu Val Val Ala Leu Ser Arg Val Asp Asn Ala Leu Leu Lys Phe
    3065            3070                3075

Val Asp Tyr Lys Gly Thr Phe Leu Thr Arg Glu Ala Leu Glu Ala
    3080            3085                3090

Leu Ser Leu Gly Arg Pro Lys Lys Lys Asn Ile Thr Lys Ala Glu
    3095            3100                3105

Ala Gln Trp Leu Leu Cys Pro Glu Asp Gln Met Glu Glu Leu Pro
    3110            3115                3120

Asp Trp Phe Ala Ala Gly Glu Pro Ile Phe Leu Glu Ala Asn Ile
    3125            3130                3135

Lys His Asp Arg Tyr His Leu Val Gly Asp Ile Ala Thr Ile Lys
    3140            3145                3150

Glu Lys Ala Lys Gln Leu Gly Ala Thr Asp Ser Thr Lys Ile Ser
    3155            3160                3165

Lys Glu Val Gly Ala Lys Val Tyr Ser Met Lys Leu Ser Asn Trp
    3170            3175                3180

Val Met Gln Glu Glu Asn Lys Gln Gly Asn Leu Thr Pro Leu Phe
    3185            3190                3195

Glu Glu Leu Leu Gln Gln Cys Pro Pro Gly Gly Gln Asn Lys Thr
    3200            3205                3210
```

-continued

```
Ala His Met Val Ser Ala Tyr Gln Leu Ala Gln Gly Asn Trp Met
3215                3220                3225

Pro Thr Ser Cys His Val Phe Met Gly Thr Val Ser Ala Arg Arg
3230                3235                3240

Thr Lys Thr His Pro Tyr Glu Ala Tyr Val Lys Leu Arg Glu Leu
3245                3250                3255

Val Glu Glu His Lys Met Lys Thr Leu Cys Pro Gly Ser Ser Leu
3260                3265                3270

Gly Arg His Asn Asp Trp Ile Ile Gly Lys Ile Lys Tyr Gln Gly
3275                3280                3285

Asn Leu Arg Thr Lys His Met Leu Asn Pro Gly Lys Val Ala Glu
3290                3295                3300

Gln Leu Cys Arg Glu Gly His Arg His Asn Val Tyr Asn Lys Thr
3305                3310                3315

Ile Ser Ser Val Met Thr Ala Thr Gly Ile Arg Leu Glu Lys Leu
3320                3325                3330

Pro Val Val Arg Ala Gln Thr Asp Pro Thr Asn Phe His Gln Ala
3335                3340                3345

Ile Arg Asp Lys Ile Asp Lys Glu Glu Asn Leu Gln Thr Pro Gly
3350                3355                3360

Leu His Lys Lys Leu Met Glu Val Phe Asn Ala Leu Lys Arg Pro
3365                3370                3375

Glu Leu Glu Ser Ser Tyr Asp Ala Val Glu Trp Glu Glu Leu Glu
3380                3385                3390

Arg Gly Ile Asn Arg Lys Gly Ala Ala Gly Phe Phe Glu Arg Lys
3395                3400                3405

Asn Ile Gly Glu Ile Leu Asp Ser Glu Lys Asn Lys Val Glu Glu
3410                3415                3420

Ile Ile Asp Asn Leu Lys Lys Gly Arg Asn Ile Lys Tyr Tyr Glu
3425                3430                3435

Thr Ala Ile Pro Lys Asn Glu Lys Arg Asp Val Asn Asp Asp Trp
3440                3445                3450

Thr Ala Gly Asp Phe Val Asp Glu Lys Lys Pro Arg Val Ile Gln
3455                3460                3465

Tyr Pro Glu Ala Lys Thr Arg Leu Ala Ile Thr Lys Val Met Tyr
3470                3475                3480

Lys Trp Val Lys Gln Lys Pro Val Val Ile Pro Gly Tyr Glu Gly
3485                3490                3495

Lys Thr Pro Leu Phe Gln Ile Phe Asp Lys Val Lys Lys Glu Trp
3500                3505                3510

Asp Gln Phe Gln Asn Pro Val Ala Val Ser Phe Asp Thr Lys Ala
3515                3520                3525

Trp Asp Thr Gln Val Thr Thr Lys Asp Leu Glu Leu Ile Arg Asp
3530                3535                3540

Ile Gln Lys Tyr Tyr Phe Lys Lys Lys Trp His Lys Phe Ile Asp
3545                3550                3555

Thr Leu Thr Thr His Met Ser Glu Val Pro Val Ile Ser Ala Asp
3560                3565                3570

Gly Glu Val Tyr Ile Arg Lys Gly Gln Arg Gly Ser Gly Gln Pro
3575                3580                3585

Asp Thr Ser Ala Gly Asn Ser Met Leu Asn Val Leu Thr Met Val
3590                3595                3600
```

Tyr Ala Phe Cys Glu Ala Thr Gly Val Pro Tyr Lys Ser Phe Asp
3605                3610                3615

Arg Val Ala Lys Ile His Val Cys Gly Asp Asp Gly Phe Leu Ile
3620                3625                3630

Thr Glu Arg Ala Leu Gly Glu Lys Phe Ala Ser Lys Gly Val Gln
3635                3640                3645

Ile Leu Tyr Glu Ala Gly Lys Pro Gln Lys Ile Thr Glu Gly Asp
3650                3655                3660

Lys Met Lys Val Ala Tyr Gln Phe Asp Asp Ile Glu Phe Cys Ser
3665                3670                3675

His Thr Pro Ile Gln Val Arg Trp Ser Asp Asn Thr Ser Ser Tyr
3680                3685                3690

Met Pro Gly Arg Asn Thr Thr Thr Ile Leu Ala Lys Met Ala Thr
3695                3700                3705

Arg Leu Asp Ser Ser Gly Glu Arg Gly Thr Ile Ala Tyr Glu Lys
3710                3715                3720

Ala Val Ala Phe Ser Phe Leu Leu Met Tyr Ser Trp Asn Pro Leu
3725                3730                3735

Ile Arg Arg Ile Cys Leu Leu Val Leu Ser Thr Glu Leu Gln Val
3740                3745                3750

Lys Pro Gly Lys Ser Thr Thr Tyr Tyr Tyr Glu Gly Asp Pro Ile
3755                3760                3765

Ser Ala Tyr Lys Glu Val Ile Gly His Asn Leu Phe Asp Leu Lys
3770                3775                3780

Arg Thr Ser Phe Glu Lys Leu Ala Lys Leu Asn Leu Ser Met Ser
3785                3790                3795

Val Leu Gly Ala Trp Thr Arg His Thr Ser Lys Arg Leu Leu Gln
3800                3805                3810

Asp Cys Val Asn Ile Gly Val Lys Glu Gly Asn Trp Leu Val Asn
3815                3820                3825

Ala Asp Arg Leu Val Ser Ser Lys Thr Gly Asn Arg Tyr Ile Pro
3830                3835                3840

Gly Glu Gly His Thr Leu Gln Gly Arg His Tyr Glu Glu Leu Val
3845                3850                3855

Leu Ala Arg Lys Gln Ile Asn Asn Phe Gln Gly Thr Asp Arg Tyr
3860                3865                3870

Asn Leu Gly Pro Ile Val Asn Met Val Leu Arg Arg Leu Arg Val
3875                3880                3885

Met Met Met Thr Leu Ile Gly Arg Gly Ala
3890                3895

<210> SEQ ID NO 14
<211> LENGTH: 3897
<212> TYPE: PRT
<213> ORGANISM: CSFV

<400> SEQUENCE: 14

Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Arg Pro Leu
                20                  25                  30

Phe Gly Asp Pro Ser Glu Val His Pro Gln Ser Thr Leu Lys Leu Pro
            35                  40                  45

His Asp Arg Gly Arg Gly Asn Ile Lys Thr Thr Leu Lys Asn Leu Pro
        50                  55                  60

```
Arg Lys Gly Asp Cys Arg Ser Gly Asn His Leu Gly Pro Val Ser Gly
 65                  70                  75                  80

Ile Tyr Val Lys Pro Gly Pro Val Phe Tyr Gln Asp Tyr Met Gly Pro
                 85                  90                  95

Val Tyr His Arg Ala Pro Leu Glu Phe Phe Asp Glu Val Gln Phe Cys
            100                 105                 110

Glu Val Thr Lys Arg Ile Gly Arg Val Thr Gly Ser Asp Gly Lys Leu
            115                 120                 125

Tyr His Thr Tyr Val Cys Ile Asp Gly Cys Ile Leu Leu Lys Leu Ala
            130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Asp Gly Ala Ser Gly Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Arg Pro Pro Asp Ala Thr
            195                 200                 205

Ile Val Val Glu Gly Val Lys Tyr Gln Val Lys Lys Gly Lys Val
            210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
            275                 280                 285

Leu Arg Gly Val Asn Arg Ser Leu His Gly Ile Trp Pro Gly Lys Ile
            290                 295                 300

Cys Lys Gly Val Pro Thr His Leu Ala Thr Asp Val Glu Leu Lys Glu
305                 310                 315                 320

Ile Gln Gly Met Met Asp Ala Ser Glu Gly Thr Asn Tyr Thr Cys Cys
            325                 330                 335

Lys Leu Gln Arg His Glu Trp Asn Lys Gly Trp Cys Asn Trp His Asn
            340                 345                 350

Ile Asp Pro Trp Ile Gln Leu Met Asn Arg Thr Gln Ala Asp Leu Ala
            355                 360                 365

Glu Gly Pro Pro Val Lys Glu Cys Ala Val Thr Cys Arg Tyr Asp Lys
            370                 375                 380

Asp Ala Asp Ile Asn Val Val Thr Gln Ala Arg Asn Arg Pro Thr Thr
385                 390                 395                 400

Leu Thr Gly Cys Lys Lys Gly Lys Asn Phe Ser Phe Ala Gly Thr Val
                405                 410                 415

Ile Glu Ser Pro Cys Asn Phe Asn Val Ser Val Glu Asp Thr Leu Tyr
            420                 425                 430

Gly Asp His Glu Cys Gly Ser Leu Leu Gln Asp Ala Ala Leu Tyr Leu
            435                 440                 445

Val Asp Gly Met Thr Asn Thr Ile Glu Asn Ala Arg Gln Gly Ala Ala
            450                 455                 460

Arg Val Thr Ser Trp Leu Gly Arg Gln Leu Arg Thr Ala Gly Lys Arg
465                 470                 475                 480
```

```
Leu Glu Gly Arg Ser Lys Thr Trp Phe Gly Ala Tyr Ala Leu Ser Pro
            485                 490                 495

Tyr Cys Asn Val Thr Ser Lys Ile Gly Tyr Ile Trp Tyr Thr Asn Asn
        500                 505                 510

Cys Thr Pro Ala Cys Leu Pro Lys Asn Thr Lys Ile Ile Gly Pro Gly
            515                 520                 525

Lys Phe Asp Thr Asn Ala Glu Asp Gly Lys Ile Leu His Glu Met Gly
        530                 535                 540

Gly His Leu Ser Glu Phe Leu Leu Leu Ser Leu Val Val Leu Ser Asp
545                 550                 555                 560

Phe Ala Pro Glu Thr Ala Ser Ala Leu Tyr Leu Ile Leu His Tyr Val
            565                 570                 575

Ile Pro Gln Pro His Asp Glu Pro Glu Gly Cys Asp Thr Asn Gln Leu
        580                 585                 590

Asn Leu Thr Val Glu Leu Arg Thr Glu Asp Val Ile Pro Ser Ser Val
            595                 600                 605

Trp Asn Val Gly Lys Tyr Val Cys Val Arg Pro Asp Trp Trp Pro Tyr
        610                 615                 620

Glu Thr Glu Val Ala Leu Leu Phe Glu Glu Val Gly Gln Val Val Lys
625                 630                 635                 640

Leu Ala Leu Arg Ala Leu Arg Asp Leu Thr Arg Val Trp Asn Ser Ala
            645                 650                 655

Ser Thr Ile Ala Phe Leu Ile Cys Leu Ile Lys Val Leu Arg Gly Gln
        660                 665                 670

Ile Val Gln Gly Val Val Trp Leu Leu Val Thr Gly Ala Gln Gly
        675                 680                 685

Arg Leu Ala Cys Lys Glu Asp Tyr Arg Tyr Ala Ile Ser Ser Thr Asp
            690                 695                 700

Glu Ile Gly Leu Leu Gly Ala Gly Gly Leu Thr Thr Thr Trp Lys Glu
705                 710                 715                 720

Tyr Asn His Asp Leu Gln Leu Asn Asp Gly Thr Val Lys Ala Ser Cys
            725                 730                 735

Val Ala Gly Ser Phe Lys Val Thr Ala Leu Asn Val Val Ser Arg Arg
        740                 745                 750

Tyr Leu Ala Ser Leu His Lys Lys Ala Leu Pro Thr Ser Val Thr Phe
            755                 760                 765

Glu Leu Leu Phe Asp Gly Thr Asn Pro Ser Thr Glu Glu Met Gly Asp
        770                 775                 780

Asp Phe Arg Ser Gly Leu Cys Pro Phe Asp Thr Ser Pro Val Val Lys
785                 790                 795                 800

Gly Lys Tyr Asn Thr Thr Leu Leu Asn Gly Ser Ala Phe Tyr Leu Val
            805                 810                 815

Cys Pro Ile Gly Trp Thr Gly Val Ile Glu Cys Thr Ala Val Ser Lys
        820                 825                 830

Asp Thr Leu Arg Thr Glu Val Val Lys Thr Phe Arg Arg Asp Lys Pro
            835                 840                 845

Phe Pro His Arg Met Asp Cys Val Thr Thr Val Glu Asn Glu Asp
        850                 855                 860

Leu Phe Tyr Cys Lys Leu Gly Gly Asn Trp Thr Cys Val Lys Gly Glu
865                 870                 875                 880

Pro Val Val Tyr Thr Gly Gly Leu Val Lys Gln Cys Arg Trp Cys Gly
            885                 890                 895

Phe Asp Phe Asp Gly Pro Asp Gly Leu Pro His Tyr Pro Ile Gly Lys
```

-continued

```
              900             905             910
Cys Ile Leu Ala Asn Glu Thr Gly Tyr Arg Ile Val Asp Ser Thr Asp
            915             920             925
Cys Asn Arg Asp Gly Val Val Ile Ser Thr Glu Gly Ser His Glu Cys
            930             935             940
Leu Ile Gly Asn Thr Thr Val Lys Val His Ala Ser Asp Glu Arg Leu
945             950             955             960
Gly Pro Met Pro Cys Arg Pro Lys Glu Ile Val Ser Ser Ala Gly Pro
                965             970             975
Val Lys Lys Thr Ser Cys Thr Phe Asn Tyr Thr Lys Thr Leu Lys Asn
            980             985             990
Arg Tyr Tyr Glu Pro Arg Asp Ser Tyr Phe Gln Gln Tyr Met Leu Lys
            995            1000            1005
Gly Glu Tyr Gln Tyr Trp Phe Asp Leu Asp Ala Thr Asp Arg His
    1010            1015            1020
Ser Asp Tyr Phe Ala Glu Phe Val Val Leu Val Val Val Ala Leu
    1025            1030            1035
Leu Gly Gly Arg Tyr Val Leu Trp Leu Ile Val Thr Tyr Val Val
    1040            1045            1050
Leu Thr Glu Gln Leu Ala Ala Gly Leu Pro Leu Gly Gln Gly Glu
    1055            1060            1065
Val Val Leu Ile Gly Asn Leu Ile Thr His Thr Asp Ile Glu Val
    1070            1075            1080
Val Val Tyr Phe Leu Leu Leu Tyr Leu Val Met Arg Asp Glu Pro
    1085            1090            1095
Ile Lys Lys Trp Ile Leu Leu Leu Phe His Ala Met Thr Asn Asn
    1100            1105            1110
Pro Val Lys Thr Ile Thr Val Ala Leu Leu Met Val Ser Gly Val
    1115            1120            1125
Ala Lys Gly Gly Lys Ile Asp Gly Gly Trp Gln Arg Leu Pro Gly
    1130            1135            1140
Thr Ser Phe Asp Ile Gln Leu Ala Leu Thr Val Ile Val Val Ala
    1145            1150            1155
Val Met Leu Leu Ala Lys Arg Asp Pro Thr Thr Val Pro Leu Val
    1160            1165            1170
Ile Thr Val Ala Pro Leu Arg Thr Ala Lys Met Thr Asn Gly Leu
    1175            1180            1185
Ser Thr Asp Ile Ala Ile Ala Thr Val Ser Ala Ala Leu Leu Thr
    1190            1195            1200
Trp Thr Tyr Ile Ser Asp Tyr Tyr Arg Tyr Lys Thr Trp Leu Gln
    1205            1210            1215
Tyr Leu Ile Ser Thr Val Thr Gly Ile Phe Leu Ile Arg Val Leu
    1220            1225            1230
Lys Gly Ile Gly Glu Leu Asp Leu His Thr Pro Thr Leu Pro Ser
    1235            1240            1245
His Arg Pro Leu Phe Phe Ile Leu Val Tyr Leu Ile Ser Thr Ala
    1250            1255            1260
Val Val Thr Arg Trp Asn Leu Asp Ile Ala Gly Leu Leu Leu Gln
    1265            1270            1275
Cys Val Pro Thr Leu Leu Met Val Phe Thr Met Trp Ala Asp Ile
    1280            1285            1290
Leu Thr Leu Ile Leu Ile Leu Pro Thr Tyr Glu Leu Thr Lys Leu
    1295            1300            1305
```

-continued

Tyr Tyr Leu Lys Glu Val Arg Ile Gly Ala Glu Lys Gly Trp Leu
    1310            1315            1320

Trp Lys Thr Asn Phe Lys Arg Val Asn Asp Ile Tyr Glu Val Asp
    1325            1330            1335

Gln Ala Gly Glu Gly Val Tyr Leu Phe Pro Ser Lys Gln Lys Thr
    1340            1345            1350

Ser Ser Met Thr Gly Thr Met Leu Pro Leu Ile Lys Ala Ile Leu
    1355            1360            1365

Ile Ser Cys Val Ser Asn Lys Trp Gln Phe Ile Tyr Leu Leu Tyr
    1370            1375            1380

Leu Ile Phe Glu Val Ser Tyr Tyr Leu His Lys Lys Ile Ile Asp
    1385            1390            1395

Glu Ile Ala Gly Gly Thr Asn Phe Ile Ser Arg Leu Val Ala Ala
    1400            1405            1410

Leu Ile Glu Val Asn Trp Ala Phe Asp Asn Glu Glu Val Arg Gly
    1415            1420            1425

Leu Lys Lys Phe Phe Leu Leu Ser Ser Arg Val Lys Glu Leu Ile
    1430            1435            1440

Ile Lys His Lys Val Arg Asn Glu Val Met Val Arg Trp Phe Gly
    1445            1450            1455

Asp Glu Glu Val Tyr Gly Met Pro Lys Leu Val Gly Leu Val Lys
    1460            1465            1470

Ala Ala Thr Leu Ser Lys Asn Lys His Cys Ile Leu Cys Thr Val
    1475            1480            1485

Cys Glu Asp Arg Glu Trp Arg Gly Glu Thr Cys Pro Lys Cys Gly
    1490            1495            1500

Arg Phe Gly Pro Pro Met Thr Cys Gly Met Thr Leu Ala Asp Phe
    1505            1510            1515

Glu Glu Lys His Tyr Lys Arg Ile Phe Phe Arg Glu Asp Gln Ser
    1520            1525            1530

Glu Gly Pro Val Arg Glu Glu Tyr Ala Gly Tyr Leu Gln Tyr Arg
    1535            1540            1545

Ala Arg Gly Gln Leu Phe Leu Arg Asn Leu Pro Val Leu Ala Thr
    1550            1555            1560

Lys Val Lys Met Leu Leu Val Gly Asn Leu Gly Thr Glu Val Gly
    1565            1570            1575

Asp Leu Glu His Leu Gly Trp Val Leu Arg Gly Pro Ala Val Cys
    1580            1585            1590

Lys Lys Val Thr Glu His Glu Lys Cys Thr Thr Ser Met Met Asp
    1595            1600            1605

Lys Leu Thr Ala Phe Phe Gly Val Met Pro Arg Gly Thr Thr Pro
    1610            1615            1620

Arg Ala Pro Val Arg Phe Pro Thr Ser Leu Leu Lys Ile Arg Arg
    1625            1630            1635

Gly Leu Glu Thr Gly Trp Ala Tyr Thr His Gln Gly Gly Ile Ser
    1640            1645            1650

Ser Val Asp His Val Thr Cys Gly Lys Asp Leu Leu Val Cys Asp
    1655            1660            1665

Thr Met Gly Arg Thr Arg Val Val Cys Gln Ser Asn Asn Lys Met
    1670            1675            1680

Thr Asp Glu Ser Glu Tyr Gly Val Lys Thr Asp Ser Gly Cys Pro
    1685            1690            1695

```
Glu Gly Ala Arg Cys Tyr Val Phe Asn Pro Glu Ala Val Asn Ile
1700                1705                1710

Ser Gly Thr Lys Gly Ala Met Val His Leu Gln Lys Thr Gly Gly
1715                1720                1725

Glu Phe Thr Cys Val Thr Ala Ser Gly Thr Pro Ala Phe Phe Asp
1730                1735                1740

Leu Lys Asn Leu Lys Gly Trp Ser Gly Leu Pro Ile Phe Glu Ala
1745                1750                1755

Ser Ser Gly Arg Val Val Gly Arg Val Lys Val Gly Lys Asn Glu
1760                1765                1770

Asp Ser Lys Pro Thr Lys Leu Met Ser Gly Ile Gln Thr Val Ser
1775                1780                1785

Lys Ser Thr Thr Asp Leu Thr Glu Met Val Lys Lys Ile Thr Thr
1790                1795                1800

Met Ser Arg Gly Glu Phe Arg Gln Ile Thr Leu Ala Thr Gly Ala
1805                1810                1815

Gly Lys Thr Thr Glu Leu Pro Arg Ser Val Ile Glu Glu Ile Gly
1820                1825                1830

Arg His Lys Arg Val Leu Val Leu Ile Pro Leu Arg Ala Ala Ala
1835                1840                1845

Glu Ser Val Tyr Gln Tyr Met Arg Gln Lys His Pro Ser Ile Ala
1850                1855                1860

Phe Asn Leu Arg Ile Gly Glu Met Lys Glu Gly Asp Met Ala Thr
1865                1870                1875

Gly Ile Thr Tyr Ala Ser Tyr Gly Tyr Phe Cys Gln Met Pro Gln
1880                1885                1890

Pro Lys Leu Arg Ala Ala Met Val Glu Tyr Ser Phe Ile Phe Leu
1895                1900                1905

Asp Glu Tyr His Cys Ala Thr Pro Glu Gln Leu Ala Ile Met Gly
1910                1915                1920

Lys Ile His Arg Phe Ser Glu Asn Leu Arg Val Val Ala Met Thr
1925                1930                1935

Ala Thr Pro Val Gly Thr Val Thr Thr Thr Gly Gln Lys His Pro
1940                1945                1950

Ile Glu Glu Phe Ile Ala Pro Asp Val Met Lys Gly Lys Asp Leu
1955                1960                1965

Gly Ser Glu Tyr Leu Asp Ile Ala Gly Leu Lys Ile Pro Val Glu
1970                1975                1980

Glu Met Lys Ser Asn Met Leu Val Phe Val Pro Thr Arg Asn Met
1985                1990                1995

Ala Val Glu Thr Ala Lys Lys Leu Lys Ala Lys Gly Tyr Asn Ser
2000                2005                2010

Gly Tyr Tyr Tyr Ser Gly Glu Asp Pro Ser Asn Leu Arg Val Val
2015                2020                2025

Thr Ser Gln Ser Pro Tyr Val Val Val Ala Thr Asn Ala Ile Glu
2030                2035                2040

Ser Gly Val Thr Leu Pro Asp Leu Asp Val Val Val Asp Thr Gly
2045                2050                2055

Leu Lys Cys Glu Lys Arg Ile Arg Leu Ser Pro Lys Met Pro Phe
2060                2065                2070

Ile Val Thr Gly Leu Lys Arg Met Ala Val Thr Ile Gly Glu Gln
2075                2080                2085

Ala Gln Arg Arg Gly Arg Val Gly Arg Val Lys Pro Gly Arg Tyr
```

-continued

```
                2090                2095                2100
Tyr Arg Ser Gln Glu Thr Pro Val Gly Ser Lys Asp Tyr His Tyr
                2105                2110                2115
Asp Leu Leu Gln Ala Gln Arg Tyr Gly Ile Glu Asp Gly Ile Asn
                2120                2125                2130
Ile Thr Lys Ser Phe Arg Glu Met Asn Tyr Asp Trp Ser Leu Tyr
                2135                2140                2145
Glu Glu Asp Ser Leu Met Ile Thr Gln Leu Glu Ile Leu Asn Asn
                2150                2155                2160
Leu Leu Ile Ser Asp Glu Leu Pro Met Ala Val Lys Asn Ile Met
                2165                2170                2175
Ala Arg Thr Asp His Pro Glu Pro Ile Gln Leu Ala Tyr Asn Ser
                2180                2185                2190
Tyr Glu Thr Gln Val Pro Val Leu Phe Pro Lys Ile Lys Asn Gly
                2195                2200                2205
Glu Val Thr Asp Ser Tyr Asp Asn Tyr Thr Phe Leu Asn Ala Arg
                2210                2215                2220
Lys Leu Gly Asp Asp Val Pro Pro Tyr Val Tyr Ala Thr Glu Asp
                2225                2230                2235
Glu Asp Leu Ala Val Glu Leu Leu Gly Leu Asp Trp Pro Asp Pro
                2240                2245                2250
Gly Asn Gln Gly Thr Val Glu Thr Gly Arg Ala Leu Lys Gln Val
                2255                2260                2265
Val Gly Leu Ser Thr Ala Glu Asn Ala Leu Leu Val Ala Leu Phe
                2270                2275                2280
Gly Tyr Val Gly Tyr Gln Ala Leu Ser Lys Arg His Ile Pro Val
                2285                2290                2295
Val Thr Asp Ile Tyr Ser Ile Glu Asp His Arg Leu Glu Asp Thr
                2300                2305                2310
Thr His Leu Gln Tyr Ala Pro Asn Ala Ile Lys Thr Glu Gly Lys
                2315                2320                2325
Glu Thr Glu Leu Lys Glu Leu Ala Gln Gly Asp Val Gln Arg Cys
                2330                2335                2340
Val Glu Ala Met Thr Asn Tyr Ala Arg Glu Gly Ile Gln Phe Met
                2345                2350                2355
Lys Ser Gln Ala Leu Lys Val Lys Glu Thr Pro Thr Tyr Lys Glu
                2360                2365                2370
Thr Met Asp Thr Val Thr Asp Tyr Val Lys Lys Phe Met Glu Ala
                2375                2380                2385
Leu Ala Asp Ser Lys Glu Asp Ile Ile Lys Tyr Gly Leu Trp Gly
                2390                2395                2400
Thr His Thr Ala Leu Tyr Lys Ser Ile Ser Ala Arg Leu Gly Gly
                2405                2410                2415
Glu Thr Ala Phe Ala Thr Leu Val Val Lys Trp Leu Ala Phe Gly
                2420                2425                2430
Gly Glu Ser Ile Ala Asp His Val Lys Gln Ala Ala Thr Asp Leu
                2435                2440                2445
Val Val Tyr Tyr Ile Ile Asn Arg Pro Gln Phe Pro Gly Asp Thr
                2450                2455                2460
Glu Thr Gln Gln Asp Gly Arg Lys Phe Val Ala Ser Leu Leu Ala
                2465                2470                2475
Ser Ala Leu Ala Thr Tyr Thr Tyr Lys Ser Trp Asn Tyr Asn Asn
                2480                2485                2490
```

```
Leu Ser Lys Ile Val Glu Pro Ala Leu Ala Thr Leu Pro Tyr Ala
2495                2500                2505

Ala Thr Ala Leu Lys Leu Phe Ala Pro Thr Arg Leu Glu Ser Val
2510                2515                2520

Val Ile Leu Ser Thr Ala Ile Tyr Lys Thr Tyr Leu Ser Ile Arg
2525                2530                2535

Arg Gly Lys Ser Asp Gly Leu Leu Gly Thr Gly Val Ser Ala Ala
2540                2545                2550

Met Glu Ile Met Ser Gln Asn Pro Val Ser Val Gly Ile Ala Val
2555                2560                2565

Met Leu Gly Val Gly Ala Val Ala Ala His Asn Ala Ile Glu Ala
2570                2575                2580

Ser Glu Gln Lys Arg Thr Leu Leu Met Lys Val Phe Val Lys Asn
2585                2590                2595

Phe Leu Asp Gln Ala Ala Thr Asp Glu Leu Val Lys Glu Ser Pro
2600                2605                2610

Glu Lys Ile Ile Met Ala Leu Phe Glu Ala Val Gln Thr Val Gly
2615                2620                2625

Asn Pro Leu Arg Leu Val Tyr His Leu Tyr Gly Val Phe Tyr Lys
2630                2635                2640

Gly Trp Glu Ala Lys Glu Leu Ala Gln Arg Thr Ala Gly Arg Asn
2645                2650                2655

Leu Phe Thr Leu Ile Met Phe Glu Ala Val Glu Leu Leu Gly Val
2660                2665                2670

Asp Ser Glu Gly Lys Val Arg Gln Leu Ser Ser Asn Tyr Ile Leu
2675                2680                2685

Glu Leu Leu Tyr Lys Phe Arg Asp Ser Ile Lys Ser Ser Val Arg
2690                2695                2700

Glu Met Ala Ile Ser Trp Ala Pro Ala Pro Phe Ser Cys Asp Trp
2705                2710                2715

Thr Pro Thr Asp Asp Arg Ile Gly Leu Pro Gln Asp Asn Phe His
2720                2725                2730

Gln Val Glu Thr Lys Cys Pro Cys Gly Tyr Lys Met Lys Ala Val
2735                2740                2745

Lys Asn Cys Ala Gly Glu Leu Arg Leu Leu Glu Glu Glu Gly Ser
2750                2755                2760

Phe Leu Cys Arg Asn Lys Phe Gly Arg Gly Ser Arg Asn Tyr Arg
2765                2770                2775

Val Thr Lys Tyr Tyr Asp Asp Asn Leu Leu Glu Ile Lys Pro Val
2780                2785                2790

Ile Arg Met Glu Gly His Val Glu Leu Tyr Tyr Lys Gly Ala Thr
2795                2800                2805

Ile Lys Leu Asp Phe Asn Asn Ser Lys Thr Ile Leu Ala Thr Asp
2810                2815                2820

Lys Trp Glu Val Asp His Ser Thr Leu Val Arg Val Leu Lys Arg
2825                2830                2835

His Thr Gly Ala Gly Tyr His Gly Ala Tyr Leu Gly Glu Lys Pro
2840                2845                2850

Asn His Lys His Leu Ile Glu Arg Asp Cys Ala Thr Ile Thr Lys
2855                2860                2865

Asp Lys Val Cys Phe Leu Lys Met Lys Arg Gly Cys Ala Phe Thr
2870                2875                2880
```

-continued

Tyr Asp Leu Ser Leu His Asn Leu Thr Arg Leu Ile Glu Leu Val
2885                     2890                2895

His Lys Asn Asn Leu Glu Asp Lys Glu Ile Pro Ala Ala Thr Val
2900                     2905                2910

Thr Thr Trp Leu Ala Tyr Thr Phe Val Asn Glu Asp Ile Gly Thr
2915                     2920                2925

Ile Lys Pro Ala Phe Gly Glu Lys Val Thr Leu Glu Met Gln Glu
2930                     2935                2940

Glu Ile Thr Leu Gln Pro Ala Val Val Val Asp Thr Thr Asp Val
2945                     2950                2955

Ala Val Thr Val Val Gly Glu Ala Pro Thr Met Thr Thr Gly Glu
2960                     2965                2970

Thr Pro Thr Val Phe Thr Ser Ser Gly Ser Gly Leu Lys Ser Gln
2975                     2980                2985

Gln Val Leu Lys Leu Gly Val Gly Glu Gly Gln Tyr Pro Gly Thr
2990                     2995                3000

Asn Pro Gln Arg Ala Ser Leu His Glu Ala Ile Gln Gly Ala Asp
3005                     3010                3015

Glu Arg Pro Ser Val Leu Ile Leu Gly Ser Asp Lys Ala Thr Ser
3020                     3025                3030

Asn Arg Val Lys Thr Ala Lys Asn Val Lys Val Tyr Arg Gly Arg
3035                     3040                3045

Asp Pro Leu Glu Val Arg Asp Met Met Arg Arg Gly Lys Ile Leu
3050                     3055                3060

Val Val Ala Leu Ser Arg Val Asp Asn Ala Leu Leu Lys Phe Val
3065                     3070                3075

Asp Tyr Lys Gly Thr Phe Leu Thr Arg Glu Ala Leu Glu Ala Leu
3080                     3085                3090

Ser Leu Gly Arg Pro Lys Lys Lys Asn Ile Thr Lys Ala Glu Ala
3095                     3100                3105

Gln Trp Leu Leu Cys Pro Glu Asp Gln Met Glu Glu Leu Pro Asp
3110                     3115                3120

Trp Phe Ala Ala Gly Glu Pro Ile Phe Leu Glu Ala Asn Ile Lys
3125                     3130                3135

His Asp Arg Tyr His Leu Val Gly Asp Ile Ala Thr Ile Lys Glu
3140                     3145                3150

Lys Ala Lys Gln Leu Gly Ala Thr Asp Ser Thr Lys Ile Ser Lys
3155                     3160                3165

Glu Val Gly Ala Lys Val Tyr Ser Met Lys Leu Ser Asn Trp Val
3170                     3175                3180

Met Gln Glu Glu Asn Lys Gln Gly Asn Leu Thr Pro Leu Phe Glu
3185                     3190                3195

Glu Leu Leu Gln Gln Cys Pro Pro Gly Gly Gln Asn Lys Thr Ala
3200                     3205                3210

His Met Val Ser Ala Tyr Gln Leu Ala Gln Gly Asn Trp Met Pro
3215                     3220                3225

Thr Ser Cys His Val Phe Met Gly Thr Val Ser Ala Arg Arg Thr
3230                     3235                3240

Lys Thr His Pro Tyr Glu Ala Tyr Val Lys Leu Arg Glu Leu Val
3245                     3250                3255

Glu Glu His Lys Met Lys Thr Leu Cys Pro Gly Ser Ser Leu Gly
3260                     3265                3270

Arg His Asn Asp Trp Ile Ile Gly Lys Ile Lys Tyr Gln Gly Asn

```
             3275                3280                3285
Leu Arg Thr Lys His Met Leu Asn Pro Gly Lys Val Ala Glu Gln
        3290                3295                3300
Leu Cys Arg Glu Gly His Arg His Asn Val Tyr Asn Lys Thr Ile
        3305                3310                3315
Ser Ser Val Met Thr Ala Thr Gly Ile Arg Leu Glu Lys Leu Pro
        3320                3325                3330
Val Val Arg Ala Gln Thr Asp Pro Thr Asn Phe His Gln Ala Ile
        3335                3340                3345
Arg Asp Lys Ile Asp Lys Glu Glu Asn Leu Gln Thr Pro Gly Leu
        3350                3355                3360
His Lys Lys Leu Met Glu Val Phe Asn Ala Leu Lys Arg Pro Glu
        3365                3370                3375
Leu Glu Ser Ser Tyr Asp Ala Val Glu Trp Glu Lys Leu Glu Arg
        3380                3385                3390
Gly Ile Asn Arg Lys Gly Ala Ala Gly Phe Phe Glu Arg Lys Asn
        3395                3400                3405
Ile Gly Glu Ile Leu Asp Ser Glu Lys Asn Lys Val Glu Glu Ile
        3410                3415                3420
Ile Asp Asn Leu Lys Lys Gly Arg Asn Ile Lys Tyr Tyr Glu Thr
        3425                3430                3435
Ala Ile Pro Lys Asn Glu Lys Arg Asp Val Asn Asp Asp Trp Thr
        3440                3445                3450
Ala Gly Asp Phe Val Asp Glu Lys Lys Pro Arg Val Ile Gln Tyr
        3455                3460                3465
Pro Glu Ala Lys Thr Arg Leu Ala Ile Thr Lys Val Met Tyr Lys
        3470                3475                3480
Trp Val Lys Gln Lys Pro Val Val Ile Pro Gly Tyr Glu Gly Lys
        3485                3490                3495
Thr Pro Leu Phe Gln Ile Phe Asp Lys Val Lys Lys Glu Trp Asp
        3500                3505                3510
Gln Phe Gln Asn Pro Val Ala Val Ser Phe Asp Thr Lys Ala Trp
        3515                3520                3525
Asp Thr Gln Val Thr Thr Lys Asp Leu Glu Leu Ile Arg Asp Ile
        3530                3535                3540
Gln Lys Tyr Tyr Phe Lys Lys Trp His Lys Phe Ile Asp Thr
        3545                3550                3555
Leu Thr Thr His Met Ser Glu Val Pro Val Ile Ser Ala Asp Gly
        3560                3565                3570
Glu Val Tyr Ile Arg Lys Gly Gln Arg Gly Ser Gly Gln Pro Asp
        3575                3580                3585
Thr Ser Ala Gly Asn Ser Met Leu Asn Val Leu Thr Met Val Tyr
        3590                3595                3600
Ala Phe Cys Glu Ala Thr Gly Val Pro Tyr Lys Ser Phe Asp Arg
        3605                3610                3615
Val Ala Lys Ile His Val Cys Gly Asp Asp Gly Phe Leu Ile Thr
        3620                3625                3630
Glu Arg Ala Leu Gly Glu Lys Phe Ala Ser Lys Gly Val Gln Ile
        3635                3640                3645
Leu Tyr Glu Ala Gly Lys Pro Gln Lys Ile Thr Glu Gly Asp Lys
        3650                3655                3660
Met Lys Val Ala Tyr Gln Phe Asp Asp Ile Glu Phe Cys Ser His
        3665                3670                3675
```

```
Thr Pro Ile Gln Val Arg Trp Ser Asp Asn Thr Ser  Ser Tyr Met
    3680                3685                 3690

Pro Gly Arg Asn Thr Thr Thr Ile Leu Ala Lys Met  Ala Thr Arg
    3695                3700                 3705

Leu Asp Ser Ser Gly Glu Arg Gly Thr Ile Ala Tyr  Glu Lys Ala
    3710                3715                 3720

Val Ala Phe Ser Phe Leu Leu Met Tyr Ser Trp Asn  Pro Leu Ile
    3725                3730                 3735

Arg Arg Ile Cys Leu Leu Val Leu Ser Thr Glu Leu  Gln Val Lys
    3740                3745                 3750

Pro Gly Lys Ser Thr Thr Tyr Tyr Tyr Glu Gly Asp  Pro Ile Ser
    3755                3760                 3765

Ala Tyr Lys Glu Val Ile Gly His Asn Leu Phe Asp  Leu Lys Arg
    3770                3775                 3780

Thr Ser Phe Glu Lys Leu Ala Lys Leu Asn Leu Ser  Met Ser Val
    3785                3790                 3795

Leu Gly Ala Trp Thr Arg His Thr Ser Lys Arg Leu  Leu Gln Asp
    3800                3805                 3810

Cys Val Asn Ile Gly Val Lys Glu Gly Asn Trp Leu  Val Asn Ala
    3815                3820                 3825

Asp Arg Leu Val Ser Ser Lys Thr Gly Asn Arg Tyr  Ile Pro Gly
    3830                3835                 3840

Glu Gly His Thr Leu Gln Gly Arg His Tyr Glu Glu  Leu Val Leu
    3845                3850                 3855

Ala Arg Lys Gln Ile Asn Asn Phe Gln Gly Thr Asp  Arg Tyr Asn
    3860                3865                 3870

Leu Gly Pro Ile Val Asn Met Val Leu Arg Arg Leu  Arg Val Met
    3875                3880                 3885

Met Met Thr Leu Ile Gly Arg Gly Ala
    3890                3895

<210> SEQ ID NO 15
<211> LENGTH: 3732
<212> TYPE: PRT
<213> ORGANISM: CSFV

<400> SEQUENCE: 15

Met Gly Ser Asp Asp Gly Ala Ser Gly Ser Lys Glu Lys Lys Pro Asp
1               5                   10                  15

Arg Ile Asn Lys Gly Lys Leu Lys Ile Ala Pro Lys Glu His Glu Lys
            20                  25                  30

Asp Ser Arg Thr Arg Pro Pro Asp Ala Thr Ile Val Val Glu Gly Val
        35                  40                  45

Lys Tyr Gln Val Lys Lys Lys Gly Lys Val Gly Lys Asn Thr Gln
    50                  55                  60

Asp Gly Leu Tyr His Asn Lys Asn Lys Pro Pro Glu Ser Arg Lys Lys
65                  70                  75                  80

Leu Glu Lys Ala Leu Leu Ala Trp Ala Val Ile Ala Ile Met Leu Tyr
                85                  90                  95

Gln Pro Val Glu Ala Glu Asn Ile Thr Gln Trp Asn Leu Ser Asp Asn
            100                 105                 110

Gly Thr Asn Gly Ile Gln His Ala Met Tyr Leu Arg Gly Val Asn Arg
        115                 120                 125

Ser Leu His Gly Ile Trp Pro Gly Lys Ile Cys Lys Gly Val Pro Thr
```

```
            130                 135                 140
His Leu Ala Thr Asp Val Glu Leu Lys Glu Ile Gln Gly Met Met Asp
145                 150                 155                 160

Ala Ser Glu Gly Thr Asn Tyr Thr Cys Cys Lys Leu Gln Arg His Glu
                165                 170                 175

Trp Asn Lys His Gly Trp Cys Asn Trp His Asn Ile Asp Pro Trp Ile
                180                 185                 190

Gln Leu Met Asn Arg Thr Gln Ala Asp Leu Ala Glu Gly Pro Pro Val
            195                 200                 205

Lys Glu Cys Ala Val Thr Cys Arg Tyr Asp Lys Asp Ala Asp Ile Asn
210                 215                 220

Val Val Thr Gln Ala Arg Asn Arg Pro Thr Thr Leu Thr Gly Cys Lys
225                 230                 235                 240

Lys Gly Lys Asn Phe Ser Phe Ala Gly Thr Val Ile Glu Ser Pro Cys
                245                 250                 255

Asn Phe Asn Val Ser Val Glu Asp Thr Leu Tyr Gly Asp His Glu Cys
                260                 265                 270

Gly Ser Leu Leu Gln Asp Ala Ala Leu Tyr Leu Val Asp Gly Met Thr
            275                 280                 285

Asn Thr Ile Glu Asn Ala Arg Gln Gly Ala Ala Arg Val Thr Ser Trp
            290                 295                 300

Leu Gly Arg Gln Leu Arg Thr Ala Gly Lys Arg Leu Glu Gly Arg Ser
305                 310                 315                 320

Lys Thr Trp Phe Gly Ala Tyr Ala Leu Ser Pro Tyr Cys Asn Val Thr
                325                 330                 335

Ser Lys Ile Gly Tyr Ile Trp Tyr Thr Asn Asn Cys Thr Pro Ala Cys
                340                 345                 350

Leu Pro Lys Asn Thr Lys Ile Ile Gly Pro Gly Lys Phe Asp Thr Asn
                355                 360                 365

Ala Glu Asp Gly Lys Ile Leu His Glu Met Gly Gly His Leu Ser Glu
            370                 375                 380

Phe Leu Leu Leu Ser Leu Val Val Leu Ser Asp Phe Ala Pro Glu Thr
385                 390                 395                 400

Ala Ser Ala Leu Tyr Leu Ile Leu His Tyr Val Ile Pro Gln Pro His
                405                 410                 415

Asp Glu Pro Glu Gly Cys Asp Thr Asn Gln Leu Asn Leu Thr Val Glu
            420                 425                 430

Leu Arg Thr Glu Asp Val Ile Pro Ser Ser Val Trp Asn Val Gly Lys
                435                 440                 445

Tyr Val Cys Val Arg Pro Asp Trp Trp Pro Tyr Glu Thr Glu Val Ala
            450                 455                 460

Leu Leu Phe Glu Glu Val Gly Gln Val Val Lys Leu Ala Leu Arg Ala
465                 470                 475                 480

Leu Arg Asp Leu Thr Arg Val Trp Asn Ser Ala Ser Thr Ile Ala Phe
                485                 490                 495

Leu Ile Cys Leu Ile Lys Val Leu Arg Gly Gln Ile Val Gln Gly Val
                500                 505                 510

Val Trp Leu Leu Leu Val Thr Gly Ala Gln Gly Arg Leu Ala Cys Lys
            515                 520                 525

Glu Asp Tyr Arg Tyr Ala Ile Ser Ser Thr Asp Glu Ile Gly Leu Leu
            530                 535                 540

Gly Ala Gly Gly Leu Thr Thr Thr Trp Lys Glu Tyr Asn His Asp Leu
545                 550                 555                 560
```

```
Gln Leu Asn Asp Gly Thr Val Lys Ala Ser Cys Val Ala Gly Ser Phe
                565                 570                 575

Lys Val Thr Ala Leu Asn Val Val Ser Arg Arg Tyr Leu Ala Ser Leu
            580                 585                 590

His Lys Lys Ala Leu Pro Thr Ser Val Thr Phe Glu Leu Leu Phe Asp
        595                 600                 605

Gly Thr Asn Pro Ser Thr Glu Glu Met Gly Asp Asp Phe Arg Ser Gly
    610                 615                 620

Leu Cys Pro Phe Asp Thr Ser Pro Val Val Lys Gly Lys Tyr Asn Thr
625                 630                 635                 640

Thr Leu Leu Asn Gly Ser Ala Phe Tyr Leu Val Cys Pro Ile Gly Trp
                645                 650                 655

Thr Gly Val Ile Glu Cys Thr Ala Val Ser Lys Asp Thr Leu Arg Thr
            660                 665                 670

Glu Val Val Lys Thr Phe Arg Arg Asp Lys Pro Phe Pro His Arg Met
        675                 680                 685

Asp Cys Val Thr Thr Val Glu Asn Glu Asp Leu Phe Tyr Cys Lys
    690                 695                 700

Leu Gly Gly Asn Trp Thr Cys Val Lys Gly Glu Pro Val Val Tyr Thr
705                 710                 715                 720

Gly Gly Leu Val Lys Gln Cys Arg Trp Cys Gly Phe Asp Phe Asp Gly
                725                 730                 735

Pro Asp Gly Leu Pro His Tyr Pro Ile Gly Lys Cys Ile Leu Ala Asn
            740                 745                 750

Glu Thr Gly Tyr Arg Ile Val Asp Ser Thr Asp Cys Asn Arg Asp Gly
        755                 760                 765

Val Val Ile Ser Thr Glu Gly Ser His Glu Cys Leu Ile Gly Asn Thr
    770                 775                 780

Thr Val Lys Val His Ala Ser Asp Glu Arg Leu Gly Pro Met Pro Cys
785                 790                 795                 800

Arg Pro Lys Glu Ile Val Ser Ser Ala Gly Pro Val Lys Lys Thr Ser
                805                 810                 815

Cys Thr Phe Asn Tyr Thr Lys Thr Leu Lys Asn Arg Tyr Tyr Glu Pro
            820                 825                 830

Arg Asp Ser Tyr Phe Gln Gln Tyr Met Leu Lys Gly Glu Tyr Gln Tyr
        835                 840                 845

Trp Phe Asp Leu Asp Ala Thr Asp His Ser Asp Tyr Phe Ala Glu
    850                 855                 860

Phe Val Val Leu Val Val Ala Leu Leu Gly Arg Tyr Val Leu
865                 870                 875                 880

Trp Leu Ile Val Thr Tyr Val Leu Thr Glu Gln Leu Ala Ala Gly
                885                 890                 895

Leu Pro Leu Gly Gln Gly Glu Val Val Leu Ile Gly Asn Leu Ile Thr
            900                 905                 910

His Thr Asp Ile Glu Val Val Tyr Phe Leu Leu Tyr Leu Val
        915                 920                 925

Met Arg Asp Glu Pro Ile Lys Lys Trp Ile Leu Leu Phe His Ala
    930                 935                 940

Met Thr Asn Asn Pro Val Lys Thr Ile Thr Val Ala Leu Leu Met Val
945                 950                 955                 960

Ser Gly Val Ala Lys Gly Gly Lys Ile Asp Gly Gly Trp Gln Arg Leu
                965                 970                 975
```

-continued

```
Pro Gly Thr Ser Phe Asp Ile Gln Leu Ala Leu Thr Val Ile Val Val
                980                 985                 990

Ala Val Met Leu Leu Ala Lys Arg Asp Pro Thr Thr Val Pro Leu Val
        995                 1000                1005

Ile Thr Val Ala Pro Leu Arg Thr Ala Lys Met Thr Asn Gly Leu
    1010                1015                1020

Ser Thr Asp Ile Ala Ile Ala Thr Val Ser Ala Ala Leu Leu Thr
    1025                1030                1035

Trp Thr Tyr Ile Ser Asp Tyr Tyr Arg Tyr Lys Thr Trp Leu Gln
    1040                1045                1050

Tyr Leu Ile Ser Thr Val Thr Gly Ile Phe Leu Ile Arg Val Leu
    1055                1060                1065

Lys Gly Ile Gly Glu Leu Asp Leu His Thr Pro Thr Leu Pro Ser
    1070                1075                1080

His Arg Pro Leu Phe Phe Ile Leu Val Tyr Leu Ile Ser Thr Ala
    1085                1090                1095

Val Val Thr Arg Trp Asn Leu Asp Ile Ala Gly Leu Leu Leu Gln
    1100                1105                1110

Cys Val Pro Thr Leu Leu Met Val Phe Thr Met Trp Ala Asp Ile
    1115                1120                1125

Leu Thr Leu Ile Leu Ile Leu Pro Thr Tyr Glu Leu Thr Lys Leu
    1130                1135                1140

Tyr Tyr Leu Lys Glu Val Arg Ile Gly Ala Glu Lys Gly Trp Leu
    1145                1150                1155

Trp Lys Thr Asn Phe Lys Arg Val Asn Asp Ile Tyr Glu Val Asp
    1160                1165                1170

Gln Ala Gly Glu Gly Val Tyr Leu Phe Pro Ser Lys Gln Lys Thr
    1175                1180                1185

Ser Ser Met Thr Gly Thr Met Leu Pro Leu Ile Lys Ala Ile Leu
    1190                1195                1200

Ile Ser Cys Val Ser Asn Lys Trp Gln Phe Ile Tyr Leu Leu Tyr
    1205                1210                1215

Leu Ile Phe Glu Val Ser Tyr Tyr Leu His Lys Lys Ile Ile Asp
    1220                1225                1230

Glu Ile Ala Gly Gly Thr Asn Phe Ile Ser Arg Leu Val Ala Ala
    1235                1240                1245

Leu Ile Glu Val Asn Trp Ala Phe Asp Asn Glu Glu Val Arg Gly
    1250                1255                1260

Leu Lys Lys Phe Phe Leu Leu Ser Ser Arg Val Lys Glu Leu Ile
    1265                1270                1275

Ile Lys His Lys Val Arg Asn Glu Val Met Val Arg Trp Phe Gly
    1280                1285                1290

Asp Glu Glu Val Tyr Gly Met Pro Lys Leu Val Gly Leu Val Lys
    1295                1300                1305

Ala Ala Thr Leu Ser Lys Asn Lys His Cys Ile Leu Cys Thr Val
    1310                1315                1320

Cys Glu Asp Arg Glu Trp Arg Gly Glu Thr Cys Pro Lys Cys Gly
    1325                1330                1335

Arg Phe Gly Pro Pro Met Thr Cys Gly Met Thr Leu Ala Asp Phe
    1340                1345                1350

Glu Glu Lys His Tyr Lys Arg Ile Phe Phe Arg Glu Asp Gln Ser
    1355                1360                1365

Glu Gly Pro Val Arg Glu Glu Tyr Ala Gly Tyr Leu Gln Tyr Arg
```

-continued

```
            1370                1375                1380

Ala Arg Gly Gln Leu Phe Leu Arg Asn Leu Pro Val Leu Ala Thr
            1385                1390                1395

Lys Val Lys Met Leu Leu Val Gly Asn Leu Gly Thr Glu Val Gly
            1400                1405                1410

Asp Leu Glu His Leu Gly Trp Val Leu Arg Gly Pro Ala Val Cys
            1415                1420                1425

Lys Lys Val Thr Glu His Glu Lys Cys Thr Thr Ser Met Met Asp
            1430                1435                1440

Lys Leu Thr Ala Phe Phe Gly Val Met Pro Arg Gly Thr Thr Pro
            1445                1450                1455

Arg Ala Pro Val Arg Phe Pro Thr Ser Leu Leu Lys Ile Arg Arg
            1460                1465                1470

Gly Leu Glu Thr Gly Trp Ala Tyr Thr His Gln Gly Gly Ile Ser
            1475                1480                1485

Ser Val Asp His Val Thr Cys Gly Lys Asp Leu Leu Val Cys Asp
            1490                1495                1500

Thr Met Gly Arg Thr Arg Val Val Cys Gln Ser Asn Asn Lys Met
            1505                1510                1515

Thr Asp Glu Ser Glu Tyr Gly Val Lys Thr Asp Ser Gly Cys Pro
            1520                1525                1530

Glu Gly Ala Arg Cys Tyr Val Phe Asn Pro Glu Ala Val Asn Ile
            1535                1540                1545

Ser Gly Thr Lys Gly Ala Met Val His Leu Gln Lys Thr Gly Gly
            1550                1555                1560

Glu Phe Thr Cys Val Thr Ala Ser Gly Thr Pro Ala Phe Phe Asp
            1565                1570                1575

Leu Lys Asn Leu Lys Gly Trp Ser Gly Leu Pro Ile Phe Glu Ala
            1580                1585                1590

Ser Ser Gly Arg Val Val Gly Arg Val Lys Val Gly Lys Asn Glu
            1595                1600                1605

Asp Ser Lys Pro Thr Lys Leu Met Ser Gly Ile Gln Thr Val Ser
            1610                1615                1620

Lys Ser Thr Thr Asp Leu Thr Glu Met Val Lys Lys Ile Thr Thr
            1625                1630                1635

Met Ser Arg Gly Glu Phe Arg Gln Ile Thr Leu Ala Thr Gly Ala
            1640                1645                1650

Gly Lys Thr Thr Glu Leu Pro Arg Ser Val Ile Glu Glu Ile Gly
            1655                1660                1665

Arg His Lys Arg Val Leu Val Leu Ile Pro Leu Arg Ala Ala Ala
            1670                1675                1680

Glu Ser Val Tyr Gln Tyr Met Arg Gln Lys His Pro Ser Ile Ala
            1685                1690                1695

Phe Asn Leu Arg Ile Gly Glu Met Lys Glu Gly Asp Met Ala Thr
            1700                1705                1710

Gly Ile Thr Tyr Ala Ser Tyr Gly Tyr Phe Cys Gln Met Pro Gln
            1715                1720                1725

Pro Lys Leu Arg Ala Ala Met Val Glu Tyr Ser Phe Ile Phe Leu
            1730                1735                1740

Asp Glu Tyr His Cys Ala Thr Pro Glu Gln Leu Ala Ile Met Gly
            1745                1750                1755

Lys Ile His Arg Phe Ser Glu Asn Leu Arg Val Val Ala Met Thr
            1760                1765                1770
```

```
Ala Thr Pro Val Gly Thr Val Thr Thr Thr Gly Gln Lys His Pro
1775             1780                1785

Ile Glu Glu Phe Ile Ala Pro Asp Val Met Lys Gly Lys Asp Leu
1790             1795                1800

Gly Ser Glu Tyr Leu Asp Ile Ala Gly Leu Lys Ile Pro Val Glu
1805             1810                1815

Glu Met Lys Ser Asn Met Leu Val Phe Val Pro Thr Arg Asn Met
1820             1825                1830

Ala Val Glu Thr Ala Lys Lys Leu Lys Ala Lys Gly Tyr Asn Ser
1835             1840                1845

Gly Tyr Tyr Tyr Ser Gly Glu Asp Pro Ser Asn Leu Arg Val Val
1850             1855                1860

Thr Ser Gln Ser Pro Tyr Val Val Val Ala Thr Asn Ala Ile Glu
1865             1870                1875

Ser Gly Val Thr Leu Pro Asp Leu Asp Val Val Val Asp Thr Gly
1880             1885                1890

Leu Lys Cys Glu Lys Arg Ile Arg Leu Ser Pro Lys Met Pro Phe
1895             1900                1905

Ile Val Thr Gly Leu Lys Arg Met Ala Val Thr Ile Gly Glu Gln
1910             1915                1920

Ala Gln Arg Arg Gly Arg Val Gly Arg Val Lys Pro Gly Arg Tyr
1925             1930                1935

Tyr Arg Ser Gln Glu Thr Pro Val Gly Ser Lys Asp Tyr His Tyr
1940             1945                1950

Asp Leu Leu Gln Ala Gln Arg Tyr Gly Ile Glu Asp Gly Ile Asn
1955             1960                1965

Ile Thr Lys Ser Phe Arg Glu Met Asn Tyr Asp Trp Ser Leu Tyr
1970             1975                1980

Glu Glu Asp Ser Leu Met Ile Thr Gln Leu Glu Ile Leu Asn Asn
1985             1990                1995

Leu Leu Ile Ser Asp Glu Leu Pro Met Ala Val Lys Asn Ile Met
2000             2005                2010

Ala Arg Thr Asp His Pro Glu Pro Ile Gln Leu Ala Tyr Asn Ser
2015             2020                2025

Tyr Glu Thr Gln Val Pro Val Leu Phe Pro Lys Ile Lys Asn Gly
2030             2035                2040

Glu Val Thr Asp Ser Tyr Asp Asn Tyr Thr Phe Leu Asn Ala Arg
2045             2050                2055

Lys Leu Gly Asp Asp Val Pro Pro Tyr Val Tyr Ala Thr Glu Asp
2060             2065                2070

Glu Asp Leu Ala Val Glu Leu Leu Gly Leu Asp Trp Pro Asp Pro
2075             2080                2085

Gly Asn Gln Gly Thr Val Glu Thr Gly Arg Ala Leu Lys Gln Val
2090             2095                2100

Val Gly Leu Ser Thr Ala Glu Asn Ala Leu Leu Val Ala Leu Phe
2105             2110                2115

Gly Tyr Val Gly Tyr Gln Ala Leu Ser Lys Arg His Ile Pro Val
2120             2125                2130

Val Thr Asp Ile Tyr Ser Ile Glu Asp His Arg Leu Glu Asp Thr
2135             2140                2145

Thr His Leu Gln Tyr Ala Pro Asn Ala Ile Lys Thr Glu Gly Lys
2150             2155                2160
```

-continued

```
Glu Thr Glu Leu Lys Glu Leu Ala Gln Gly Asp Val Gln Arg Cys
    2165                2170                2175
Val Glu Ala Met Thr Asn Tyr Ala Arg Glu Gly Ile Gln Phe Met
    2180                2185                2190
Lys Ser Gln Ala Leu Lys Val Lys Glu Thr Pro Thr Tyr Lys Glu
    2195                2200                2205
Thr Met Asp Thr Val Thr Asp Tyr Val Lys Lys Phe Met Glu Ala
    2210                2215                2220
Leu Ala Asp Ser Lys Glu Asp Ile Ile Lys Tyr Gly Leu Trp Gly
    2225                2230                2235
Thr His Thr Ala Leu Tyr Lys Ser Ile Ser Ala Arg Leu Gly Gly
    2240                2245                2250
Glu Thr Ala Phe Ala Thr Leu Val Val Lys Trp Leu Ala Phe Gly
    2255                2260                2265
Gly Glu Ser Ile Ala Asp His Val Lys Gln Ala Ala Thr Asp Leu
    2270                2275                2280
Val Val Tyr Tyr Ile Ile Asn Arg Pro Gln Phe Pro Gly Asp Thr
    2285                2290                2295
Glu Thr Gln Gln Asp Gly Arg Lys Phe Val Ala Ser Leu Leu Ala
    2300                2305                2310
Ser Ala Leu Ala Thr Tyr Thr Tyr Lys Ser Trp Asn Tyr Asn Asn
    2315                2320                2325
Leu Ser Lys Ile Val Glu Pro Ala Leu Ala Thr Leu Pro Tyr Ala
    2330                2335                2340
Ala Thr Ala Leu Lys Leu Phe Ala Pro Thr Arg Leu Glu Ser Val
    2345                2350                2355
Val Ile Leu Ser Thr Ala Ile Tyr Lys Thr Tyr Leu Ser Ile Arg
    2360                2365                2370
Arg Gly Lys Ser Asp Gly Leu Leu Gly Thr Gly Val Ser Ala Ala
    2375                2380                2385
Met Glu Ile Met Ser Gln Asn Pro Val Ser Val Gly Ile Ala Val
    2390                2395                2400
Met Leu Gly Val Gly Ala Val Ala Ala His Asn Ala Ile Glu Ala
    2405                2410                2415
Ser Glu Gln Lys Arg Thr Leu Leu Met Lys Val Phe Val Lys Asn
    2420                2425                2430
Phe Leu Asp Gln Ala Ala Thr Asp Glu Leu Val Lys Glu Ser Pro
    2435                2440                2445
Glu Lys Ile Ile Met Ala Leu Phe Glu Ala Val Gln Thr Val Gly
    2450                2455                2460
Asn Pro Leu Arg Leu Val Tyr His Leu Tyr Gly Val Phe Tyr Lys
    2465                2470                2475
Gly Trp Glu Ala Lys Glu Leu Ala Gln Arg Thr Ala Gly Arg Asn
    2480                2485                2490
Leu Phe Thr Leu Ile Met Phe Glu Ala Val Glu Leu Leu Gly Val
    2495                2500                2505
Asp Ser Glu Gly Lys Val Arg Gln Leu Ser Ser Asn Tyr Ile Leu
    2510                2515                2520
Glu Leu Leu Tyr Lys Phe Arg Asp Ser Ile Lys Ser Ser Val Arg
    2525                2530                2535
Glu Met Ala Ile Ser Trp Ala Pro Ala Pro Phe Ser Cys Asp Trp
    2540                2545                2550
Thr Pro Thr Asp Asp Arg Ile Gly Leu Pro Gln Asp Asn Phe His
```

```
            2555                2560                2565
Gln Val Glu Thr Lys Cys Pro Cys Gly Tyr Lys Met Lys Ala Val
    2570                2575                2580

Lys Asn Cys Ala Gly Glu Leu Arg Leu Leu Glu Glu Glu Gly Ser
    2585                2590                2595

Phe Leu Cys Arg Asn Lys Phe Gly Arg Gly Ser Arg Asn Tyr Arg
    2600                2605                2610

Val Thr Lys Tyr Tyr Asp Asp Asn Leu Leu Glu Ile Lys Pro Val
    2615                2620                2625

Ile Arg Met Glu Gly His Val Glu Leu Tyr Tyr Lys Gly Ala Thr
    2630                2635                2640

Ile Lys Leu Asp Phe Asn Asn Ser Lys Thr Ile Leu Ala Thr Asp
    2645                2650                2655

Lys Trp Glu Val Asp His Ser Thr Leu Val Arg Val Leu Lys Arg
    2660                2665                2670

His Thr Gly Ala Gly Tyr His Gly Ala Tyr Leu Gly Glu Lys Pro
    2675                2680                2685

Asn His Lys His Leu Ile Glu Arg Asp Cys Ala Thr Ile Thr Lys
    2690                2695                2700

Asp Lys Val Cys Phe Leu Lys Met Lys Arg Gly Cys Ala Phe Thr
    2705                2710                2715

Tyr Asp Leu Ser Leu His Asn Leu Thr Arg Leu Ile Glu Leu Val
    2720                2725                2730

His Lys Asn Asn Leu Glu Asp Lys Glu Ile Pro Ala Ala Thr Val
    2735                2740                2745

Thr Thr Trp Leu Ala Tyr Thr Phe Val Asn Glu Asp Ile Gly Thr
    2750                2755                2760

Ile Lys Pro Ala Phe Gly Glu Lys Val Thr Leu Glu Met Gln Glu
    2765                2770                2775

Glu Ile Thr Leu Gln Pro Ala Val Val Val Asp Thr Thr Asp Val
    2780                2785                2790

Ala Val Thr Val Val Gly Glu Ala Pro Thr Met Thr Thr Gly Glu
    2795                2800                2805

Thr Pro Thr Val Phe Thr Ser Ser Gly Ser Gly Leu Lys Ser Gln
    2810                2815                2820

Gln Val Leu Lys Leu Gly Val Gly Glu Gly Gln Tyr Pro Gly Thr
    2825                2830                2835

Asn Pro Gln Arg Ala Ser Leu His Glu Ala Ile Gln Gly Ala Asp
    2840                2845                2850

Glu Arg Pro Ser Val Leu Ile Leu Gly Ser Asp Lys Ala Thr Ser
    2855                2860                2865

Asn Arg Val Lys Thr Ala Lys Asn Val Lys Val Tyr Arg Gly Arg
    2870                2875                2880

Asp Pro Leu Glu Val Arg Asp Met Met Arg Arg Gly Lys Ile Leu
    2885                2890                2895

Val Val Ala Leu Ser Arg Val Asp Asn Ala Leu Leu Lys Phe Val
    2900                2905                2910

Asp Tyr Lys Gly Thr Phe Leu Thr Arg Glu Ala Leu Glu Ala Leu
    2915                2920                2925

Ser Leu Gly Arg Pro Lys Lys Lys Asn Ile Thr Lys Ala Glu Ala
    2930                2935                2940

Gln Trp Leu Leu Cys Pro Glu Asp Gln Met Glu Glu Leu Pro Asp
    2945                2950                2955
```

-continued

```
Trp Phe Ala Ala Gly Glu Pro Ile Phe Leu Glu Ala Asn Ile Lys
    2960            2965            2970

His Asp Arg Tyr His Leu Val Gly Asp Ile Ala Thr Ile Lys Glu
    2975            2980            2985

Lys Ala Lys Gln Leu Gly Ala Thr Asp Ser Thr Lys Ile Ser Lys
    2990            2995            3000

Glu Val Gly Ala Lys Val Tyr Ser Met Lys Leu Ser Asn Trp Val
    3005            3010            3015

Met Gln Glu Glu Asn Lys Gln Gly Asn Leu Thr Pro Leu Phe Glu
    3020            3025            3030

Glu Leu Leu Gln Gln Cys Pro Pro Gly Gly Gln Asn Lys Thr Ala
    3035            3040            3045

His Met Val Ser Ala Tyr Gln Leu Ala Gln Gly Asn Trp Met Pro
    3050            3055            3060

Thr Ser Cys His Val Phe Met Gly Thr Val Ser Ala Arg Arg Thr
    3065            3070            3075

Lys Thr His Pro Tyr Glu Ala Tyr Val Lys Leu Arg Glu Leu Val
    3080            3085            3090

Glu Glu His Lys Met Lys Thr Leu Cys Pro Gly Ser Ser Leu Gly
    3095            3100            3105

Arg His Asn Asp Trp Ile Ile Gly Lys Ile Lys Tyr Gln Gly Asn
    3110            3115            3120

Leu Arg Thr Lys His Met Leu Asn Pro Gly Lys Val Ala Glu Gln
    3125            3130            3135

Leu Cys Arg Glu Gly His Arg His Asn Val Tyr Asn Lys Thr Ile
    3140            3145            3150

Ser Ser Val Met Thr Ala Thr Gly Ile Arg Leu Glu Lys Leu Pro
    3155            3160            3165

Val Val Arg Ala Gln Thr Asp Pro Thr Asn Phe His Gln Ala Ile
    3170            3175            3180

Arg Asp Lys Ile Asp Lys Glu Glu Asn Leu Gln Thr Pro Gly Leu
    3185            3190            3195

His Lys Lys Leu Met Glu Val Phe Asn Ala Leu Lys Arg Pro Glu
    3200            3205            3210

Leu Glu Ser Ser Tyr Asp Ala Val Glu Trp Glu Glu Leu Glu Arg
    3215            3220            3225

Gly Ile Asn Arg Lys Gly Ala Ala Gly Phe Phe Glu Arg Lys Asn
    3230            3235            3240

Ile Gly Glu Ile Leu Asp Ser Glu Lys Asn Lys Val Glu Glu Ile
    3245            3250            3255

Ile Asp Asn Leu Lys Lys Gly Arg Asn Ile Lys Tyr Tyr Glu Thr
    3260            3265            3270

Ala Ile Pro Lys Asn Glu Lys Arg Asp Val Asn Asp Asp Trp Thr
    3275            3280            3285

Ala Gly Asp Phe Val Asp Glu Lys Lys Pro Arg Val Ile Gln Tyr
    3290            3295            3300

Pro Glu Ala Lys Thr Arg Leu Ala Ile Thr Lys Val Met Tyr Lys
    3305            3310            3315

Trp Val Lys Gln Lys Pro Val Val Ile Pro Gly Tyr Glu Gly Lys
    3320            3325            3330

Thr Pro Leu Phe Gln Ile Phe Asp Lys Val Lys Lys Glu Trp Asp
    3335            3340            3345
```

```
Gln Phe Gln Asn Pro Val Ala Val Ser Phe Asp Thr Lys Ala Trp
    3350                3355                3360
Asp Thr Gln Val Thr Thr Lys Asp Leu Glu Leu Ile Arg Asp Ile
    3365                3370                3375
Gln Lys Tyr Tyr Phe Lys Lys Trp His Lys Phe Ile Asp Thr
    3380                3385                3390
Leu Thr Thr His Met Ser Glu Val Pro Val Ile Ser Ala Asp Gly
    3395                3400                3405
Glu Val Tyr Ile Arg Lys Gly Gln Arg Gly Ser Gly Gln Pro Asp
    3410                3415                3420
Thr Ser Ala Gly Asn Ser Met Leu Asn Val Leu Thr Met Val Tyr
    3425                3430                3435
Ala Phe Cys Glu Ala Thr Gly Val Pro Tyr Lys Ser Phe Asp Arg
    3440                3445                3450
Val Ala Lys Ile His Val Cys Gly Asp Asp Gly Phe Leu Ile Thr
    3455                3460                3465
Glu Arg Ala Leu Gly Glu Lys Phe Ala Ser Lys Gly Val Gln Ile
    3470                3475                3480
Leu Tyr Glu Ala Gly Lys Pro Gln Lys Ile Thr Glu Gly Asp Lys
    3485                3490                3495
Met Lys Val Ala Tyr Gln Phe Asp Asp Ile Glu Phe Cys Ser His
    3500                3505                3510
Thr Pro Ile Gln Val Arg Trp Ser Asp Asn Thr Ser Ser Tyr Met
    3515                3520                3525
Pro Gly Arg Asn Thr Thr Thr Ile Leu Ala Lys Met Ala Thr Arg
    3530                3535                3540
Leu Asp Ser Ser Gly Glu Arg Gly Thr Ile Ala Tyr Glu Lys Ala
    3545                3550                3555
Val Ala Phe Ser Phe Leu Leu Met Tyr Ser Trp Asn Pro Leu Ile
    3560                3565                3570
Arg Arg Ile Cys Leu Leu Val Leu Ser Thr Glu Leu Gln Val Lys
    3575                3580                3585
Pro Gly Lys Ser Thr Thr Tyr Tyr Tyr Glu Gly Asp Pro Ile Ser
    3590                3595                3600
Ala Tyr Lys Glu Val Ile Gly His Asn Leu Phe Asp Leu Lys Arg
    3605                3610                3615
Thr Ser Phe Glu Lys Leu Ala Lys Leu Asn Leu Ser Met Ser Val
    3620                3625                3630
Leu Gly Ala Trp Thr Arg His Thr Ser Lys Arg Leu Leu Gln Asp
    3635                3640                3645
Cys Val Asn Ile Gly Val Lys Glu Gly Asn Trp Leu Val Asn Ala
    3650                3655                3660
Asp Arg Leu Val Ser Ser Lys Thr Gly Asn Arg Tyr Ile Pro Gly
    3665                3670                3675
Glu Gly His Thr Leu Gln Gly Arg His Tyr Glu Glu Leu Val Leu
    3680                3685                3690
Ala Arg Lys Gln Ile Asn Asn Phe Gln Gly Thr Asp Arg Tyr Asn
    3695                3700                3705
Leu Gly Pro Ile Val Asn Met Val Leu Arg Arg Leu Arg Val Met
    3710                3715                3720
Met Met Thr Leu Ile Gly Arg Gly Ala
    3725                3730
```

<210> SEQ ID NO 16
<211> LENGTH: 3731
<212> TYPE: PRT
<213> ORGANISM: CSFV

<400> SEQUENCE: 16

```
Met Gly Ser Asp Asp Gly Ala Ser Gly Ser Lys Glu Lys Pro Asp
 1               5                  10                  15

Arg Ile Asn Lys Gly Lys Leu Lys Ile Ala Pro Lys Glu His Glu Lys
                20                  25                  30

Asp Ser Arg Thr Arg Pro Pro Asp Ala Thr Ile Val Val Glu Gly Val
                35                  40                  45

Lys Tyr Gln Val Lys Lys Gly Lys Val Lys Gly Lys Asn Thr Gln
     50                  55                  60

Asp Gly Leu Tyr His Asn Lys Asn Lys Pro Pro Glu Ser Arg Lys Lys
 65                  70                  75                  80

Leu Glu Lys Ala Leu Leu Ala Trp Ala Val Ile Ala Ile Met Leu Tyr
                 85                  90                  95

Gln Pro Val Glu Ala Glu Asn Ile Thr Gln Trp Asn Leu Ser Asp Asn
                100                 105                 110

Gly Thr Asn Gly Ile Gln His Ala Met Tyr Leu Arg Gly Val Asn Arg
                115                 120                 125

Ser Leu His Gly Ile Trp Pro Gly Lys Ile Cys Lys Gly Val Pro Thr
                130                 135                 140

His Leu Ala Thr Asp Val Glu Leu Lys Glu Ile Gln Gly Met Met Asp
145                 150                 155                 160

Ala Ser Glu Gly Thr Asn Tyr Thr Cys Cys Lys Leu Gln Arg His Glu
                165                 170                 175

Trp Asn Lys Gly Trp Cys Asn Trp His Asn Ile Asp Pro Trp Ile Gln
                180                 185                 190

Leu Met Asn Arg Thr Gln Ala Asp Leu Ala Glu Gly Pro Pro Val Lys
                195                 200                 205

Glu Cys Ala Val Thr Cys Arg Tyr Asp Lys Asp Ala Asp Ile Asn Val
                210                 215                 220

Val Thr Gln Ala Arg Asn Arg Pro Thr Thr Leu Thr Gly Cys Lys Lys
225                 230                 235                 240

Gly Lys Asn Phe Ser Phe Ala Gly Thr Val Ile Glu Ser Pro Cys Asn
                245                 250                 255

Phe Asn Val Ser Val Glu Asp Thr Leu Tyr Gly Asp His Glu Cys Gly
                260                 265                 270

Ser Leu Leu Gln Asp Ala Ala Leu Tyr Leu Val Asp Gly Met Thr Asn
                275                 280                 285

Thr Ile Glu Asn Ala Arg Gln Gly Ala Ala Arg Val Thr Ser Trp Leu
                290                 295                 300

Gly Arg Gln Leu Arg Thr Ala Gly Lys Arg Leu Glu Gly Arg Ser Lys
305                 310                 315                 320

Thr Trp Phe Gly Ala Tyr Ala Leu Ser Pro Tyr Cys Asn Val Thr Ser
                325                 330                 335

Lys Ile Gly Tyr Ile Trp Tyr Thr Asn Asn Cys Thr Pro Ala Cys Leu
                340                 345                 350

Pro Lys Asn Thr Lys Ile Ile Gly Pro Gly Lys Phe Asp Thr Asn Ala
                355                 360                 365

Glu Asp Gly Lys Ile Leu His Glu Met Gly Gly His Leu Ser Glu Phe
                370                 375                 380
```

```
Leu Leu Leu Ser Leu Val Val Leu Ser Asp Phe Ala Pro Glu Thr Ala
385                 390                 395                 400

Ser Ala Leu Tyr Leu Ile Leu His Tyr Val Ile Pro Gln Pro His Asp
            405                 410                 415

Glu Pro Glu Gly Cys Asp Thr Asn Gln Leu Asn Leu Thr Val Glu Leu
        420                 425                 430

Arg Thr Glu Asp Val Ile Pro Ser Ser Val Trp Asn Val Gly Lys Tyr
    435                 440                 445

Val Cys Val Arg Pro Asp Trp Pro Tyr Glu Thr Glu Val Ala Leu
450                 455                 460

Leu Phe Glu Glu Val Gly Gln Val Val Lys Leu Ala Leu Arg Ala Leu
465                 470                 475                 480

Arg Asp Leu Thr Arg Val Trp Asn Ser Ala Ser Thr Ile Ala Phe Leu
            485                 490                 495

Ile Cys Leu Ile Lys Val Leu Arg Gly Gln Ile Val Gln Gly Val Val
            500                 505                 510

Trp Leu Leu Leu Val Thr Gly Ala Gln Gly Arg Leu Ala Cys Lys Glu
    515                 520                 525

Asp Tyr Arg Tyr Ala Ile Ser Ser Thr Asp Glu Ile Gly Leu Leu Gly
    530                 535                 540

Ala Gly Gly Leu Thr Thr Thr Trp Lys Glu Tyr Asn His Asp Leu Gln
545                 550                 555                 560

Leu Asn Asp Gly Thr Val Lys Ala Ser Cys Val Ala Gly Ser Phe Lys
            565                 570                 575

Val Thr Ala Leu Asn Val Val Ser Arg Arg Tyr Leu Ala Ser Leu His
        580                 585                 590

Lys Lys Ala Leu Pro Thr Ser Val Thr Phe Glu Leu Leu Phe Asp Gly
        595                 600                 605

Thr Asn Pro Ser Thr Glu Glu Met Gly Asp Asp Phe Arg Ser Gly Leu
    610                 615                 620

Cys Pro Phe Asp Thr Ser Pro Val Val Lys Gly Lys Tyr Asn Thr Thr
625                 630                 635                 640

Leu Leu Asn Gly Ser Ala Phe Tyr Leu Val Cys Pro Ile Gly Trp Thr
            645                 650                 655

Gly Val Ile Glu Cys Thr Ala Val Ser Lys Asp Thr Leu Arg Thr Glu
        660                 665                 670

Val Val Lys Thr Phe Arg Arg Asp Lys Pro Phe Pro His Arg Met Asp
        675                 680                 685

Cys Val Thr Thr Thr Val Glu Asn Glu Asp Leu Phe Tyr Cys Lys Leu
    690                 695                 700

Gly Gly Asn Trp Thr Cys Val Lys Gly Glu Pro Val Val Tyr Thr Gly
705                 710                 715                 720

Gly Leu Val Lys Gln Cys Arg Trp Cys Gly Phe Asp Phe Asp Gly Pro
            725                 730                 735

Asp Gly Leu Pro His Tyr Pro Ile Gly Lys Cys Ile Leu Ala Asn Glu
        740                 745                 750

Thr Gly Tyr Arg Ile Val Asp Ser Thr Asp Cys Asn Arg Asp Gly Val
    755                 760                 765

Val Ile Ser Thr Glu Gly Ser His Glu Cys Leu Ile Gly Asn Thr Thr
        770                 775                 780

Val Lys Val His Ala Ser Asp Glu Arg Leu Gly Pro Met Pro Cys Arg
785                 790                 795                 800

Pro Lys Glu Ile Val Ser Ser Ala Gly Pro Val Lys Lys Thr Ser Cys
```

-continued

```
                805                 810                 815
Thr Phe Asn Tyr Thr Lys Thr Leu Lys Asn Arg Tyr Tyr Glu Pro Arg
                820                 825                 830
Asp Ser Tyr Phe Gln Gln Tyr Met Leu Lys Gly Glu Tyr Gln Tyr Trp
                835                 840                 845
Phe Asp Leu Asp Ala Thr Asp Arg His Ser Asp Tyr Phe Ala Glu Phe
850                 855                 860
Val Val Leu Val Val Ala Leu Leu Gly Gly Arg Tyr Val Leu Trp
865                 870                 875                 880
Leu Ile Val Thr Tyr Val Val Leu Thr Glu Gln Leu Ala Ala Gly Leu
                885                 890                 895
Pro Leu Gly Gln Gly Glu Val Val Leu Ile Gly Asn Leu Ile Thr His
                900                 905                 910
Thr Asp Ile Glu Val Val Val Tyr Phe Leu Leu Leu Tyr Leu Val Met
                915                 920                 925
Arg Asp Glu Pro Ile Lys Lys Trp Ile Leu Leu Leu Phe His Ala Met
                930                 935                 940
Thr Asn Asn Pro Val Lys Thr Ile Thr Val Ala Leu Leu Met Val Ser
945                 950                 955                 960
Gly Val Ala Lys Gly Gly Lys Ile Asp Gly Gly Trp Gln Arg Leu Pro
                965                 970                 975
Gly Thr Ser Phe Asp Ile Gln Leu Ala Leu Thr Val Ile Val Val Ala
                980                 985                 990
Val Met Leu Leu Ala Lys Arg Asp Pro Thr Thr Val Pro Leu Val Ile
                995                 1000                1005
Thr Val Ala Pro Leu Arg Thr Ala Lys Met Thr Asn Gly Leu Ser
                1010                1015                1020
Thr Asp Ile Ala Ile Ala Thr Val Ser Ala Ala Leu Leu Thr Trp
                1025                1030                1035
Thr Tyr Ile Ser Asp Tyr Tyr Arg Tyr Lys Thr Trp Leu Gln Tyr
                1040                1045                1050
Leu Ile Ser Thr Val Thr Gly Ile Phe Leu Ile Arg Val Leu Lys
                1055                1060                1065
Gly Ile Gly Glu Leu Asp Leu His Thr Pro Thr Leu Pro Ser His
                1070                1075                1080
Arg Pro Leu Phe Phe Ile Leu Val Tyr Leu Ile Ser Thr Ala Val
                1085                1090                1095
Val Thr Arg Trp Asn Leu Asp Ile Ala Gly Leu Leu Gln Cys
                1100                1105                1110
Val Pro Thr Leu Leu Met Val Phe Thr Met Trp Ala Asp Ile Leu
                1115                1120                1125
Thr Leu Ile Leu Ile Leu Pro Thr Tyr Glu Leu Thr Lys Leu Tyr
                1130                1135                1140
Tyr Leu Lys Glu Val Arg Ile Gly Ala Glu Lys Gly Trp Leu Trp
                1145                1150                1155
Lys Thr Asn Phe Lys Arg Val Asn Asp Ile Tyr Glu Val Asp Gln
                1160                1165                1170
Ala Gly Glu Gly Val Tyr Leu Phe Pro Ser Lys Gln Lys Thr Ser
                1175                1180                1185
Ser Met Thr Gly Thr Met Leu Pro Leu Ile Lys Ala Ile Leu Ile
                1190                1195                1200
Ser Cys Val Ser Asn Lys Trp Gln Phe Ile Tyr Leu Leu Tyr Leu
                1205                1210                1215
```

-continued

```
Ile Phe Glu Val Ser Tyr Tyr Leu His Lys Lys Ile Ile Asp Glu
1220                1225                1230

Ile Ala Gly Gly Thr Asn Phe Ile Ser Arg Leu Val Ala Ala Leu
1235                1240                1245

Ile Glu Val Asn Trp Ala Phe Asp Asn Glu Glu Val Arg Gly Leu
1250                1255                1260

Lys Lys Phe Phe Leu Leu Ser Ser Arg Val Lys Glu Leu Ile Ile
1265                1270                1275

Lys His Lys Val Arg Asn Glu Val Met Val Arg Trp Phe Gly Asp
1280                1285                1290

Glu Glu Val Tyr Gly Met Pro Lys Leu Val Gly Leu Val Lys Ala
1295                1300                1305

Ala Thr Leu Ser Lys Asn Lys His Cys Ile Leu Cys Thr Val Cys
1310                1315                1320

Glu Asp Arg Glu Trp Arg Gly Glu Thr Cys Pro Lys Cys Gly Arg
1325                1330                1335

Phe Gly Pro Pro Met Thr Cys Gly Met Thr Leu Ala Asp Phe Glu
1340                1345                1350

Glu Lys His Tyr Lys Arg Ile Phe Phe Arg Glu Asp Gln Ser Glu
1355                1360                1365

Gly Pro Val Arg Glu Glu Tyr Ala Gly Tyr Leu Gln Tyr Arg Ala
1370                1375                1380

Arg Gly Gln Leu Phe Leu Arg Asn Leu Pro Val Leu Ala Thr Lys
1385                1390                1395

Val Lys Met Leu Leu Val Gly Asn Leu Gly Thr Glu Val Gly Asp
1400                1405                1410

Leu Glu His Leu Gly Trp Val Leu Arg Gly Pro Ala Val Cys Lys
1415                1420                1425

Lys Val Thr Glu His Glu Lys Cys Thr Thr Ser Met Met Asp Lys
1430                1435                1440

Leu Thr Ala Phe Phe Gly Val Met Pro Arg Gly Thr Thr Pro Arg
1445                1450                1455

Ala Pro Val Arg Phe Pro Thr Ser Leu Leu Lys Ile Arg Arg Gly
1460                1465                1470

Leu Glu Thr Gly Trp Ala Tyr Thr His Gln Gly Gly Ile Ser Ser
1475                1480                1485

Val Asp His Val Thr Cys Gly Lys Asp Leu Leu Val Cys Asp Thr
1490                1495                1500

Met Gly Arg Thr Arg Val Val Cys Gln Ser Asn Asn Lys Met Thr
1505                1510                1515

Asp Glu Ser Glu Tyr Gly Val Lys Thr Asp Ser Gly Cys Pro Glu
1520                1525                1530

Gly Ala Arg Cys Tyr Val Phe Asn Pro Glu Ala Val Asn Ile Ser
1535                1540                1545

Gly Thr Lys Gly Ala Met Val His Leu Gln Lys Thr Gly Gly Glu
1550                1555                1560

Phe Thr Cys Val Thr Ala Ser Gly Thr Pro Ala Phe Phe Asp Leu
1565                1570                1575

Lys Asn Leu Lys Gly Trp Ser Gly Leu Pro Ile Phe Glu Ala Ser
1580                1585                1590

Ser Gly Arg Val Val Gly Arg Val Lys Val Gly Lys Asn Glu Asp
1595                1600                1605
```

-continued

```
Ser Lys Pro Thr Lys Leu Met Ser Gly Ile Gln Thr Val Ser Lys
    1610                1615                1620

Ser Thr Thr Asp Leu Thr Glu Met Val Lys Lys Ile Thr Thr Met
    1625                1630                1635

Ser Arg Gly Glu Phe Arg Gln Ile Thr Leu Ala Thr Gly Ala Gly
    1640                1645                1650

Lys Thr Thr Glu Leu Pro Arg Ser Val Ile Glu Glu Ile Gly Arg
    1655                1660                1665

His Lys Arg Val Leu Val Leu Ile Pro Leu Arg Ala Ala Ala Glu
    1670                1675                1680

Ser Val Tyr Gln Tyr Met Arg Gln Lys His Pro Ser Ile Ala Phe
    1685                1690                1695

Asn Leu Arg Ile Gly Glu Met Lys Glu Gly Asp Met Ala Thr Gly
    1700                1705                1710

Ile Thr Tyr Ala Ser Tyr Gly Tyr Phe Cys Gln Met Pro Gln Pro
    1715                1720                1725

Lys Leu Arg Ala Ala Met Val Glu Tyr Ser Phe Ile Phe Leu Asp
    1730                1735                1740

Glu Tyr His Cys Ala Thr Pro Glu Gln Leu Ala Ile Met Gly Lys
    1745                1750                1755

Ile His Arg Phe Ser Glu Asn Leu Arg Val Val Ala Met Thr Ala
    1760                1765                1770

Thr Pro Val Gly Thr Val Thr Thr Gly Gln Lys His Pro Ile
    1775                1780                1785

Glu Glu Phe Ile Ala Pro Asp Val Met Lys Gly Lys Asp Leu Gly
    1790                1795                1800

Ser Glu Tyr Leu Asp Ile Ala Gly Leu Lys Ile Pro Val Glu Glu
    1805                1810                1815

Met Lys Ser Asn Met Leu Val Phe Val Pro Thr Arg Asn Met Ala
    1820                1825                1830

Val Glu Thr Ala Lys Lys Leu Lys Ala Lys Gly Tyr Asn Ser Gly
    1835                1840                1845

Tyr Tyr Tyr Ser Gly Glu Asp Pro Ser Asn Leu Arg Val Val Thr
    1850                1855                1860

Ser Gln Ser Pro Tyr Val Val Ala Thr Asn Ala Ile Glu Ser
    1865                1870                1875

Gly Val Thr Leu Pro Asp Leu Asp Val Val Val Asp Thr Gly Leu
    1880                1885                1890

Lys Cys Glu Lys Arg Ile Arg Leu Ser Pro Lys Met Pro Phe Ile
    1895                1900                1905

Val Thr Gly Leu Lys Arg Met Ala Val Thr Ile Gly Glu Gln Ala
    1910                1915                1920

Gln Arg Arg Gly Arg Val Gly Arg Val Lys Pro Gly Arg Tyr Tyr
    1925                1930                1935

Arg Ser Gln Glu Thr Pro Val Gly Ser Lys Asp Tyr His Tyr Asp
    1940                1945                1950

Leu Leu Gln Ala Gln Arg Tyr Gly Ile Glu Asp Gly Ile Asn Ile
    1955                1960                1965

Thr Lys Ser Phe Arg Glu Met Asn Tyr Asp Trp Ser Leu Tyr Glu
    1970                1975                1980

Glu Asp Ser Leu Met Ile Thr Gln Leu Glu Ile Leu Asn Asn Leu
    1985                1990                1995

Leu Ile Ser Asp Glu Leu Pro Met Ala Val Lys Asn Ile Met Ala
```

```
                2000                2005                2010
Arg Thr Asp His Pro Glu Pro Ile Gln Leu Ala Tyr Asn Ser Tyr
    2015                2020                2025

Glu Thr Gln Val Pro Val Leu Phe Pro Lys Ile Lys Asn Gly Glu
    2030                2035                2040

Val Thr Asp Ser Tyr Asp Asn Tyr Thr Phe Leu Asn Ala Arg Lys
    2045                2050                2055

Leu Gly Asp Asp Val Pro Pro Tyr Val Tyr Ala Thr Glu Asp Glu
    2060                2065                2070

Asp Leu Ala Val Glu Leu Leu Gly Leu Asp Trp Pro Asp Pro Gly
    2075                2080                2085

Asn Gln Gly Thr Val Glu Thr Gly Arg Ala Leu Lys Gln Val Val
    2090                2095                2100

Gly Leu Ser Thr Ala Glu Asn Ala Leu Leu Val Ala Leu Phe Gly
    2105                2110                2115

Tyr Val Gly Tyr Gln Ala Leu Ser Lys Arg His Ile Pro Val Val
    2120                2125                2130

Thr Asp Ile Tyr Ser Ile Glu Asp His Arg Leu Glu Asp Thr Thr
    2135                2140                2145

His Leu Gln Tyr Ala Pro Asn Ala Ile Lys Thr Glu Gly Lys Glu
    2150                2155                2160

Thr Glu Leu Lys Glu Leu Ala Gln Gly Asp Val Gln Arg Cys Val
    2165                2170                2175

Glu Ala Met Thr Asn Tyr Ala Arg Glu Gly Ile Gln Phe Met Lys
    2180                2185                2190

Ser Gln Ala Leu Lys Val Lys Glu Thr Pro Thr Tyr Lys Glu Thr
    2195                2200                2205

Met Asp Thr Val Thr Asp Tyr Val Lys Lys Phe Met Glu Ala Leu
    2210                2215                2220

Ala Asp Ser Lys Glu Asp Ile Ile Lys Tyr Gly Leu Trp Gly Thr
    2225                2230                2235

His Thr Ala Leu Tyr Lys Ser Ile Ser Ala Arg Leu Gly Gly Glu
    2240                2245                2250

Thr Ala Phe Ala Thr Leu Val Lys Trp Leu Ala Phe Gly Gly
    2255                2260                2265

Glu Ser Ile Ala Asp His Val Lys Gln Ala Ala Thr Asp Leu Val
    2270                2275                2280

Val Tyr Tyr Ile Ile Asn Arg Pro Gln Phe Pro Gly Asp Thr Glu
    2285                2290                2295

Thr Gln Gln Asp Gly Arg Lys Phe Val Ala Ser Leu Leu Ala Ser
    2300                2305                2310

Ala Leu Ala Thr Tyr Thr Tyr Lys Ser Trp Asn Tyr Asn Asn Leu
    2315                2320                2325

Ser Lys Ile Val Glu Pro Ala Leu Ala Thr Leu Pro Tyr Ala Ala
    2330                2335                2340

Thr Ala Leu Lys Leu Phe Ala Pro Thr Arg Leu Glu Ser Val Val
    2345                2350                2355

Ile Leu Ser Thr Ala Ile Tyr Lys Thr Tyr Leu Ser Ile Arg Arg
    2360                2365                2370

Gly Lys Ser Asp Gly Leu Leu Gly Thr Gly Val Ser Ala Ala Met
    2375                2380                2385

Glu Ile Met Ser Gln Asn Pro Val Ser Val Gly Ile Ala Val Met
    2390                2395                2400
```

```
Leu Gly Val Gly Ala Val Ala  Ala His Asn Ala Ile  Glu Ala Ser
    2405            2410                2415

Glu Gln Lys Arg Thr Leu Leu  Met Lys Val Phe Val  Lys Asn Phe
    2420            2425                2430

Leu Asp Gln Ala Ala Thr Asp  Glu Leu Val Lys Glu  Ser Pro Glu
    2435            2440                2445

Lys Ile Ile Met Ala Leu Phe  Glu Ala Val Gln Thr  Val Gly Asn
    2450            2455                2460

Pro Leu Arg Leu Val Tyr His  Leu Tyr Gly Val Phe  Tyr Lys Gly
    2465            2470                2475

Trp Glu Ala Lys Glu Leu Ala  Gln Arg Thr Ala Gly  Arg Asn Leu
    2480            2485                2490

Phe Thr Leu Ile Met Phe Glu  Ala Val Glu Leu Leu  Gly Val Asp
    2495            2500                2505

Ser Glu Gly Lys Val Arg Gln  Leu Ser Ser Asn Tyr  Ile Leu Glu
    2510            2515                2520

Leu Leu Tyr Lys Phe Arg Asp  Ser Ile Lys Ser Ser  Val Arg Glu
    2525            2530                2535

Met Ala Ile Ser Trp Ala Pro  Ala Pro Phe Ser Cys  Asp Trp Thr
    2540            2545                2550

Pro Thr Asp Asp Arg Ile Gly  Leu Pro Gln Asp Asn  Phe His Gln
    2555            2560                2565

Val Glu Thr Lys Cys Pro Cys  Gly Tyr Lys Met Lys  Ala Val Lys
    2570            2575                2580

Asn Cys Ala Gly Glu Leu Arg  Leu Leu Glu Glu Glu  Gly Ser Phe
    2585            2590                2595

Leu Cys Arg Asn Lys Phe Gly  Arg Gly Ser Arg Asn  Tyr Arg Val
    2600            2605                2610

Thr Lys Tyr Tyr Asp Asp Asn  Leu Leu Glu Ile Lys  Pro Val Ile
    2615            2620                2625

Arg Met Glu Gly His Val Glu  Leu Tyr Tyr Lys Gly  Ala Thr Ile
    2630            2635                2640

Lys Leu Asp Phe Asn Asn Ser  Lys Thr Ile Leu Ala  Thr Asp Lys
    2645            2650                2655

Trp Glu Val Asp His Ser Thr  Leu Val Arg Val Leu  Lys Arg His
    2660            2665                2670

Thr Gly Ala Gly Tyr His Gly  Ala Tyr Leu Gly Glu  Lys Pro Asn
    2675            2680                2685

His Lys His Leu Ile Glu Arg  Asp Cys Ala Thr Ile  Thr Lys Asp
    2690            2695                2700

Lys Val Cys Phe Leu Lys Met  Lys Arg Gly Cys Ala  Phe Thr Tyr
    2705            2710                2715

Asp Leu Ser Leu His Asn Leu  Thr Arg Leu Ile Glu  Leu Val His
    2720            2725                2730

Lys Asn Asn Leu Glu Asp Lys  Glu Ile Pro Ala Ala  Thr Val Thr
    2735            2740                2745

Thr Trp Leu Ala Tyr Thr Phe  Val Asn Glu Asp Ile  Gly Thr Ile
    2750            2755                2760

Lys Pro Ala Phe Gly Glu Lys  Val Thr Leu Glu Met  Gln Glu Glu
    2765            2770                2775

Ile Thr Leu Gln Pro Ala Val  Val Val Asp Thr Thr  Asp Val Ala
    2780            2785                2790
```

```
Val Thr Val Val Gly Glu Ala Pro Thr Met Thr Thr Gly Glu Thr
    2795            2800                2805
Pro Thr Val Phe Thr Ser Ser Gly Ser Gly Leu Lys Ser Gln Gln
    2810            2815                2820
Val Leu Lys Leu Gly Val Gly Glu Gly Gln Tyr Pro Gly Thr Asn
    2825            2830                2835
Pro Gln Arg Ala Ser Leu His Glu Ala Ile Gln Gly Ala Asp Glu
    2840            2845                2850
Arg Pro Ser Val Leu Ile Leu Gly Ser Asp Lys Ala Thr Ser Asn
    2855            2860                2865
Arg Val Lys Thr Ala Lys Asn Val Lys Val Tyr Arg Gly Arg Asp
    2870            2875                2880
Pro Leu Glu Val Arg Asp Met Met Arg Arg Gly Lys Ile Leu Val
    2885            2890                2895
Val Ala Leu Ser Arg Val Asp Asn Ala Leu Leu Lys Phe Val Asp
    2900            2905                2910
Tyr Lys Gly Thr Phe Leu Thr Arg Glu Ala Leu Glu Ala Leu Ser
    2915            2920                2925
Leu Gly Arg Pro Lys Lys Lys Asn Ile Thr Lys Ala Glu Ala Gln
    2930            2935                2940
Trp Leu Leu Cys Pro Glu Asp Gln Met Glu Glu Leu Pro Asp Trp
    2945            2950                2955
Phe Ala Ala Gly Glu Pro Ile Phe Leu Glu Ala Asn Ile Lys His
    2960            2965                2970
Asp Arg Tyr His Leu Val Gly Asp Ile Ala Thr Ile Lys Glu Lys
    2975            2980                2985
Ala Lys Gln Leu Gly Ala Thr Asp Ser Thr Lys Ile Ser Lys Glu
    2990            2995                3000
Val Gly Ala Lys Val Tyr Ser Met Lys Leu Ser Asn Trp Val Met
    3005            3010                3015
Gln Glu Glu Asn Lys Gln Gly Asn Leu Thr Pro Leu Phe Glu Glu
    3020            3025                3030
Leu Leu Gln Gln Cys Pro Pro Gly Gly Gln Asn Lys Thr Ala His
    3035            3040                3045
Met Val Ser Ala Tyr Gln Leu Ala Gln Gly Asn Trp Met Pro Thr
    3050            3055                3060
Ser Cys His Val Phe Met Gly Thr Val Ser Ala Arg Arg Thr Lys
    3065            3070                3075
Thr His Pro Tyr Glu Ala Tyr Val Lys Leu Arg Glu Leu Val Glu
    3080            3085                3090
Glu His Lys Met Lys Thr Leu Cys Pro Gly Ser Ser Leu Gly Arg
    3095            3100                3105
His Asn Asp Trp Ile Ile Gly Lys Ile Lys Tyr Gln Gly Asn Leu
    3110            3115                3120
Arg Thr Lys His Met Leu Asn Pro Gly Lys Val Ala Glu Gln Leu
    3125            3130                3135
Cys Arg Glu Gly His Arg His Asn Val Tyr Asn Lys Thr Ile Ser
    3140            3145                3150
Ser Val Met Thr Ala Thr Gly Ile Arg Leu Glu Lys Leu Pro Val
    3155            3160                3165
Val Arg Ala Gln Thr Asp Pro Thr Asn Phe His Gln Ala Ile Arg
    3170            3175                3180
Asp Lys Ile Asp Lys Glu Glu Asn Leu Gln Thr Pro Gly Leu His
```

-continued

```
              3185                3190                3195

Lys  Lys  Leu  Met  Glu  Val  Phe  Asn  Ala  Leu  Lys  Arg  Pro  Glu  Leu
              3200                3205                3210

Glu  Ser  Ser  Tyr  Asp  Ala  Val  Glu  Trp  Glu  Glu  Leu  Glu  Arg  Gly
              3215                3220                3225

Ile  Asn  Arg  Lys  Gly  Ala  Ala  Gly  Phe  Phe  Glu  Arg  Lys  Asn  Ile
              3230                3235                3240

Gly  Glu  Ile  Leu  Asp  Ser  Glu  Lys  Asn  Lys  Val  Glu  Glu  Ile  Ile
              3245                3250                3255

Asp  Asn  Leu  Lys  Lys  Gly  Arg  Asn  Ile  Lys  Tyr  Tyr  Glu  Thr  Ala
              3260                3265                3270

Ile  Pro  Lys  Asn  Glu  Lys  Arg  Asp  Val  Asn  Asp  Asp  Trp  Thr  Ala
              3275                3280                3285

Gly  Asp  Phe  Val  Asp  Glu  Lys  Lys  Pro  Arg  Val  Ile  Gln  Tyr  Pro
              3290                3295                3300

Glu  Ala  Lys  Thr  Arg  Leu  Ala  Ile  Thr  Lys  Val  Met  Tyr  Lys  Trp
              3305                3310                3315

Val  Lys  Gln  Lys  Pro  Val  Val  Ile  Pro  Gly  Tyr  Glu  Gly  Lys  Thr
              3320                3325                3330

Pro  Leu  Phe  Gln  Ile  Phe  Asp  Lys  Val  Lys  Lys  Glu  Trp  Asp  Gln
              3335                3340                3345

Phe  Gln  Asn  Pro  Val  Ala  Val  Ser  Phe  Asp  Thr  Lys  Ala  Trp  Asp
              3350                3355                3360

Thr  Gln  Val  Thr  Thr  Lys  Asp  Leu  Glu  Leu  Ile  Arg  Asp  Ile  Gln
              3365                3370                3375

Lys  Tyr  Tyr  Phe  Lys  Lys  Lys  Trp  His  Lys  Phe  Ile  Asp  Thr  Leu
              3380                3385                3390

Thr  Thr  His  Met  Ser  Glu  Val  Pro  Val  Ile  Ser  Ala  Asp  Gly  Glu
              3395                3400                3405

Val  Tyr  Ile  Arg  Lys  Gly  Gln  Arg  Gly  Ser  Gly  Gln  Pro  Asp  Thr
              3410                3415                3420

Ser  Ala  Gly  Asn  Ser  Met  Leu  Asn  Val  Leu  Thr  Met  Val  Tyr  Ala
              3425                3430                3435

Phe  Cys  Glu  Ala  Thr  Gly  Val  Pro  Tyr  Lys  Ser  Phe  Asp  Arg  Val
              3440                3445                3450

Ala  Lys  Ile  His  Val  Cys  Gly  Asp  Asp  Gly  Phe  Leu  Ile  Thr  Glu
              3455                3460                3465

Arg  Ala  Leu  Gly  Glu  Lys  Phe  Ala  Ser  Lys  Gly  Val  Gln  Ile  Leu
              3470                3475                3480

Tyr  Glu  Ala  Gly  Lys  Pro  Gln  Lys  Ile  Thr  Glu  Gly  Asp  Lys  Met
              3485                3490                3495

Lys  Val  Ala  Tyr  Gln  Phe  Asp  Asp  Ile  Glu  Phe  Cys  Ser  His  Thr
              3500                3505                3510

Pro  Ile  Gln  Val  Arg  Trp  Ser  Asp  Asn  Thr  Ser  Ser  Tyr  Met  Pro
              3515                3520                3525

Gly  Arg  Asn  Thr  Thr  Thr  Ile  Leu  Ala  Lys  Met  Ala  Thr  Arg  Leu
              3530                3535                3540

Asp  Ser  Ser  Gly  Glu  Arg  Gly  Thr  Ile  Ala  Tyr  Glu  Lys  Ala  Val
              3545                3550                3555

Ala  Phe  Ser  Phe  Leu  Leu  Met  Tyr  Ser  Trp  Asn  Pro  Leu  Ile  Arg
              3560                3565                3570

Arg  Ile  Cys  Leu  Leu  Val  Leu  Ser  Thr  Glu  Leu  Gln  Val  Lys  Pro
              3575                3580                3585
```

```
Gly Lys Ser Thr Thr Tyr Tyr Tyr Glu Gly Asp Pro Ile Ser Ala
    3590                3595                3600

Tyr Lys Glu Val Ile Gly His Asn Leu Phe Asp Leu Lys Arg Thr
    3605                3610                3615

Ser Phe Glu Lys Leu Ala Lys Leu Asn Leu Ser Met Ser Val Leu
    3620                3625                3630

Gly Ala Trp Thr Arg His Thr Ser Lys Arg Leu Leu Gln Asp Cys
    3635                3640                3645

Val Asn Ile Gly Val Lys Glu Gly Asn Trp Leu Val Asn Ala Asp
    3650                3655                3660

Arg Leu Val Ser Ser Lys Thr Gly Asn Arg Tyr Ile Pro Gly Glu
    3665                3670                3675

Gly His Thr Leu Gln Gly Arg His Tyr Glu Glu Leu Val Leu Ala
    3680                3685                3690

Arg Lys Gln Ile Asn Asn Phe Gln Gly Thr Asp Arg Tyr Asn Leu
    3695                3700                3705

Gly Pro Ile Val Asn Met Val Leu Arg Arg Leu Arg Val Met Met
    3710                3715                3720

Met Thr Leu Ile Gly Arg Gly Ala
    3725                3730

<210> SEQ ID NO 17
<211> LENGTH: 10
<212> TYPE: PRT
<213> ORGANISM: CSFV

<400> SEQUENCE: 17

Thr Ala Val Ser Pro Thr Thr Leu Arg Thr
1               5                   10

<210> SEQ ID NO 18
<211> LENGTH: 9
<212> TYPE: PRT
<213> ORGANISM: CSFV

<400> SEQUENCE: 18

Thr Ala Val Asn Lys Asp Thr Leu Arg
1               5

<210> SEQ ID NO 19
<211> LENGTH: 9
<212> TYPE: PRT
<213> ORGANISM: CSFV

<400> SEQUENCE: 19

Thr Ala Val Asn Gln Asp Thr Leu Arg
1               5

<210> SEQ ID NO 20
<211> LENGTH: 9
<212> TYPE: PRT
<213> ORGANISM: CSFV

<400> SEQUENCE: 20

Thr Ala Val Ser Ala Ala Thr Val Arg
1               5

<210> SEQ ID NO 21
<211> LENGTH: 9
<212> TYPE: PRT
```

```
<213> ORGANISM: CSFV

<400> SEQUENCE: 21

Thr Ala Val Ser Ala Ser Ser Val Arg
1               5

<210> SEQ ID NO 22
<211> LENGTH: 10
<212> TYPE: PRT
<213> ORGANISM: CSFV

<400> SEQUENCE: 22

Thr Ala Val Ser Lys Asp Thr Leu Arg Thr
1               5                   10

<210> SEQ ID NO 23
<211> LENGTH: 10
<212> TYPE: PRT
<213> ORGANISM: CSFV

<400> SEQUENCE: 23

Thr Ala Val Ser Gln Asp Thr Leu Arg Thr
1               5                   10

<210> SEQ ID NO 24
<211> LENGTH: 10
<212> TYPE: PRT
<213> ORGANISM: CSFV

<400> SEQUENCE: 24

Thr Ala Val Ser Ala Ala Thr Leu Arg Thr
1               5                   10

<210> SEQ ID NO 25
<211> LENGTH: 10
<212> TYPE: PRT
<213> ORGANISM: CSFV

<400> SEQUENCE: 25

Thr Ala Val Ser Ala Ser Ser Leu Arg Thr
1               5                   10

<210> SEQ ID NO 26
<211> LENGTH: 9
<212> TYPE: PRT
<213> ORGANISM: CSFV

<400> SEQUENCE: 26

Thr Ala Val Ala Ser Ser Leu Arg Thr
1               5

<210> SEQ ID NO 27
<211> LENGTH: 9
<212> TYPE: PRT
<213> ORGANISM: CSFV

<400> SEQUENCE: 27

Thr Ala Val Ala Ser Ser Val Arg Thr
1               5

<210> SEQ ID NO 28
<211> LENGTH: 10
<212> TYPE: PRT
<213> ORGANISM: CSFV
```

```
<400> SEQUENCE: 28

Thr Ala Val Asn Lys Asp Thr Leu Arg Thr
1               5                   10

<210> SEQ ID NO 29
<211> LENGTH: 10
<212> TYPE: PRT
<213> ORGANISM: CSFV

<400> SEQUENCE: 29

Thr Ala Val Asn Gln Asp Thr Leu Arg Thr
1               5                   10

<210> SEQ ID NO 30
<211> LENGTH: 10
<212> TYPE: PRT
<213> ORGANISM: CSFV

<400> SEQUENCE: 30

Thr Ala Val Ser Ala Ala Thr Val Arg Thr
1               5                   10

<210> SEQ ID NO 31
<211> LENGTH: 10
<212> TYPE: PRT
<213> ORGANISM: CSFV

<400> SEQUENCE: 31

Thr Ala Val Ser Ala Ser Ser Val Arg Thr
1               5                   10

<210> SEQ ID NO 32
<211> LENGTH: 13
<212> TYPE: PRT
<213> ORGANISM: CSFV

<400> SEQUENCE: 32

Ser Leu His Gly Ile Trp Pro Glu Lys Ile Cys Lys Gly
1               5                   10

<210> SEQ ID NO 33
<211> LENGTH: 20
<212> TYPE: PRT
<213> ORGANISM: CSFV

<400> SEQUENCE: 33

Leu Gln Arg His Glu Trp Asn Lys His Gly Trp Cys Asn Trp Tyr Asn
1               5                   10                  15

Ile Asp Pro Trp
            20

<210> SEQ ID NO 34
<211> LENGTH: 13
<212> TYPE: PRT
<213> ORGANISM: CSFV

<400> SEQUENCE: 34

Ser Leu His Gly Ile Trp Pro Glu Lys Ile Cys Thr Gly
1               5                   10

<210> SEQ ID NO 35
<211> LENGTH: 20
<212> TYPE: PRT
<213> ORGANISM: CSFV
```

```
<400> SEQUENCE: 35

Leu Gln Arg His Glu Trp Asn Lys His Gly Trp Cys Asn Trp Phe His
1               5                   10                  15

Ile Glu Pro Trp
            20

<210> SEQ ID NO 36
<211> LENGTH: 11
<212> TYPE: PRT
<213> ORGANISM: CSFV

<400> SEQUENCE: 36

Ser Leu His Gly Ile Trp Pro Glu Lys Ile Cys
1               5                   10

<210> SEQ ID NO 37
<211> LENGTH: 12
<212> TYPE: PRT
<213> ORGANISM: CSFV

<400> SEQUENCE: 37

Arg His Glu Trp Asn Lys His Gly Trp Cys Asn Trp
1               5                   10

<210> SEQ ID NO 38
<211> LENGTH: 12
<212> TYPE: RNA
<213> ORGANISM: HCLV

<400> SEQUENCE: 38
cuuuuuucuu uu                                                        12
```

UNITED STATES PATENT AND TRADEMARK OFFICE
CERTIFICATE OF CORRECTION

| | |
|---|---|
| PATENT NO. | : 9,993,544 B2 |
| APPLICATION NO. | : 15/312249 |
| DATED | : June 12, 2018 |
| INVENTOR(S) | : Gregor Meyers et al. |

Page 1 of 1

It is certified that error appears in the above-identified patent and that said Letters Patent is hereby corrected as shown below:

On the Title Page
At Column 2, Line 3, (57) ABSTRACT, "position 44" should read --position 144--
At Column 2, Line 4, (57) ABSTRACT, "position 45" should read --position 145--

In the Specification
At Column 2, Line 39, "positions 40 to 48" should read --positions 140 to 148--
At Column 3, Line 26, "position 44" should read --position 144--
At Column 3, Line 28, "position 45" should read --position 145--
At Column 3, Line 44, "positions 40 to 48" should read --positions 140 to 148--
At Column 4, Line 7, "residues 40 to 48" should read --residues 140 to 148--
At Column 4, Line 61, "positions 44, 45, and 46" should read --positions 144, 145, and 146--
At Column 4, Line 67, "position 44" should read --position 144--
At Column 5, Line 1, "position 45" should read --position 145--
At Column 5, Line 34, "position 44" should read --position 144--
At Column 5, Line 36, "position 45" should read --position 145--
At Column 10, Line 10, "position 44" should read --position 144--
At Column 10, Line 11, "position 45" should read --position 145--
At Column 10, Line 38, "position 44" should read --position 144--
At Column 10, Line 40, "position 45" should read --position 145--
At Column 13, Line 59, "position 44" should read --position 144--
At Column 13, Line 61, "position 45" should read --position 145--
At Column 19, Line 9, "position 44" should read --position 144--
At Column 19, Line 11, "position 45" should read --position 145--

In the Claims
At Column 329, Line 40 (Claim 1), please replace "position 44" with --position 144--
At Column 329, Line 42 (Claim 1), please replace "position 45" with --position 145--
At Column 330, Line 45 (Claim 10), "position 44" should read --position 144--
At Column 330, Line 46 (Claim 10), "position 45" should read --position 145--

Signed and Sealed this
Twelfth Day of March, 2019

Andrei Iancu
*Director of the United States Patent and Trademark Office*